US010189838B2

(12) United States Patent
Wang et al.

(10) Patent No.: US 10,189,838 B2
(45) Date of Patent: Jan. 29, 2019

(54) AZA-OXO-INDOLES FOR THE TREATMENT AND PROPHYLAXIS OF RESPIRATORY SYNCYTIAL VIRUS INFECTION

(71) Applicant: Hoffmann-La Roche Inc., Little Falls, NJ (US)

(72) Inventors: Lisha Wang, Shanghai (CN); Lu Gao, Shanghai (CN); Mengwei Huang, Shanghai (CN); Lei Guo, Shanghai (CN); Chungen Liang, Shanghai (CN); Wei Zhu, Shanghai (CN); Song Feng, Shanghai (CN); Xiufang Zheng, Shanghai (CN); Weixing Zhang, Shanghai (CN); Guolong Wu, Shanghai (CN); Baoxia Wang, Shanghai (CN); Hongying Yun, Shanghai (CN)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/942,725

(22) Filed: Nov. 16, 2015

(65) Prior Publication Data
US 2016/0068531 A1 Mar. 10, 2016
US 2018/0072726 A9 Mar. 15, 2018

Related U.S. Application Data

(63) Continuation of application No. PCT/EP2014/059699, filed on May 13, 2014.

(30) Foreign Application Priority Data

May 14, 2013 (WO) ................ PCT/CN2013/075594

(51) Int. Cl.
C07D 519/00 (2006.01)
C07D 471/10 (2006.01)
C07D 471/04 (2006.01)

(52) U.S. Cl.
CPC ......... *C07D 471/10* (2013.01); *C07D 471/04* (2013.01); *C07D 519/00* (2013.01)

(58) Field of Classification Search
CPC ..................... C07D 471/10; C07D 519/00
See application file for complete search history.

(56) References Cited

U.S. PATENT DOCUMENTS

2016/0318943 A1* 11/2016 He ...................... C07D 403/06

FOREIGN PATENT DOCUMENTS

| CN | 104693211 | * | 6/2015 |
|---|---|---|---|
| TW | 201305157 A1 | | 2/2013 |
| TW | 201305158 A1 | | 2/2013 |
| WO | 02/062290 A2 | | 8/2002 |
| WO | 2012/080446 A1 | | 6/2012 |
| WO | 2013/068769 A1 | | 5/2013 |
| WO | WO 2014/060411 | * | 4/2014 |

OTHER PUBLICATIONS

EP 159431.9, Priority document for WO 2014/060411 filed Mar. 15, 2013 for WO 2014/060411.*
Machine translation for CN 104693211 (Jun. 10, 2015).*
He et al. Chemical Abstracts vol. 163 No. 118683 Abstract for CN 104693211 (2015).*
(Author Not Identified) Ansel's Pharmaceutical Dosage Forms and Drug Delivery Systems (Table of Contents only, in 6 pages), Allen et al., 8th edition, Philadelphia, PA:Lippincott Williams & Wilkins, ( 2004).
(Author Not Identified) Handbook of Pharmaceutical Excipients (Cover and Table of Contents only, total in 6 pages), Rowe et al., 5th edition, Grayslake, IL:Pharmaceutical Press, ( 2005).
(Author Not Identified) Remington: The Science and Practice of Pharmacy (Cover and Table of Contents only, total in 4 pages), Gennaro et al., 20th edition, Philadelphia, PA:Lippincott Williams & Wilkins, ( 2000).
Ansel et al. Pharmaceutical Dosage Forms and Drug Delivery Systems (total in 6 pages), Balado et al., Sixth edition, Malvern, PA:Williams & Wilkins,:Table of Contents & 196-197.
Bastin et al., "Salt selection and optimisation procedures for pharmaceutical new chemical entities" Organic Process Res & Dev 4:427-435 ( 2000).
Combrink et al., "Respiratory syncytial virus fusion inhibitors. Part 6: an examination of the effect of structural variation of the benzimidazol-2-one heterocycle moiety" Bioorganic & Medicinal Chemistry Letters 17(17):4784-4790 (Aug. 4, 2007).
DeVincenzo et al., "A randomized, double-blind, placebo-controlled study of an RNAi-based therapy directed against respiratory syncytial virus" PNAS 107(19):8800-8805 (May 11, 2010).
Feltes et al., "A Randomized Controlled Trial of Motavizumab Versus Palivizumab for the Prophylaxis of Serious Respiratory Syncytial Virus Disease in Children with Hemodynamically Significant Congenital Heart Disease" Pediatric Research 70(2):186-191 ( 2011).

(Continued)

*Primary Examiner* — Emily A Bernhardt
(74) *Attorney, Agent, or Firm* — Lily J. Ackerman

(57) ABSTRACT

The invention provides novel compounds having the general formula:

wherein $R^1$, $R^2$, $R^3$, $R^4$, $R^5$, $R^6$, $W^1$, $W^2$, $W^3$, A and X are as described herein, compositions including the compounds and methods of using the compounds for the treatment and prophylaxis of respiratory syncytial virus infection.

11 Claims, No Drawings

(56) References Cited

OTHER PUBLICATIONS

Feltes et al., "Palivizumab prophylaxis reduces hospitalization due to respiratory syncytial viurs in young children with hemodynamically significant congenital heart disease" The Journal of Pediatrics 143(4):532-540 (Oct. 2003).
International Preliminary Report on Patentability issued in International Application No. PCT/EP2014/059669, dated Nov. 17, 2015 (in 8 pages).
International Search Report issued in International Application No. PCT/EP2014/059699, dated Aug. 25, 2014 (in 7 pages).
Sin et al., "Respiratory syncytial virus fusion inhibitors. Part 7: Structure-activity" Bioorganic & Medicinal Chemistry Letters 19(16):4857-4862 (Aug 15, 2009).
The IMpact-RSV Study Group (No authors listed), "Palivizumab, a Humanized Respiratory Syncytial Virus Monoclonal Antibody, Reduces Hospitalization From Respiratory Syncytial Virus Infection in High-risk Infants" Pediatrics 102(3):531-537 ( Sep. 1998).
Wandstrat, "Respiratory syncytial virus immune globulin intravenous" Ann Pharmacother 31(1):83-88 ( 1997).
Written Opinion of International Searching Authority issued in International Application No. PCT/EP2014/059699, dated Aug. 25, 2014 (in 7 pages).
Zamora et al., "RNA Interference Therapy in Lung Transplant Patients Infected with Respiratory Syncytial Virus" Am J Resp Crit Care 183:531-538 ( 2011).

* cited by examiner

AZA-OXO-INDOLES FOR THE TREATMENT AND PROPHYLAXIS OF RESPIRATORY SYNCYTIAL VIRUS INFECTION

The present invention relates to organic compounds useful for therapy and/or prophylaxis in a mammal, and in particular to respiratory syncytial virus (RSV) inhibitors useful for treating RSV infection.

CROSS REFERENCE TO RELATED APPLICATIONS

This Application is a continutaion of International Application No. PCT/EP2014/059699 having an international filing date of May 13, 2014, which claims benefit of priority to International Application No. PCT/CN2013/075594 having an international filing date of May 14, 2013, the entire contents of which are incorporated herein by reference.

FIELD OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and elder children, RSV infection is mainly associated with upper respiratory track symptoms. Severe case of RSV infection often leads to bronchiolitis and pneumonia, which requires hospitalization. High-risk factors for lower respiratory tract infections include premature birth, congenital heart disease, chronic pulmonary disease, and immunocompromised conditions. A severe infection at young age may lead to recurrent wheezing and asthma. For the elderly, RSV-related mortality rate becomes higher with advancing age.

RSV Fusion (F) protein is a surface glycoprotein on the viral envelope which, together with the G surface glycoprotein, mediates viral entry into host cell. The F protein initiates viral penetration by fusing viral and host cellular membranes and subsequently promotes viral spread after infection by melding infected cells to adjacent uninfected cells, resulting in characteristic syncytial formation. By inhibiting viral entry and spread, it is expected that treatment with chemicals described here will decrease the duration and severity of respiratory symptoms and subsequent risk of prolonged hospitalization and complications. It is also expected to limit the ability of individuals to transmit RSV within households, nursing homes and the hospital setting to other hosts potentially at high risk of complications.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophylaxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 August; 70(2):186-91).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor, RSV-604, in stem cell transplantation patients by February 2010 (www.clinicaltrials.gov), but has not released the final results. Most of other small molecules were put on hold for various reasons.

RNAi therapeutics against RSV has also been thoroughly studied. ALN-RSV01 (Alnylam Pharmaceuticals, MA, USA) is a siRNA targeting on RSV gene. A nasal spray administered for two days before and for three days after RSV inoculation decreased infection rate among adult volunteers (DeVincenzo J. et al, Proc Natl Acad Sci USA. 2010 May 11; 107(19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 February 15; 183(4): 531-8). Additional Phase IIb clinical trials in similar patient population for ALN-RSVO1 are on-going (www.clinicaltrials.gov).

Nevertheless, safe and effective treatment for RSV disease is needed urgently.

SUMMARY OF THE INVENTION

Objects of the present invention are novel compounds of formula I, their manufacture, medicaments based on a compound in accordance with the invention and their production as well as the use of compounds of formula I for the treatment or prophylaxis of RSV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_xH_{2x}$" alone or in combination signifies a saturated, linear- or branched chain alkyl group containing 2 to 6, particularly 2 to 4 carbon atoms. Particular "$C_xH_{2x}$" groups are saturated, linear alkyl chain containing 2 to 6, particularly 2 to 4 carbon atoms.

The term "$C_yH_{2y}$" alone or in combination signifies a saturated, linear- or branched chain alkyl group containing 1 to 6, particularly 1 to 4 carbon atoms. Particular "$C_yH_{2y}$" groups are saturated, linear alkyl chain containing 1 to 6, particularly 1 to 4 carbon atoms.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "cyano" alone or in combination refers to the group —CN.

The term "amino", alone or in combination, refers to primary (—NH$_2$), secondary (—NH—) or tertiary amino

The term "halogen" means fluorine, chlorine, bromine or iodine. Halogen is particularly fluorine, chlorine or bromine.

The term "hydroxy" alone or in combination refers to the group —OH.

The term "carbonyl" alone or in combination refers to the group —C(O)—.

The term "sulfonyl" alone or in combination refers to the group —S(O)$_2$—.

The term "sulfinyl" alone or in combination refers to the group —S(O)—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of RSV Fusion Protein

The present invention provides (i) novel compounds having the general formula I:

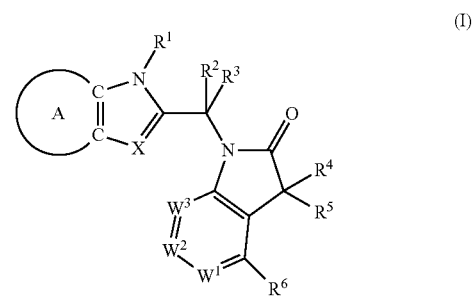

wherein

A is phenyl or pyridinyl, which is unsubstituted or substituted by $C_{1-6}$alkyl, $C_{1-6}$alkoxy, halogen, trifluoromethyl or cyano;

X is nitrogen, —CH or —CR$^7$; provided that when X is —CR$^7$, R$^1$ is hydrogen, wherein R$^7$ is $C_{1-6}$ alkylsulfonyl-C$_y$H$_{2y}$—;

when X is nitrogen or —CH, R$^1$ is $C_{1-6}$ alkylsulfonylphenyl-C$_y$H$_{2y}$—, thietan-3-yl-C$_y$H$_{2y}$—, dioxothietan-3-yl-C$_y$H$_{2y}$—, oxetan-3-yl-C$_y$H$_{2y}$—, aminooxetan-3-yl-C$_x$H$_{2x}$—, hydroxy-C$_x$H$_{2x}$—, $C_{1-6}$ alkylsufinyl-C$_y$H$_{2y}$—, trifluoromethyl-C$_y$H$_{2y}$-aminocarbonyl-O—C$_x$H$_{2x}$—,

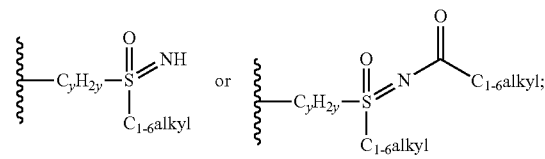

or —C$_y$H$_{2y}$—SO$_2$R$^8$, wherein R$^8$ is $C_{1-6}$alkyl, cycloalkyl, $C_{1-6}$alkylcarbonylamino, $C_{1-6}$alkylamino, diC$_{1-6}$alkylamino, amino, morpholinyl, pyrrolidinyl, piperazinyl,

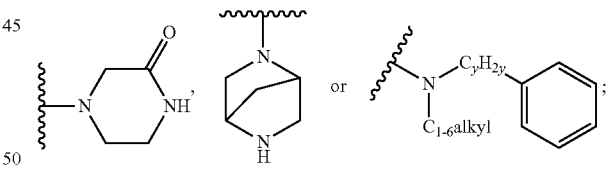

or —C$_y$H$_{2y}$—COR$^9$, wherein R$^9$ is $C_{1-6}$alkoxy, amino, hydroxy, cycloalkylsulfonylamino, cycloalkylsulfonylamino(C$_{1-6}$alkyl) or $C_{1-6}$ alkylsulfonylamino(C$_{1-6}$alkyl); or —C$_x$H$_{2x}$—NR$^{10}$R$^{11}$, wherein R$^{10}$ is hydrogen, R$^{11}$ is hydrogen, $C_{1-6}$alkoxycarbonyl, $C_{1-6}$alkylcarbonyl, $C_{1-6}$alkylsulfonyl, hydroxy-C$_x$H$_{2x}$— or

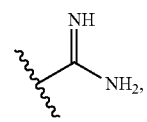

or R$^{10}$ and R$^{11}$, together with the nitrogen atom, to which they are attached, form

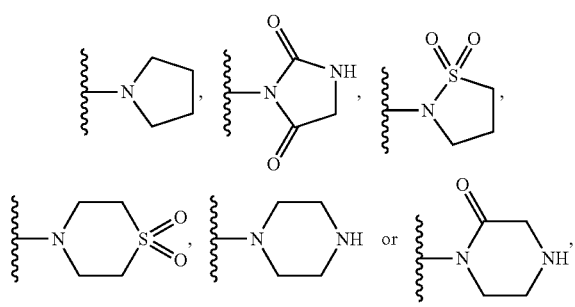

which is unsubstituted or substituted by hydroxy, $C_{1-6}$alkylcarbonyl or $C_{1-6}$ alkylsulfonyl;

$R^2$ and $R^3$ are hydrogen or deuterium simultaneously;

$R^4$ and $R^5$, with the carbon atom to which they are attached, form cycloalkyl;

$R^6$ is hydrogen or halogen;

$W^1$ is nitrogen or —$CR^{12}$, wherein $R^{12}$ is hydrogen or halogen;

$W^2$ is —CH or nitrogen;

$W^3$ is —CH or nitrogen; provided that at most one of $W^1$, $W^2$ and $W^3$ is nitrogen;

x is 2-6;

y is 1-6;

or pharmaceutically acceptable salt thereof.

Another embodiment of present invention is (ii) a compound of formula I, wherein A is phenyl, which is unsubstituted or once or twice substituted by $C_{1-6}$alkyl, $C_{1-6}$alkoxy, halogen, trifluoromethyl or cyano; or pyridinyl, which is unsubstituted or once substituted by $C_{1-6}$ alkyl or halogen;

X is nitrogen, —CH or —$CR^7$; provided that when X is —$CR^7$, $R^1$ is hydrogen, wherein $R^7$ is $C_{1-6}$ alkylsulfonyl-$C_yH_{2y}$—;

when X is nitrogen or —CH, $R^1$ is $C_{1-6}$ alkylsulfonylphenyl-$C_yH_{2y}$—, thietan-3-yl-$C_yH_{2y}$—, dioxothietan-3-yl-$C_yH_{2y}$—, oxetan-3-yl-$C_yH_{2y}$—, aminooxetan-3-yl-$C_xH_{2x}$—, hydroxy-$C_xH_{2x}$—, $C_{1-6}$ alkylsufinyl-$C_yH_{2y}$—, trifluoromethyl-$C_yH_{2y}$-aminocarbonyl-O—$C_xH_{2x}$—,

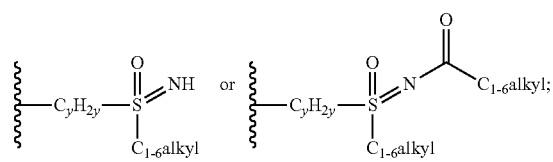

or —$C_yH_{2y}$—$SO_2R^8$, wherein $R^8$ is $C_{1-6}$alkyl, cycloalkyl, $C_{1-6}$alkylcarbonylamino, $C_{1-6}$alkylamino, di$C_{1-6}$alkylamino, amino, morpholinyl, pyrrolidinyl, piperazinyl,

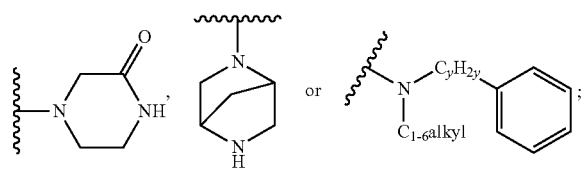

or —$C_yH_{2y}$—$COR^9$, wherein $R^9$ is $C_{1-6}$alkoxy, amino, hydroxy, cycloalkylsulfonylamino, cycloalkylsulfonylamino($C_{1-6}$alkyl) or $C_{1-6}$ alkylsulfonylamino($C_{1-6}$alkyl); or —$C_xH_{2x}$—$NR^{10}R^{11}$, wherein $R^{10}$ is hydrogen, $R^{11}$ is hydrogen, $C_{1-6}$alkoxycarbonyl, $C_{1-6}$alkylcarbonyl, $C_{1-6}$alkylsulfonyl, hydroxy-$C_xH_{2x}$— or

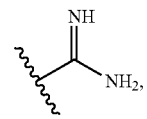

or $R^{10}$ and $R^{11}$, together with the nitrogen atom, to which they are attached, form

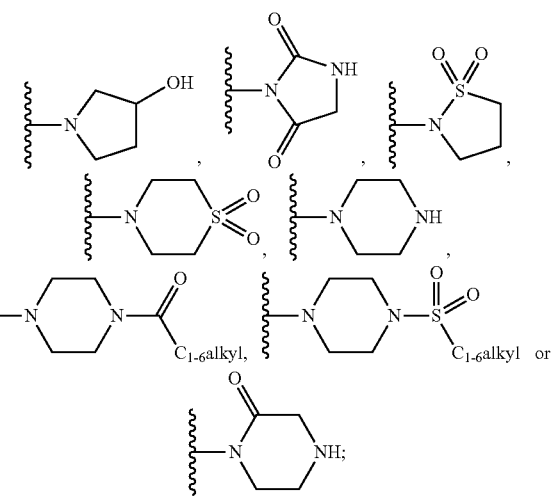

$R^2$ and $R^3$ are hydrogen or deuterium simultaneously;

$R^4$ and $R^5$, with the carbon atom to which they are attached, form cycloalkyl;

$R^6$ is hydrogen or halogen;

$W^1$ is nitrogen or —$CR^{12}$, wherein $R^{12}$ is hydrogen or halogen;

$W^2$ is —CH or nitrogen;

$W^3$ is —CH or nitrogen; provided that at most one of $W^1$, $W^2$ and $W^3$ is nitrogen;

x is 2-6;

y is 1-6;

or pharmaceutically acceptable salt thereof.

Further embodiment of present invention is (iii) a compound of formula I, wherein A is phenyl, which is unsubstituted or once or twice substituted by methyl, ethyl, fluoro, chloro, bromo, methoxy, trifluoromethyl or cyano; or pyridinyl, which is unsubstituted or once substituted by methyl or chloro;

X is nitrogen, —CH or —$CR^7$; provided that when X is —$CR^7$, $R^1$ is hydrogen, wherein $R^7$ is ethylsulfonylethyl, methylsulfonylethyl or methylsulfonylpropyl;

when X is nitrogen or —CH, $R^1$ is acetylaminoethyl, acetylaminosulfonylpropyl, 4-acetylpiperazin-1-ylethyl, aminocarbonylethyl, aminocarbonylpropyl, aminoethyl, 3-aminooxetan-3-ylmethyl, aminosulfonylpropyl, carboxyethyl, cyclopropylsulfonylaminocarbonylethyl, cyclopropylsulfonylamino(methyl)carbonylethyl, cyclopropylsulfonylethyl, cyclopropylsulfonylpropyl, dimethylaminosulfonylethyl, dimethylaminosulfonylpropyl, ethoxycarbonylethyl, ethylsulfonylethyl, ethylsulfonylpropyl, hydroxyethylaminopropyl, hydroxypropyl, methoxycarbonylaminopropyl, methoxycarbonylpropyl, methylaminosulfonylpropyl, methylsulfinylpropyl, methylsulfonylamino(methyl)carbonylethyl, methylsulfonylaminoethyl, methylsulfonylaminopropyl, methylsulfonylbutyl, methylsulfonylethyl, methylsulfonylphenylmethyl, 4-(methylsulfonyl)piperazin-1-ylethyl, methylsulfonylpropyl, oxetan-3-ylethyl, oxetan-3-ylmethyl, piperazin-1-ylethyl, piperazin-1-ylsulfonylpropyl, thietan-3-ylethyl, (2,2,2-trifluoroethyl)carbamoyloxypropyl,

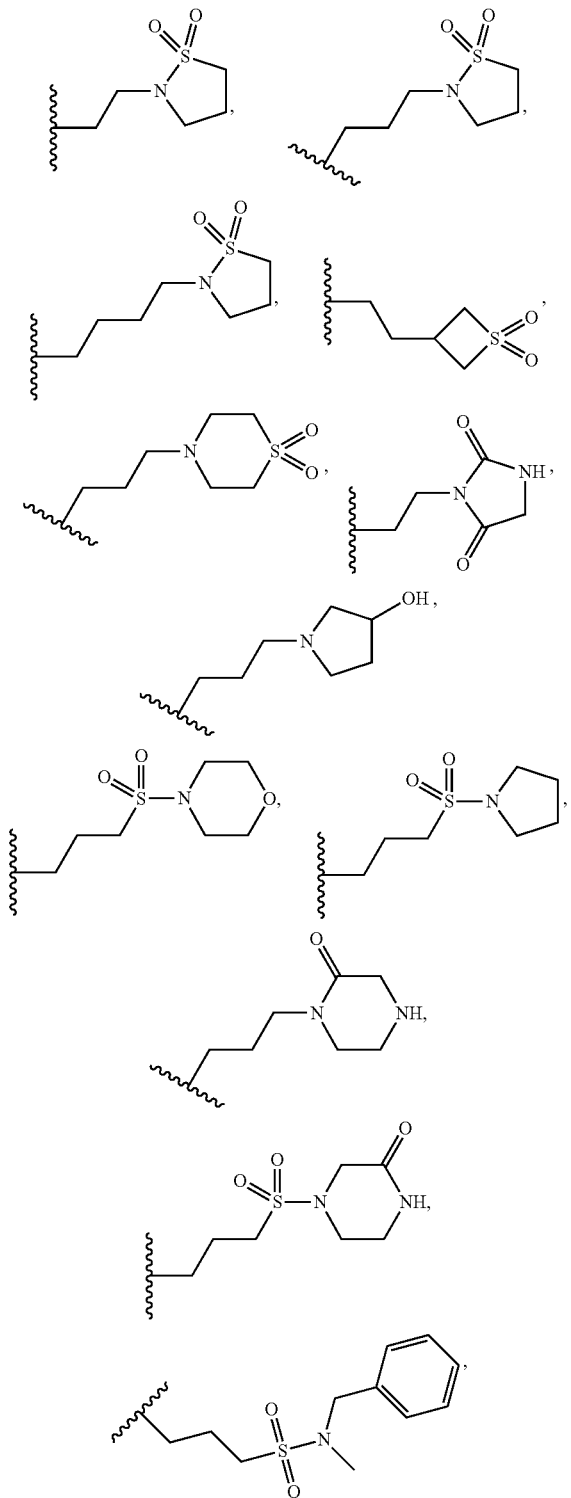

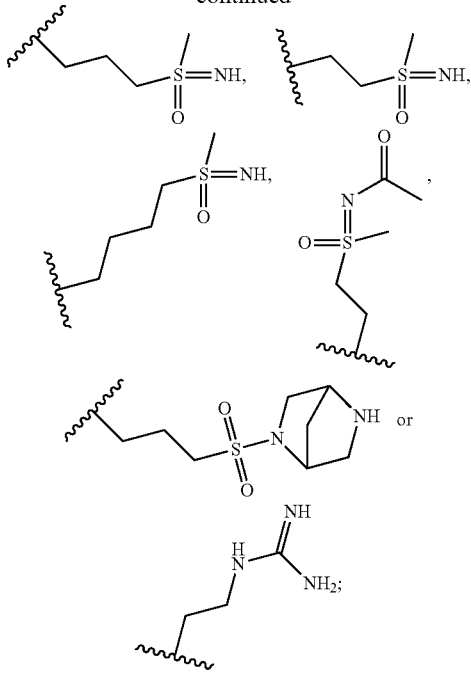

$R^2$ and $R^3$ are hydrogen or deuterium simultaneously;

$R^4$ and $R^5$, with the carbon atom to which they are attached, form cyclopropyl, cyclobutyl or cyclopentyl;

$R^6$ is hydrogen, fluoro, chloro or bromo;

$W^1$ is nitrogen, —CH or —CF;

$W^2$ is —CH or nitrogen;

$W^3$ is —CH or nitrogen; provided that at most one of $W^1$, $W^2$ and $W^3$ is nitrogen; or pharmaceutically acceptable salt thereof.

Another embodiment of present invention is (iv) a compound of formula I or a pharmaceutically acceptable salt thereof, wherein A is phenyl, which is unsubstituted or once or twice substituted by $C_{1-6}$alkyl, $C_{1-6}$alkoxy, halogen, trifluoromethyl or cyano; or pyridinyl, which is unsubstituted or once substituted by $C_{1-6}$ alkyl or halogen;

X is nitrogen, —CH or —CR$^7$; provided that when X is —CR$^7$, R$^1$ is hydrogen, wherein R$^7$ is $C_{1-6}$ alkylsulfonyl-$C_yH_{2y}$—;

when X is nitrogen or —CH, R$^1$ is $C_{1-6}$ alkylsulfonylphenyl-$C_yH_{2y}$—, thietan-3-yl-$C_yH_{2y}$—, dioxothietan-3-yl-$C_yH_{2y}$—, oxetan-3-yl-$C_yH_{2y}$—, aminooxetan-3-yl-$C_xH_{2x}$—, hydroxy-$C_xH_{2x}$—, $C_{1-6}$alkylsufinyl-$C_yH_{2y}$—, trifluoroethyl-$C_yH_{2y}$-aminocarbonyl-O—$C_xH_{2x}$—,

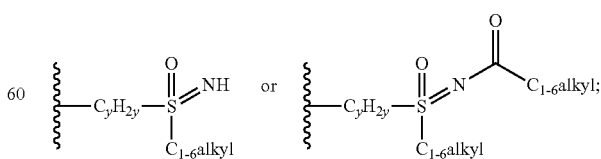

or —$C_yH_{2y}$—SO$_2$R$^8$, wherein R$^8$ is $C_{1-6}$alkyl, cycloalkyl, $C_{1-6}$alkylcarbonylamino, $C_{1-6}$alkylamino, diC$_{1-6}$alkylamino, amino, morpholinyl, pyrrolidinyl, piperazinyl,

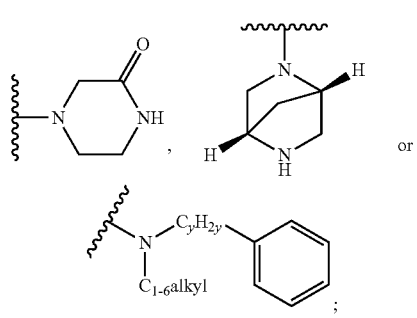

or —C$_y$H$_{2y}$—COR$^9$, wherein R$^9$ is C$_{1-6}$alkoxy, amino, hydroxy, cycloalkylsulfonylamino, cycloalkylsulfonylamino(C$_{1-6}$alkyl) or C$_{1-6}$ alkylsulfonylamino(C$_{1-6}$alkyl); or —C$_x$H$_{2x}$—NR$^{10}$R$^{11}$, wherein R$^{10}$ is hydrogen, R$^{11}$ is hydrogen, C$_{1-6}$alkoxycarbonyl, C$_{1-6}$alkylcarbonyl, C$_{1-6}$alkylsulfonyl, hydroxy-C$_x$H$_{2x}$— or

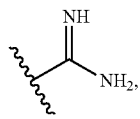

or R$^{10}$ and R$^{11}$, together with the nitrogen atom, to which they are attached, form

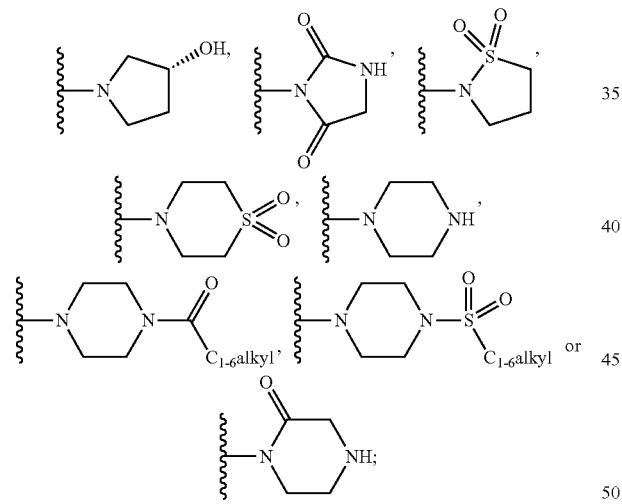

R$^2$ and R$^3$ are hydrogen or deuterium simultaneously;
R$^4$ and R$^5$, with the carbon atom to which they are attached, form cycloalkyl;
R$^6$ is hydrogen;
W$^1$ is —CH;
W$^2$ is nitrogen;
W$^3$ is —CH;
x is 2-6;
y is 1-6.

Further embodiment of present invention is (v) a compound of formula I or a pharmaceutically acceptable salt thereof, wherein A is phenyl, which is unsubstituted or once or twice substituted by methyl, ethyl, fluoro, chloro, bromo, methoxy, trifluoromethyl or cyano; or pyridinyl; which is unsubstituted or once substituted by methyl or chloro;

X is nitrogen, —CH or —CR$^7$; provided that
when X is —CR$^7$, R$^1$ is hydrogen, wherein R$^7$ is methylsulfonylethyl or methylsulfonylpropyl;
when X is nitrogen or —CH, R$^1$ is acetylaminoethyl, acetylaminosulfonylpropyl, 4-acetylpiperazin-1-ylethyl, aminocarbonylethyl, aminocarbonylpropyl, aminoethyl, 3-aminooxetan-3-ylmethyl, aminosulfonylpropyl, carboxyethyl, cyclopropylsulfonylaminocarbonylethyl, cyclopropylsulfonylamino(methyl)carbonylethyl, cyclopropylsulfonylethyl, cyclopropylsulfonylpropyl, dimethylaminosulfonylethyl, dimethylaminosulfonylpropyl, ethoxycarbonylethyl, ethylsulfonylethyl, ethylsulfonylpropyl, hydroxyethylaminopropyl, hydroxypropyl, methoxycarbonylaminopropyl, methoxycarbonylpropyl, methylaminosulfonylpropyl, methylsulfinylpropyl, methylsulfonylamino(methyl)carbonylethyl, methylsulfonylaminoethyl, methylsulfonylaminopropyl, methylsulfonylbutyl, methylsulfonylethyl, methylsulfonylphenylmethyl, 4-(methylsulfonyl)piperazin-1-ylethyl, methylsulfonylpropyl, oxetan-3-ylethyl, oxetan-3-ylmethyl, piperazin-1-ylethyl, piperazin-1-ylsulfonylpropyl, thietan-3-ylethyl, (2,2,2-trifluoroethyl)carbamoyloxypropyl,

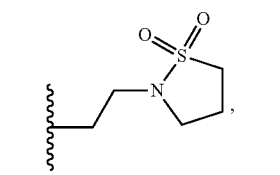

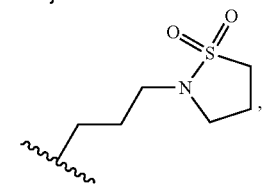

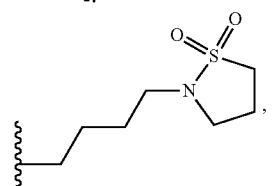

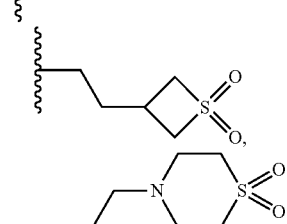

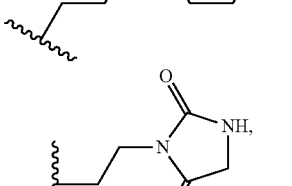

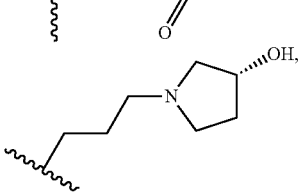

-continued

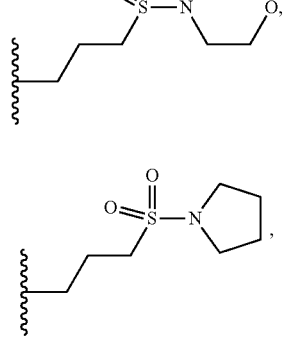

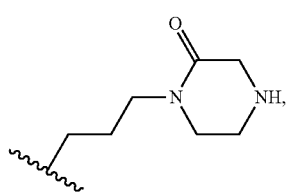

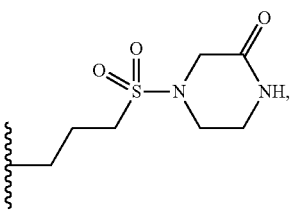

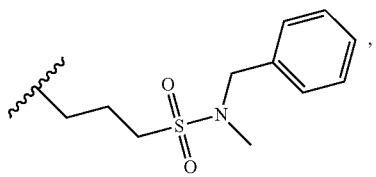

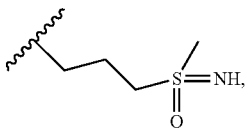

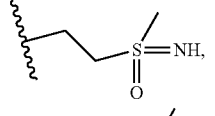

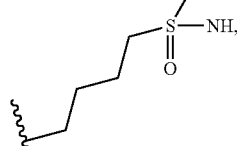

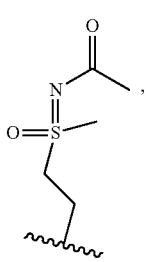

-continued

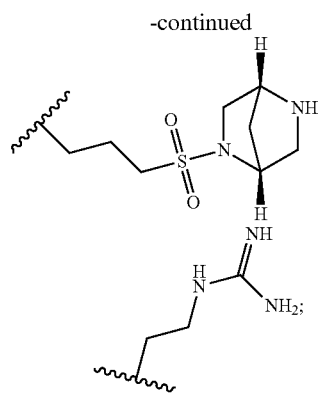

$R^2$ and $R^3$ are hydrogen or deuterium simultaneously;

$R^4$ and $R^5$, with the carbon atom to which they are attached, form cyclopropyl, cyclobutyl or cyclopentyl;

$R^6$ is hydrogen;

$W^1$ is —CH;

$W^2$ is nitrogen;

$W^3$ is —CH.

Still further embodiment of present invention is (vi) a compound of formula I or a pharmaceutically acceptable salt thereof, wherein A is phenyl, which is unsubstituted or once or twice substituted by $C_{1-6}$alkyl, $C_{1-6}$alkoxy, halogen, trifluoromethyl or cyano; or pyridinyl, which is unsubstituted or once substituted by $C_{1-6}$ alkyl or halogen;

X is nitrogen, —CH or —$CR^7$; provided that when X is —$CR^7$, $R^1$ is hydrogen, wherein $R^7$ is $C_{1-6}$ alkylsulfonyl-$C_yH_{2y}$— when X is nitrogen or —CH, $R^1$ is $C_{1-6}$ alkylsulfonylphenyl-$C_yH_{2y}$—, thietan-3-yl-$C_yH_{2y}$—, dioxothietan-3-yl-$C_yH_{2y}$—, oxetan-3-yl-$C_yH_{2y}$—, aminooxetan-3-yl-$C_xH_{2x}$—, hydroxy-$C_xH_{2x}$—, $C_{1-6}$alkylsufinyl-$C_yH_{2y}$—, trifluoromethyl-$C_yH_{2y}$-aminocarbonyl-O—$C_xH_{2x}$—,

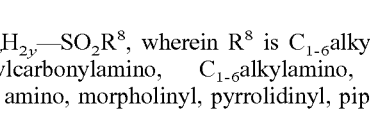

or —$C_yH_{2y}$—$SO_2R^8$, wherein $R^8$ is $C_{1-6}$alkyl, cycloalkyl, $C_{1-6}$alkylcarbonylamino, $C_{1-6}$alkylamino, di$C_{1-6}$alkylamino, amino, morpholinyl, pyrrolidinyl, piperazinyl,

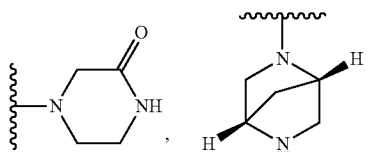

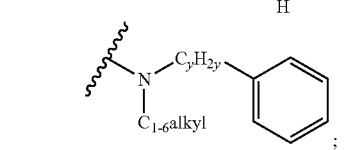

or —$C_yH_{2y}$—$COR^9$, wherein $R^9$ is $C_{1-6}$alkoxy, amino, hydroxy, cycloalkylsulfonylamino, cycloalkylsulfonylamino(C$_{1-6}$alkyl) or C$_{1-6}$ alkylsulfonylamino(C$_{1-6}$alkyl); or —C$_x$H$_{2x}$—NR$^{10}$R$^{11}$, wherein R$^{10}$ is hydrogen, R$^{11}$ is hydrogen, C$_{1-6}$alkoxycarbonyl, C$_{1-6}$alkylcarbonyl, C$_{1-6}$alkylsulfonyl, hydroxy-C$_x$H$_{2x}$— or

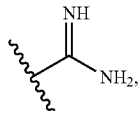

or R$^{10}$ and R$^{11}$, together with the nitrogen atom, to which they are attached, form

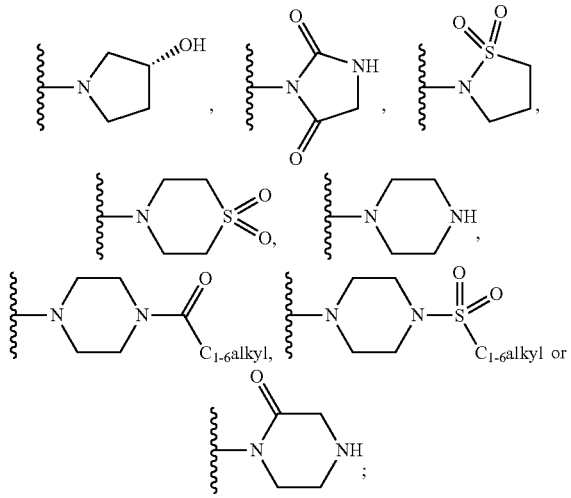

R$^2$ and R$^3$ are hydrogen or deuterium simultaneously;
R$^4$ and R$^5$, with the carbon atom to which they are attached, form cyclopropyl;
R$^6$ is hydrogen;
W$^1$ is —CH;
W$^2$ is nitrogen;
W$^3$ is —CH;
x is 2-6;
y is 1-6.

More further embodiment of present invention is (vii) a compound of formula I or a pharmaceutically acceptable salt thereof, wherein A is phenyl, which is unsubstituted or once or twice substituted by methyl, ethyl, fluoro, chloro, bromo, methoxy, trifluoromethyl or cyano; or pyridinyl, which is unsubstituted or once substituted by methyl or chloro;

X is nitrogen, —CH or —CR$^7$; provided that when X is —CR$^7$, R$^1$ is hydrogen, wherein R$^7$ is methylsulfonylethyl or methylsulfonylpropyl;

when X is nitrogen or —CH, R$^1$ is acetylaminoethyl, acetylaminosulfonylpropyl, 4-acetylpiperazin-1-ylethyl, aminocarbonylethyl, aminocarbonylpropyl, aminoethyl, 3-aminooxetan-3-ylmethyl, aminosulfonylpropyl, carboxyethyl, cyclopropylsulfonylaminocarbonylethyl, cyclopropylsulfonylamino(methyl)carbonylethyl, cyclopropylsulfonylethyl, cyclopropylsulfonylpropyl, dimethylaminosulfonylethyl, dimethylaminosulfonylpropyl, ethoxycarbonylethyl, ethylsulfonylethyl, ethylsulfonylpropyl, hydroxyethylaminopropyl, hydroxypropyl, methoxycarbonylaminopropyl, methoxycarbonylpropyl, methylaminosulfonylpropyl, methylsulfinylpropyl, methylsulfonylamino(methyl)carbonylethyl, methylsulfonylaminoethyl, methylsulfonylaminopropyl, methylsulfonylbutyl, methylsulfonylethyl, methylsulfonylphenylmethyl, 4-(methylsulfonyl)piperazin-1-ylethyl, methylsulfonylpropyl, oxetan-3-ylethyl, oxetan-3-ylmethyl, piperazin-1-ylethyl, piperazin-1-ylsulfonylpropyl, thietan-3-ylethyl, (2,2,2-trifluoroethyl)carbamoyloxypropyl,

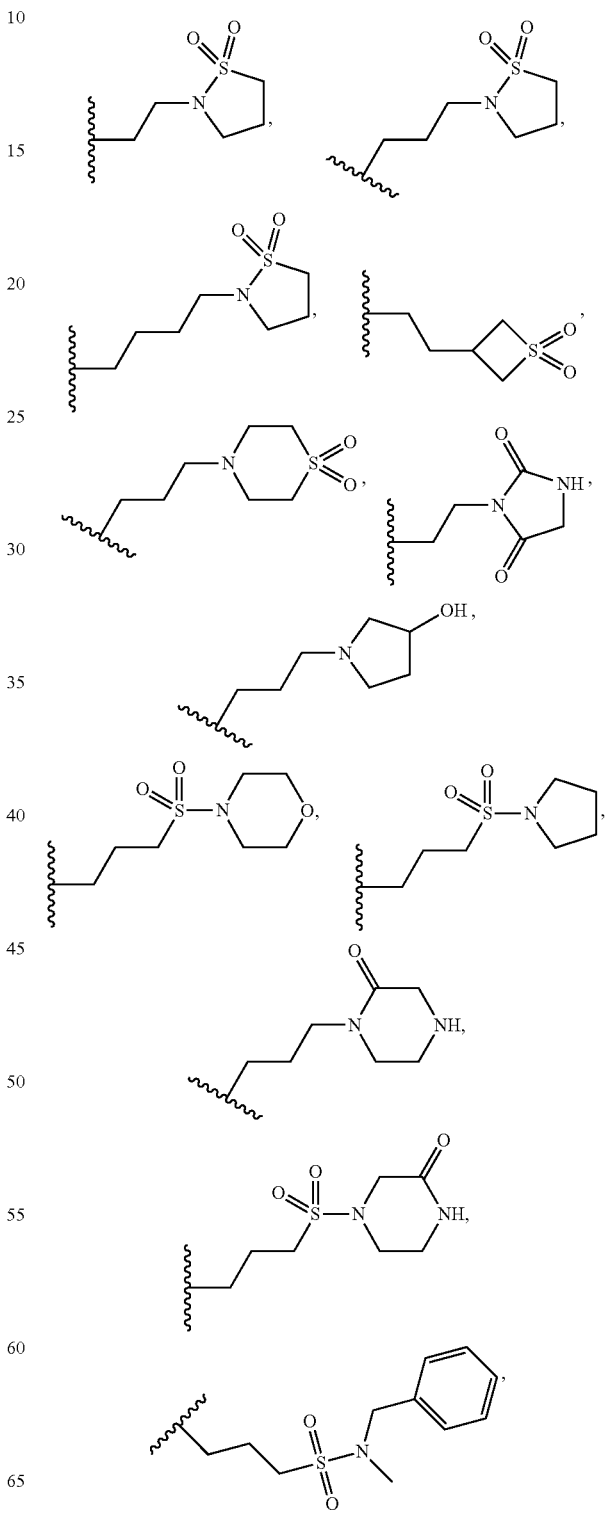

-continued

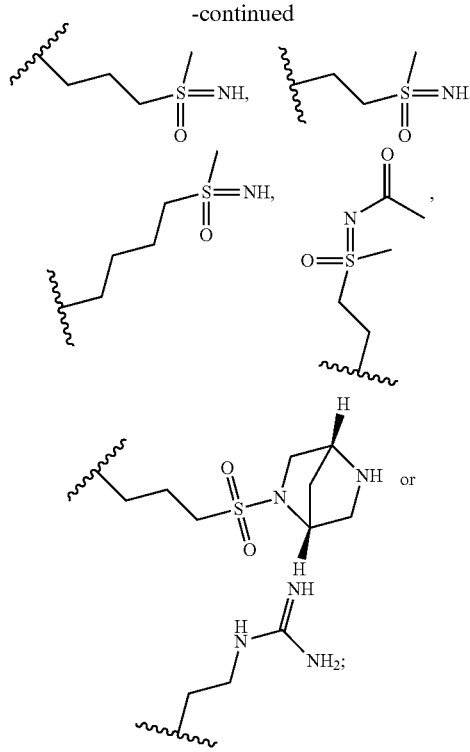

$R^2$ and $R^3$ are hydrogen or deuterium simultaneously;
$R^4$ and $R^5$, with the carbon atom to which they are attached, form cyclopropyl;
$R^6$ is hydrogen;
$W^1$ is —CH;
$W^2$ is nitrogen;
$W^3$ is —CH.

Still further embodiment of present invention is (viii) a compound of formula I or a pharmaceutically acceptable salt thereof, wherein
A is phenyl or pyridinyl, which is once substituted by halogen;
X is —CH;
$R^1$ is $C_{1-6}$ alkylsulfonyl-$C_yH_{2y}$—;
$R^2$ is hydrogen;
$R^3$ is hydrogen;
$R^4$ and $R^5$, with the carbon atom to which they are attached, form cyclobutyl or cyclopentyl;
$R^6$ is hydrogen;
$W^1$ is —CH;
$W^2$ is nitrogen;
$W^3$ is —CH;
y is 1-6.

More further embodiment of present invention is (ix) a compound of formula I or a pharmaceutically acceptable salt thereof, wherein
A is

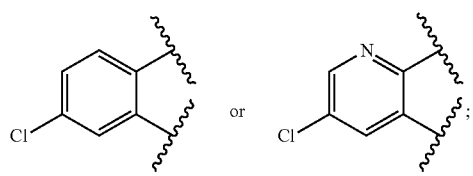 [SMILES: *c1ccc(Cl)cc1* ; *c1cc(Cl)cnc1*]

X is —CH;
$R^1$ is methylsulfonylethyl or methylsulfonylpropyl;
$R^2$ is hydrogen;
$R^3$ is hydrogen;
$R^4$ and $R^5$, with the carbon atom to which they are attached, form cyclobutyl or cyclopentyl;
$R^6$ is hydrogen;
$W^1$ is —CH;
$W^2$ is nitrogen;
$W^3$ is —CH.

Another embodiment of present invention is (x) a compound of formula I or a pharmaceutically acceptable salt thereof, wherein
A is phenyl or pyridinyl, which is once substituted by halogen;
X is nitrogen, —CH or —$CR^7$; provided that
when X is —$CR^7$, $R^1$ is hydrogen, wherein $R^7$ is $C_{1-6}$ alkylsulfonyl-$C_yH_{2y}$—;
when X is nitrogen or —CH, $R^1$ is $C_{1-6}$ alkylsulfonyl-$C_yH_{2y}$— or aminocarbonyl-$C_yH_{2y}$—;
$R^2$ is hydrogen;
$R^3$ is hydrogen;
$R^4$ and $R^5$, with the carbon atom to which they are attached, form cycloalkyl;
$R^6$ is hydrogen or halogen;
$W^1$ is nitrogen or —$CR^{12}$, wherein $R^{12}$ is hydrogen or halogen;
$W^2$ is —CH;
$W^3$ is —CH or nitrogen; provided that $W^1$ and $W^3$ are not nitrogen simultaneously;
x is 2-6;
y is 1-6.

Further embodiment of present invention is (xi) a compound of formula I or a pharmaceutically acceptable salt thereof, wherein
A is

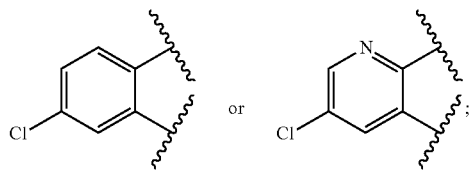

X is nitrogen, —CH or —$CR^7$; provided that
when X is —$CR^7$, $R^1$ is hydrogen, wherein $R^7$ is ethylsulfonylethyl;
when X is nitrogen or —CH, $R^1$ is ethylsulfonylethyl, methylsulfonylethyl,
methylsulfonylpropyl or aminocarbonylethyl;
$R^2$ is hydrogen;
$R^3$ is hydrogen;
$R^4$ and $R^5$, with the carbon atom to which they are attached, form cyclopropyl;
$R^6$ is hydrogen, fluoro, chloro or bromo;
$W^1$ is nitrogen, —CH or —CF;
$W^2$ is —CH;
$W^3$ is —CH or nitrogen;
provided that $W^1$ and $W^3$ are not nitrogen simultaneously.

Particular compounds of formula I, including their activity data, NMR data and MS data are summarized in the following Table 1 and 2.

TABLE 1

Structure, name and activity data of particular compounds

| Example No. | Structure | Name | CPE Long EC$_{50}$ (μM) |
|---|---|---|---|
| 1-1 | 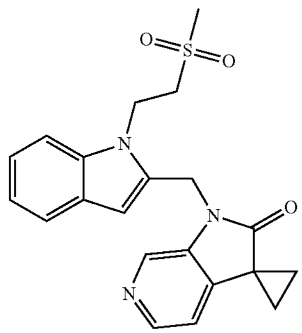 [SMILES: CS(=O)(=O)CCn1c(CN2C(=O)C3(CC3)c3ccncc32)cc2ccccc21] | 1'-({1-[2-(Methylsulfonyl)ethyl]-1H-indol-2-yl}methyl)spiro[cyclopropane-1,3'-pyrrolo[2,3-c]pyridin]-2'(1'H)-one | 0.22 |
| 1-2 | 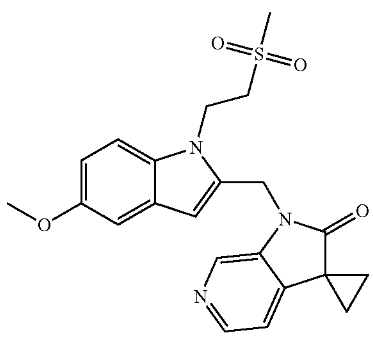 [SMILES: COc1ccc2c(c1)cc(CN1C(=O)C3(CC3)c3ccncc31)n2CCS(C)(=O)=O] | 1'-({5-Methoxy-1-[2-(methylsulfonyl)ethyl]-1H-indol-2-yl}methyl)spiro[cyclopropane-1,3'-pyrrolo[2,3-c]pyridin]-2'(1'H)-one | 0.074 |
| 1-3 | 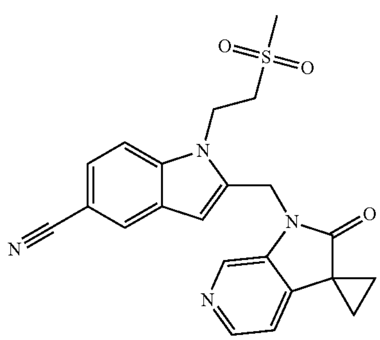 [SMILES: CS(=O)(=O)CCn1c(CN2C(=O)C3(CC3)c3ccncc32)cc2cc(C#N)ccc21] | 1-[2-(Methylsulfonyl)ethyl]-2-[(2'-oxospiro[cyclopropane-1,3'-pyrrolo[2,3-c]pyridin]-1'(2'H)-yl)methyl]-1H-indole-5-carbonitrile | 0.938 |
| 1-4 | 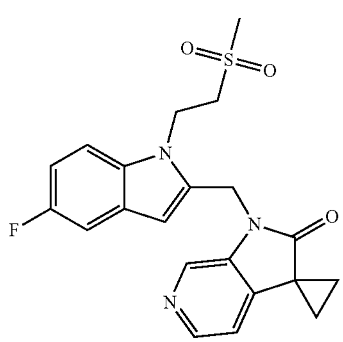 [SMILES: CS(=O)(=O)CCn1c(CN2C(=O)C3(CC3)c3ccncc32)cc2cc(F)ccc21] | 1'-({5-Fluoro-1-[2-(methylsulfonyl)ethyl]-1H-indol-2-yl}methyl)spiro[cyclopropane-1,3'-pyrrolo[2,3-c]pyridin]-2'(1'H)-one | 0.189 |

TABLE 1-continued

Structure, name and activity data of particular compounds

| Example No. | Structure | Name | CPE Long $EC_{50}$ (μM) |
|---|---|---|---|
| 1-5 | 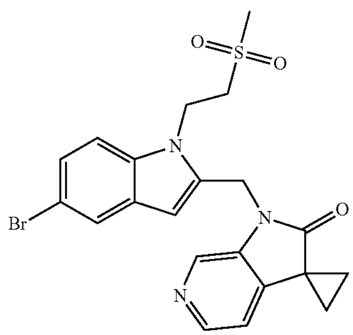 [SMILES: CS(=O)(=O)CCn1c(CN2C(=O)C3(CC3)c3ccncc32)cc2cc(Br)ccc21] | 1'-({5-Bromo-1-[2-(methylsulfonyl)ethyl]-1H-indol-2-yl}methyl)spiro[cyclopropane-1,3'-pyrrolo[2,3-c]pyridin]-2'(1'H)-one | 0.014 |
| 1-6 | 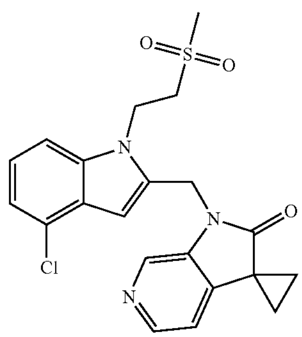 [SMILES: CS(=O)(=O)CCn1c(CN2C(=O)C3(CC3)c3ccncc32)cc2c(Cl)cccc21] | 1'-({4-Chloro-1-[2-(methylsulfonyl)ethyl]-1H-indol-2-yl}methyl)spiro[cyclopropane-1,3'-pyrrolo[2,3-c]pyridin]-2'(1'H)-one | 1.671 |
| 1-7 | 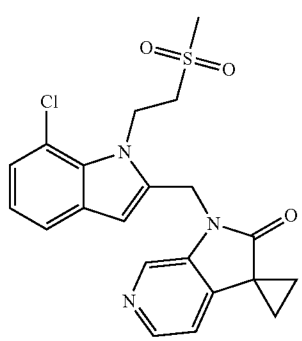 [SMILES: CS(=O)(=O)CCn1c(CN2C(=O)C3(CC3)c3ccncc32)cc2cccc(Cl)c21] | 1'-({7-Chloro-1-[2-(methylsulfonyl)ethyl]-1H-indol-2-yl}methyl)spiro[cyclopropane-1,3'-pyrrolo[2,3-c]pyridin]-2'(1'H)-one | 0.164 |
| 1-8 | 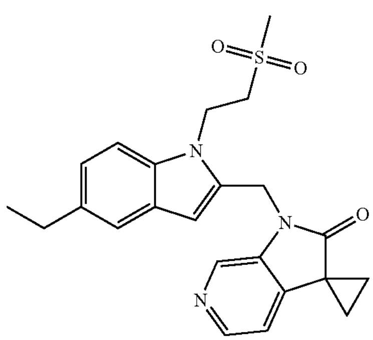 [SMILES: CCc1ccc2c(c1)cc(CN1C(=O)C3(CC3)c3ccncc31)n2CCS(C)(=O)=O] | 1'-({5-Ethyl-1-[2-(methylsulfonyl)ethyl]-1H-indol-2-yl}methyl)spiro[cyclopropane-1,3'-pyrrolo[2,3-c]pyridin]-2'(1'H)-one | 0.22 |

TABLE 1-continued

Structure, name and activity data of particular compounds

| Example No. | Structure | Name | CPE Long EC$_{50}$ (μM) |
|---|---|---|---|
| 1-9 | 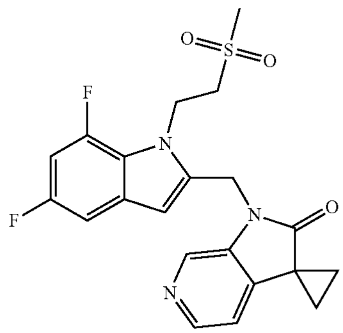 [SMILES: CS(=O)(=O)CCn1c(CN2C(=O)C3(CC3)c3ccncc32)cc2cc(F)cc(F)c21] | 1'-({5,7-Difluoro-1-[2-(methylsulfonyl)ethyl]-1H-indol-2-yl}methyl)spiro[cyclopropane-1,3'-pyrrolo[2,3-c]pyridin]-2'(1'H)-one | 0.024 |
| 1-10 | 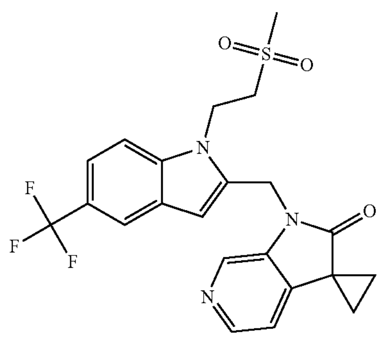 [SMILES: CS(=O)(=O)CCn1c(CN2C(=O)C3(CC3)c3ccncc32)cc2cc(C(F)(F)F)ccc21] | 1'-({1-[2-(Methylsulfonyl)ethyl]-5-(trifluoromethyl)-1H-indol-2-yl}methyl)spiro[cyclopropane-1,3'-pyrrolo[2,3-pyridin]-2'(1'H)-one | 0.557 |
| 1-11 | 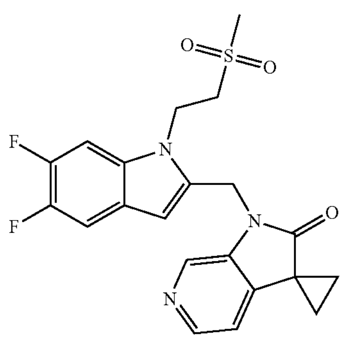 [SMILES: CS(=O)(=O)CCn1c(CN2C(=O)C3(CC3)c3ccncc32)cc2cc(F)c(F)cc21] | 1'-({5,6-Difluoro-1-[2-(methylsulfonyl)ethyl]-1H-indol-2-yl}methyl)spiro[cyclopropane-1,3'-pyrrolo[2,3-c]pyridin]-2'(1'H)-one | 0.935 |
| 1-12 | 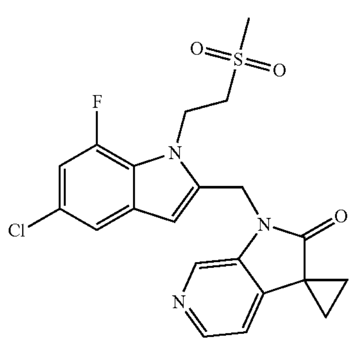 [SMILES: CS(=O)(=O)CCn1c(CN2C(=O)C3(CC3)c3ccncc32)cc2cc(Cl)cc(F)c21] | 1'-({5-Chloro-7-fluoro-1-[2-(methylsulfonyl)ethyl]-1H-indol-2-yl}methyl)spiro[cyclopropane-1,3'-pyrrolo[2,3-c]pyridin]-2'(1'H)-one | 0.0034 |

TABLE 1-continued

Structure, name and activity data of particular compounds

| Example No. | Structure | Name | CPE Long $EC_{50}$ (μM) |
|---|---|---|---|
| 1-13 | 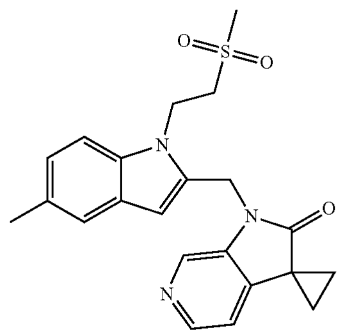 [SMILES: Cc1ccc2c(c1)cc(CN1C(=O)C3(CC3)c3ccncc31)n2CCS(C)(=O)=O] | 1'-({5-Methyl-1-[2-(methylsulfonyl)ethyl]-1H-indol-2-yl}methyl)spiro[cyclopropane-1,3'-pyrrolo[2,3-c]pyridin]-2'(1'H)-one | 0.009 |
| 1-14 | 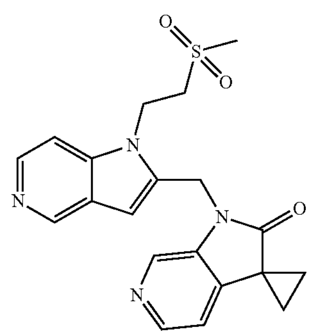 [SMILES: CS(=O)(=O)CCn1c(CN2C(=O)C3(CC3)c3ccncc32)cc2cnccc21] | 1'-({1-[2-(Methylsulfonyl)ethyl]-1H-pyrrolo[3,2-c]pyridin-2-yl}methyl)spiro[cyclopropane-1,3'-pyrrolo[2,3-c]pyridin]-2'(1'H)-one | 0.0778 |
| 2-1 | 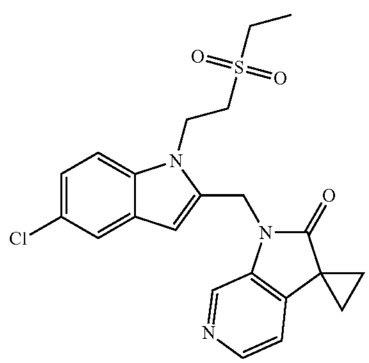 [SMILES: CCS(=O)(=O)CCn1c(CN2C(=O)C3(CC3)c3ccncc32)cc2cc(Cl)ccc21] | 1'-({5-Chloro-1-[2-(ethylsulfonyl)ethyl]-1H-indol-2-yl}methyl)spiro[cyclopropane-1,3'-pyrrolo[2,3-c]pyridin]-2'(1'H)-one | 0.00767 |
| 2-2 | 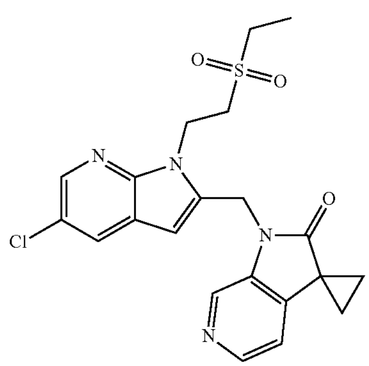 [SMILES: CCS(=O)(=O)CCn1c(CN2C(=O)C3(CC3)c3ccncc32)cc2cc(Cl)cnc21] | 1'-({5-Chloro-1-[2-(ethylsulfonyl)ethyl]-1H-pyrrolo[2,3-b]pyridin-2-yl}methyl)spiro[cyclopropane-1,3'-pyrrolo[2,3-c]pyridin]-2'(1'H)-one | 0.019 |

TABLE 1-continued

Structure, name and activity data of particular compounds

| Example No. | Structure | Name | CPE Long EC$_{50}$ (μM) |
|---|---|---|---|
| 2-3 | 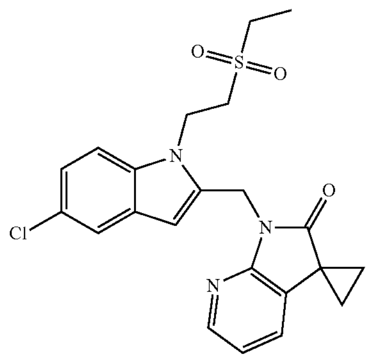 [SMILES: CCS(=O)(=O)CCn1c(CN2C(=O)C3(CC3)c3cccnc32)cc2cc(Cl)ccc21] | 1'-({5-Chloro-1-[2-(ethylsulfonyl)ethyl]-1H-indol-2-yl}methyl)spiro[cyclopropane-1,3'-pyrrolo[2,3-b]pyridin]-2'(1'H)-one | 0.247 |
| 2-4 | 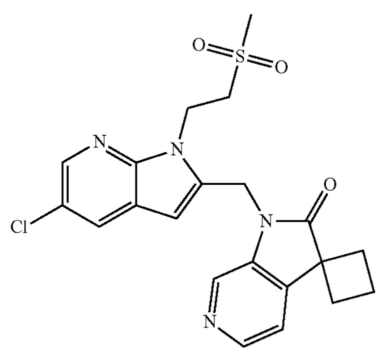 [SMILES: CS(=O)(=O)CCn1c(CN2C(=O)C3(CCC3)c3ccncc32)cc2cc(Cl)cnc21] | 1'-({5-Chloro-1-[2-(methylsulfonyl)ethyl]-1H-pyrrolo[2,3-b]pyridin-2-yl}methyl)spiro[cyclobutane-1,3'-pyrrolo[2,3-c]pyridin]-2'(1'H)-one | 0.02881 |
| 2-5 | 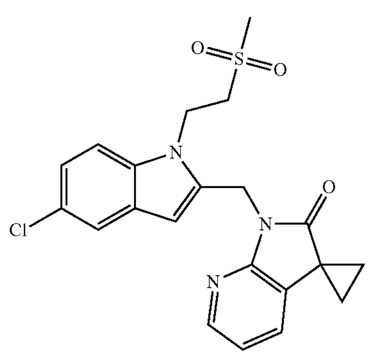 [SMILES: CS(=O)(=O)CCn1c(CN2C(=O)C3(CC3)c3cccnc32)cc2cc(Cl)ccc21] | 1'-({5-Chloro-1-[2-(methylsulfonyl)ethyl]-1H-indol-2-yl}methyl)spiro[cyclopropane-1,3'-pyrrolo[2,3-b]pyridin]-2'(1'H)-one | 0.169 |
| 2-6 | 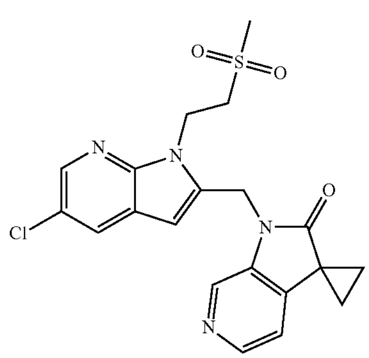 [SMILES: CS(=O)(=O)CCn1c(CN2C(=O)C3(CC3)c3ccncc32)cc2cc(Cl)cnc21] | 1'-({5-Chloro-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one | 0.02734 |

TABLE 1-continued

Structure, name and activity data of particular compounds

| Example No. | Structure | Name | CPE Long EC$_{50}$ (μM) |
|---|---|---|---|
| 2-7 | 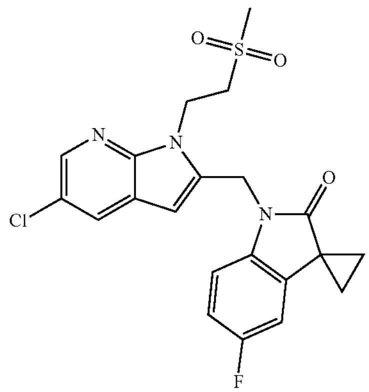 [SMILES: CS(=O)(=O)CCn1c(CN2C(=O)C3(CC3)c3cc(F)ccc32)cc2cc(Cl)cnc21] | 1'-({5-Chloro-1-[2-(methylsulfonyl)ethyl]-1H-pyrrolo[2,3-b]pyridin-2-yl}methyl)-5'-fluorospiro[cyclopropane-1,3'-indol]-2'(1'H)-one | 0.7495 |
| 2-8 | 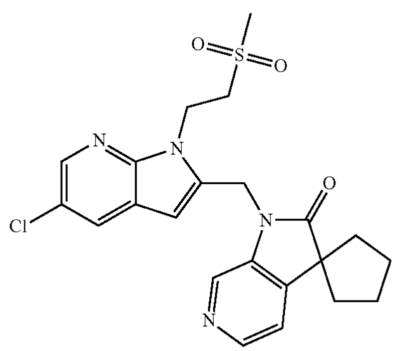 [SMILES: CS(=O)(=O)CCn1c(CN2C(=O)C3(CCCC3)c3ccncc32)cc2cc(Cl)cnc21] | 1'-({5-Chloro-1-[2-(methylsulfonyl)ethyl]-1H-pyrrolo[2,3-b]pyridin-2-yl}methyl)spiro[cyclopentane-1,3'-pyrrolo[2,3-c]pyridin]-2'(1'H)-one | 0.919 |
| 2-9 | 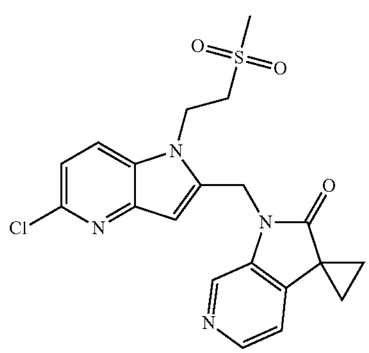 [SMILES: CS(=O)(=O)CCn1c(CN2C(=O)C3(CC3)c3ccncc32)cc2nc(Cl)ccc21] | 1'-({5-Chloro-1-[2-(methylsulfonyl)ethyl]-1H-pyrrolo[3,2-b]pyridin-2-yl}methyl)spiro[cyclopropane-1,3'-pyrrolo[2,3-c]pyridin]-2'(1'H)-one | 0.063 |
| 3-1 | 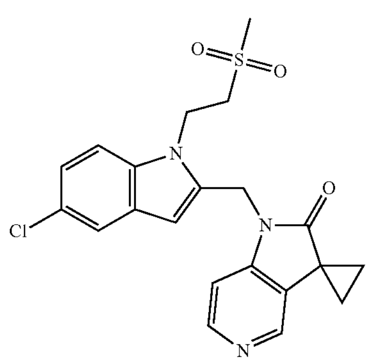 [SMILES: CS(=O)(=O)CCn1c(CN2C(=O)C3(CC3)c3cnccc32)cc2cc(Cl)ccc21] | 1'-({5-Chloro-1-[2-(methylsulfonyl)ethyl]-1H-indol-2-yl}methyl)spiro[cyclopropane-1,3'-pyrrolo[3,2-c]pyridin]-2'(1'H)-one | 0.201 |

TABLE 1-continued

Structure, name and activity data of particular compounds

| Example No. | Structure | Name | CPE Long EC$_{50}$ (μM) |
|---|---|---|---|
| 3-2 | 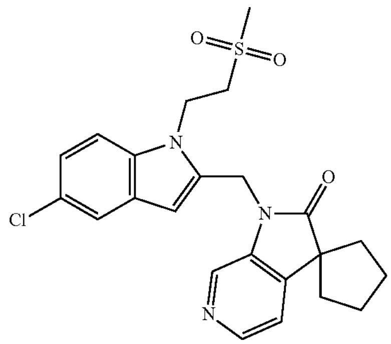 [SMILES: CS(=O)(=O)CCn1c(CN2C(=O)C3(CCCC3)c3ccncc32)cc2cc(Cl)ccc21] | 1'-({5-Chloro-1-[2-(methylsulfonyl)ethyl]-1H-indol-2-yl}methyl)spiro[cyclopentane-1,3'-pyrrolo[2,3-c]pyridin]-2'(1'H)-one | 0.29 |
| 3-3 | 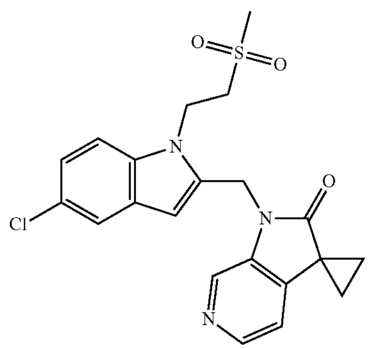 [SMILES: CS(=O)(=O)CCn1c(CN2C(=O)C3(CC3)c3ccncc32)cc2cc(Cl)ccc21] | 1'-({5-Chloro-1-[2-(methylsulfonyl)ethyl]-1H-indol-2-yl}methyl)spiro[cyclopropane-1,3'-pyrrolo[2,3-c]pyridin]-2'(1'H)-one | 0.018 |
| 4-1 | 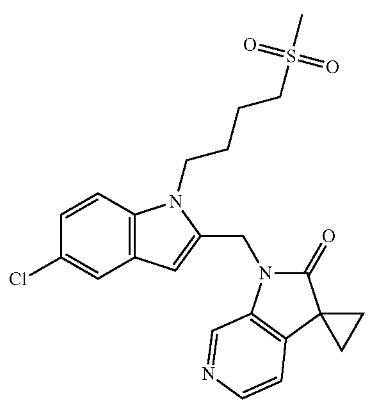 [SMILES: CS(=O)(=O)CCCCn1c(CN2C(=O)C3(CC3)c3ccncc32)cc2cc(Cl)ccc21] | 1'-({5-Chloro-1-[4-(methylsulfonyl)butyl]-1H-indol-2-yl}methyl)spiro[cyclopropane-1,3'-pyrrolo[2,3-c]pyridin]-2'(1'H)-one | 0.0059 |
| 4-2 | 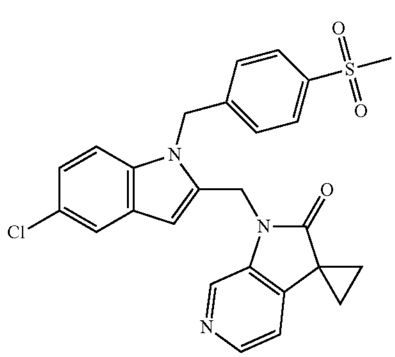 [SMILES: CS(=O)(=O)c1ccc(Cn2c(CN3C(=O)C4(CC4)c4ccncc43)cc3cc(Cl)ccc32)cc1] | 1'-({5-Chloro-1-[4-(methylsulfonyl)benzyl]-1H-indol-2-yl}methyl)spiro[cyclopropane-1,3'-pyrrolo[2,3-c]pyridin]-2'(1'H)-one | 0.2751 |

TABLE 1-continued

Structure, name and activity data of particular compounds

| Example No. | Structure | Name | CPE Long EC$_{50}$ (μM) |
|---|---|---|---|
| 4-3 | 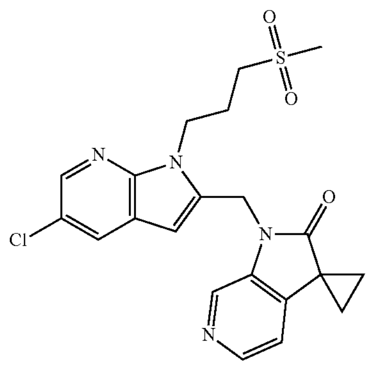 [SMILES: CS(=O)(=O)CCCn1c(CN2C(=O)C3(CC3)c3ccncc32)cc2cc(Cl)cnc21] | 1'-({5-Chloro-1-[3-(methylsulfonyl)propyl]-1H-pyrrolo[2,3-b]pyridin-2-yl}methyl)spiro[cyclopropane-1,3'-pyrrolo[2,3-c]pyridin]-2'(1'H)-one | 0.03793 |
| 4-4 | 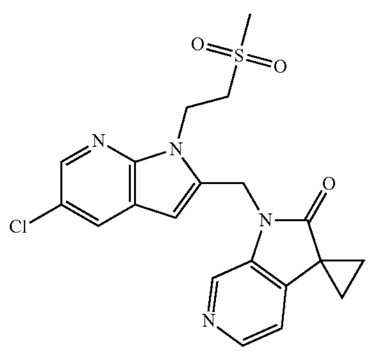 [SMILES: CS(=O)(=O)CCn1c(CN2C(=O)C3(CC3)c3ccncc32)cc2cc(Cl)cnc21] | 1'-({5-Methyl-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one | 0.064 |
| 4-5 | 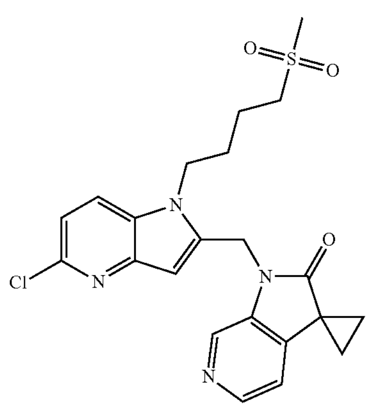 [SMILES: CS(=O)(=O)CCCCn1c(CN2C(=O)C3(CC3)c3ccncc32)cc2nc(Cl)ccc21] | 1'-({5-Chloro-1-[4-(methylsulfonyl)butyl]-1H-pyrrolo[3,2-b]pyridin-2-yl}methyl)spiro[cyclopropane-1,3'-pyrrolo[2,3-c]pyridin]-2'(1'H)-one | 0.0221 |
| 4-6 | 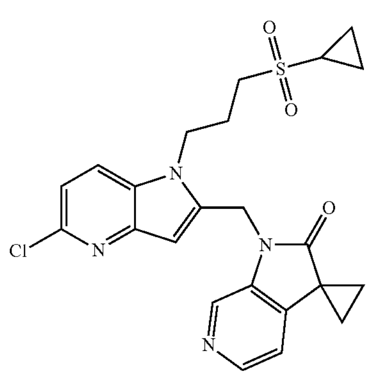 [SMILES: O=C1N(Cc2cc3nc(Cl)ccc3n2CCCS(=O)(=O)C2CC2)c2cnccc2C12CC2] | 1'-({5-Chloro-1-[3-(cyclopropylsulfonyl)propyl]-1H-pyrrolo[3,2-b]pyridin-2-yl}methyl)spiro[cyclopropane-1,3'-pyrrolo[2,3-c]pyridin]-2'(1'H)-one | 0.029 |

TABLE 1-continued

Structure, name and activity data of particular compounds

| Example No. | Structure | Name | CPE Long EC$_{50}$ (μM) |
|---|---|---|---|
| 4-7 | 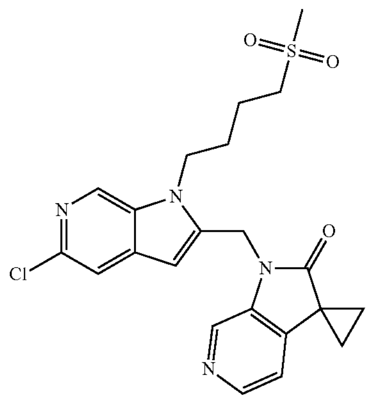 [SMILES: CS(=O)(=O)CCCCn1c(CN2C(=O)C3(CC3)c3ccncc32)cc2cc(Cl)ncc21] | 1'-({5-Chloro-1-[4-(methylsulfonyl)butyl]-1H-pyrrolo[2,3-c]pyridin-2-yl}methyl)spiro[cyclopropane-1,3'-pyrrolo[2,3-c]pyridin]-2'(1'H)-one | 0.027 |
| 4-8 | 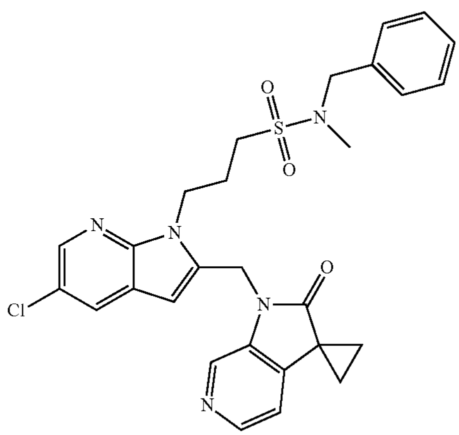 [SMILES: CN(Cc1ccccc1)S(=O)(=O)CCCn1c(CN2C(=O)C3(CC3)c3ccncc32)cc2cc(Cl)cnc21] | N-Benzyl-3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide | 0.7775 |
| 4-9 | 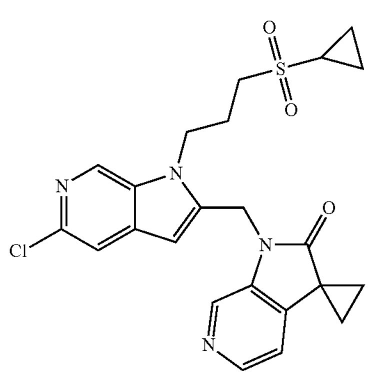 [SMILES: O=C1N(Cc2cc3cc(Cl)ncc3n2CCCS(=O)(=O)C2CC2)c2cnccc2C12CC2] | 1'-({5-Chloro-1-[3-(cyclopropylsulfonyl)propyl]-1H-pyrrolo[2,3-c]pyridin-2-yl}methyl)spiro[cyclopropane-1,3'-pyrrolo[2,3-c]pyridin]-2'(1'H)-one | 0.0487 |

TABLE 1-continued

Structure, name and activity data of particular compounds

| Example No. | Structure | Name | CPE Long EC$_{50}$ (μM) |
|---|---|---|---|
| 4-10 | 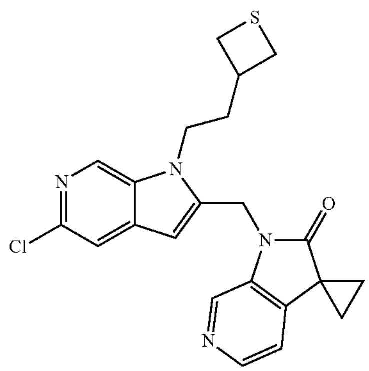 [SMILES: O=C1N(Cc2cc3cc(Cl)ncc3n2CCC2CSC2)c2cnccc2C12CC2] | 1'-({5-Chloro-1-[2-(thietan-3-yl)ethyl]-1H-pyrrolo[2,3-c]pyridin-2-yl}methyl)spiro[cyclopropane-1,3'-pyrrolo[2,3-c]pyridin]-2'(1'H)-one | 0.074 |
| 4-11 | 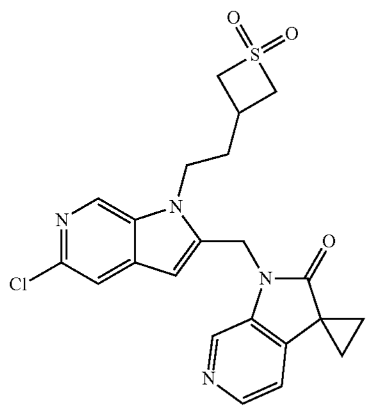 [SMILES: O=C1N(Cc2cc3cc(Cl)ncc3n2CCC2CS(=O)(=O)C2)c2cnccc2C12CC2] | 1'-({5-Chloro-1-[2-(1,1-dioxidothietan-3-yl)ethyl]-1H-pyrrolo[2,3-c]pyridin-2-yl}methyl)spiro[cyclopropane-1,3'-pyrrolo[2,3-c]pyridin]-2'(1'H)-one | 0.018 |
| 4-12 | 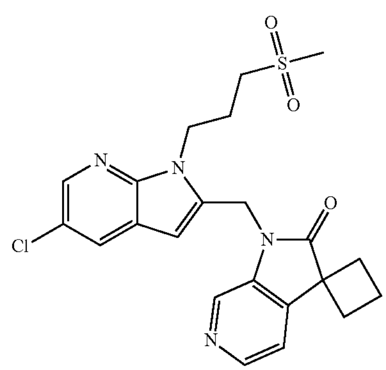 [SMILES: CS(=O)(=O)CCCn1c(CN2C(=O)C3(CCC3)c3ccncc32)cc2cc(Cl)cnc21] | 1'-({5-Chloro-1-[3-(methylsulfonyl)propyl]-1H-pyrrolo[2,3-b]pyridin-2-yl}methyl)spiro[cyclobutane-1,3'-pyrrolo[2,3-c]pyridin]-2'(1'H)-one | 0.05675 |
| 4-13 | 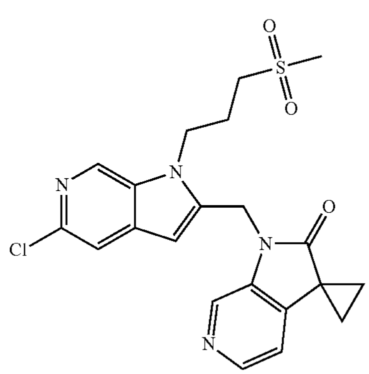 | 1'-({5-Chloro-1-[3-(methylsulfonyl)propyl]-1H-pyrrolo[2,3-c]pyridin-2-yl}methyl)spiro[cyclopropane-1,3'-pyrrolo[2,3-c]pyridin]-2'(1'H)-one | 0.026 |

TABLE 1-continued

Structure, name and activity data of particular compounds

| Example No. | Structure | Name | CPE Long EC$_{50}$ (μM) |
|---|---|---|---|
| 4-14 | 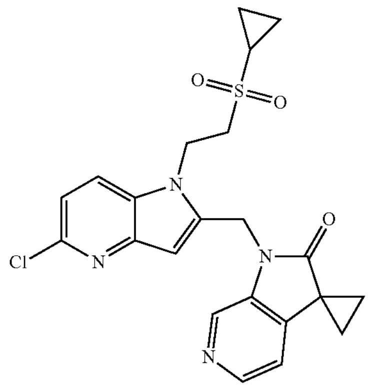 [SMILES: O=C1N(Cc2cc3nc(Cl)ccc3n2CCS(=O)(=O)C2CC2)c2cnccc2C12CC2] | 1'-({5-Chloro-1-[2-(cyclopropylsulfonyl)ethyl]-1H-pyrrolo[3,2-b]pyridin-2-yl}methyl)spiro[cyclopropane-1,3'-pyrrolo[2,3-c]pyridin]-2'(1'H)-one | 0.072 |
| 4-15 | 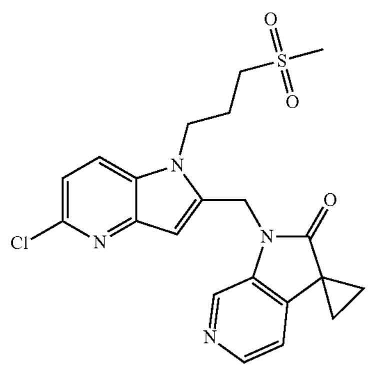 [SMILES: CS(=O)(=O)CCCn1c(CN2C(=O)C3(CC3)c3ccncc32)cc2nc(Cl)ccc21] | 1'-({5-Chloro-1-[3-(methylsulfonyl)propyl]-1H-pyrrolo[3,2-b]pyridin-2-yl}methyl)spiro[cyclopropane-1,3'-pyrrolo[2,3-c]pyridin]-2'(1'H)-one | 0.018 |
| 4-16 | 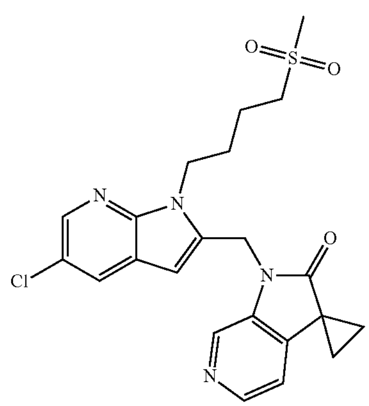 [SMILES: CS(=O)(=O)CCCCn1c(CN2C(=O)C3(CC3)c3ccncc32)cc2cc(Cl)cnc21] | 1'-({5-Chloro-1-[4-(methylsulfonyl)butyl]-1H-pyrrolo[2,3-b]pyridin-2-yl}methyl)spiro[cyclopropane-1,3'-pyrrolo[2,3-c]pyridin]-2'(1'H)-one | 0.0549 |
| 5-1 | 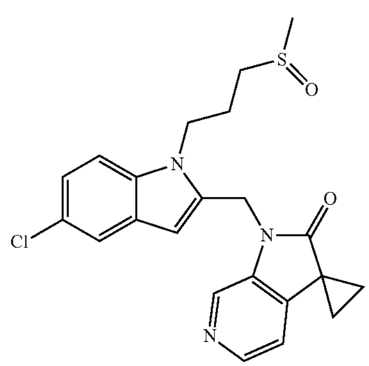 [SMILES: CS(=O)CCCn1c(CN2C(=O)C3(CC3)c3ccncc32)cc2cc(Cl)ccc21] | 1'-({5-Chloro-1-[3-(methylsulfinyl)propyl]-1H-indol-2-yl}methyl)spiro[cyclopropane-1,3'-pyrrolo[2,3-c]pyridin]-2'(1'H)-one | 0.009 |

TABLE 1-continued

Structure, name and activity data of particular compounds

| Example No. | Structure | Name | CPE Long EC$_{50}$ (μM) |
|---|---|---|---|
| 5-2 | 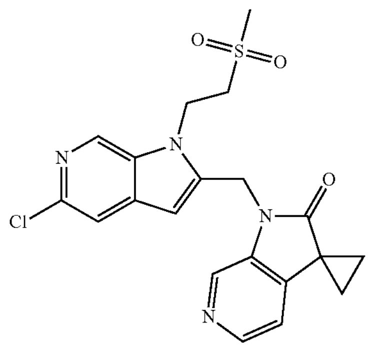 [SMILES: CS(=O)(=O)CCn1c(CN2C(=O)C3(CC3)c3ccncc32)cc2cc(Cl)ncc21] | 1'-({5-Chloro-1-[2-(methylsulfonyl)ethyl]-1H-pyrrolo[2,3-c]pyridin-2-yl}methyl)spiro[cyclopropane-1,3'-pyrrolo[2,3-c]pyridin]-2'(1'H)-one | 0.269 |
| 6 | 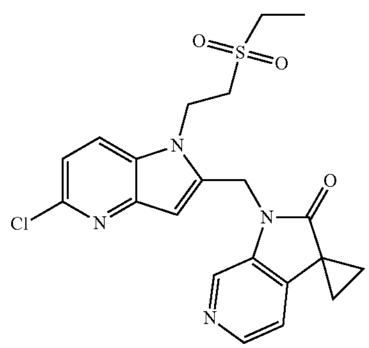 [SMILES: CCS(=O)(=O)CCn1c(CN2C(=O)C3(CC3)c3ccncc32)cc2nc(Cl)ccc21] | 1'-({5-Chloro-1-[2-(ethylsulfonyl)ethyl]-1H-pyrrolo[3,2-b]pyridin-2-yl}methyl)spiro[cyclopropane-1,3'-pyrrolo[2,3-c]pyridin]-2'(1'H)-one | 0.131 |
| 7-1 | 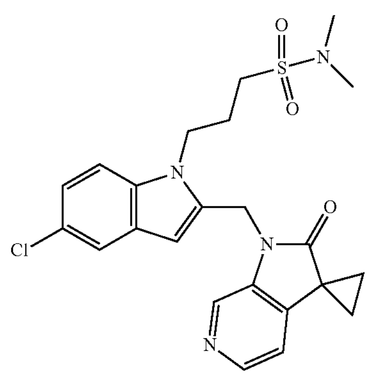 [SMILES: CN(C)S(=O)(=O)CCCn1c(CN2C(=O)C3(CC3)c3ccncc32)cc2cc(Cl)ccc21] | 3-{5-Chloro-2-[(2'-oxospiro[cyclopropane-1,3'-pyrrolo[2,3-c]pyridin]-1'(2'H)-yl)methyl]-1H-indol-1-yl}-N,N-dimethylpropane-1-sulfonamide | 0.007 |
| 7-2 | 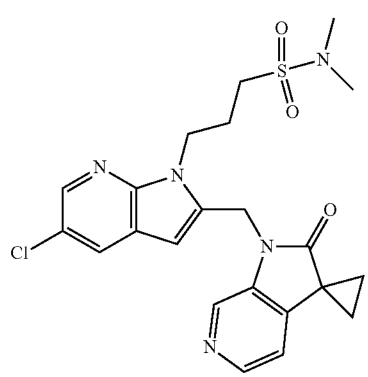 [SMILES: CN(C)S(=O)(=O)CCCn1c(CN2C(=O)C3(CC3)c3ccncc32)cc2cc(Cl)cnc21] | 3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-dimethylpropane-1-sulfonamide | 0.064 |

TABLE 1-continued

Structure, name and activity data of particular compounds

| Example No. | Structure | Name | CPE Long EC$_{50}$ (μM) |
|---|---|---|---|
| 7-3 | 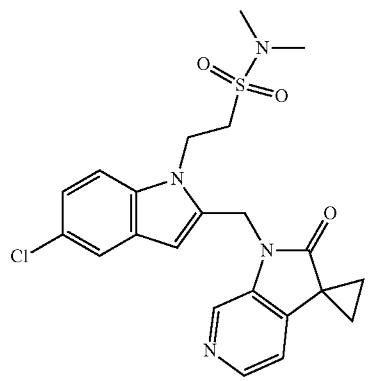 [SMILES: CN(C)S(=O)(=O)CCn1c(CN2C(=O)C3(CC3)c3ccncc32)cc2cc(Cl)ccc21] | 2-{5-Chloro-2-[(2'-oxospiro[cyclopropane-1,3'-pyrrolo[2,3-c]pyridin]-1'(2'H)-yl)methyl]-1H-indol-1-yl}-N,N-dimethylethanesulfonamide | 0.023 |
| 7-4 | 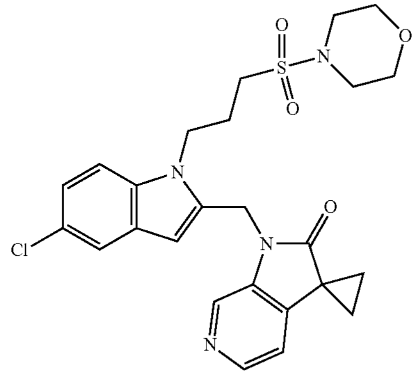 [SMILES: O=C1N(Cc2cc3cc(Cl)ccc3n2CCCS(=O)(=O)N2CCOCC2)c2cnccc2C12CC2] | 1'-({5-Chloro-1-[3-(morpholin-4-ylsulfonyl)propyl]-1H-indol-2-yl}methyl)spiro[cyclopropane-1,3'-pyrrolo[2,3-c]pyridin]-2'(1'H)-one | 0.014 |
| 7-5 | 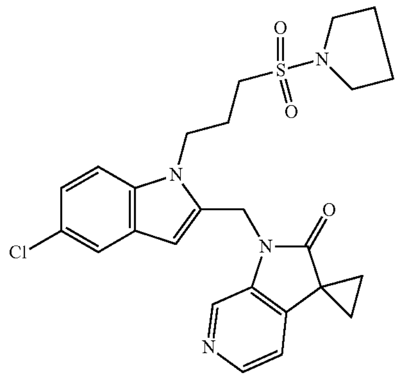 [SMILES: O=C1N(Cc2cc3cc(Cl)ccc3n2CCCS(=O)(=O)N2CCCC2)c2cnccc2C12CC2] | 1'-({5-Chloro-1-[3-(pyrrolidin-1-ylsulfonyl)propyl]-1H-indol-2-yl}methyl)spiro[cyclopropane-1,3'-pyrrolo[2,3-c]pyridin]-2'(1'H)-one | 0.02 |

TABLE 1-continued

Structure, name and activity data of particular compounds

| Example No. | Structure | Name | CPE Long $EC_{50}$ (μM) |
|---|---|---|---|
| 7-6 | 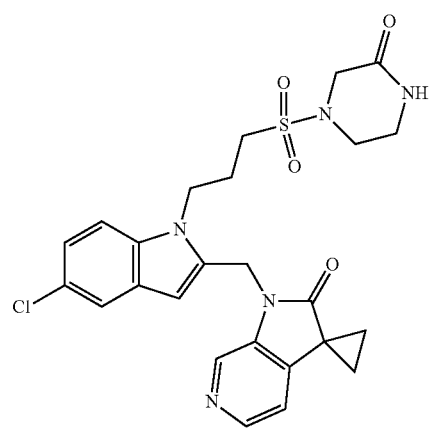 [SMILES: O=C1CN(S(=O)(=O)CCCn2c(CN3C(=O)C4(CC4)c4ccncc43)cc3cc(Cl)ccc32)CCN1] | 1'-[(5-Chloro-1-{3-[(3-oxopiperazin-1-yl)sulfonyl]propyl}-1H-indol-2-yl)methyl]spiro[cyclopropane-1,3'-pyrrolo[2,3-c]pyridin]-2'(1'H)-one | 0.007 |
| 7-7 | 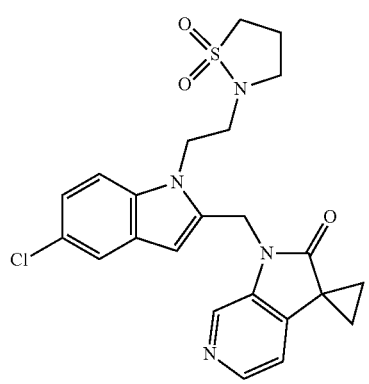 [SMILES: O=C1N(Cc2cc3cc(Cl)ccc3n2CCN2CCCS2(=O)=O)c2cnccc2C12CC2] | 1'-({5-Chloro-1-[2-(1,1-dioxido-1,2-thiazolidin-2-yl)ethyl]-1H-indol-2-yl}methyl)spiro[cyclopropane-1,3'-pyrrolo[2,3-c]pyridin]-2'(1'H)-one | 0.035 |
| 7-8 | 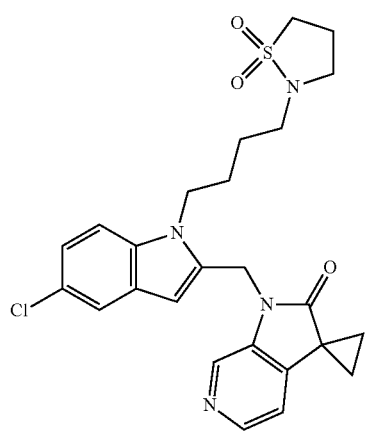 [SMILES: O=C1N(Cc2cc3cc(Cl)ccc3n2CCCCN2CCCS2(=O)=O)c2cnccc2C12CC2] | 1'-({5-Chloro-1-[4-(1,1-dioxido-1,2-thiazolidin-2-yl)butyl]-1H-indol-2-yl}methyl)spiro[cyclopropane-1,3'-pyrrolo[2,3-c]pyridin]-2'(1'H)-one | 0.018 |

TABLE 1-continued

Structure, name and activity data of particular compounds

| Example No. | Structure | Name | CPE Long EC$_{50}$ (μM) |
|---|---|---|---|
| 7-9 | 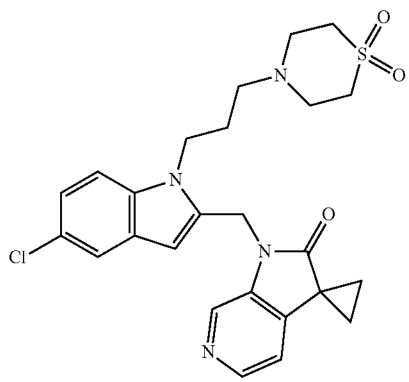 [SMILES: O=C1N(Cc2cc3cc(Cl)ccc3n2CCCN2CCS(=O)(=O)CC2)c2cnccc2C12CC2] | 1'-({5-Chloro-1-[3-(1,1-dioxidothiomorpholin-4-yl)propyl]-1H-indol-2-yl}methyl)spiro[cyclopropane-1,3'-pyrrolo[2,3-c]pyridin]-2'(1'H)-one | 0.797 |
| 7-10 | 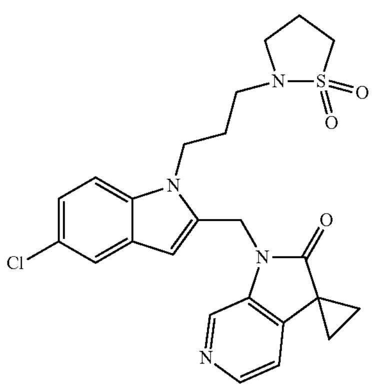 [SMILES: O=C1N(Cc2cc3cc(Cl)ccc3n2CCCN2CCCS2(=O)=O)c2cnccc2C12CC2] | 1'-({5-Chloro-1-[3-(1,1-dioxido-1,2-thiazolidin-2-yl)propyl]-1H-indol-2-yl}methyl)spiro[cyclopropane-1,3'-pyrrolo[2,3-c]pyridin]-2'(1'H)-one | 0.029 |
| 8 | 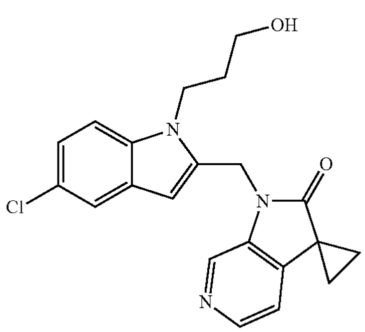 [SMILES: O=C1N(Cc2cc3cc(Cl)ccc3n2CCCO)c2cnccc2C12CC2] | 1'-{[5-Chloro-1-(3-hydroxypropyl)-1H-indol-2-yl]methyl}spiro[cyclopropane-1,3'-pyrrolo[2,3-c]pyridin]-2'(1'H)-one | 0.058 |
| 9 | 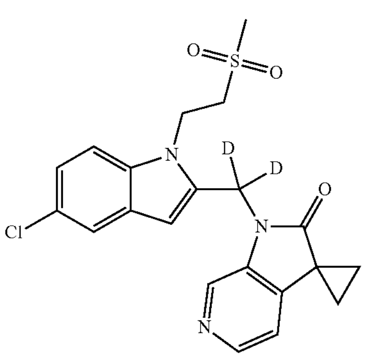 [SMILES: [2H]C([2H])(c1cc2cc(Cl)ccc2n1CCS(C)(=O)=O)N1C(=O)C2(CC2)c2ccncc21] | 1'-[{5-Chloro-1-[2-(methylsulfonyl)ethyl]-1H-indol-2-yl}($^2$H$_2$)methyl]spiro[cyclopropane-1,3'-pyrrolo[2,3-c]pyridin]-2'(1'H)-one | 0.019 |

TABLE 1-continued

Structure, name and activity data of particular compounds

| Example No. | Structure | Name | CPE Long EC$_{50}$ (μM) |
|---|---|---|---|
| 10 | 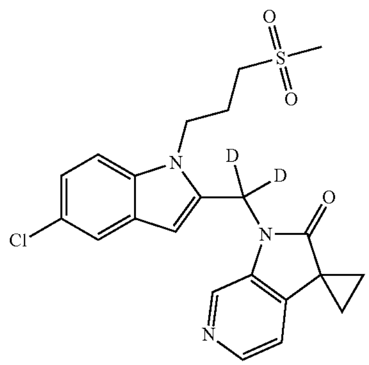 [SMILES: [2H]C([2H])(c1cc2cc(Cl)ccc2n1CCCS(C)(=O)=O)N1C(=O)C2(CC2)c2ccncc21] | 1'-[{5-Chloro-1-[3-(methylsulfonyl)propyl]-1H-indol-2-yl}($^2$H$_2$)methyl]spiro[cyclopropane-1,3'-pyrrolo[2,3-c]pyridin]-2'(1'H)-one | 0.019 |
| 11 | 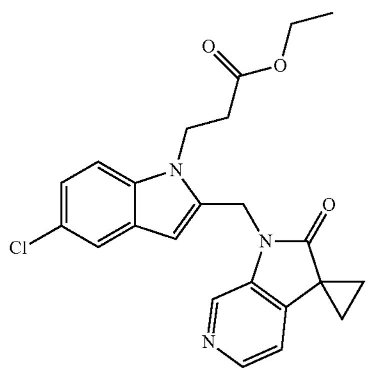 [SMILES: CCOC(=O)CCn1c(CN2C(=O)C3(CC3)c3ccncc32)cc2cc(Cl)ccc21] | Ethyl 3-{5-chloro-2-[(2'-oxospiro[cyclopropane-1,3'-pyrrolo[2,3-c]pyridin]-1'(2'H)-yl)methyl]-1H-indol-1-yl}propanoate | 0.019 |
| 12 | 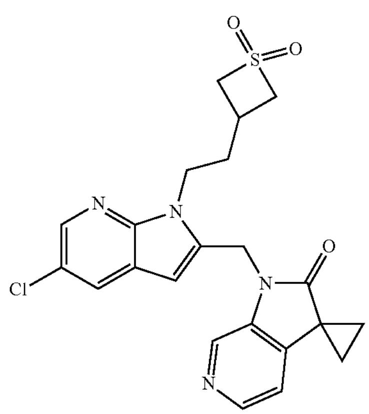 [SMILES: O=C1N(Cc2cc3cc(Cl)cnc3n2CCC2CS(=O)(=O)C2)c2cnccc2C12CC2] | 1'-({5-Chloro-1-[2-(1,1-dioxidothietan-3-yl)ethyl]-1H-pyrrolo[2,3-b]pyridin-2-yl}methyl)spiro[cyclopropane-1,3'-pyrrolo[2,3-c]pyridin]-2'(1'H)-one | 0.029 |
| 13 | 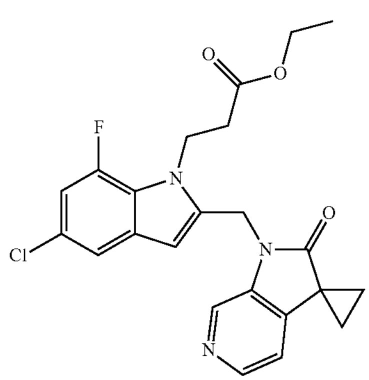 [SMILES: CCOC(=O)CCn1c(CN2C(=O)C3(CC3)c3ccncc32)cc2cc(Cl)cc(F)c21] | Ethyl 3-{5-chloro-7-fluoro-2-[(2'-oxospiro[cyclopropane-1,3'-pyrrolo[2,3-c]pyridin]-1'(2'H)-yl)methyl]-1H-indol-1-yl}propanoate | 0.018 |

TABLE 1-continued

Structure, name and activity data of particular compounds

| Example No. | Structure | Name | CPE Long EC$_{50}$ (μM) |
|---|---|---|---|
| 14-1 | 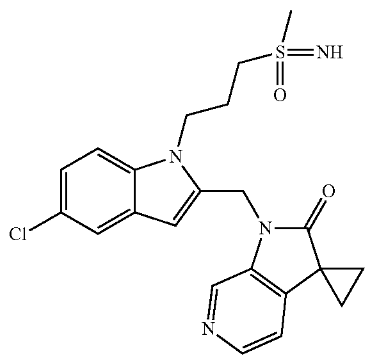 [SMILES: CS(=N)(=O)CCCn1c(CN2C(=O)C3(CC3)c3ccncc32)cc2cc(Cl)ccc21] | 1'-({5-Chloro-1-[3-(S-methylsulfomidoyl)propyl]-1H-indol-2-yl}methyl)spiro[cyclopropane-1,3'-pyrrolo[2,3-c]pyridin]-2'(1'H)-one | 0.006 |
| 14-2 | 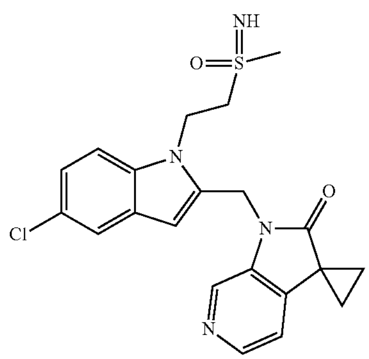 [SMILES: CS(=N)(=O)CCn1c(CN2C(=O)C3(CC3)c3ccncc32)cc2cc(Cl)ccc21] | 1'-({5-Chloro-1-[2-(S-methylsulfonimidoyl)ethyl]-1H-indol-2-yl}methyl)spiro[cyclopropane-1,3'-pyrrolo[2,3-c]pyridin]-2'(1'H)-one | 0.007 |
| 14-3 | 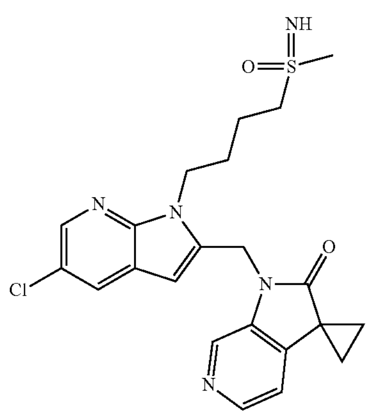 [SMILES: CS(=N)(=O)CCCCn1c(CN2C(=O)C3(CC3)c3ccncc32)cc2cc(Cl)cnc21] | 1'-({5-Chloro-1-[4-(S-methylsulfonimidoyl)butyl]-1H-pyrrolo[2,3-b]pyridin-2-yl}methyl)spiro[cyclopropane-1,3'-pyrrolo[2,3-c]pyridin]-2'(1'H)-one | 0.074 |
| 14-4 | 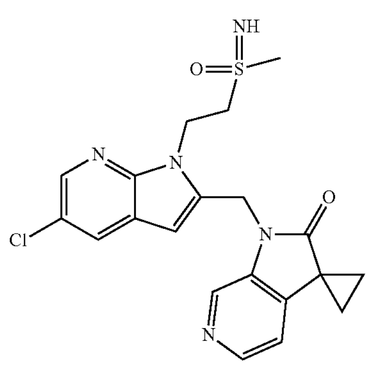 [SMILES: CS(=N)(=O)CCn1c(CN2C(=O)C3(CC3)c3ccncc32)cc2cc(Cl)cnc21] | 1'-({5-Chloro-1-[2-(S-methylsulfonimidoyl)ethyl]-1H-pyrrolo[2,3-b]pyridin-2-yl}methyl)spiro[cyclopropane-1,3'-pyrrolo[2,3-c]pyridin]-2'(1'H)-one | 0.172 |

TABLE 1-continued

Structure, name and activity data of particular compounds

| Example No. | Structure | Name | CPE Long EC$_{50}$ (μM) |
|---|---|---|---|
| 15 | 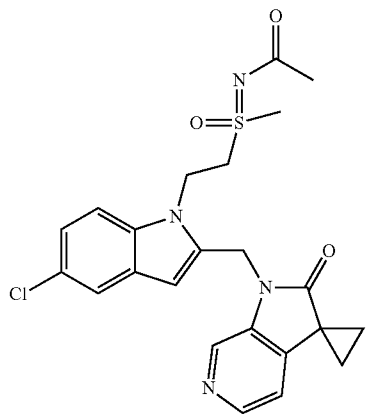 [SMILES: CC(=O)N=S(C)(=O)CCn1c(CN2C(=O)C3(CC3)c3ccncc32)cc2cc(Cl)ccc21] | N-[(2-{5-Chloro-2-[(2'-oxospiro[cyclopropane-1,3'-pyrrolo[2,3-c]pyridin]-1'(2'H)-yl)methyl]-1H-indol-1-yl}ethyl)(methyl)oxido-λ$^6$-sulfanylidene]acetamide | 0.025 |
| 16-1 | 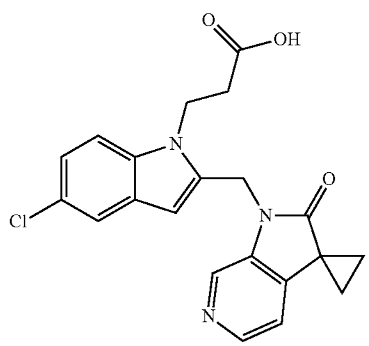 [SMILES: O=C(O)CCn1c(CN2C(=O)C3(CC3)c3ccncc32)cc2cc(Cl)ccc21] | 3-{5-Chloro-2-[(2'-oxospiro[cyclopropane-1,3'-pyrrolo[2,3-c]pyridin]-1'(2'H)-yl)methyl]-1H-indol-1-yl}propanoic acid | 0.3895 |
| 16-2 | 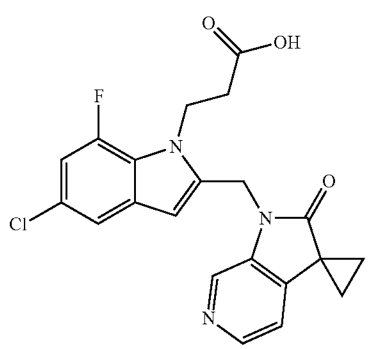 [SMILES: O=C(O)CCn1c(CN2C(=O)C3(CC3)c3ccncc32)cc2cc(Cl)cc(F)c21] | 3-{5-Chloro-7-fluoro-2-[(2'-oxospiro[cyclopropane-1,3'-pyrrolo[2,3-c]pyridin]-1'(2'H)-yl)methyl]-1H-indol-1-yl}propanoic acid | 0.3 |
| 17 | 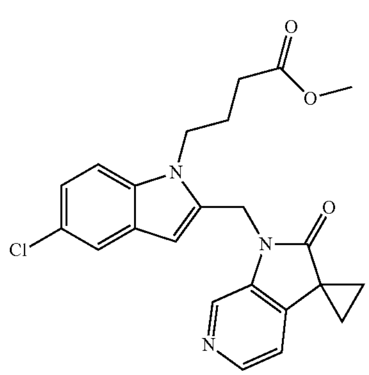 [SMILES: COC(=O)CCCn1c(CN2C(=O)C3(CC3)c3ccncc32)cc2cc(Cl)ccc21] | Methyl 4-{5-chloro-2-[(2'-oxospiro[cyclopropane-1,3'-pyrrolo[2,3-c]pyridin]-1'(2'H)-yl)methyl]-1H-indol-1-yl}butanoate | 0.01862 |

TABLE 1-continued

Structure, name and activity data of particular compounds

| Example No. | Structure | Name | CPE Long EC$_{50}$ (μM) |
|---|---|---|---|
| 18-1 | 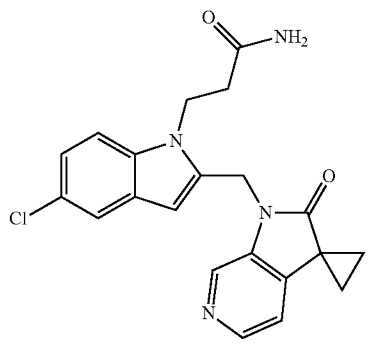 [SMILES: NC(=O)CCn1c(CN2C(=O)C3(CC3)c3ccncc32)cc2cc(Cl)ccc21] | 3-{5-Chloro-2-[(2'-oxospiro[cyclopropane-1,3'-pyrrolo[2,3-c]pyridin]-1'(2'H)-yl)methyl]-1H-indol-1-yl}propanamide | 0.017 |
| 18-2 | 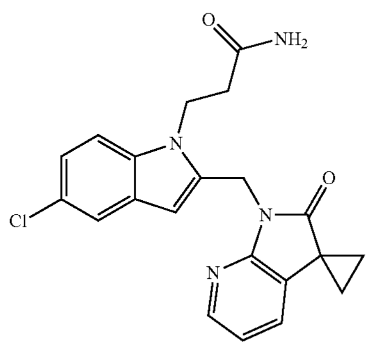 [SMILES: NC(=O)CCn1c(CN2C(=O)C3(CC3)c3cccnc32)cc2cc(Cl)ccc21] | 3-{5-Chloro-2-[(2'-oxospiro[cyclopropane-1,3'-pyrrolo[2,3-b]pyridin]-1'(2'H)-yl)methyl]-1H-indol-1-yl}propanamide | 0.711 |
| 18-3 | 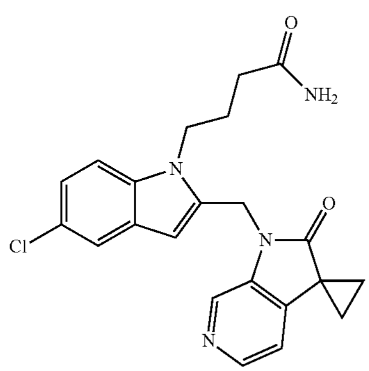 | 4-{5-Chloro-2-[(2'-oxospiro[cyclopropane-1,3'-pyrrolo[2,3-c]pyridin]-1'(2'H)-yl)methyl]-1H-indol-1-yl}butanamide | 0.011 |
| 19-1 | 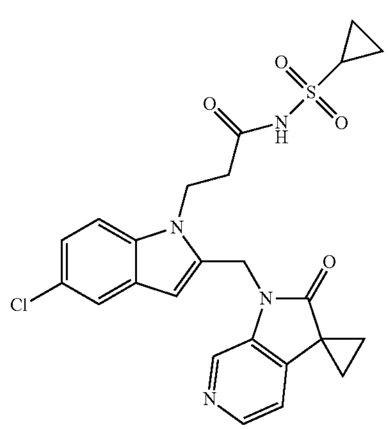 [SMILES: O=C(CCn1c(CN2C(=O)C3(CC3)c3ccncc32)cc2cc(Cl)ccc21)NS(=O)(=O)C1CC1] | 3-{5-Chloro-2-[(2'-oxospiro[cyclopropane-1,3'-pyrrolo[2,3-c]pyridin]-1'(2'H)-yl)methyl]-1H-indol-1-yl}-N-(cyclopropylsulfonyl)propanamide | 1.184 |

TABLE 1-continued

Structure, name and activity data of particular compounds

| Example No. | Structure | Name | CPE Long EC$_{50}$ (μM) |
|---|---|---|---|
| 19-2 | 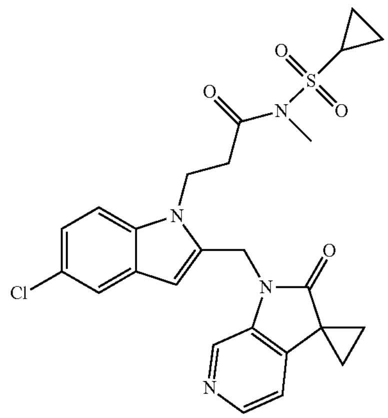 [SMILES: CN(C(=O)CCn1c(CN2C(=O)C3(CC3)c3ccncc32)cc2cc(Cl)ccc21)S(=O)(=O)C1CC1] | 3-{5-Chloro-2-[(2'-oxospiro[cyclopropane-1,3'-pyrrolo[2,3-c]pyridin]-1'(2'H)-yl)methyl]-1H-indol-1-yl}-N-(cyclopropylsulfonyl)-N-methylpropanamide | 0.059 |
| 19-3 | 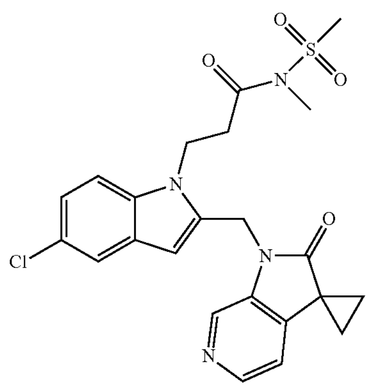 [SMILES: CN(C(=O)CCn1c(CN2C(=O)C3(CC3)c3ccncc32)cc2cc(Cl)ccc21)S(C)(=O)=O] | 3-{5-Chloro-2-[(2'-oxospiro[cyclopropane-1,3'-pyrrolo[2,3-c]pyridin]-1'(2'H)-yl)methyl]-1H-indol-1-yl}-N-methyl-N-(methylsulfonyl)propanamide | 0.047 |
| 20 | 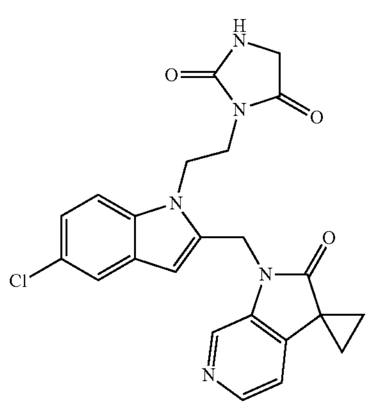 [SMILES: O=C1CNC(=O)N1CCn1c(CN2C(=O)C3(CC3)c3ccncc32)cc2cc(Cl)ccc21] | 3-(2-{5-Chloro-2-[(2'-oxospiro[cyclopropane-1,3'-pyrrolo[2,3-c]pyridin]-1'(2'H)-yl)methyl]-1H-indol-1-yl}ethyl)imidazolidine-2,4-dione | 3.484 |

TABLE 1-continued

Structure, name and activity data of particular compounds

| Example No. | Structure | Name | CPE Long EC$_{50}$ (μM) |
|---|---|---|---|
| 21 | 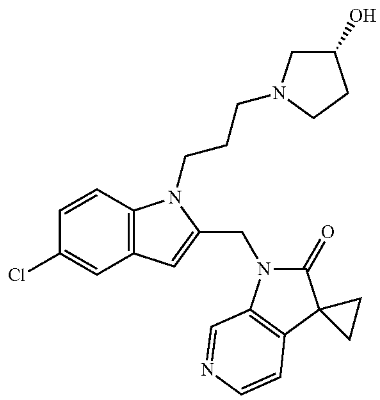 [SMILES: O=C1N(Cc2cc3cc(Cl)ccc3n2CCCN2CC[C@@H](O)C2)c2cnccc2C12CC2] | 1'-[(5-Chloro-1-{3-[(3R)-3-hydroxypyrrolidin-1-yl]propyl}-1H-indol-2-yl)methyl]spiro[cyclopropane-1,3'-pyrrolo[2,3-c]pyridin]-2'(1'H)-one | 0.544 |
| 22-1 | 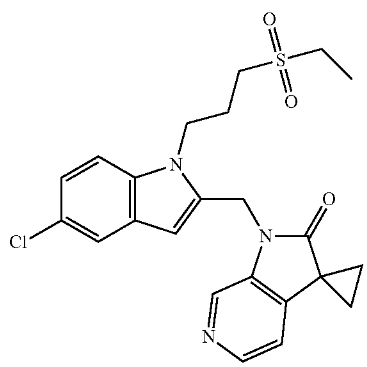 [SMILES: CCS(=O)(=O)CCCn1c(CN2C(=O)C3(CC3)c3ccncc32)cc2cc(Cl)ccc21] | 1'-({5-Chloro-1-[3-(ethylsulfonyl)propyl]-1H-indol-2-yl}methyl)spiro[cyclopropane-1,3'-pyrrolo[2,3-c]pyridin]-2'(1'H)-one | 0.003 |
| 22-2 | 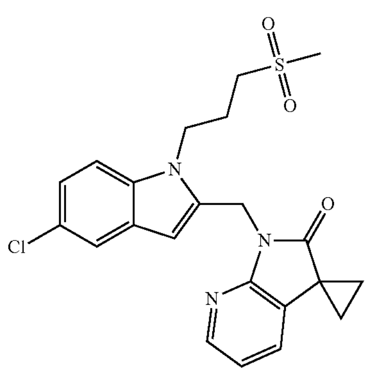 [SMILES: CS(=O)(=O)CCCn1c(CN2C(=O)C3(CC3)c3cccnc32)cc2cc(Cl)ccc21] | 1'-({5-Chloro-1-[3-(methylsulfonyl)propyl]-1H-indol-2-yl}methyl)spiro[cyclopropane-1,3'-pyrrolo[2,3-b]pyridin]-2'(1'H)-one | 0.088 |
| 22-3 | 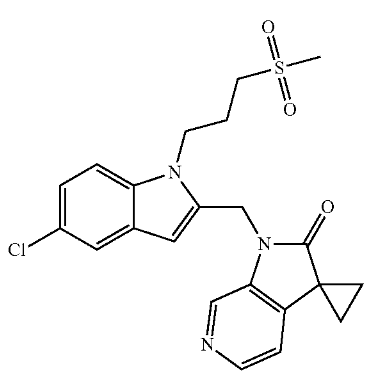 | 1'-({5-Chloro-1-[3-(methylsulfonyl)propyl]-1H-indol-2-yl}methyl)spiro[cyclopropane-1,3'-pyrrolo[2,3-c]pyridin]-2'(1'H)-one | 0.003 |

TABLE 1-continued

Structure, name and activity data of particular compounds

| Example No. | Structure | Name | CPE Long EC$_{50}$ (μM) |
|---|---|---|---|
| 23 | 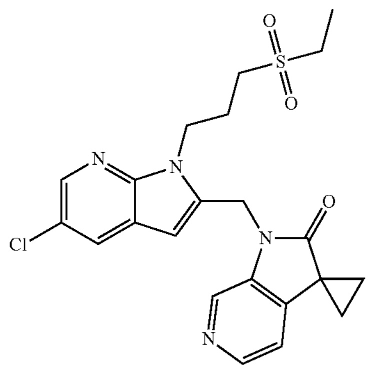 [SMILES: CCS(=O)(=O)CCCn1c(CN2C(=O)C3(CC3)c3ccncc32)cc2cc(Cl)cnc21] | 1'-({5-Chloro-1-[3-(ethylsulfonyl)propyl]-1H-pyrrolo[2,3-b]pyridin-2-yl}methyl)spiro[cyclopropane-1,3'-pyrrolo[2,3-c]pyridin]-2'(1'H)-one | 0.063 |
| 24-1 | 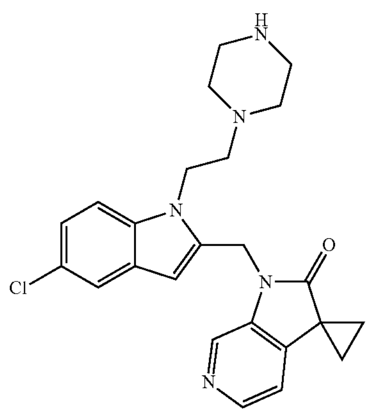 [SMILES: O=C1N(Cc2cc3cc(Cl)ccc3n2CCN2CCNCC2)c2cnccc2C12CC2] | 1'-({5-Chloro-1-[2-(piperazin-1-yl)ethyl]-1H-indol-2-yl}methyl)spiro[cyclopropane-1,3'-pyrrolo[2,3-c]pyridin]-2'(1'H)-one | 0.068 |
| 24-2 | 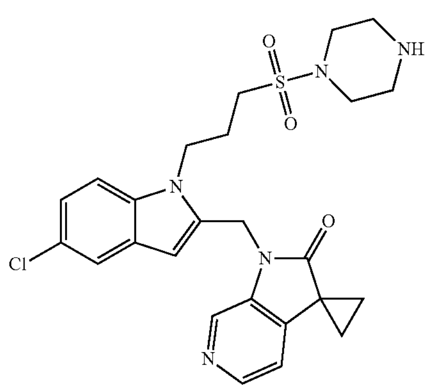 [SMILES: O=C1N(Cc2cc3cc(Cl)ccc3n2CCCS(=O)(=O)N2CCNCC2)c2cnccc2C12CC2] | 1'-({5-Chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one | 0.015 |

TABLE 1-continued

Structure, name and activity data of particular compounds

| Example No. | Structure | Name | CPE Long EC$_{50}$ (μM) |
|---|---|---|---|
| 24-3 | 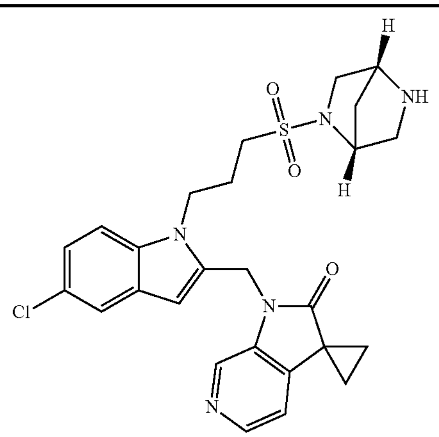 | 1'-[(5-Chloro-1-{3-[(1R,4R)-2,5-diazabicyclo[2.2.1]hept-2-ylsulfonyl]propyl}-1H-indol-2-yl)methyl]spiro[cyclopropane-1,3'-pyrrolo[2,3-c]pyridin]-2'(1'H)-one | 0.019 |
| 24-4 | 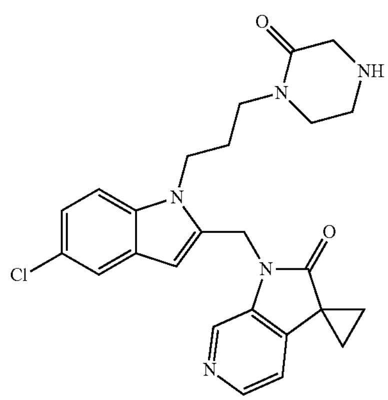 [SMILES: O=C1CNCCN1CCCn1c(CN2C(=O)C3(CC3)c3ccncc32)cc2cc(Cl)ccc21] | 1'-({5-Chloro-1-[3-(2-oxopiperazin-1-yl)propyl]-1H-indol-2-yl}methyl)spiro[cyclopropane-1,3'-pyrrolo[2,3-c]pyridin]-2'(1'H)-one | 0.03 |
| 24-5 | 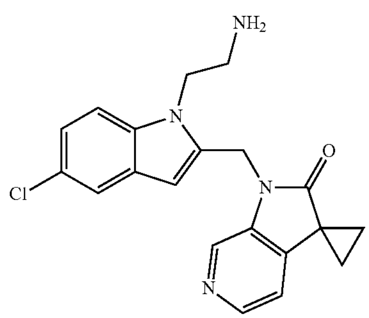 | 1'-{[1-(2-Aminoethyl)-5-chloro-1H-indol-2-yl]methyl}spiro[cyclopropane-1,3'-pyrrolo[2,3-c]pyridin]-2'(1'H)-one | 0.064 |
| 25-1 | 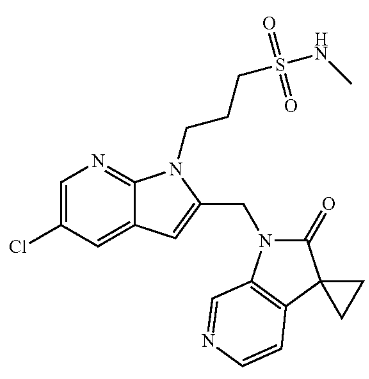 [SMILES: CNS(=O)(=O)CCCn1c(CN2C(=O)C3(CC3)c3ccncc32)cc2cc(Cl)cnc21] | 3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide | 0.057 |

TABLE 1-continued

Structure, name and activity data of particular compounds

| Example No. | Structure | Name | CPE Long EC$_{50}$ (μM) |
|---|---|---|---|
| 25-2 | 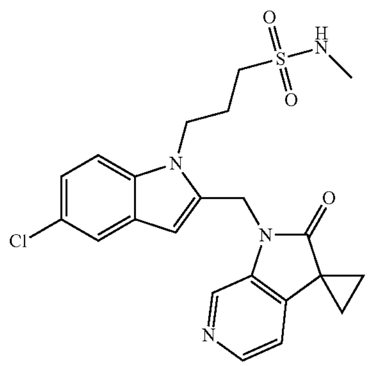 [SMILES: CNS(=O)(=O)CCCn1c(CN2C(=O)C3(CC3)c3ccncc32)cc2cc(Cl)ccc21] | 3-{5-Chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide | 0.011 |
| 25-3 | 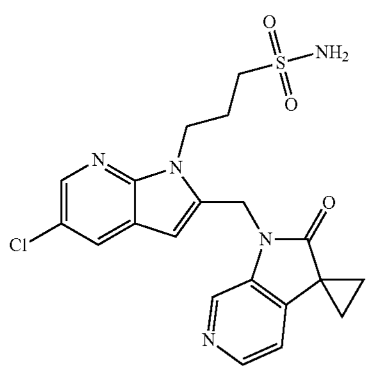 [SMILES: NS(=O)(=O)CCCn1c(CN2C(=O)C3(CC3)c3ccncc32)cc2cc(Cl)cnc21] | 3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propane-1-sulfonamide | 0.041 |
| 26-1 | 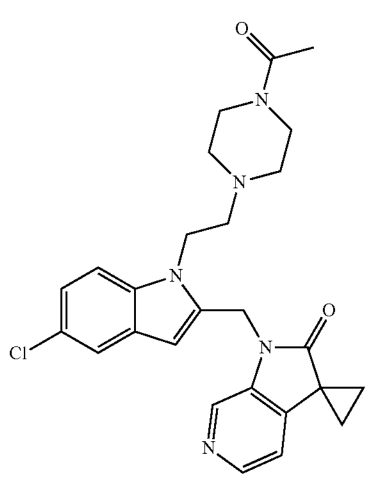 [SMILES: CC(=O)N1CCN(CCn2c(CN3C(=O)C4(CC4)c4ccncc43)cc3cc(Cl)ccc32)CC1] | 1'-({1-[2-(4-Acetylpiperazin-1-yl)ethyl]-5-chloro-1H-indol-2-yl}methyl)spiro[cyclopropane-1,3'-pyrrolo[2,3-c]pyridin]-2'(1'H)-one | 0.025 |

TABLE 1-continued

Structure, name and activity data of particular compounds

| Example No. | Structure | Name | CPE Long EC$_{50}$ (μM) |
|---|---|---|---|
| 26-2 | 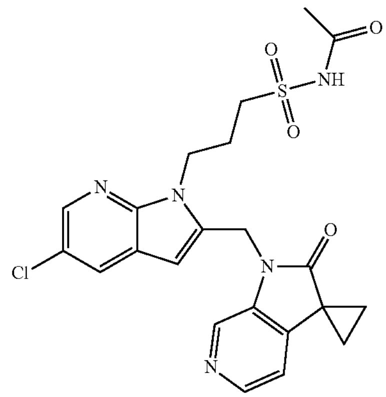 [SMILES: CC(=O)NS(=O)(=O)CCCn1c(CN2C(=O)C3(CC3)c3ccncc32)cc2cc(Cl)cnc21] | N-[(3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propyl)sulfonyl]acetamide | 1.917 |
| 26-3 | 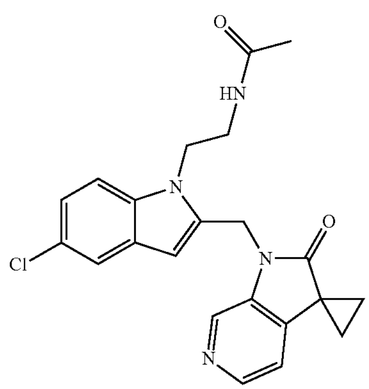 [SMILES: CC(=O)NCCn1c(CN2C(=O)C3(CC3)c3ccncc32)cc2cc(Cl)ccc21] | N-(2-{5-Chloro-2-[(2'-oxospiro[cyclopropane-1,3'-pyrrolo[2,3-c]pyridin]-1'(2'H)-yl)methyl]-1H-indol-1-yl}ethyl)acetamide | 0.025 |
| 27-1 | 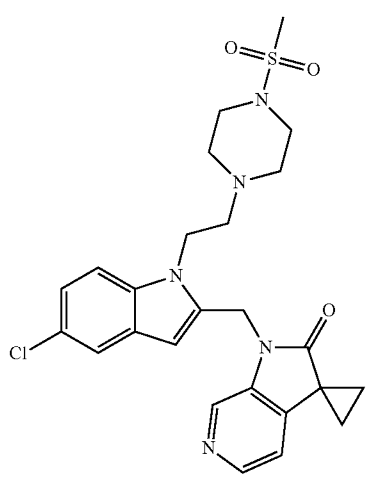 [SMILES: CS(=O)(=O)N1CCN(CCn2c(CN3C(=O)C4(CC4)c4ccncc43)cc3cc(Cl)ccc32)CC1] | 1'-[(5-Chloro-1-{2-[4-(methylsulfonyl)piperazin-1-yl]ethyl}-1H-indol-2-yl)methyl]spiro[cyclopropane-1,3'-pyrrolo[2,3-c]pyridin]-2'(1'H)-one | 0.006 |

TABLE 1-continued

Structure, name and activity data of particular compounds

| Example No. | Structure | Name | CPE Long EC$_{50}$ (μM) |
|---|---|---|---|
| 27-2 | 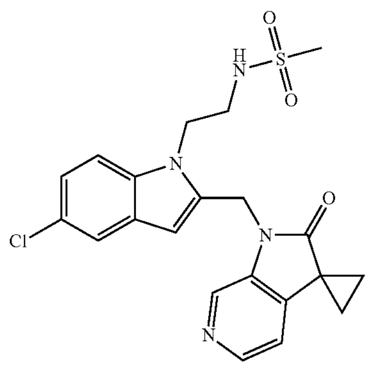 [SMILES: CS(=O)(=O)NCCn1c(CN2C(=O)C3(CC3)c3ccncc32)cc2cc(Cl)ccc21] | N-(2-{5-Chloro-2-[(2'-oxospiro[cyclopropane-1,3'-pyrrolo[2,3-c]pyridin]-1'(2'H)-yl)methyl]-1H-indol-1-yl}ethyl)methanesulfonamide | 0.0115 |
| 27-3 | 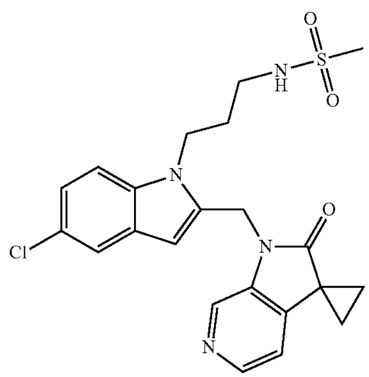 [SMILES: CS(=O)(=O)NCCCn1c(CN2C(=O)C3(CC3)c3ccncc32)cc2cc(Cl)ccc21] | N-(3-{5-chloro-2-[(2'-oxospiro[cyclopropane-1,3'-pyrrolo[2,3-c]pyridin]-1'(2'H)-yl)methyl]-1H-indol-1-yl}propyl)methanesulfonamide | 0.4987 |
| 28 | 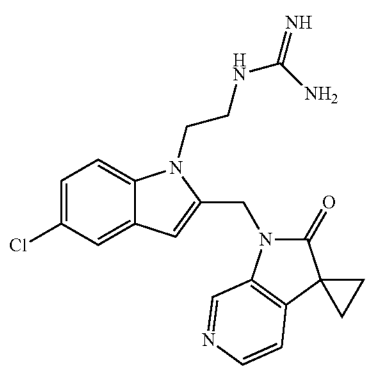 [SMILES: N=C(N)NCCn1c(CN2C(=O)C3(CC3)c3ccncc32)cc2cc(Cl)ccc21] | 1-(2-{5-Chloro-2-[(2'-oxospiro[cyclopropane-1,3'-pyrrolo[2,3-c]pyridin]-1'(2'H)-yl)methyl]-1H-indol-1-yl}ethyl)urea | 0.064 |
| 29 | 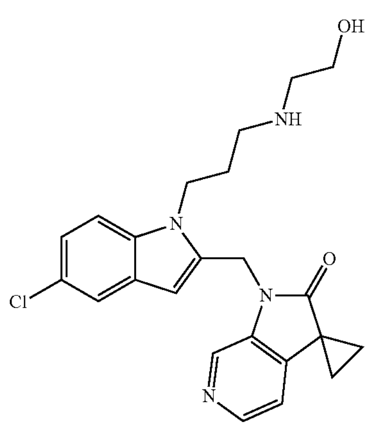 [SMILES: O=C1N(Cc2cc3cc(Cl)ccc3n2CCCNCCO)c2cnccc2C12CC2] | 1'-[(5-Chloro-1-{3-[(2-hydroxyethyl)amino]propyl}-1H-indol-2-yl)methyl]spiro[cyclopropane-1,3'-pyrrolo[2,3-c]pyridin]-2'(1'H)-one | 0.244 |

TABLE 1-continued

Structure, name and activity data of particular compounds

| Example No. | Structure | Name | CPE Long EC$_{50}$ (µM) |
|---|---|---|---|
| 30 | 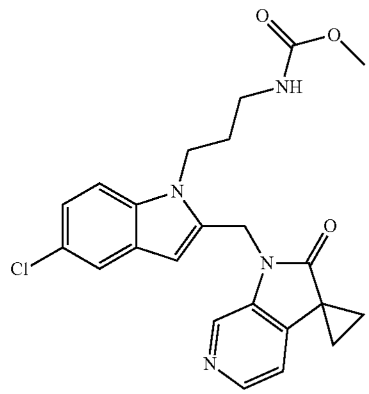 [SMILES: COC(=O)NCCCn1c(CN2C(=O)C3(CC3)c3ccncc32)cc2cc(Cl)ccc21] | Methyl (3-{5-chloro-2-[(2'-oxospiro[cyclopropane-1,3'-pyrrolo[2,3-c]pyridin]-1'(2'H)-yl)methyl]-1H-indol-1-yl}propyl)carbamate | 0.02 |
| 31 | 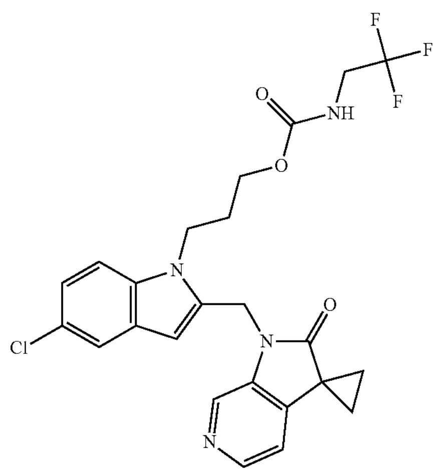 [SMILES: O=C(NCC(F)(F)F)OCCCn1c(CN2C(=O)C3(CC3)c3ccncc32)cc2cc(Cl)ccc21] | 3-{5-Chloro-2-[(2'-oxospiro[cyclopropane-1,3'-pyrrolo[2,3-c]pyridin]-1'(2'H)-yl)methyl]-1H-indol-1-yl}propyl(2,2,2-trifluoroethyl)carbamate | 0.052 |
| 32-1 | 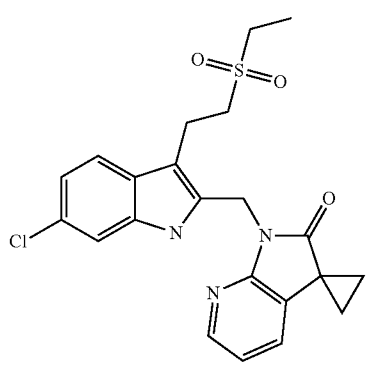 [SMILES: CCS(=O)(=O)CCc1c(CN2C(=O)C3(CC3)c3cccnc32)[nH]c2cc(Cl)ccc12] | 1'-({6-Chloro-3-[2-(ethylsulfonyl)ethyl]-1H-indol-2-yl}methyl)spiro[cyclopropane-1,3'-pyrrolo[2,3-b]pyridin]-2'(1'H)-one | 0.009 |

TABLE 1-continued

Structure, name and activity data of particular compounds

| Example No. | Structure | Name | CPE Long EC$_{50}$ (μM) |
|---|---|---|---|
| 32-2 | 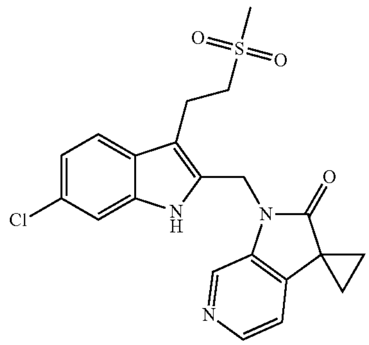 [SMILES: CS(=O)(=O)CCc1c(CN2C(=O)C3(CC3)c3ccncc32)[nH]c2cc(Cl)ccc12] | 1'-({6-Chloro-3-[2-(methylsulfonyl)ethyl]-1H-indol-2-yl}methyl)spiro[cyclopropane-1,3'-pyrrolo[2,3-c]pyridin]-2'(1'H)-one | 0.005 |
| 33 | 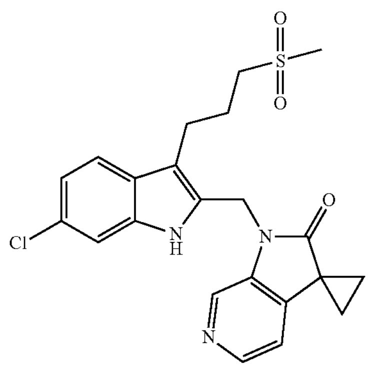 [SMILES: CS(=O)(=O)CCCc1c(CN2C(=O)C3(CC3)c3ccncc32)[nH]c2cc(Cl)ccc12] | 1'-({6-Chloro-3-[3-(methylsulfonyl)propyl]-1H-indol-2-yl}methyl)spiro[cyclopropane-1,3'-pyrrolo[2,3-c]pyridin]-2'(1'H)-one | 0.006 |
| 34-1 | 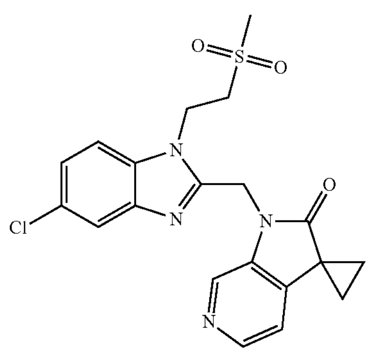 [SMILES: CS(=O)(=O)CCn1c(CN2C(=O)C3(CC3)c3ccncc32)nc2cc(Cl)ccc21] | 1'-({5-Chloro-1-[2-(methylsulfonyl)ethyl]-1H-benzimidazol-2-yl}methyl)spiro[cyclopropane-1,3'-pyrrolo[2,3-c]pyridin]-2'(1'H)-one | 0.012 |
| 34-2 | 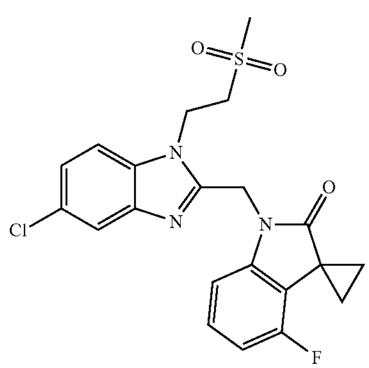 [SMILES: CS(=O)(=O)CCn1c(CN2C(=O)C3(CC3)c3c(F)cccc32)nc2cc(Cl)ccc21] | 1'-({5-Chloro-1-[2-(methylsulfonyl)ethyl]-1H-benzimidazol-2-yl}methyl)-4'-fluorospiro[cyclopropane-1,3'-indol]-2'(1'H)-one | 0.02 |

TABLE 1-continued

Structure, name and activity data of particular compounds

| Example No. | Structure | Name | CPE Long EC$_{50}$ (μM) |
|---|---|---|---|
| 34-3 | 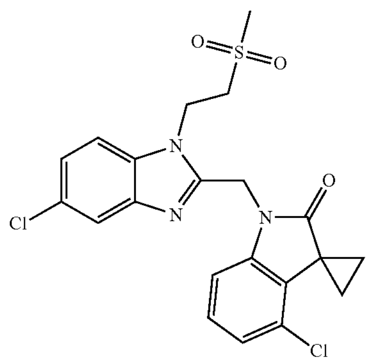 [SMILES: CS(=O)(=O)CCn1c(CN2C(=O)C3(CC3)c3c(Cl)cccc32)nc2cc(Cl)ccc21] | 4'-Chloro-1'-({5-chloro-1-[2-(methylsulfonyl)ethyl]-1H-benzimidazol-2-yl}methyl)spiro[cyclopropane-1,3'-indol]-2'(1'H)-one | 0.066 |
| 34-4 | 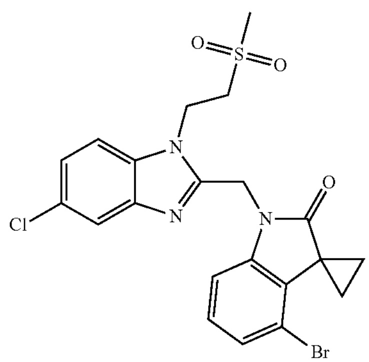 [SMILES: CS(=O)(=O)CCn1c(CN2C(=O)C3(CC3)c3c(Br)cccc32)nc2cc(Cl)ccc21] | 4'-Bromo-1'-({5-chloro-1-[2-(methylsulfonyl)ethyl]-1H-benzimidazol-2-yl}methyl)spiro[cyclopropane-1,3'-indol]-2'(1'H)-one | 0.205 |
| 34-5 | 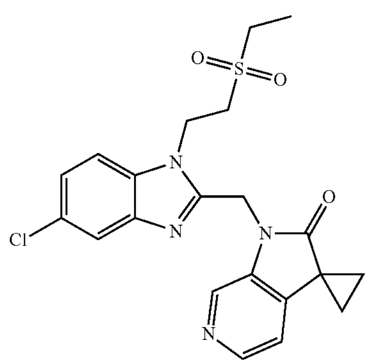 [SMILES: CCS(=O)(=O)CCn1c(CN2C(=O)C3(CC3)c3ccncc32)nc2cc(Cl)ccc21] | 1'-({5-Chloro-1-[2-(ethylsulfonyl)ethyl]-1H-benzimidazol-2-yl}methyl)spiro[cyclopropane-1,3'-pyrrolo[2,3-c]pyridin]-2'(1'H)-one | 0.013 |
| 35 | 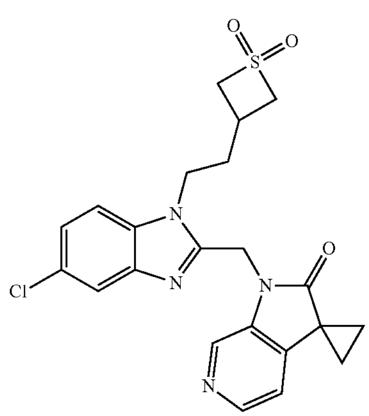 [SMILES: O=C1N(Cc2nc3cc(Cl)ccc3n2CCC2CS(=O)(=O)C2)c2cnccc2C12CC2] | 1'-({5-Chloro-1-[2-(1,1-dioxidothietan-3-yl)ethyl]-1H-benzimidazol-2-yl}methyl)spiro[cyclopropane-1,3'-pyrrolo[2,3-c]pyridin]-2'(1'H)-one | 0.0011 |

TABLE 1-continued

Structure, name and activity data of particular compounds

| Example No. | Structure | Name | CPE Long EC$_{50}$ (μM) |
|---|---|---|---|
| 36-1 | 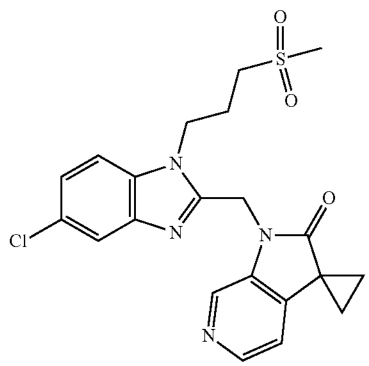 [SMILES: CS(=O)(=O)CCCn1c(CN2C(=O)C3(CC3)c3ccncc32)nc2cc(Cl)ccc21] | 1'-({5-Chloro-1-[3-(methylsulfonyl)propyl]-1H-benzimidazol-2-yl}methyl)spiro[cyclopropane-1,3'-pyrrolo[2,3-c]pyridin]-2'(1'H)-one | 0.002 |
| 36-2 | 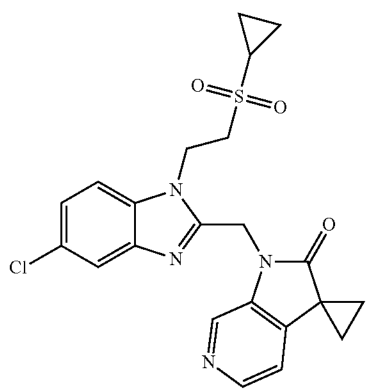 [SMILES: O=C1N(Cc2nc3cc(Cl)ccc3n2CCS(=O)(=O)C2CC2)c2cnccc2C12CC2] | 1'-({5-Chloro-1-[2-(cyclopropylsulfonyl)ethyl]-1H-benzimidazol-2-yl}methyl)spiro[cyclopropane-1,3'-pyrrolo[2,3-c]pyridin]-2'(1'H)-one | 0.008 |
| 37-1 | 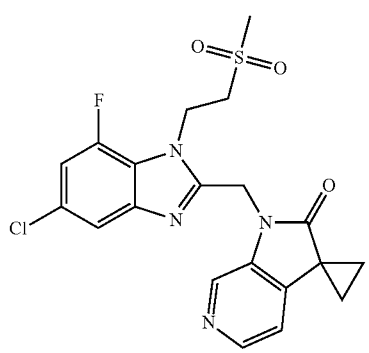 [SMILES: CS(=O)(=O)CCn1c(CN2C(=O)C3(CC3)c3ccncc32)nc2cc(Cl)cc(F)c21] | 1'-({5-Chloro-7-fluoro-1-[2-(methylsulfonyl)ethyl]-1H-benzimidazol-2-yl}methyl)spiro[cyclopropane-1,3'-pyrrolo[2,3-c]pyridin]-2'(1'H)-one | 0.009 |
| 37-2 | 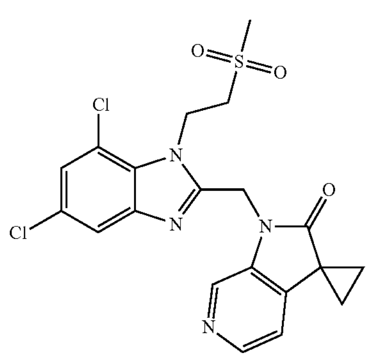 [SMILES: CS(=O)(=O)CCn1c(CN2C(=O)C3(CC3)c3ccncc32)nc2cc(Cl)cc(Cl)c21] | 1'-({5,7-Dichloro-1-[2-(methylsulfonyl)ethyl]-1H-benzimidazol-2-yl}methyl)spiro[cyclopropane-1,3'-pyrrolo[2,3-c]pyridin]-2'(1'H)-one | 0.0168 |

TABLE 1-continued

Structure, name and activity data of particular compounds

| Example No. | Structure | Name | CPE Long EC$_{50}$ (μM) |
|---|---|---|---|
| 38-1 | 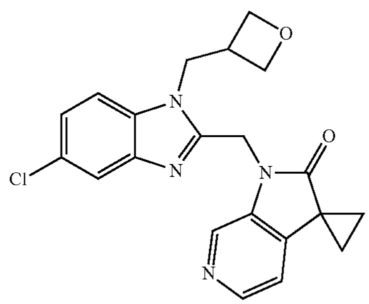 [SMILES: O=C1N(Cc2nc3cc(Cl)ccc3n2CC2COC2)c2cnccc2C12CC2] | 1'-{[5-Chloro-1-(oxetan-3-ylmethyl)-1H-benzimidazol-2-yl]methyl}spiro[cyclopropane-1,3'-pyrrolo[2,3-c]pyridin]-2'(1'H)-one | 0.003 |
| 38-2 | 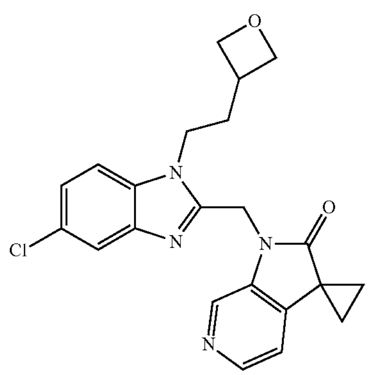 [SMILES: O=C1N(Cc2nc3cc(Cl)ccc3n2CCC2COC2)c2cnccc2C12CC2] | 1'-({5-Chloro-1-[2-(oxetan-3-yl)ethyl]-1H-benzimidazol-2-yl}methyl)spiro[cyclopropane-1,3'-pyrrolo[2,3-c]pyridin]-2'(1'H)-one | 0.003 |
| 38-3 | 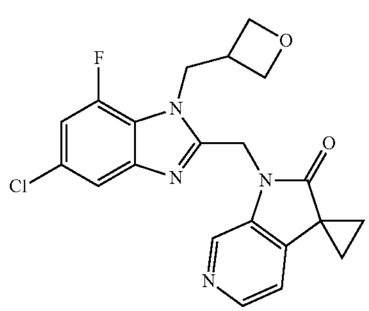 [SMILES: O=C1N(Cc2nc3cc(Cl)cc(F)c3n2CC2COC2)c2cnccc2C12CC2] | 1'-{[5-Chloro-7-fluoro-1-(oxetan-3-ylmethyl)-1H-benzimidazol-2-yl]methyl}spiro[cyclopropane-1,3'-pyrrolo[2,3-c]pyridin]-2'(1'H)-one | 0.030 |
| 39-1 | 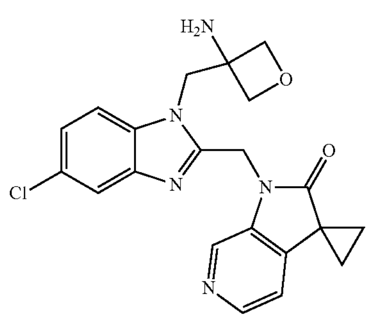 [SMILES: NC1(Cn2c(CN3C(=O)C4(CC4)c4ccncc43)nc3cc(Cl)ccc32)COC1] | 1'-({1-[(3-Aminooxetan-3-yl)methyl]-5-chloro-1H-benzimidazol-2-yl}methyl)spiro[cyclopropane-1,3'-pyrrolo[2,3-c]pyridin]-2'(1'H)-one | 0.018 |

TABLE 1-continued

Structure, name and activity data of particular compounds

| Example No. | Structure | Name | CPE Long EC$_{50}$ (μM) |
|---|---|---|---|
| 39-2 | 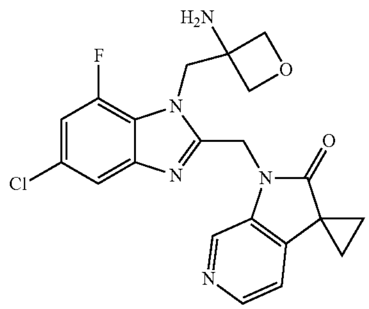 [SMILES: NC1(Cn2c(CN3C(=O)C4(CC4)c4ccncc43)nc3cc(Cl)cc(F)c32)COC1] | 1'-({1-[(3-Aminooxetan-3-yl)methyl]-5-chloro-7-fluoro-1H-benzimidazol-2-yl}methyl)spiro[cyclopropane-1,3'-pyrrolo[2,3-c]pyridin]-2'(1'H)-one | 0.227 |

TABLE 2

NMR and MS data of particular compounds

| Example No. | $^1$H NMR data | MW data |
|---|---|---|
| 1-1 | $^1$H NMR (400 MHz, CD$_3$OD) δ ppm 8.45-8.40 (m, 1 H), 7.69-7.58 (m, 1 H), 7.54-7.52 (m, 1 H), 7.47-7.45 (m, 1 H), 7.25-7.17 (m, 2 H), 7.11-7.07 (m, 1 H), 6.50 (s, 1 H), 5.42 (s, 2 H), 4.81-4.78 (t, 2 H), 3.59-3.55 (t, 2 H), 2.82 (s, 3 H), 1.94-1.90 (m, 4 H) | MS obsd. (ESI$^+$) [(M + H)$^+$] 396 |
| 1-2 | $^1$H NMR (400 MHz, CDCl$_3$) δ ppm 8.47 (s, 1 H), 8.32-8.31 (d, J = 4.4 Hz, 1 H), 7.26-7.21 (m, 1 H), 7.02 (m, 1 H), 6.92-6.89 (m, 1 H), 6.84-6.83 (m, 1 H), 6.58 (s, 1 H), 5.22 (s, 2 H), 4.75-4.72 (t, 2 H), 3.82 (s, 3 H), 3.39-3.35 (t, 2 H), 2.74 (s, 3 H), 1.93-1.90 (m, 2 H), 1.72-1.69 (m, 2 H) | MS obsd. (ESI$^+$) [(M + H)$^+$] 426 |
| 1-3 | $^1$H NMR (400 MHz, CD$_3$OD) δ ppm 8.19 (s, 1 H), 8.11-8.10 (m, 1 H), 7.75 (m, 1 H), 7.33 (m, 2 H), 6.81-6.80 (m, 1 H), 6.48 (s, 1 H), 5.16 (s, 2 H), 4.68-4.64 (t, 2 H), 3.84-3.38 (t, 2 H), 2.73 (s, 3 H), 1.80-1.78 (m, 2 H), 1.65-1.63 (m, 2 H) | MS obsd. (ESI$^+$) [(M + H)$^+$] 421 |
| 1-4 | $^1$H NMR (400 MHz, CD$_3$OD) δ ppm 8.42-8.39 (m, 1 H), 8.27-8.26 (m, 1 H), 7.45-7.44 (m, 1 H), 7.44-7.20 (m, 2 H), 7.98-7.01 (m, 1 H), 6.46 (s, 1 H), 5.41 (s, 2 H), 4.81-4.78 (t, 2 H), 3.61-3.58 (t, 2 H), 2.86 (s, 3 H), 1.92 (t, 4 H) | MS obsd. (ESI$^+$) [(M + H)$^+$] 414 |
| 1-5 | $^1$H NMR (400 MHz, DMSO-d$_6$) δ ppm 8.38 (s, 1 H), 8.26-8.25 (d, J = 4.8 Hz, 1 H), 7.67 (m, 1 H), 7.45-7.43 (d, J = 8.8 Hz, 1 H), 7.28-7.25 (dd, J = 6.8, 0.8 Hz, 1 H), 7.18-7.17 (d, J = 4.8 Hz, 1 H), 6.30 (s, 1 H), 5.34 (s, 2 H), 4.73-4.70 (t, 2 H), 3.64-3.60 (t, 2 H), 3.00 (s, 3 H), 1.89-1.84 (m, 2 H), 1.74-1.72 (m, 2 H) | MS obsd. (ESI$^+$) [(M + H)$^+$] 474 |
| 1-6 | $^1$H NMR (400 MHz, CDCl$_3$) δ ppm 8.54 (s, 1 H), 8.37 (d, J = 4.8 Hz, 1 H), 7.27 (s, 1 H), 7.18 (m, 2 H), 6.88 (d, J = 4.8 Hz, 1 H), 6.81 (s, 1 H), 5.29 (s, 2 H), 4.81 (t, J = 6.0 Hz, 2 H), 3.41 (t, J = 7.2 Hz, 2 H), 2.85 (s, 3 H), 1.97 (t, J = 4.8 Hz, 2 H), 1.76 (t, J = 3.0 Hz, 2 H) | MS obsd. (ESI$^+$) [(M + H)$^+$] 430 |
| 1-7 | $^1$H NMR (400 MHz, CDCl$_3$) δ ppm 8.43 (s, 1 H), 8.40-8.30 (d, J = 4.8 Hz, 1 H), 7.50-7.40 (d, J = 7.6 Hz, 1 H), 7.22-7.16 (d, J = 7.2 Hz, 1 H), 7.10-7.00 (t, J = 8.0 Hz, 1 H), 6.90-6.82 (d, J = 4.8 Hz, 1 H), 6.60 (s, 1 H), 5.30 (s, 2 H), 5.15-5.08 (t, J = 6.8 Hz, 2 H), 3.52-3.42 (t, J = 7.2 Hz, 2 H), 2.86 (s, 3 H), 2.00-1.96 (m, 2 H), 1.65-1.60 (m, 2 H) | MS obsd. (ESI$^+$) [(M + H)$^+$] 430 |
| 1-8 | $^1$H NMR (400 MHz, CDCl$_3$) δ ppm 8.49 (s, 1 H), 8.40-8.30 (d, J = 4.8 Hz, 1 H), 7.39 (s, 1 H), 7.24 (s, 1 H), 7.15-7.10 (dd, J = 8.4, 1.6 Hz, 1 H), 6.90-6.80 (d, J = 4.8 Hz, 1 H), 6.61 (s, 1 H), 5.24 (s, 2 H), 4.80-4.70 (t, J = 7.2 Hz, 2 H), 3.42-3.32 (t, J = 6.8 Hz, 2 H), 2.80-2.60 (m, 5 H), 2.00-1.90 (m, 2 H), 1.75-1.68 (m, 2 H), 1.30-1.20 (t, J = 7.6 Hz, 3 H) | MS obsd. (ESI$^+$) [(M + H)$^+$] 424 |
| 1-9 | $^1$H NMR (400 MHz, CDCl$_3$) δ ppm 8.41 (s, 1 H), 8.40-8.30 (d, J = 4.8 Hz, 1 H), 7.10-6.98 (d, J = 2.0 Hz, 1 H), 6.90-6.80 (d, J = 4.8 Hz, 1 H), 6.80-6.70 (t, J = 11.6 Hz, 1 H), 6.54 (s, 1 H), 5.28 (s, 2 H), 4.90-4.80 (t, J = 6.8 Hz, 2 H), 3.50-3.38 (t, J = 6.8 Hz, 2 H), 2.83 (s, 3 H), 2.00-1.90 (m, 2 H), 1.80-1.68 (m, 2 H) | MS obsd. (ESI$^+$) [(M + H)$^+$] 432 |

TABLE 2-continued

NMR and MS data of particular compounds

| Example No. | ¹H NMR data | MW data |
|---|---|---|
| 1-10 | ¹H NMR (400 MHz, CDCl₃) δ ppm 8.45 (s, 1 H), 8.40-8.30 (d, J = 4.8 Hz, 1 H), 7.87 (s, 1 H), 7.52-7.38 (m, 2 H), 6.90-6.80 (d, J = 4.8 Hz, 1 H), 6.75 (s, 1 H), 5.28 (s, 2 H), 4.90-4.78 (t, J = 7.2 Hz, 2 H), 3.42-3.38 (t, J = 7.2 Hz, 2 H), 2.83 (s, 3 H), 2.00-1.90 (m, 2 H), 1.75-1.65 (m, 2 H) | MS obsd. (ESI⁺) [(M + H)⁺] 464 |
| 1-11 | ¹H NMR (400 MHz, CDCl₃) δ ppm 8.44 (s, 1 H), 8.40-8.30 (d, J = 4.8 Hz, 1 H), 7.40-7.28 (t, J = 8.0 Hz, 1 H), 7.20-7.10 (dd, J = 6.8, 4.0 Hz, 1 H), 6.90-6.80 (t, J = 0.8 Hz, 1 H), 6.60 (s, 1 H), 5.23 (s, 2 H), 4.75-4.68 (t, J = 6.8 Hz, 2 H), 3.40-3.30 (t, J = 7.2 Hz, 2 H), 2.83 (s, 3 H), 2.00-1.90 (m, 2 H), 1.75-1.68 (m, 2 H) | MS obsd. (ESI⁺) [(M + H)⁺] 432 |
| 1-12 | ¹H NMR (400 MHz, CDCl₃) δ ppm 8.39 (s, 1 H), 8.40-8.30 (d, J = 4.8 Hz, 1 H), 7.35-7.28 (d, J = 1.6 Hz, 1 H), 7.00-6.90 (dd, J = 12.4, 1.6 Hz, 1 H), 6.90-6.80 (d, J = 4.8 Hz, 1 H), 6.52 (s, 1 H), 5.27 (s, 2 H), 4.90-4.80 (t, J = 7.2 Hz, 2 H), 3.45-3.35 (t, J = 6.8 Hz, 2 H), 2.83 (s, 3 H), 2.00-1.90 (m, 2 H), 1.72-1.60 (m, 2 H) | MS obsd. (ESI⁺) [(M + H)⁺] 448 |
| 1-13 | ¹H NMR (400 MHz, CDCl₃) δ ppm 8.49 (s, 1 H), 8.32 (d, J = 3.2 Hz, 1 H), 7.37 (s, 1 H), 7.24-7.22 (dd, J = 10.4, 8.4 Hz, 1 H), 7.09-7.07 (d, J = 8.8 Hz, 1 H), 6.84-6.82 (d, J = 4.4 Hz, 1 H), 6.59 (s, 1 H), 5.24 (s, 2 H), 4.77-4.73 (q, J = 6.8 Hz, 2 H), 3.52-3.39 (q, J = 6.8 Hz, 2 H), 2.75 (s, 3 H), 2.42 (s, 3 H), 1.94-1.91 (m, 2 H), 1.72-1.69 (m, 2 H) | MS obsd. (ESI⁺) [(M + H)⁺] 410 |
| 1-14 | ¹H NMR (400 MHz, DMSO-d₆) δ ppm 8.72 (s, 1 H), 8.39 (s, 1 H), 8.25 (d, J = 4.8 Hz, 1 H), 8.21 (d, J = 5.6 Hz, 1 H), 7.48 (d, J = 5.6 Hz, 1 H), 7.18 (d, J = 4.8 Hz, 1 H), 6.44 (s, 1 H), 5.36 (s, 2 H), 4.75-4.72 (m, 2 H), 3.67-3.64 (m, 2 H), 3.02 (s, 3 H), 1.85-1.72 (m, 4 H) | MS obsd. (ESI⁺) [(M + H)⁺] 397 |
| 2-1 | ¹H NMR (400 MHz, CD₃OD) δ ppm 8.43-8.33 (m, 1 H), 8.30-8.20 (m, 1 H), 7.51 (s, 1 H), 7.49-7.40 (m, 1 H), 7.17 (d, J = 4.80 Hz, 2 H), 6.44 (s, 1 H), 5.41 (s, 2 H), 4.80-4.73 (m, 2 H), 3.54 (t, J = 6.69 Hz, 2 H), 2.93 (q, J = 7.58 Hz, 2 H), 1.96-1.85 (m, 4 H), 1.26 (t, J = 7.45 Hz, 3 H) | MS obsd. (ESI⁺) [(M + H)⁺] 444 |
| 2-2 | ¹H NMR (400 MHz, CD₃OD) δ ppm 8.39 (s, 1 H), 8.28 (d, J = 5.05 Hz, 1 H), 8.24 (d, J = 2.02 Hz, 1 H), 7.92 (d, J = 2.27 Hz, 1 H), 7.21 (d, J = 4.80 Hz, 1 H), 6.39 (s, 1 H), 5.47 (s, 2 H), 4.84 (t, J = 6.57 Hz, 2 H), 3.72 (t, J = 6.57 Hz, 2 H), 3.07-2.96 (m, 2 H), 1.99-1.88 (m, 4 H), 1.28 (t, J = 7.45 Hz, 3 H) | MS obsd. (ESI⁺) [(M + H)⁺] 445 |
| 2-3 | ¹H NMR (400 MHz, DMSO-d₆) δ ppm 8.20-8.10 (m, 1 H), 7.58-7.45 (m, 3 H), 7.17 (dd, J = 8.84, 1.77 Hz, 1 H), 7.05 (dd, J = 7.20, 5.43 Hz, 1 H), 6.30 (s, 1 H), 5.24 (s, 2 H), 4.87 (t, J = 6.95 Hz, 2 H), 3.66 (t, J = 7.07 Hz, 2 H), 3.10 (q, J = 7.49 Hz, 2 H), 1.83-1.73 (m, 2 H), 1.71-1.61 (m, 2 H), 1.26-1.13 (m, 3 H) | MS obsd. (ESI⁺) [(M + H)⁺] 444 |
| 2-4 | ¹H NMR (400 MHz, CDCl₃) δ ppm 8.56-8.46 (m, 1 H), 8.42 (s, 1 H), 8.24 (d, J = 2.27 Hz, 1 H), 7.80 (d, J = 2.27 Hz, 1 H), 7.68 (d, J = 5.05 Hz, 1 H), 6.35 (s, 1 H), 5.36-5.24 (m, 2 H), 4.88-4.75 (m, 2 H), 3.75 (t, J = 6.19 Hz, 2 H), 2.87-2.70 (m, 5 H), 2.55-2.29 (m, 4 H) | MS obsd. (ESI⁺) [(M + H)⁺] 445 |
| 2-5 | ¹H NMR (400 MHz, DMSO-d₆) δ ppm 8.16 (dd, J = 5.05, 1.52 Hz, 1 H), 7.56-7.45 (m, 3 H), 7.16 (dd, J = 8.72, 2.15 Hz, 1 H), 7.05 (dd, J = 7.33, 5.31 Hz, 1 H), 6.31 (s, 1 H), 5.24 (s, 2 H), 4.87 (t, J = 7.07 Hz, 2 H), 3.70 (t, J = 7.20 Hz, 2 H), 3.01 (s, 3 H), 1.81-1.74 (m, 2 H), 1.69-1.62 (m, 2 H) | MS obsd. (ESI⁺) [(M + H)⁺] 430 |
| 2-6 | ¹H NMR (400 MHz, DMSO-d₆) δ ppm 8.40 (s, 1 H), 8.33-8.25 (m, 2 H), 8.04 (d, J = 2.27 Hz, 1 H), 7.21 (dd, J = 4.80, 0.51 Hz, 1 H), 6.30 (s, 1 H), 5.41 (s, 2 H), 4.79 (t, J = 6.95 Hz, 2 H), 3.74 (t, J = 6.95 Hz, 2 H), 3.08 (s, 3 H), 1.92-1.85 (m, 2 H), 1.80-1.73 (m, 2 H) | MS obsd. (ESI⁺) [(M + H)⁺] 431 |
| 2-7 | ¹H NMR (400 MHz, CD₃OD) δ ppm 8.27 (d, J = 2.27 Hz, 1 H), 7.96 (d, J = 2.27 Hz, 1 H), 7.15 (d, J = 4.30 Hz, 1 H), 6.95 (d, J = 8.34 Hz, 2 H), 6.38 (s, 1 H), 5.40 (s, 2 H), 4.87 (t, J = 6.82 Hz, 2 H), 3.75 (t, J = 6.82 Hz, 2 H), 3.01 (s, 3 H), 1.85-1.73 (m, 4 H) | MS obsd. (ESI⁺) [(M + H)⁺] 448 |
| 2-8 | ¹H NMR (400 MHz, CD₃OD) δ ppm 8.34-8.31 (m, 2 H), 8.24 (d, J = 2.27 Hz, 1 H), 7.92 (d, J = 2.27 Hz, 1 H), 7.46 (dd, J = 4.80, 0.76 Hz, 1 H), 6.33 (s, 1 H), 5.38 (s, 2 H), 4.86-4.83 (m, 2 H), 3.82 (t, J = 6.57 Hz, 2 H), 2.95 (s, 3 H), 2.29-2.19 (m, 2 H), 2.13 (d, J = 7.33 Hz, 4 H), 2.06-1.96 (m, 2 H) | MS obsd. (ESI⁺) [(M + H)⁺] 459 |
| 2-9 | ¹H NMR (400 MHz, CDCl₃) δ ppm 8.46 (s, 1 H), 8.38 (d, J = 4.80 Hz, 1 H), 7.69 (d, J = 8.59 Hz, 1 H), 7.20 (d, J = 8.59 Hz, 1 H), 6.88 (d, J = 4.80 Hz, 1 H), 6.80 (s, 1 H), 5.34-5.17 (m, 2 H), 4.80 (t, J = 7.07 Hz, 2 H), 3.42 (t, J = 7.07 Hz, 2 H), 2.88 (s, 3 H), 2.00-1.93 (m, 2 H), 1.76 (q, J = 4.38 Hz, 2 H) | MS obsd. (ESI⁺) [(M + H)⁺] 431 |

TABLE 2-continued

NMR and MS data of particular compounds

| Example No. | $^1$H NMR data | MW data |
|---|---|---|
| 3-1 | $^1$H NMR (400 MHz, CD$_3$OD) δ ppm 8.35 (d, J = 5.3 Hz, 1 H), 8.13 (s, 1 H), 7.53-7.42 (m, 2 H), 7.29 (d, J = 5.6 Hz, 1 H), 7.20 (dd, J = 8.8, 1.8 Hz, 1 H), 6.41 (s, 1 H), 5.38 (s, 2 H), 4.81 (t, J = 6.8 Hz, 2 H), 3.57-3.65 (m, 2 H), 2.86 (s, 3 H), 1.88 (d, J = 11.1 Hz, 4 H) | MS obsd. (ESI$^+$) [(M + H)$^+$] 430 |
| 3-2 | $^1$H NMR (400 MHz, CD$_3$OD) δ ppm 8.37-8.28 (m, 2 H), 7.53-7.40 (m, 3 H), 7.20 (dd, J = 8.7, 1.9 Hz, 1 H), 6.37 (s, 1 H), 5.33 (s, 2 H), 4.80 (t, J = 6.7 Hz, 2 H), 3.67 (t, J = 6.7 Hz, 2 H), 2.86 (s, 3 H), 2.26-1.96 (m, 8 H) | MS obsd. (ESI$^+$) [(M + H)$^+$] 458 |
| 3-3 | $^1$H NMR (400 MHz, CDCl$_3$) δ ppm 8.45 (s, 1 H), 8.34 (d, J = 4.8 Hz, 1 H), 7.55 (d, J = 1.6 Hz, 1 H), 7.27 (d, J = 6.0 Hz, 1 H), 7.21 (d, J = 6.0 Hz, 1 H), 6.84 (d, J = 5.2 Hz, 1 H), 6.61 (s, 1 H), 5.24 (s, 2 H), 4.77 (t, J = 7.2 Hz, 2 H), 3.38 (t, J = 7.0 Hz, 2 H), 2.80 (s, 3 H), 1.93 (q, J = 4 Hz, 2 H), 1.72 (q, J = 4 Hz, 2 H) | MS obsd. (ESI$^+$) [(M + H)$^+$] 430 |
| 4-1 | $^1$H NMR (400 MHz, CD$_3$OD) δ ppm 8.37 (s, 1 H), 8.25 (d, J = 4.80 Hz, 1 H), 7.52 (d, J = 2.02 Hz, 1 H), 7.41 (d, J = 8.59 Hz, 1 H), 7.20-7.11 (m, 2 H), 6.59 (s, 1 H), 5.33 (s, 2 H), 4.30 (t, J = 7.33 Hz, 2 H), 3.17-3.07 (m, 2 H), 1.95-1.76 (m, 8 H) | MS obsd. (ESI$^+$) [(M + H)$^+$] 458 |
| 4-2 | $^1$H NMR (400 MHz, CDCl$_3$) δ ppm 8.39 (s, 1 H), 8.16 (d, J = 4.80 Hz, 1 H), 7.68 (d, J = 1.77 Hz, 1 H), 7.48 (d, J = 8.34 Hz, 2 H), 7.21-7.08 (m, 2 H), 7.00 (s, 1 H), 6.85 (d, J = 4.80 Hz, 1 H), 6.63 (d, J = 8.08 Hz, 2 H), 5.63 (s, 2 H), 5.33 (s, 2 H), 3.03 (s, 3 H), 1.46 (d, J = 3.28 Hz, 4 H) | MS obsd. (ESI$^+$) [(M + H)$^+$] 493 |
| 4-3 | $^1$H NMR (400 MHz, DMSO-d$_6$) δ ppm 8.43 (s, 1 H), 8.31-8.23 (m, 2 H), 8.06 (d, J = 2.27 Hz, 1 H), 7.20 (d, J = 4.80 Hz, 1 H), 6.48 (s, 1 H), 5.34 (s, 2 H), 4.44 (t, J = 7.33 Hz, 2 H), 3.22-3.09 (m, 2 H), 2.98 (s, 3 H), 2.09 (q, J = 7.71 Hz, 2 H), 1.91-1.84 (m, 2 H), 1.80-1.74 (m, 2 H) | MS obsd. (ESI$^+$) [(M + H)$^+$] 445 |
| 4-4 | $^1$H NMR (400 MHz, CD$_3$OD) δ ppm 8.38 (s, 1 H), 8.26 (d, J = 4.80 Hz, 1 H), 8.14 (d, J = 1.26 Hz, 1 H), 7.73 (s, 1 H), 7.17 (d, J = 5.05 Hz, 1 H), 6.38 (s, 1 H), 5.44 (s, 2 H), 4.82 (t, J = 6.69 Hz, 2 H), 3.72 (t, J = 6.69 Hz, 2 H), 2.89 (s, 3 H), 2.42 (s, 3 H), 1.98-1.85 (m, 4 H) | MS obsd. (ESI$^+$) [(M + H)$^+$] 411 |
| 4-5 | $^1$H NMR (400 MHz, CD$_3$OD) δ ppm 8.36 (s, 1 H), 8.27 (d, J = 5.05 Hz, 1 H), 7.97 (d, J = 8.59 Hz, 1 H), 7.27-7.15 (m, 2 H), 6.64 (s, 1 H), 5.40 (s, 2 H), 4.38 (t, J = 6.95 Hz, 2 H), 3.17 (t, J = 6.95 Hz, 2 H), 2.96 (s, 3 H), 1.94 (s, 4 H), 1.91-1.79 (m, 4 H) | MS obsd. (ESI$^+$) [(M + H)$^+$] 459 |
| 4-6 | $^1$H NMR (400 MHz, CD$_3$OD) δ ppm 8.37 (s, 1 H), 8.28 (d, J = 5.05 Hz, 1 H), 8.00 (d, J = 8.59 Hz, 1 H), 7.24 (d, J = 8.59 Hz, 1 H), 7.18 (d, J = 4.80 Hz, 1 H), 6.63 (s, 1 H), 5.41 (s, 2 H), 4.55-4.45 (m, 2 H), 3.22 (t, J = 7.45 Hz, 2 H), 2.68-2.56 (m, 1 H), 2.29-2.14 (m, 2 H), 2.00-1.85 (m, 4 H), 1.19-1.00 (m, 5 H) | MS obsd. (ESI$^+$) [(M + H)$^+$] 471 |
| 4-7 | $^1$H NMR (400 MHz, CD$_3$OD) δ ppm 8.66-8.58 (m, 1 H), 8.33 (s, 1 H), 8.28 (d, J = 4.80 Hz, 1 H), 7.57 (s, 1 H), 7.18 (d, J = 5.05 Hz, 1 H), 6.61 (s, 1 H), 5.39 (s, 2 H), 4.44 (br. s., 2 H), 3.23-3.12 (m, 2 H), 2.96 (s, 3 H), 2.00-1.84 (m, 8 H) | MS obsd. (ESI$^+$) [(M + H)$^+$] 459 |
| 4-8 | $^1$H NMR (400 MHz, CD$_3$OD) δ ppm 8.38 (d, J = 0.76 Hz, 1 H), 8.27 (d, J = 5.05 Hz, 1 H), 8.22 (d, J = 2.27 Hz, 1 H), 7.99 (d, J = 2.27 Hz, 1 H), 7.29 (s, 5 H), 7.20-7.16 (m, 1 H), 6.62 (s, 1 H), 5.38 (s, 2 H), 4.55-4.44 (m, 2 H), 4.26 (s, 2 H), 3.14-3.04 (m, 2 H), 2.70 (s, 3 H), 2.22-2.09 (m, 2 H), 1.99-1.88 (m, 4 H) | MS obsd. (ESI$^+$) [(M + H)$^+$] 550 |
| 4-9 | $^1$H NMR (400 MHz, CD$_3$OD) δ ppm 8.66 (s, 1 H), 8.36 (s, 1 H), 8.28 (s, 1 H), 7.57 (d, J = 0.76 Hz, 1 H), 7.19 (d, J = 5.05 Hz, 1 H), 6.60 (s, 1 H), 5.40 (s, 2 H), 4.57 (t, J = 7.58 Hz, 2 H), 3.25 (t, J = 8.08 Hz, 2 H), 2.69-2.59 (m, 1 H), 2.26 (quin, J = 7.71 Hz, 2 H), 1.99-1.90 (m, 4 H) | MS obsd. (ESI$^+$) [(M + H)$^+$] 471 |
| 4-10 | $^1$H NMR (400 MHz, CD$_3$OD) δ ppm 8.57 (s, 1 H), 8.32 (s, 1 H), 8.28 (d, J = 5.05 Hz, 1 H), 7.56 (d, J = 0.76 Hz, 1 H), 7.19 (d, J = 4.29 Hz, 1 H), 6.60 (s, 1 H), 5.37 (s, 2 H), 4.33 (t, J = 7.58 Hz, 2 H), 3.16 (t, J = 8.84 Hz, 2 H), 3.01 (t, J = 8.84 Hz, 2 H), 2.07-1.97 (m, 3 H), 1.97-1.89 (m, 4 H) | MS obsd. (ESI$^+$) [(M + H)$^+$] 425 |
| 4-11 | $^1$H NMR (400 MHz, CD$_3$OD) δ ppm 8.62 (s, 1 H), 8.36 (s, 1 H), 8.28 (d, J = 5.31 Hz, 1 H), 7.58 (d, J = 0.76 Hz, 1 H), 7.18 (d, J = 5.31 Hz, 1 H), 6.65 (s, 1 H), 5.38 (s, 2 H), 4.48-4.38 (m, 2 H), 4.29-4.19 (m, 2 H), 3.91 (dd, J = 14.65, 6.32 Hz, 2 H), 2.73-2.60 (m, 1 H), 2.22-2.12 (m, 2 H), 1.99-1.86 (m, 4 H) | MS obsd. (ESI$^+$) [(M + H)$^+$] 457 |
| 4-12 | $^1$H NMR (400 MHz, DMSO-d$_6$) δ ppm 8.39 (d, J = 4.55 Hz, 1 H), 8.34 (s, 1 H), 8.25 (d, J = 2.27 Hz, 1 H), 8.04 (d, J = 2.02 Hz, 1 H), 7.76 (d, J = 4.80 Hz, 1 H), 6.40 (s, 1 H), 5.23 (s, 2 H), 4.45 (t, J = 7.33 Hz, 2 H), 3.23-3.13 (m, 2 H), 2.98 (s, 3 H), 2.61-2.53 (d, J = 9.09 Hz, 2 H), 2.47-2.38 (m, 2 H), 2.36-2.24 (m, 2 H), 2.20-2.05 (m, 2 H) | MS obsd. (ESI$^+$) [(M + H)$^+$] 459 |

TABLE 2-continued

NMR and MS data of particular compounds

| Example No. | $^1$H NMR data | MW data |
|---|---|---|
| 4-13 | $^1$H NMR (400 MHz, DMSO-$d_6$) δ ppm 8.74 (s, 1 H), 8.40 (s, 1 H), 8.29 (d, J = 4.80 Hz, 1 H), 7.57 (s, 1 H), 7.21 (d, J = 4.80 Hz, 1 H), 6.44 (s, 1 H), 5.34 (s, 2 H), 4.49 (t, J = 7.58 Hz, 9 H), 3.24-3.14 (m, 2 H), 3.00 (s, 3 H), 2.14-2.05 (t, J = 7.33 Hz, 2 H), 1.93-1.81 (m, 2 H), 1.81-1.66 (m, 2 H) | MS obsd. (ESI$^+$) [(M + H)$^+$] 445 |
| 4-14 | $^1$H NMR (400 MHz, DMSO-$d_6$) δ ppm 8.41 (s, 1 H), 8.29 (d, J = 4.80 Hz, 1 H), 7.99 (d, J = 8.59 Hz, 1 H), 7.29-7.13 (m, 2 H), 6.43 (s, 1 H), 5.41 (s, 2 H), 4.81 (t, J = 6.82 Hz, 2 H), 3.71 (t, J = 6.82 Hz, 2 H), 2.75-2.64 (m, 1 H), 1.93-1.85 (m, 2 H), 1.82-1.66 (m, 2 H), 1.00 (d, J = 6.32 Hz, 4 H) | MS obsd. (ESI$^+$) [(M + H)$^+$] 457 |
| 4-15 | $^1$H NMR (400 MHz, DMSO-$d_6$) δ ppm 8.44 (s, 1 H), 8.28 (d, J = 4.80 Hz, 1 H), 8.04 (d, J = 8.59 Hz, 1 H), 7.27-7.13 (m, 2 H), 6.61 (s, 1 H), 5.34 (s, 2 H), 4.41 (t, J = 7.45 Hz, 2 H), 3.19-3.09 (m, 2 H), 2.98 (s, 3 H), 2.01 (q, J = 7.64 Hz, 2 H), 1.90-1.83 (m, 2 H), 1.80-1.71 (m, 2 H) | MS obsd. (ESI$^+$) [(M + H)$^+$] 445 |
| 4-16 | $^1$H NMR (400 MHz, DMSO-$d_6$) δ ppm 8.39 (s, 1 H), 8.28 (d, J = 4.80 Hz, 1 H,) 8.25 (d, J = 2.27 Hz, 1 H), 8.06 (d, J = 2.27 Hz, 1 H), 7.20 (d, J = 4.80 Hz, 1 H), 6.52 (s, 1 H), 5.34 (s, 2 H), 4.34 (t, J = 6.69 Hz, 2 H), 3.14 (t, J = 7.07 Hz, 2 H), 2.94 (s, 3 H), 1.93-1.86 (m, 2 H), 1.79-1.63 (m, 6 H) | MS obsd. (ESI$^+$) [(M + H)$^+$] 459 |
| 5-1 | $^1$H NMR (400 MHz, CDCl$_3$) δ ppm 8.53 (s, 1 H), 8.35 (d, J = 5.05 Hz, 1 H), 7.52 (d, J = 1.77 Hz, 1 H), 7.32-7.12 (m, 1 H), 6.99 (d, J = 5.05 Hz, 1 H), 6.57 (s, 1 H), 5.27 (s, 1 H), 4.40 (t, J = 7.45 Hz, 2 H), 2.76-2.60 (m, 2 H), 2.56 (s, 3 H), 2.18 (dq, J = 14.97, 7.56 Hz, 2 H), 2.11-1.96 (m, 2 H), 1.84 (d, J = 4.04 Hz, 2 H) | MS obsd. (ESI$^+$) [(M + H)$^+$] 428 |
| 5-2 | $^1$H NMR (400 MHz, CDCl$_3$) δ ppm 8.54 (s, 1 H), 8.47-8.34 (m, 2 H), 7.49 (s, 1 H), 6.92 (d, J = 4.55 Hz, 1 H), 6.54 (s, 1 H), 5.33 (s, 2 H), 4.89 (t, J = 6.69 Hz, 2 H), 3.52 (t, J = 6.57 Hz, 2 H), 2.89 (s, 2 H), 2.00 (q, J = 3.96 Hz, 2 H), 1.78 (q, J = 4.38 Hz, 2 H), 1.28 (s, 1 H) | MS obsd. (ESI$^+$) [(M + H)$^+$] 431 |
| 6 | $^1$H NMR (400 MHz, CD$_3$OD) δ ppm 8.39 (s, 1 H), 8.29 (d, J = 4.80 Hz, 1 H), 8.00 (d, J = 8.59 Hz, 1 H), 7.25 (d, J = 8.59 Hz, 1 H), 7.19 (d, J = 4.80 Hz, 1 H), 6.45 (s, 1 H), 5.49 (s, 2 H), 3.63 (t, J = 6.57 Hz, 2 H), 3.04 (q, J = 7.33 Hz, 2 H), 2.06 (s, 3 H), 1.93 (s, 3 H), 1.31 (t, J = 7.45 Hz, 3 H) | MS obsd. (ESI$^+$) [(M + H)$^+$] 445 |
| 7-1 | $^1$H NMR (400 MHz, CD$_3$OD) δ ppm 8.43-8.21 (m, 2 H), 7.54 (d, J = 1.8 Hz, 1 H), 7.45 (d, J = 8.8 Hz, 1 H), 7.24-7.08 (m, 2 H), 6.59 (s, 1 H), 5.33 (s, 2 H), 4.46-4.33 (m, 2 H), 3.08-2.98 (m, 2 H), 2.82 (s, 6 H), 2.07 (t, J = 7.7 Hz, 2 H), 1.97-1.86 (m, 4 H) | MS obsd. (ESI$^+$) [(M + H)$^+$] 473 |
| 7-2 | $^1$H NMR (400 MHz, CD$_3$OD) δ ppm 8.37 (s, 1 H), 8.23 (d, J = 2.0 Hz, 2 H), 7.98 (d, J = 2.3 Hz, 1 H), 7.17 (d, J = 4.8 Hz, 1 H), 6.60 (s, 1 H), 5.38 (s, 2 H), 4.49 (t, J = 7.5 Hz, 2 H), 3.11-3.00 (m, 2 H), 2.81 (s, 6 H), 2.14 (br. s., 2 H), 1.93 (d, J = 6.8 Hz, 4 H) | MS obsd. (ESI$^+$) [(M + H)$^+$] 474 |
| 7-3 | $^1$H NMR (400 MHz, CD$_3$OD) δ ppm 8.37 (s, 1 H), 8.26 (d, J = 5.1 Hz, 1 H), 7.51 (d, J = 2.0 Hz, 1 H), 7.42 (d, J = 8.6 Hz, 1 H), 7.25-7.13 (m, 2 H), 6.44 (s, 1 H), 5.39 (s, 2 H), 4.74 (t, J = 6.9 Hz, 2 H), 3.40-3.36 (m, 2 H), 2.82 (s, 6 H), 1.98-1.86 (m, 4 H) | MS obsd. (ESI$^+$) [(M + H)$^+$] 459 |
| 7-4 | $^1$H NMR (400 MHz, CD$_3$OD) δ ppm 8.38 (s, 1 H), 8.26 (d, J = 5.1 Hz, 1 H), 7.54 (d, J = 1.8 Hz, 1 H), 7.45 (d, J = 8.8 Hz, 1 H), 7.23-7.12 (m, 2 H), 6.59 (s, 1 H), 5.33 (s, 2 H), 4.47-4.36 (m, 2 H), 3.73-3.64 (m, 4 H), 3.23-3.15 (m, 4 H), 3.11-3.00 (m, 2 H), 2.09 (t, J = 7.6 Hz, 2 H), 1.99-1.83 (m, 4 H) | MS obsd. (ESI+) [(M + H)$^+$] 515 |
| 7-5 | $^1$H NMR (400 MHz, CD$_3$OD) δ ppm 8.38 (s, 1 H), 8.26 (d, J = 4.8 Hz, 1 H), 7.53 (d, J = 2.0 Hz, 1 H), 7.45 (d, J = 8.8 Hz, 1 H), 7.21-7.12 (m, 2 H), 6.59 (s, 1 H), 5.32 (s, 2 H), 4.48-4.33 (m, 2 H), 3.26 (t, J = 6.7 Hz, 4 H), 3.09-3.02 (m, 2 H), 2.13-2.03 (m, 2 H), 1.96-1.85 (m, 8 H) | MS obsd. (ESI$^+$) [(M + H)$^+$] 499 |
| 7-6 | $^1$H NMR (400 MHz, CD$_3$OD) δ ppm 8.42-8.35 (m, 1 H), 8.29-8.24 (m, 1 H), 7.57-7.51 (m, 1 H), 7.48-7.42 (m, 1 H), 7.22-7.13 (m, 2 H), 6.61-6.55 (m, 1 H), 5.36-5.29 (m, 2 H), 4.45-4.36 (m, 2 H), 3.91-3.85 (m, 2 H), 3.50-3.44 (m, 2 H), 3.39-3.34 (m, 2 H), 3.18-3.11 (m, 2 H), 2.15-2.04 (m, 2 H), 1.97-1.87 (m, 4 H) | MS obsd. (ESI$^+$) [(M + H)$^+$] 528 |
| 7-7 | $^1$H NMR (400 MHz, CD$_3$OD) δ ppm 8.34 (d, J = 0.76 Hz, 1 H), 8.27 (d, J = 5.05 Hz, 1 H), 7.53-7.45 (m, 2 H), 7.21-7.12 (m, 2 H), 6.39 (s, 1 H), 5.38 (s, 2 H), 4.48 (t, J = 6.06 Hz, 2 H), 3.37 (t, J = 6.06 Hz, 2 H), 3.20-3.08 (m, 2 H), 2.88 (t, J = 6.82 Hz, 2 H), 2.20 (dd, J = 8.34, 6.82 Hz, 2 H), 1.92 (s, 4 H) | MS obsd. (ESI$^+$) [(M + H)$^+$] 471 |

TABLE 2-continued

NMR and MS data of particular compounds

| Example No. | $^1$H NMR data | MW data |
| --- | --- | --- |
| 7-8 | $^1$H NMR (400 MHz, CD$_3$OD) δ ppm 8.34 (s, 1 H), 8.25 (d, J = 4.80 Hz, 1 H), 7.50 (d, J = 1.77 Hz, 1 H), 7.41 (d, J = 8.84 Hz, 1 H), 7.19-7.07 (m, 2 H), 6.54 (d, J = 0.51 Hz, 1 H), 5.31 (s, 2 H), 4.25 (d, J = 8.08 Hz, 2 H), 3.21-3.07 (m, 4 H), 2.94 (t, J = 6.69 Hz, 2 H), 2.33-2.21 (m, 2 H), 1.74-1.54 (m, 4 H) | MS obsd. (ESI$^+$) [(M + H)$^+$] 499 |
| 7-9 | $^1$H NMR (400 MHz, CD$_3$OD) δ ppm 8.35-8.41 (m, 1 H), 8.30-8.24 (m, 1 H), 7.55-7.47 (m, 2 H), 7.24-7.15 (m, 2 H), 6.46-6.41 (m, 1 H), 5.46-5.41 (m, 2 H), 4.84-4.78 (m, 2 H), 3.72-3.64 (m, 2 H), 3.26-3.17 (m, 4 H), 2.92-2.80 (m, 4 H), 2.11-2.01 (m, 2 H), 1.95-1.88 (m, 4 H) | MS obsd. (ESI$^+$) [(M + H)$^+$] 499 |
| 7-10 | $^1$H NMR (400 MHz, CDCl$_3$) δ ppm 8.40 (s, 1 H), 8.33 (d, J = 4.77 Hz, 1 H), 7.54 (d, J = 1.76 Hz, 1 H), 7.26 (s, 1 H), 7.17 (dd, J = 8.78, 2.01 Hz, 1 H), 6.84 (d, J = 4.77 Hz, 1 H), 6.55 (s, 1 H), 5.23 (s, 2 H), 4.39-4.28 (m, 2 H), 3.27-3.13 (m, 4 H), 3.02 (t, J = 6.53 Hz, 2 H), 2.36 (dd, J = 8.41, 7.15 Hz, 2 H), 2.08-1.98 (m, 2 H), 1.94 (q, J = 4.02 Hz, 2 H), 1.72 (q, J = 4.35 Hz, 2 H) | MS obsd. (ESI$^+$) [(M + H)$^+$] 486 |
| 8 | $^1$H NMR (400 MHz, CD$_3$OD) δ ppm 8.32 (s, 1 H), 8.24 (d, J = 5.6 Hz, 1 H), 7.48 (d, J = 2.0 Hz, 1 H), 7.41 (d, J = 8.8 Hz, 1 H), 7.16-7.10 (m, 2 H), 6.46 (s, 1 H), 5.33 (s, 2 H), 4.34 (t, J = 7.2 Hz, 2 H), 4.20 (m, 1 H), 3.54 (t, J = 6.4 Hz, 2 H), 1.91 (m, 4 H), 1.86-1.82 (m, 2 H) | MS obsd. (ESI$^+$) [(M + H)$^+$] 382 |
| 9 | $^1$H NMR (400 MHz, DMSO-d$_6$) δ ppm 8.40 (s, 1 H), 8.27 (d, J = 4.80 Hz, 1 H), 7.55 (d, J = 1.77 Hz, 1 H), 7.51 (d, J = 8.84 Hz, 1 H), 7.22-7.14 (m, 2 H), 6.34 (s, 1 H), 4.74 (t, J = 6.82 Hz, 2 H), 3.64 (t, J = 6.95 Hz, 2 H), 3.01 (s, 3 H), 1.90-1.83 (m, 2 H), 1.79-1.71 (m, 2 H) | MS obsd. (ESI$^+$) [(M + H)$^+$] 432 |
| 10 | $^1$H NMR (400 MHz, DMSO-d$_6$) δ ppm 8.41 (s, 1 H), 8.27 (d, J = 4.80 Hz, 1 H), 7.64-7.45 (m, 2 H), 7.25-7.11 (m, 2 H), 6.50 (s, 1 H), 4.37 (t, J = 7.58 Hz, 2 H), 3.21-3.10 (m, 2 H), 2.98 (s, 3 H), 1.99 (q, J = 7.71 Hz, 2 H), 1.92-1.82 (m, 2 H), 1.82-1.68 (m, 2 H) | MS obsd. (ESI$^+$) [(M + H)$^+$] 446 |
| 11 | $^1$H NMR (400 MHz, CD$_3$OD) δ ppm 8.34 (s, 1 H), 8.26 (d, J = 5.05 Hz, 1 H), 7.49 (d, J = 2.02 Hz, 1 H), 7.39 (d, J = 8.59 Hz, 1 H), 7.20-7.12 (m, 2 H), 6.45 (s, 1 H), 5.39 (s, 2 H), 4.56 (t, J = 7.07 Hz, 2 H), 4.08 (q, J = 7.16 Hz, 2 H), 2.70 (t, J = 7.07 Hz, 2 H), 1.91 (d, J = 1.77 Hz, 4 H), 1.17 (t, J = 7.20 Hz, 3 H) | MS obsd. (ESI$^+$) [(M + H)$^+$] 424 |
| 12 | $^1$H NMR (400 MHz, CD$_3$OD) δ ppm 8.37 (br. s., 1 H), 8.24 (s, 1 H), 8.28 (s, 1 H), 7.97 (br. s., 1 H), 7.18 (br. s., 1 H), 6.61 (br. s., 1 H), 5.37 (br. s., 2 H), 4.41 (br. s., 2 H), 4.17 (d, J = 9.85 Hz, 2 H), 3.86 (br. s., 2 H), 2.55 (br. s., 1 H), 2.06 (br. s., 2 H), 1.93 (br. s., 4 H) | MS obsd. (ESI$^+$) [(M + H)$^+$] 457 |
| 13 | $^1$H NMR (400 MHz, DMSO-d$_6$) δ ppm 8.37 (s, 1 H), 8.27 (d, J = 4.8 Hz, 1 H), 7.47-7.38 (m, 1 H), 7.20 (d, J = 4.8 Hz, 1 H), 7.10 (dd, J = 1.6, 12.5 Hz, 1 H), 6.47 (d, J = 1.8 Hz, 1 H), 5.33 (s, 2 H), 4.58 (t, J = 7.2 Hz, 2 H), 4.11-3.98 (m, 2 H), 2.72 (t, J = 7.2 Hz, 2 H), 1.91-1.82 (m, 2 H), 1.73 (q, J = 4.0 Hz, 2 H), 1.17-1.08 (m, 3 H) | MS obsd. (ESI$^+$) [(M + H)$^+$] 442 |
| 14-1 | $^1$H NMR (400 MHz, DMSO-d$_6$) δ ppm 8.41 (s, 1 H), 8.27 (d, J = 4.55 Hz, 1 H), 7.58 (br. s., 2 H), 7.26-7.09 (m, 2 H), 6.48 (s, 1 H), 6.21-5.94 (m, 1 H), 5.29 (br. s., 2 H), 4.39 (br. s., 2 H), 3.77 (br. s., 1 H), 3.14-3.02 (br. s., 2 H), 2.96-2.80 (m, 5 H), 2.09-1.93 (br. s., 2 H), 1.86 (br. s., 2 H), 1.77 (d, J = 3.54 Hz, 2 H) | MS obsd. (ESI$^+$) [(M + H)$^+$] 443 |
| 14-2 | $^1$H NMR (400 MHz, DMSO-d$_6$) δ ppm 8.42 (s, 1 H), 8.28 (d, J = 4.80 Hz, 1 H), 7.61-7.48 (m, 2 H), 7.26-7.00 (m, 2 H), 6.33 (s, 1 H), 5.38 (s, 2 H), 4.77-4.57 (m, 2 H), 3.99 (s, 1 H), 3.64-3.41 (m, 2 H), 2.91 (s, 3 H), 1.92-1.84 (m, 2 H), 1.81-1.70 (m, 2 H) | MS obsd. (ESI$^+$) [(M + H)$^+$] 429 |
| 14-3 | $^1$H NMR (400 MHz, DMSO-d$_6$) δ ppm 8.39 (s, 1 H), 8.31-8.20 (m, 2 H), 8.06 (d, J = 2.27 Hz, 1 H), 7.20 (d, J = 4.80 Hz, 1 H), 6.51 (s, 1 H), 5.34 (s, 2 H), 4.33 (br. s., 2 H), 3.59 (s, 1 H), 3.05 (br. s., 2 H), 2.86 (s, 3 H), 1.92-1.85 (m, 2 H), 1.80-1.64 (m, 6 H) | MS obsd. (ESI$^+$) [(M + H)$^+$] 458 |
| 14-4 | $^1$H NMR (400 MHz, DMSO-d$_6$) δ ppm 8.42 (s, 1 H), 8.32-8.23 (m, 2 H), 8.03 (d, J = 2.27 Hz, 1 H), 7.21 (d, J = 4.80 Hz, 1 H), 6.30 (s, 3 H), 5.44 (s, 2 H), 4.76 (t, J = 6.95 Hz, 2 H), 3.96 (s, 1 H), 3.65 (t, J = 6.95 Hz, 2 H), 2.94 (s, 3 H), 1.93-1.86 (m, 2 H), 1.80-1.71 (m, 2 H) | MS obsd. (ESI$^+$) [(M + H)$^+$] 430 |
| 15 | $^1$H NMR (400 MHz, DMSO-d$_6$) δ ppm 8.42 (s, 1 H), 8.28 (d, J = 4.80 Hz, 1 H), 7.60-7.48 (m, 2 H), 7.26-7.10 (m, 2 H), 6.34 (s, 1 H), 5.36 (s, 2 H), 4.91-4.65 (m, 2 H), 4.09-3.88 (m, 2 H), 1.96-1.91 (m, 3 H), 1.89-1.85 (m, 2 H), 1.79-1.67 (m, 2 H) | MS obsd. (ESI$^+$) [(M + H)$^+$] 471 |

TABLE 2-continued

NMR and MS data of particular compounds

| Example No. | ¹H NMR data | MW data |
|---|---|---|
| 16-1 | ¹H NMR (400 MHz, CD₃OD) δ ppm 8.49-8.40 (m, 2 H), 7.59 (d, J = 5.56 Hz, 1 H), 7.50 (d, J = 1.77 Hz, 1 H), 7.43 (d, J = 8.59 Hz, 1 H), 7.17 (dd, J = 8.84, 2.02 Hz, 1 H), 6.49 (s, 1 H), 5.45 (s, 2 H), 4.55 (t, J = 6.95 Hz, 2 H), 2.71 (t, J = 7.07 Hz, 2 H), 2.19-2.09 (m, 4 H) | MS obsd. (ESI⁺) [(M + H)⁺] 396 |
| 16-2 | ¹H NMR (400 MHz, DMSO-d₆) δ ppm 12.56-12.42 (m, 1 H), 8.37 (s, 1 H), 8.27 (d, J = 4.5 Hz, 1 H), 7.42 (d, J = 1.3 Hz, 1 H), 7.20 (d, J = 4.5 Hz, 1 H), 7.10 (d, J = 12.4 Hz, 1 H), 6.44 (s, 1 H), 5.35 (s, 2 H), 4.53 (t, J = 7.1 Hz, 2 H), 2.65 (t, J = 7.1 Hz, 2 H), 1.92-1.83 (m, 2 H), 1.80-1.69 (m, 2 H) | MS obsd. (ESI⁺) [(M + H)⁺] 414 |
| 17 | ¹H NMR (400 MHz, DMSO-d₆) δ ppm 8.40 (s, 1 H), 8.26 (d, J = 4.55 Hz, 1 H), 7.61-7.44 (m, 2 H), 7.21-7.10 (m, 2 H), 6.51 (s, 1 H), 5.27 (s, 2 H), 4.30-4.16 (m, 2 H), 2.36 (t, J = 7.33 Hz, 2 H), 1.89-1.82 (m, 2 H), 1.81-1.68 (m, 4 H) | MS obsd. (ESI⁺) [(M + H)⁺] 424 |
| 18-1 | ¹H NMR (400 MHz, CD₃OD) δ ppm 8.30 (s, 1 H), 8.26 (d, J = 4.80 Hz, 1 H), 7.46 (d, J = 1.77 Hz, 1 H), 7.43 (d, J = 8.84 Hz, 1 H), 7.17 (d, J = 4.80 Hz, 1 H), 7.14 (dd, J = 8.84, 2.02 Hz, 1 H), 6.34 (s, 1 H), 5.38 (s, 2 H), 4.57 (t, J = 7.07 Hz, 2 H), 2.64 (t, J = 6.95 Hz, 2 H), 1.95-1.88 (m, 4 H) | MS obsd. (ESI⁺) [(M + H)⁺] 395 |
| 18-2 | ¹H NMR (400 MHz, CD₃OD) δ ppm 8.17 (d, J = 4.3 Hz, 1 H), 7.45-7.36 (m, 3 H), 7.14-7.03 (m, 2 H), 6.28 (s, 1 H), 5.31 (s, 2 H), 4.72 (t, J = 7.1 Hz, 2 H), 2.72 (t, J = 6.9 Hz, 2 H), 1.78 (d, J = 7.8 Hz, 4 H) | MS obsd. (ESI⁺) [(M + H)⁺] 395 |
| 18-3 | ¹H NMR (400 MHz, DMSO-d₆) δ ppm 8.40 (s, 1 H), 8.26 (d, J = 4.80 Hz, 1 H), 7.57 (d, J = 2.02 Hz, 1 H), 7.51 (d, J = 8.84 Hz, 1 H), 7.33 (br. s., 1 H), 7.18 (d, J = 4.80 Hz, 1 H), 7.14 (dd, J = 8.84, 2.02 Hz, 1 H), 6.80 (br. s., 1 H), 6.51 (s, 1 H), 5.27 (s, 2 H), 4.28-4.12 (m, 2 H), 2.20-2.04 (m, 3 H), 1.89-1.80 (m, 2 H), 1.79-1.60 (m, 4 H) | MS obsd. (ESI⁺) [(M + H)⁺] 409 |
| 19-1 | ¹H NMR (400 MHz, CD₃OD) δ ppm 8.43-8.20 (m, 2 H), 7.51-7.35 (m, 2 H), 7.22-7.06 (m, 2 H), 6.40 (s, 1 H), 5.38 (s, 2 H), 4.58 (t, J = 6.95 Hz, 2 H), 2.92-2.78 (m, 1 H), 2.70 (t, J = 6.95 Hz, 2 H), 1.99-1.83 (m, 4 H), 1.17-1.06 (m, 2 H), 1.00-0.92 (m, 2 H) | MS obsd. (ESI⁺) [(M + H)⁺] 499 |
| 19-2 | ¹H NMR (400 MHz, CD₃OD) δ ppm 8.42-8.30 (m, 1 H), 8.24 (br. s., 1 H), 7.46 (d, J = 1.52 Hz, 1 H), 7.40 (d, J = 8.59 Hz, 1 H), 7.25-7.05 (m, 2 H), 6.45 (s, 1 H), 5.37 (s, 2 H), 4.60 (t, J = 6.69 Hz, 2 H), 3.21-3.12 (m, 3 H), 3.11-3.03 (m, 2 H), 2.73-2.63 (m, 1 H), 1.88 (s, 4 H), 1.10-1.01 (m, 2 H), 0.96-0.85 (m, 2 H) | MS obsd. (ESI⁺) [(M + H)⁺] 513 |
| 19-3 | ¹H NMR (400 MHz, CD₃OD) δ ppm 8.39-8.28 (m, 1 H), 8.27-8.18 (m, 1 H), 7.45 (d, J = 1.77 Hz, 1 H), 7.39 (d, J = 8.84 Hz, 1 H), 7.20-7.05 (m, 2 H), 6.42 (s, 1 H), 5.35 (s, 2 H), 4.56 (t, J = 6.95 Hz, 2 H), 3.20-3.09 (m, 6 H), 3.05 (t, J = 6.82 Hz, 2 H), 1.87 (s, 4 H) | MS obsd. (ESI⁺) [(M + H)⁺] 487 |
| 20 | ¹H NMR (400 MHz, CDCl₃) δ ppm 8.44 (s, 1 H), 8.34-8.32 (d, J = 4.8 Hz, 1 H), 7.49-7.48 (d, J = 2 Hz, 1 H), 7.24 (s, 1 H), 7.12 (d, J = 2 Hz, 1 H), 6.84-6.83 (d, J = 4.8 Hz, 1 H), 6.52 (s, 1 H), 5.24 (s, 2 H), 5.07 (s, 1 H), 4.49-4.46 (q, J = 6 Hz, 2 H), 3.90-3.86 (q, J = 6.4 Hz, 2 H), 3.65 (s, 32 H), 1.95-1.93 (m, 2 H), 1.72-1.69 (m, 2 H) | MS obsd. (ESI⁺) [(M + H)⁺] 450 |
| 21 | ¹H NMR (400 MHz, CD₃OD) δ ppm 8.33 (s, 1 H), 8.26 (d, J = 4.8 Hz, 1 H), 7.51 (d, J = 2.0 Hz, 1 H), 7.43 (d, J = 8.8 Hz, 1 H), 7.17-7.12 (m, 2 H), 6.53 (s, 1 H), 5.35 (s, 2 H), 4.33 (m, 3 H), 2.67 (m, 2 H), 2.40 (m, 2 H), 1.96-1.85 (m, 6 H), 1.31 (m, 2 H), 0.89 (m, 2 H) | MS obsd. (ESI⁺) [(M + H)⁺] 451 |
| 22-1 | ¹H NMR (400 MHz, DMSO-d₆): δ ppm 8.45-8.38 (m, 1 H), 8.27 (d, J = 4.8 Hz, 1 H), 7.61-7.51 (m, 2 H), 7.23-7.12 (m, 2 H), 6.49 (s, 1 H), 5.28 (s, 2 H), 4.38 (t, J = 7.7 Hz, 2 H), 3.11 (q, J = 7.6 Hz, 4 H), 1.98 (q, J = 7.7 Hz, 2 H), 1.89-1.82 (m, 2 H), 1.79-1.72 (m, 2 H), 1.19 (t, J = 7.5 Hz, 3 H) | MS obsd. (ESI⁺) [(M + H)⁺] 458 |
| 22-2 | ¹H NMR (400 MHz, DMSO-d₆) δ ppm 8.15 (dd, J = 5.31, 1.52 Hz, 1 H), 7.60-7.45 (m, 3 H), 7.25-6.93 (m, 3 H), 6.25 (s, 1 H), 5.20 (s, 2 H), 4.49 (t, J = 7.45 Hz, 2 H), 3.26-3.15 (m, 2 H), 3.00 (s, 3 H), 2.19-2.04 (m, 2 H), 1.84-1.74 (m, 2 H), 1.71-1.62 (m, 2 H) | MS obsd. (ESI⁺) [(M + H)⁺] 444 |
| 22-3 | ¹H NMR (400 MHz, DMSO-d₆) δ ppm 8.42 (s, 1 H), 8.27 (d, J = 4.80 Hz, 1 H), 7.63-7.49 (m, 2 H), 7.23-7.11 (m, 2 H), 6.49 (s, 1 H), 5.28 (s, 2 H), 4.38 (t, J = 7.83 Hz, 2 H), 3.22-3.11 (m, 2 H), 2.99 (s, 3 H), 2.06-1.92 (m, 2 H), 1.91-1.83 (m, 2 H), 1.79-1.73 (m, 2 H) | MS obsd. (ESI⁺) [(M + H)⁺] 444 |

TABLE 2-continued

NMR and MS data of particular compounds

| Example No. | ¹H NMR data | MW data |
|---|---|---|
| 23 | ¹H NMR (400 MHz, CD₃OD) δ ppm 8.37 (s, 1 H), 8.27 (d, J = 4.80 Hz, 1 H), 8.23 (d, J = 2.27 Hz, 1 H), 7.97 (d, J = 2.27 Hz, 1 H), 7.17 (dd, J = 5.05, 0.76 Hz, 1 H), 6.60 (s, 1 H), 5.38 (s, 2 H), 4.51 (t, J = 7.33 Hz, 2 H), 3.18-3.00 (m, 4 H), 2.18 (t, J = 7.83 Hz, 2 H), 1.99-1.86 (m, 4 H), 1.30 (t, J = 7.45 Hz, 3 H) | MS obsd. (ESI⁺) [(M + H)⁺] 459 |
| 24-1 | ¹H NMR (400 MHz, CDCl₃) δ ppm 8.38 (s, 1 H), 8.30 (d, J = 4.8 Hz, 1 H), 7.50 (s, 1 H), 7.20 (d, J = 8.8 Hz, 1 H), 7.14 (d, J = 8.8 Hz, 1 H), 6.83 (d, J = 4.0 Hz, 1 H), 6.81 (s, 1 H), 5.24 (s, 2 H), 4.30 (t, J = 6.8 Hz, 2 H), 2.88 (m, 4 H), 2.53 (t, J = 6.8 Hz, 4 H), 2.43 (s, 3 H), 1.93 (m, 2 H), 1.71 (m, 2 H) | MS obsd. (ESI⁺) [(M + H)⁺] 436 |
| 24-2 | ¹H NMR (400 MHz, CD₃OD) δ ppm 8.37 (d, J = 0.76 Hz, 1 H), 8.26 (d, J = 4.80 Hz, 2 H), 7.53 (d, J = 2.02 Hz, 1 H), 7.44 (d, J = 8.84 Hz, 1 H), 7.21-7.12 (m, 2 H), 6.58 (d, J = 0.51 Hz, 1 H), 5.32 (s, 2 H), 4.40 (s, 2 H), 3.23-3.15 (m, 4 H), 3.08-2.99 (m, 2 H), 2.90-2.83 (m, 4 H), 2.15-2.02 (m, 2 H), 1.98-1.87 (m, 4 H) | MS obsd. (ESI⁺) [(M + H)⁺] 514 |
| 24-3 | ¹H NMR (400 MHz, CD₃OD) δ ppm 8.37 (d, J = 0.51 Hz, 1 H), 8.26 (d, J = 4.80 Hz, 1 H), 7.53 (d, J = 2.02 Hz, 1 H), 7.47-7.41 (m, 1 H), 7.20-7.14 (m, 2 H), 6.57 (s, 1 H), 5.32 (s, 2 H), 4.45-4.38 (m, 2 H), 4.32-4.27 (m, 1 H), 3.82-3.76 (m, 1 H), 3.38-3.34 (m, 1 H), 3.25-3.20 (m, 1 H), 3.11-3.01 (m, 3 H), 2.93-2.89 (m, 1 H), 2.13-2.06 (m, 2 H), 1.94-1.90 (m, 4 H), 1.76-1.72 (m, 2 H) | MS obsd. (ESI⁺) [(M + H)⁺] 526 |
| 24-4 | ¹H NMR (400 MHz, CD₃OD) δ ppm 8.40-8.36 (m, 1 H), 8.27-8.22 (m, 1 H), 7.53-7.51 (m, 1 H), 7.43-7.39 (m, 1 H), 7.16 (s, 2 H), 6.61-6.59 (m, 1 H), 5.31 (s, 2 H), 4.32-4.24 (m, 2 H), 3.53-3.48 (m, 4 H), 3.42-3.37 (m, 2 H), 3.14-3.09 (m, 2 H), 2.02-1.95 (m, 2 H), 1.91 (d, J = 6.57 Hz, 4 H) | MS obsd. (ESI⁺) [(M + H)⁺] 464 |
| 24-5 | ¹H NMR (400 MHz, CD₃OD) δ ppm 8.40-8.31 (m, 1 H), 8.28-8.21 (m, 1 H), 7.55-7.38 (m, 3 H), 7.15 (s, 2 H), 6.55-6.46 (m, 1 H), 5.34 (s, 2 H), 4.40-4.28 (m, 2 H), 2.93-2.81 (m, 2 H), 1.98-1.86 (m, 4 H) | MS obsd. (ESI⁺) [(M + H)⁺] 367 |
| 25-1 | ¹H NMR (400 MHz, CD₃OD) δ ppm 8.36 (s, 1 H), 8.26 (d, J = 4.80 Hz, 1 H), 8.22 (d, J = 2.27 Hz, 1 H), 7.97 (d, J = 2.27 Hz, 1 H), 7.16 (s, 1 H), 6.60 (s, 1 H), 5.38 (s, 2 H), 4.49 (s, 2 H), 3.06 (s, 2 H), 2.65 (s, 3 H), 2.20-2.08 (m, 2 H), 1.99-1.85 (m, 4 H) | MS obsd. (ESI⁺) [(M + H)⁺] 460 |
| 25-2 | ¹H NMR (400 MHz, CD₃OD) δ ppm 8.41-8.34 (m, 1 H), 8.29-8.20 (m, 1 H), 7.56-7.51 (m, 1 H), 7.48-7.42 (m, 1 H), 7.20-7.11 (m, 2 H), 6.63-6.52 (m, 1 H), 5.33 (s, 2 H), 4.47-4.34 (m, 2 H), 3.11-3.00 (m, 2 H), 2.65 (s, 3 H), 2.13-2.01 (m, 2 H), 1.92 (d, J = 7.58 Hz, 4 H) | MS obsd. (ESI⁺) [(M + H)⁺] 459 |
| 25-3 | ¹H NMR (400 MHz, DMSO-d₆) δ ppm 8.44-8.39 (m, 1 H), 8.26 (s, 2 H), 8.07 (s, 1 H), 7.24-7.16 (m, 1 H), 6.81 (s, 2 H), 6.51 (s, 1 H), 5.33 (s, 2 H), 4.48-4.37 (m, 2 H), 3.08-2.94 (m, 2 H), 2.17-2.01 (m, 2 H), 1.92-1.84 (m, 2 H), 1.81-1.72 (m, 2 H) | MS obsd. (ESI⁺) [(M + H)⁺] 446 |
| 26-1 | ¹H NMR (400 MHz, DMSO-d₆) δ ppm 8.32 (s, 1 H), 8.25 (d, J = 4.0 Hz, 1 H), 7.51 (s, 1 H), 7.46 (d, J = 8.8 Hz, 1 H), 7.18 (d, J = 4.8 Hz, 1 H), 7.10 (dd, J = 8.8, 2.0 Hz, 1 H), 6.32 (s, 1 H), 5.32 (s, 2 H), 4.35 (t, J = 6.0 Hz, 2 H), 2.48 (s, 6 H), 2.33 (m, 4 H), 1.94 (s, 3 H), 1.86 (m, 2 H), 1.73 (m, 2 H) | MS obsd. (ESI⁺) [(M + H)⁺] 478 |
| 26-2 | ¹H NMR (400 MHz, CD₃OD) δ ppm 8.38-8.34 (m, 1 H), 8.28-8.25 (m, 1 H), 8.24-8.21 (m, 1 H), 7.98-7.94 (m, 1 H), 7.19-7.15 (m, 1 H), 6.59-6.56 (m, 1 H), 5.37 (s, 2 H), 4.54-4.43 (m, 2 H), 3.42-3.35 (m, 2 H), 2.25-2.14 (m, 2 H), 2.00 (s, 3 H), 1.94 (d, J = 12.38 Hz, 4 H) | MS obsd. (ESI⁺) [(M + H)⁺] 488 |
| 26-3 | ¹H NMR (400 MHz, DMSO-d₆) δ ppm 8.36 (s, 1 H), 8.27 (d, J = 4.77 Hz, 1 H), 8.11-8.03 (m, 1 H), 7.53 (d, J = 2.01 Hz, 1 H), 7.20 (d, J = 5.02 Hz, 1 H), 7.17-7.11 (m, 1 H), 6.28 (s, 1 H), 5.25 (s, 2 H), 4.32 (s, 2 H), 3.33-3.28 (m, 2 H), 1.86 (s, 2 H), 1.80-1.72 (m, 5 H) | MS obsd. (ESI⁺) [(M + H)⁺] 409 |
| 27-1 | ¹H NMR (400 MHz, DMSO-d₆) δ ppm 8.34 (s, 1 H), 8.25 (s, 1 H), 7.47 (m, 2 H), 7.17 (m, 2 H), 6.34 (s, 1 H), 5.31 (s, 2 H), 4.35 (s, 2 H), 3.06 (s, 6 H), 2.83 (s, 3 H), 2.65 (m, 4 H), 1.85 (m, 2 H), 1.73 (m, 2 H). | MS obsd. (ESI⁺) [(M + H)⁺] 514 |
| 27-2 | ¹H NMR (400 MHz, DMSO-d₆) δ ppm 8.42-8.33 (m, 1 H), 8.31-8.24 (m, 1 H), 7.59-7.49 (m, 1 H), 7.24-7.08 (m, 2 H), 6.32-6.21 (m, 1 H), 5.39-5.24 (m, 2 H), 4.43-4.31 (m, 2 H), 3.30-3.19 (m, 2 H), 2.77 (s, 3 H), 1.92-1.70 (m, 4 H) | MS obsd. (ESI⁺) [(M + H)⁺] 445 |
| 27-3 | ¹H NMR (400 MHz, CD₃OD) δ ppm 8.40-8.32 (m, 1 H), 8.28-8.23 (m, 1 H), 7.56-7.47 (m, 1 H), 7.45-7.36 (m, 1 H), 7.21-7.10 (m, 2 H), 6.60-6.49 (m, 1 H), 5.39-5.26 (m, 2 H), 4.34-4.29 (m, 4 H), 2.94 (s, 3 H), 1.71-1.65 (m, 2 H), 1.46-1.40, 2 H), 1.05 (s, 4 H) | MS obsd. (ESI⁺) [(M + H)⁺] 459 |

TABLE 2-continued

NMR and MS data of particular compounds

| Example No. | ¹H NMR data | MW data |
|---|---|---|
| 28 | ¹H NMR (400 MHz, CD$_3$OD) δ ppm 8.40-8.31 (m, 1 H), 8.29-8.21 (m, 1 H), 7.56-7.40 (m, 2 H), 7.15 (s, 2 H), 6.55-6.45 (m, 1 H), 5.34 (s, 2 H), 4.43-4.24 (m, 2 H), 2.93-2.78 (m, 2 H), 1.98-1.83 (m, 4 H) | MS obsd. (ESI$^+$) [(M + H)$^+$] 409 |
| 29 | ¹H NMR (400 MHz, DMSO-d$_6$) δ ppm 8.47-8.21 (m, 2 H), 7.56 (s, 2 H), 7.11 (s, 2 H), 6.45 (s, 1 H), 5.29 (s, 2 H), 4.35-4.20 (m, 2 H), 3.52-3.39 (m, 2 H), 2.55 (s, 6 H), 1.86 (s, 2 H), 1.77-1.62 (m, 2 H) | MS obsd. (ESI$^+$) [(M + H)$^+$] 425 |
| 30 | ¹H NMR (400 MHz, CDCl$_3$) δ ppm 8.47 (s, 1 H), 8.34 (d, J = 4.80 Hz, 1 H), 7.56 (d, J = 1.01 Hz, 1 H), 7.23-7.13 (m, 2 H), 6.90-6.79 (m, 1 H), 6.62 (s, 1 H), 5.20 (s, 2 H), 4.29-4.19 (m, 2 H), 4.14 (q, J = 7.24 Hz, 1 H), 3.71 (s, 3 H), 3.26 (d, J = 5.81 Hz, 2 H), 1.98 (q, J = 4.13 Hz, 2 H), 1.90 (dt, J = 14.21, 6.92 Hz, 2 H), 1.73 (d, J = 3.79 Hz, 2 H) | MS obsd. (ESI$^+$) [(M + H)$^+$] 439 |
| 31 | ¹H NMR (400 MHz, CD$_3$OD) δ ppm 8.33 (s, 1 H), 8.25 (d, J = 5.1 Hz, 1 H), 7.51 (d, J = 1.5 Hz, 1 H), 7.38 (d, J = 8.6 Hz, 1 H), 7.22-7.08 (m, 2 H), 6.54 (s, 1 H), 5.33 (s, 2 H), 4.36 (t, J = 7.3 Hz, 2 H), 4.27-4.21 (m, 1 H), 4.07 (t, J = 5.9 Hz, 2 H), 3.82 (d, J = 9.3 Hz, 2 H), 2.09-1.84 (m, 5 H) | MS obsd. (ESI$^+$) [(M + H)$^+$] 507 |
| 32-1 | ¹H NMR (400 MHz, CD$_3$OD) δ ppm 8.28-8.21 (m, 1 H), 7.55-7.47 (m, 1 H), 7.42-7.27 (m, 2 H), 7.09-6.96 (m, 2 H), 5.24 (s, 2 H), 3.43 (d, J = 3.54 Hz, 4 H), 3.10 (d, J = 7.58 Hz, 2 H), 1.83-1.66 (m, 4 H), 1.44-1.17 (m, 3 H) | MS obsd. (ESI$^+$) [(M + H)$^+$] 444 |
| 32-2 | ¹H NMR (400 MHz, CD$_3$OD) δ ppm 8.28-8.19 (m, 1 H), 8.15 (s, 1 H), 7.59-7.48 (m, 1 H), 7.33 (d, J = 1.52 Hz, 1 H), 7.15 (d, J = 4.80 Hz, 1 H), 7.10-7.00 (m, 1 H), 5.27 (s, 2 H), 2.93 (s, 3 H), 1.92 (s, 2 H), 1.90-1.83 (m, 2 H) | MS obsd. (ESI$^+$) [(M + H)$^+$] 430 |
| 33 | ¹H NMR (400 MHz, DMSO-d$_6$) δ ppm 11.24-11.10 (m, 1 H), 8.29-8.17 (m, 2 H), 7.55 (d, J = 8.59 Hz, 1 H), 7.37 (d, J = 1.77 Hz, 1 H), 7.16 (d, J = 4.80 Hz, 1 H), 7.02 (dd, J = 8.59, 1.77 Hz, 1 H), 5.15 (s, 2 H), 3.01-3.13 (m, 2 H), 2.97-2.86 (m, 5 H), 1.96-1.86 (m, 2 H), 1.85-1.79 (m, 2 H), 1.77-1.70 (m, 2 H) | MS obsd. (ESI$^+$) [(M + H)$^+$] 444 |
| 34-1 | ¹H NMR (400 MHz, CD$_3$OD) δ ppm 8.41 (s, 1 H) 8.28 (d, J = 5.05 Hz, 1 H), 7.63 (d, J = 9.09 Hz, 1 H), 7.59 (d, J = 1.52 Hz, 1 H), 7.36 (dd, J = 8.72, 1.89 Hz, 1 H), 7.18 (dd, J = 4.80, 0.76 Hz, 1 H), 5.54 (s, 2 H), 4.94 (t, J = 6.44 Hz, 2 H), 3.79 (t, J = 6.44 Hz, 2 H), 3.03 (s, 3 H), 1.87-1.95 (m, 4 H) | MS obsd. (ESI$^+$) [(M + H)$^+$] 433 |
| 34-2 | ¹H NMR (400 MHz, DMSO-d$_6$) δ ppm 7.67 (s, 1.5 H), 7.64 (s, 0.5 H), 7.32 (d, J = 8.4 Hz, 1 H), 7.24 (dd, J = 14, 7.6 Hz, 1 H), 7.03 (d, J = 8.0 Hz, 1 H), 6.85 (t, J = 9.2 Hz, 1 H), 5.41 (s, 2 H), 4.83 (t, J = 6.4 Hz, 2 H), 3.77 (t, J = 6.4 Hz, 2 H), 3.09 (s, 3 H), 1.92 (d, J = 3.2 Hz, 2 H), 1.62 (d, J = 3.2 Hz, 2 H) | MS obsd. (ESI$^+$) [(M + H)$^+$] 449 |
| 34-3 | ¹H NMR (400 MHz, DMSO-d$_6$) δ ppm 7.66 (m, 2 H), 7.32 (dd, J = 8.8, 2.0 Hz, 1 H), 7.23 (t, J = 8.0 Hz, 1 H), 7.15 (d, J = 7.2 Hz, 1 H), 7.03 (dd, J = 8.4, 0.8 Hz, 1 H), 5.41 (s, 2 H), 4.83 (t, J = 6.8 Hz, 2 H), 3.77 (t, J = 6.4 Hz, 2 H), 3.09 (s, 3 H), 1.92 (dd, J = 8.0, 4.0 Hz, 2 H), 1.56 (dd, J = 8.0, 4.0 Hz, 2 H) | MS obsd. (ESI$^+$) [(M + H)$^+$] 465 |
| 34-4 | ¹H NMR (400 MHz, DMSO-d$_6$) δ ppm 7.66 (m, 2 H), 7.32 (dd, J = 8.8, 2.0 Hz, 1 H), 7.20-7.15 (m, 3 H), 5.41 (s, 2 H), 4.83 (t, J = 6.8 Hz, 2 H), 3.77 (t, J = 6.4 Hz, 2 H), 3.09 (s, 3 H), 2.28 (dd, J = 7.6, 4.0 Hz, 2 H), 1.52 (dd, J = 7.6, 3.6 Hz, 2 H) | MS obsd. (ESI$^+$) [(M + H)$^+$] 509 |
| 34-5 | ¹H NMR (400 MHz, CD$_3$OD) δ ppm 8.41 (s, 1 H), 8.28 (d, J = 5.1 Hz, 1 H), 7.68-7.54 (m, 2 H), 7.40-7.31 (m, 1 H), 7.18 (d, J = 4.8 Hz, 1 H), 5.55 (s, 2 H), 4.94 (d, J = 6.6 Hz, 2 H), 3.73 (t, J = 6.3 Hz, 2 H), 3.12 (q, J = 7.6 Hz, 2 H), 1.92 (m, 4 H), 1.34 (t, J = 7.3 Hz, 3 H) | MS obsd. (ESI$^+$) [(M + H)$^+$] 445 |
| 35 | ¹H NMR (400 MHz, CD$_3$OD) δ ppm 8.47 (s, 1 H), 8.28 (d, J = 4.80 Hz, 1 H), 7.64 (d, J = 1.26 Hz, 1 H), 7.59 (d, J = 8.84 Hz, 1 H), 7.35 (dd, J = 8.84, 1.77 Hz, 1 H), 7.17 (d, J = 5.05 Hz, 1 H), 5.42 (s, 2 H), 4.46-4.37 (m, 2 H), 4.27 (dd, J = 13.89, 9.60 Hz, 2 H), 3.95 (dd, J = 14.02, 6.44 Hz, 2 H), 2.73-2.62 (m, 1 H), 2.20 (q, J = 7.75 Hz, 2 H), 1.99-1.86 (m, 4 H) | MS obsd. (ESI$^+$) [(M + H)$^+$] 457 |
| 36-1 | ¹H NMR (400 MHz, CD$_3$OD) δ ppm 8.43 (s, 1 H), 8.28 (d, J = 5.1 Hz, 1 H), 7.68-7.58 (m, 2 H), 7.40-7.30 (m, 1 H), 7.17 (d, J = 4.8 Hz, 1 H), 5.45 (s, 2 H), 4.57 (t, J = 7.7 Hz, 2 H), 3.28 (t, J = 7.3 Hz, 2 H), 3.02 (s, 3 H), 2.30 (br. s, 2 H), 1.92 (m, 4 H) | MS obsd. (ESI$^+$) [(M + H)$^+$] 445 |

TABLE 2-continued

NMR and MS data of particular compounds

| Example No. | ¹H NMR data | MW data |
|---|---|---|
| 36-2 | ¹H NMR (400 MHz, CD$_3$OD) δ ppm 8.41 (d, J = 0.51 Hz, 1 H), 8.28 (d, J = 4.80 Hz, 1 H), 7.63 (d, J = 8.34 Hz, 1 H), 7.59 (d, J = 1.77 Hz, 1 H), 7.37 (d, J = 2.02 Hz, 1 H), 7.18 (dd, J = 5.05, 0.76 Hz, 1 H), 5.55 (s, 2 H), 4.99-4.90 (m, 2 H), 3.79 (t, J = 6.57 Hz, 2 H), 2.65-2.54 (m, 1 H), 1.92 (d, J = 2.27 Hz, 4 H), 1.14 (br. s., 2 H), 1.09-1.00 (m, 2 H) | MS obsd. (ESI⁺) [(M + H) +9459 |
| 37-1 | ¹H NMR (400 MHz, DMSO-d$_6$) δ ppm 8.34 (s, 1 H), 8.25 (d, J = 4.8 Hz, 1 H), 7.55 (d, J = 1.6 Hz, 1 H), 7.30 (dd, J = 11.2, 1.6 Hz, 1 H), 7.17 (d, J = 1.6 Hz, 1 H), 5.46 (s, 2 H), 4.87 (d, J = 6.8 Hz, 2 H), 3.81 (d, J = 6.8 Hz, 2 H), 3.11 (s, 3 H), 1.85 (m, 2 H), 1.72 (m, 2 H) | MS obsd. (ESI⁺) [(M + H)⁺] 448 |
| 37-2 | ¹H NMR (400 MHz, DMSO-d$_6$) δ ppm 8.35 (s, 1 H), 8.25 (d, J = 4.8 Hz, 1 H), 7.70 (d, J = 1.6 Hz, 1 H), 7.43 (d, J = 2.0 Hz, 1 H), 7.17 (d, J = 4.8 Hz, 1 H), 5.49 (s, 2 H), 5.02 (t, J = 6.0 Hz, 2 H), 3.84 (t, J = 6.0 Hz, 2 H), 3.15 (s, 3 H), 1.85 (m, 2 H), 1.72 (m, 2 H) | MS obsd. (ESI⁺) [(M + H)⁺] 464 |
| 38-1 | ¹H NMR (400 MHz, CDCl$_3$) δ ppm 8.78 (s, 1 H), 8.36-8.34 (br. s, J = 4.8 Hz, 1 H), 7.75 (s, 1 H), 7.29-7.24 (m, 2 H), 6.82-6.81 (m, 1 H), 5.32 (s, 2 H), 4.71-4.63 (m, 4 H), 4.44-4.41 (m, 2 H), 3.42-3.35 (m, 1 H), 1.94-1.91 (m, 2 H), 1.73-1.70 (m, 2 H) | MS obsd. (ESI⁺) [(M + H)⁺] 395 |
| 38-2 | ¹H NMR (400 MHz, CDCl$_3$) δ ppm 8.79 (s, 1 H), 8.34 (d, J = 4.8 Hz, 1 H), 7.77 (d, J = 2.0 Hz, 1 H), 7.28 (m, 1 H), 7.20 (d, J = 8.8 Hz, 1 H), 6.81 (d, J = 5.2 Hz, 1 H), 5.30 (s, 2 H), 4.77 (t, J = 7.6 Hz, 2 H), 4.32 (t, J = 6.0 Hz, 2 H), 4.22 (t, J = 7.6 Hz, 2 H), 3.02 (m, 1 H), 2.08 (q, J = 7.6 Hz, 2 H), 1.92 (m, 2 H), 1.70 (m, 2 H) | MS obsd. (ESI⁺) [(M + H)⁺] 409 |
| 38-3 | ¹H NMR (400 MHz, CD$_3$OD) δ ppm 8.42 (s, 1 H), 8.29 (d, J = 5.02 Hz, 5 H), 7.44 (d, J = 1.51 Hz, 1 H), 7.20-7.14 (m, 2 H), 5.44 (s, 2 H), 4.85 (d, J = 7.28 Hz, 2 H), 4.80 (t, J = 6.50 Hz, 2 H), 4.57 (t, J = 6.27 Hz, 2 H), 3.65 (m, J = 7.40, 6.15 Hz, 1 H), 1.91 (s, 4 H) | MS obsd. (ESI⁺) [(M + H)⁺] 413 |
| 39-1 | ¹H NMR (400 MHz, CD$_3$OD) δ ppm 8.34 (s, 1 H), 8.27 (d, J = 5.02 Hz, 1 H), 7.72 (d, J = 8.78 Hz, 1 H), 7.57 (d, J = 1.76 Hz, 1 H), 7.34 (dd, J = 8.78, 1.76 Hz, 1 H), 7.17 (d, J = 4.77 Hz, 1 H), 5.55 (s, 2 H), 4.76 (s, 2 H), 4.70 (d, J = 6.78 Hz, 2 H), 4.48 (d, J = 6.78 Hz, 2 H), 1.90 (s, 4 H) | MS obsd. (ESI⁺) [(M + H)⁺] 410 |
| 39-2 | ¹H NMR (400 MHz, CDCl$_3$) δ ppm 8.36 (s, 1 H), 8.28-8.27 (d, J = 4.8 Hz, 1 H), 7.42 (s, 1 H), 7.19-7.14 (m, 2 H), 5.56 (s, 2 H), 4.92-4.91 (m, 1 H), 4.71-4.70 (d, J = 7.2 Hz, 1 H), 4.49-4.47 (d, J = 6.8 Hz, 1 H), 1.91-1.90 (m, 4 H) | MS obsd. (ESI⁺) [(M + H)⁺] 428 |

More particular compounds of formula I include the following:

1'-({5-Bromo-1-[2-(methylsulfonyl)ethyl]-1H-indol-2-yl}methyl)spiro[cyclopropane-1,3'-pyrrolo[2,3-c]pyridin]-2'(1'H)-one;

1'-({5-Chloro-7-fluoro-1-[2-(methylsulfonyl)ethyl]-1H-indol-2-yl}methyl)spiro[cyclopropane-1,3'-pyrrolo[2,3-c]pyridin]-2'(1'H)-one;

1'-({5-Methyl-1-[2-(methylsulfonyl)ethyl]-1H-indol-2-yl}methyl)spiro[cyclopropane-1,3'-pyrrolo[2,3-c]pyridin]-2'(1'H)-one;

1'-({5-Chloro-1-[2-(ethylsulfonyl)ethyl]-1H-indol-2-yl}methyl)spiro[cyclopropane-1,3'-pyrrolo[2,3-c]pyridin]-2'(1'H)-one;

1'-({5-Chloro-1-[2-(ethylsulfonyl)ethyl]-1H-pyrrolo[2,3-b]pyridin-2-yl}methyl)spiro[cyclopropane-1,3'-pyrrolo[2,3-c]pyridin]-2'(1'H)-one;

1'-({5-Chloro-1-[2-(methylsulfonyl)ethyl]-1H-indol-2-yl}methyl)spiro[cyclopropane-1,3'-pyrrolo[2,3-c]pyridin]-2'(1'H)-one;

1'-({5-Chloro-1-[4-(methylsulfonyl)butyl]-1H-indol-2-yl}methyl)spiro[cyclopropane-1,3'-pyrrolo[2,3-c]pyridin]-2'(1'H)-one;

1'-({5-Chloro-1-[2-(1,1-dioxidothietan-3-yl)ethyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-pyrrolo[3,2-b]pyridin-2-yl}methyl)spiro[cyclopropane-1,3'-pyrrolo[2,3-c]pyridin]-2'(1'H)-one;

1'-({5-Chloro-1-[3-(methylsulfinyl)propyl]-1H-indol-2-yl}methyl)spiro[cyclopropane-1,3'-pyrrolo[2,3-c]pyridin]-2'(1'H)-one;

3-{5-Chloro-2-[(2'-oxospiro[cyclopropane-1,3'-pyrrolo[2,3-c]pyridin]-1'(2'H)-yl)methyl]-1H-indol-1-yl}-N,N-dimethylpropane-1-sulfonamide;

1'-({5-Chloro-1-[3-(morpholin-4-ylsulfonyl)propyl]-1H-indol-2-yl}methyl)spiro[cyclopropane-1,3'-pyrrolo[2,3-c]pyridin]-2'(1'H)-one;

1'-({5-Chloro-1-[3-(pyrrolidin-1-ylsulfonyl)propyl]-1H-indol-2-yl}methyl)spiro[cyclopropane-1,3'-pyrrolo[2,3-c]pyridin]-2'(1'H)-one;

1'-[(5-Chloro-1-{3-[(3-oxopiperazin-1-yl)sulfonyl]propyl}-1H-indol-2-yl)methyl]spiro[cyclopropane-1,3'-pyrrolo[2,3-c]pyridin]-2'(1'H)-one;

1'-({5-Chloro-1-[4-(1,1-dioxido-1,2-thiazolidin-2-yl)butyl]-1H-indol-2-yl}methyl)spiro[cyclopropane-1,3'-pyrrolo[2,3-c]pyridin]-2'(1'H)-one;

1'-[{5-Chloro-1-[2-(methylsulfonyl)ethyl]-1H-indol-2-yl}(²H$_2$)methyl]spiro[cyclopropane-1,3'-pyrrolo[2,3-c]pyridin]-2'(1'H)-one;

1'-[{5-Chloro-1-[3-(methylsulfonyl)propyl]-1H-indol-2-yl}(²H$_2$)methyl]spiro[cyclopropane-1,3'-pyrrolo[2,3-c]pyridin]-2'(1'H)-one;

Ethyl 3-{5-chloro-2-[(2'-oxospiro[cyclopropane-1,3'-pyrrolo[2,3-c]pyridin]-1'(2'H)-yl)methyl]-1H-indol-1-yl}propanoate;
Ethyl 3-{5-chloro-7-fluoro-2-[(2'-oxospiro[cyclopropane-1,3'-pyrrolo[2,3-c]pyridin]-1'(2'H)-yl)methyl]-1H-indol-1-yl}propanoate;
1'-({5-Chloro-1-[3-(S-methylsulfonimidoyl)propyl]-1H-indol-2-yl}methyl)spiro[cyclopropane-1,3'-pyrrolo[2,3-c]pyridin]-2'(1'H)-one;
1'-({5-Chloro-1-[2-(S-methylsulfonimidoyl)ethyl]-1H-indol-2-yl}methyl)spiro[cyclopropane-1,3'-pyrrolo[2,3-c]pyridin]-2'(1'H)-one;
Methyl 4-{5-chloro-2-[(2'-oxospiro[cyclopropane-1,3'-pyrrolo[2,3-c]pyridin]-1'(2'H)-yl)methyl]-1H-indol-1-yl}butanoate;
3-{5-Chloro-2-[(2'-oxospiro[cyclopropane-1,3'-c]pyridin]-1'(2'H)-yl)methyl]-1H-indol-1-yl}propanamide;
4-{5-Chloro-2-[(2'-oxospiro[cyclopropane-1,3'-pyrrolo[2,3-c]pyridin]-1'(2'H)-yl)methyl]-1H-indol-1-yl}butanamide;
1'-({5-Chloro-1-[3-(ethylsulfonyl)propyl]-1H-indol-2-yl}methyl)spiro[cyclopropane-1,3'-pyrrolo[2,3-c]pyridin]-2'(1'H)-one;
1'-({5-Chloro-1-[3-(methylsulfonyl)propyl]-1H-indol-2-yl}methyl)spiro[cyclopropane-1,3'-pyrrolo[2,3-c]pyridin]-2'(1'H)-one;
1'-({5-Chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one;
1'-[(5-Chloro-1-{3-[(1R,4R)-2,5-diazabicyclo[2.2.1]hept-2-ylsulfonyl]propyl}-1H-indol-2-yl)methyl]spiro[cyclopropane-1,3'-pyrrolo[2,3-c]pyridin]-2'(1'H)-one;
3-{5-Chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide;
1'-[(5-Chloro-1-{2-[4-(methylsulfonyl)piperazin-1-yl]ethyl}-1H-indol-2-yl)methyl]spiro[cyclopropane-1,3'-pyrrolo[2,3-c]pyridin]-2'(1'H)-one;
N-(2-{5-Chloro-2-[(2'-oxospiro[cyclopropane-1,3'-pyrrolo[2,3-c]pyridin]-1'(2'H)-yl)methyl]-1H-indol-1-yl}ethyl)methanesulfonamide;
Methyl(3-{5-chloro-2-[(2'-oxospiro[cyclopropane-1,3'-pyrrolo[2,3-c]pyridin]-1'(2'H)-yl)methyl]-1H-indol-1-yl}propyl)carbamate;
1'-({6-Chloro-3-[2-(ethylsulfonyl)ethyl]-1H-indol-2-yl}methyl)spiro[cyclopropane-1,3'-pyrrolo[2,3-b]pyridin]-2'(1'H)-one;
1'-({6-Chloro-3-[2-(methylsulfonyl)ethyl]-1H-indol-2-yl}methyl)spiro[cyclopropane-1,3'-pyrrolo[2,3-c]pyridin]-2'(1'H)-one;
1'-({6-Chloro-3-[3-(methylsulfonyl)propyl]-1H-indol-2-yl}methyl)spiro[cyclopropane-1,3'-pyrrolo[2,3-c]pyridin]-2'(1'H)-one;
1'-({5-Chloro-1-[2-(methylsulfonyl)ethyl]-1H-benzimidazol-2-yl}methyl)spiro[cyclopropane-1,3'-pyrrolo[2,3-c]pyridin]-2'(1'H)-one;
1'-({5-Chloro-1-[2-(methylsulfonyl)ethyl]-1H-benzimidazol-2-yl}methyl)-4'-fluorospiro[cyclopropane-1,3'-indol]-2'(1'H)-one;
1'-({5-Chloro-1-[2-(ethylsulfonyl)ethyl]-1H-benzimidazol-2-yl}methyl)spiro[cyclopropane-1,3'-pyrrolo[2,3-c]pyridin]-2'(1'H)-one;
1'-({5-Chloro-1-[2-(1,1-dioxidothietan-3-yl)ethyl]-1H-benzimidazol-2-yl}methyl)spiro[cyclopropane-1,3'-pyrrolo[2,3-c]pyridin]-2'(1'H)-one;
1'-({5-Chloro-1-[3-(methylsulfonyl)propyl]-1H-benzimidazol-2-yl}methyl)spiro[cyclopropane-1,3'-pyrrolo[2,3-c]pyridin]-2'(1'H)-one;
1'-({5-Chloro-1-[2-(cyclopropylsulfonyl)ethyl]-1H-benzimidazol-2-yl}methyl)spiro[cyclopropane-1,3'-pyrrolo[2,3-c]pyridin]-2'(1'H)-one;
1'-({5-Chloro-7-fluoro-1-[2-(methylsulfonyl)ethyl]-1H-benzimidazol-2-yl}methyl)spiro[cyclopropane-1,3'-pyrrolo[2,3-c]pyridin]-2'(1'H)-one;
1'-({5,7-Dichloro-1-[2-(methylsulfonyl)ethyl]-1H-benzimidazol-2-yl}methyl)spiro[cyclopropane-1,3'-pyrrolo[2,3-c]pyridin]-2'(1'H)-one;
1'-{[5-Chloro-1-(oxetan-3-ylmethyl)-1H-benzimidazol-2-yl]methyl}spiro[cyclopropane-1,3'-pyrrolo[2,3-c]pyridin]-2'(1'H)-one;
1'-({5-Chloro-1-[2-(oxetan-3-yl)ethyl]-1H-benzimidazol-2-yl}methyl)spiro[cyclopropane-1,3'-pyrrolo[2,3-c]pyridin]-2'(1'H)-one; and
1'-({1-[(3-Aminooxetan-3-yl)methyl]-5-chloro-1H-benzimidazol-2-yl}methyl)spiro[cyclopropane-1,3'-pyrrolo[2,3-c]pyridin]-2'(1'H)-one.

Compound with favorable pharmacokinetics is more likely to be efficacious and safe. It is very important for a drug to have a moderate or low clearance and a long half-life, as this often lead to a good oral bioavailability and high exposure in systemic exposure. Reducing the clearance and increasing half-life time of a compound or drug could reduce the daily dose required for efficacy and therefore give a better efficacy and safety profile. From the examples below, it has been found a good SDPK profiling of this invention: good exposure at low dose, longer t ½ (more than 1 hour), low to moderate clearance and good bioavailability (see Table 3).

The single dose PK in male ICR mouse was performed to assess their pharmacokinetic properties. Two groups of animals were dosed via either bolus intravenous (IV) or oral gavage (PO) of the respective compound. The animals for oral administration were fasted overnight prior to dosing and food was resumed 4 hours postdose. Blood samples (approximately 400 μL) were collected via cardiac puncture after euthanasia by carbon dioxide inhalation at 2 minutes, 5 minutes, 15 minutes, 30 minutes, 1 hour, 2 hours, 4 hours, 6 hours, 8 hours, and 24 hours postdose for IV group, and at 5 minutes, 15 minutes, 30 minutes, 1 hour, 2 hours, 4 hours, 6 hours, 8 hours, and 24 hours postdose for PO group. Blood samples were placed into tubes containing sodium heparin and centrifuged at 8000 rpm for 6 minutes at 4° C. to separate plasma from the samples.

Following centrifugation, the resulting plasma was transferred to clean tubes for bioanalysis on LC/MS/MS. The pharmacokinetic parameters were calculated using non-compartmental module of WinNonlin® Professional 5.2.

TABLE 3

Selected Pharmacokinetics Parameters of Compounds in Male ICR Mice Following Intravenous and Oral Administration

| | $AUC_{(0-t)}$ μg/L*hr | $t_{1/2z}$ hr | CLz mL/min/kg | F % |
|---|---|---|---|---|
| Example 2-6 | | | | |
| IV (5 mg/kg) | 3510 | 0.724 | 23.7 | NA* |
| PO (25 mg/kg) | 10200 | 0.701 | NA* | 58.3 |
| Example 34-1 | | | | |
| IV (1.45 mg/kg) | 373 | 10.2 | 64.8 | NA* |
| PO (25 mg/kg)) | 3280 | 2.98 | NA* | 51.0 |

TABLE 3-continued

Selected Pharmacokinetics Parameters of Compounds in Male ICR Mice Following Intravenous and Oral Administration

| | $AUC_{(0-t)}$ µg/L*hr | $t_{1/2z}$ hr | CLz mL/min/kg | F % |
|---|---|---|---|---|
| Example 37-1 | | | | |
| IV (2 mg/kg) | 751 | 0.976 | 44.4 | NA* |
| PO (25 mmg/kg) | 9290 | 3.74 | NA* | 99 |

In the above Table 3, the abbreviations have the following meanings:
$AUC_{(0-t)}$: area under the curve from 0 to t hour;
$t_{1/2z}$: terminal half-life
CLz: clearance;
F: bioavailability;
IV: intravenous;
PO: oral gavage.
NA: not applicable Synthesis The compounds of the present invention can be prepared by any conventional means. Suitable processes for synthesizing these compounds as well as their starting materials are provided in the schemes below and in the examples. All substituents, in particular, $R^1$ to $R^6$, $W^1$ to $W^3$, A and X are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Iaa (Scheme 1)

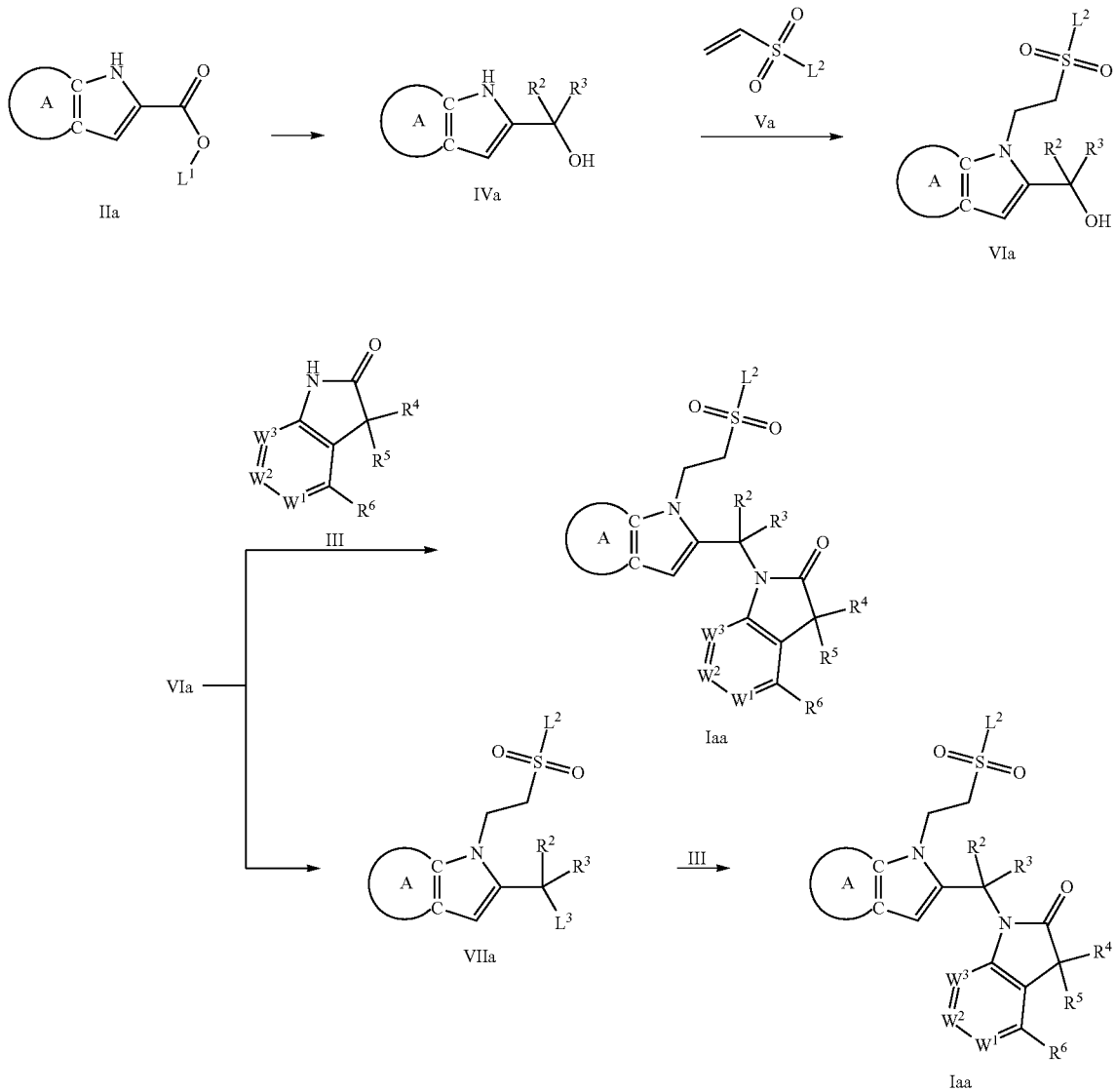

$L^1$ is $C_{1-6}$alkyl;
$L^2$ is $C_{1-6}$ alkyl;
$L^3$ is chloro or $-OSO_2CH_3$.

Compound of interest Iaa can be prepared according to Scheme 1.

Hydroxymethyl indole IVa can be prepared by reduction of $C_{1-6}$ alkyl ester IIa. The conversion can be carried out by treating $C_{1-6}$ alkyl ester IIa with lithium aluminum hydride or lithium aluminum deuteride in tetrahydrofuran at a temperature between 0° C. and room temperature for several hours.

Sulfone VIa can be prepared by coupling of hydroxymethyl indole IVa and ($C_{1-6}$ alkylsulfonyl)ethene Va. The reaction can be carried out with a suitable base such as cesium carbonate in a suitable organic solvent such as acetonitrile or N,N-dimethylformamide at a temperature between room temperature and 50° C. for several hours.

Intermediate VIIa can be prepared by treating hydroxy VIa with thionyl chloride or methanesulfonyl chloride. When $L^3$ is chloride, the reaction can be carried out by treating hydroxy VIa with thionyl chloride in dichloromethane at a temperature between room temperature and 60° C. for 30 minutes to several hours. When $L^3$ is methanesulfonate, the reaction can be carried out by treating hydroxy VIa with methanesulfonyl chloride in the presence of an organic base such as triethylamine or diisopropylethylamine in dichloromethane at a temperature between 0° C. and room temperature for one to several hours.

Compound of interest Iaa can be prepared by Mitsunobu reaction of hydroxy VIa and amide III. The reaction can be carried out in the presence of a phosphine reagent such as triphenylphosphine or tributylphosphine, and an azidocarbonyl reagent such as diethyl azodicarboxylate, diisopropyl azodicarboxylate, 1,1-(azodicarbonyl)dipiperidine or N,N,N',N'-tetramethylazodicarboxamide in an inert organic solvent such as tetrahydrofuran, diethyl ether, acetonitrile or toluene at a temperature between room temperature and 80° C. for several hours.

Compound of interest Iaa can also be prepared by reaction of intermediate VIIa and amide III. The reaction can be carried out in the presence of a base such as cesium carbonate, sodium hydride or sodium tert-butoxide in an organic solvent such as acetonitrile or N,N-dimethylformamide at a temperature between 0° C. to room temperature for one to several hours.

General Synthetic Route for Compound Iab (Scheme 2)

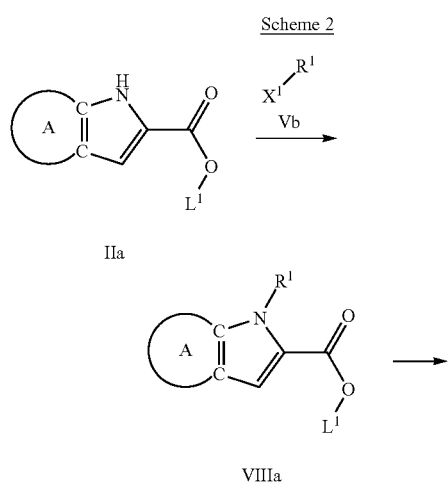

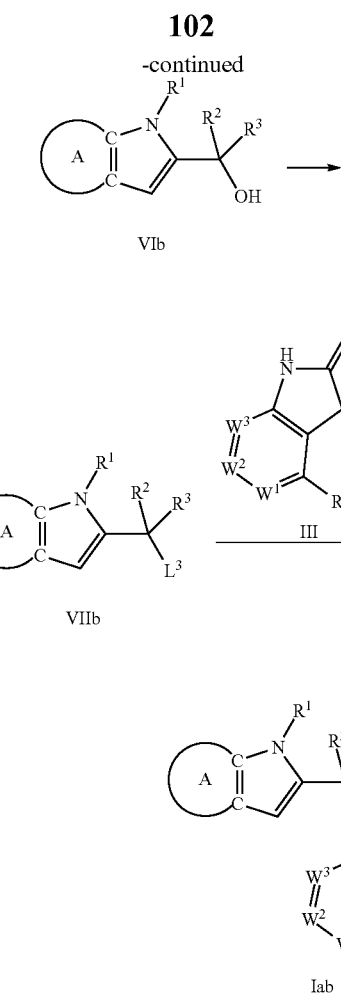

$X^1$ is chloro, bromo, iodo, 4-methylbenzenesulfonate or hydroxy;
$L^1$ is $C_{1-6}$alkyl;
$L^3$ is chloro or —OSO$_2$CH$_3$.

Compound of interest Iab can be prepared according to Scheme 2.

N-Substituted indole VIIIa can be prepared by reaction of IIa and Vb. When $X^1$ is chloro, bromo, iodo or 4-methylbenzenesulfonate, the reaction can be carried out in the presence of a base such as potassium carbonate or cesium carbonate in a suitable solvent such as acetonitrile or N,N-dimethylformamide at a temperature between 70° C. and 100° C. for several hours. When $X^1$ is hydroxy, The reaction can be carried out in the presence of a phosphine reagent such as triphenylphosphine or tributylphosphine and an azidocarbonyl reagent such as diethyl azodicarboxylate, diisopropyl azodicarboxylate, 1,1-(azodicarbonyl)dipiperidine or N,N,N',N'-tetramethylazodicarboxamide in an inert organic solvent such as tetrahydrofuran, diethyl ether, acetonitrile or toluene at a temperature between room temperature and 80° C. for several hours.

Hydroxy VIb can be prepared by reduction of $C_{1-6}$ alkyl ester VIM in the presence of lithium aluminum hydride or lithium aluminum deuteride in tetrahydrofuran at a temperature between 0° C. and room temperature for several hours.

Intermediate VIIb can be prepared by treating hydroxy VIb with thionyl chloride or methanesulfonyl chloride. When $L^3$ is chloro, the reaction can be carried out by treating hydroxy VIa with thionyl chloride in dichloromethane at a temperature between room temperature and 60° C. for 30 minutes to several hours. When L³ is methanesulfonate, the reaction can be carried out by treating hydroxy VIa with methanesulfonyl chloride in the presence of an organic base such as triethylamine or diisopropylethylamine in dichloromethane at a temperature between 0° C. and room temperature for one to several hours.

Compound of interest Iab can be prepared by reaction of intermediate VIIb and amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

General Synthetic Route for Compound Iac (Scheme 3)

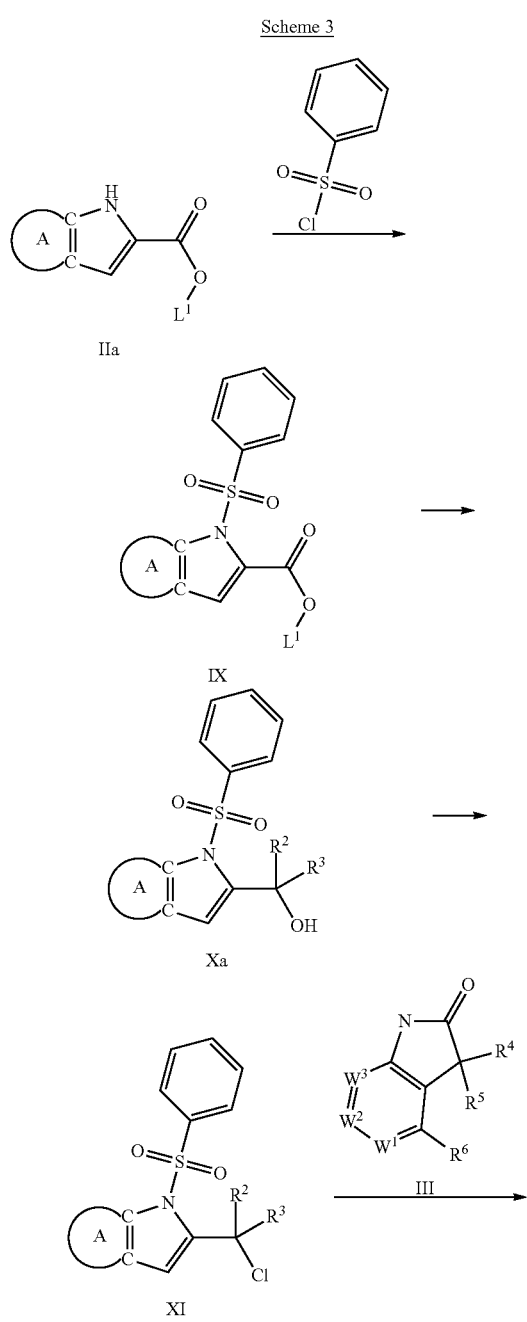

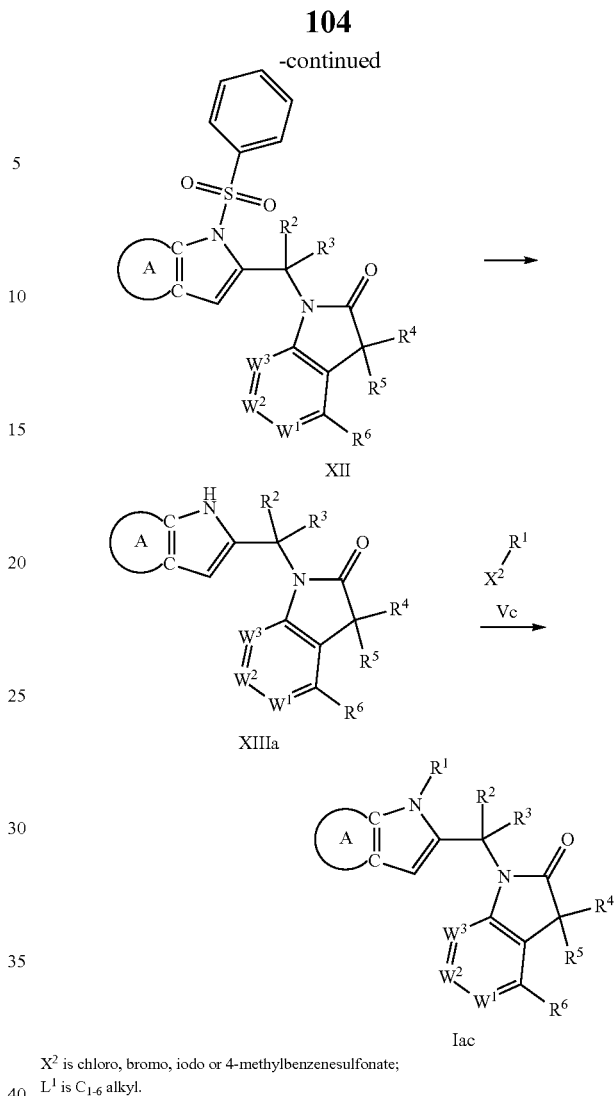

$X^2$ is chloro, bromo, iodo or 4-methylbenzenesulfonate;
$L^1$ is $C_{1-6}$ alkyl.

Compound of interest Iac can be prepared according to Scheme 3.

N-protected indole IX can be prepared by reaction of indole IIa and benzenesulfonyl chloride. The reaction can be carried out in the presence of sodium hydride in N,N-dimethylformamide at a temperature between 0° C. and room temperature for one to several hours.

Hydroxy Xa can be prepared by reduction of ester IX in the presence of lithium aluminum hydride or lithium aluminum deuteride in tetrahydrofuran at a temperature between 0° C. and room temperature for several hours.

Chloride XI can be prepared by treating hydroxy Xa with thionyl chloride. The reaction can be carried out in dichloromethane at a temperature between room temperature and 60° C. for 30 minutes to several hours.

Compound XII can be prepared by reaction of chloride XI and amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

Key intermediate XIIIa can be prepared by deprotection of benzenesulfonyl XII. The reaction can be carried out in the presence of tetrabutylammonium fluoride in tetrahydrofuran at room temperature for several hours.

Compound of interest Iac can be prepared by substitution reaction of intermediate XIIIa and intermediate Vc. The reaction can be carried out in the presence of a base such as potassium carbonate or cesium carbonate in a suitable solvent such as acetonitrile or N,N-dimethylformamide at a temperature between 70° C. and 100° C. for several hours.

General Synthetic Route for Compound Iad (Scheme 4)

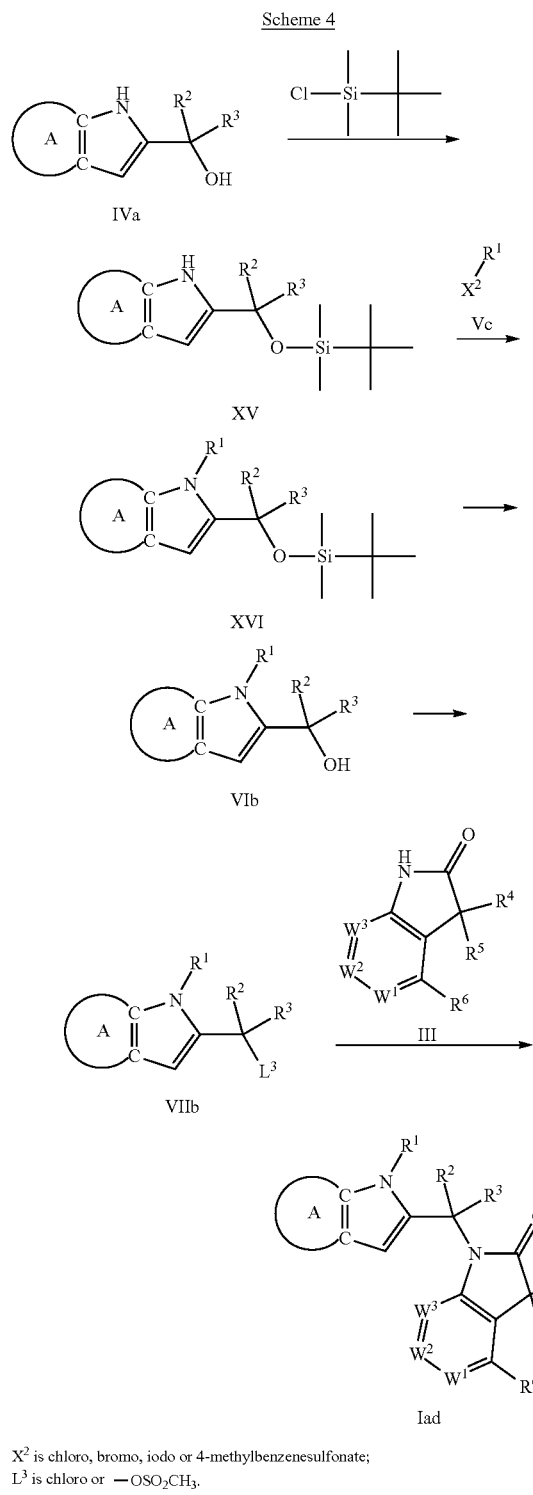

X² is chloro, bromo, iodo or 4-methylbenzenesulfonate;
L³ is chloro or —OSO₂CH₃.

Compound of interest Iad can be prepared according to Scheme 4.

Silyloxy XV can be prepared by reaction of hydroxy IVa and tert-butyl(chloro)dimethylsilane. The reaction can be carried out in the presence of imidazole in dichloromethane at room temperature for several hours.

N-Substituted indole XVI can be prepared by substitution reaction of indole XV and intermediate Vc. The reaction can be carried out in the presence of a base such as potassium carbonate or cesium carbonate in a suitable solvent such as acetonitrile or N,N-dimethylformamide at a temperature between 70° C. and 100° C. for several hours.

Hydroxy VIb can be prepared by deprotection of silyloxy XVI. The reaction can be carried out by treating silyloxy XVI with tetrabutylammonium fluoride in tetrahydrofuran at room temperature for several hours.

Compound of interest Iad can be prepared in analogy to Compound Iab in Scheme 3 starting with hydroxy VIb and amide III.

General Synthetic Route for Compounds Iae and Iaf (Scheme 5)

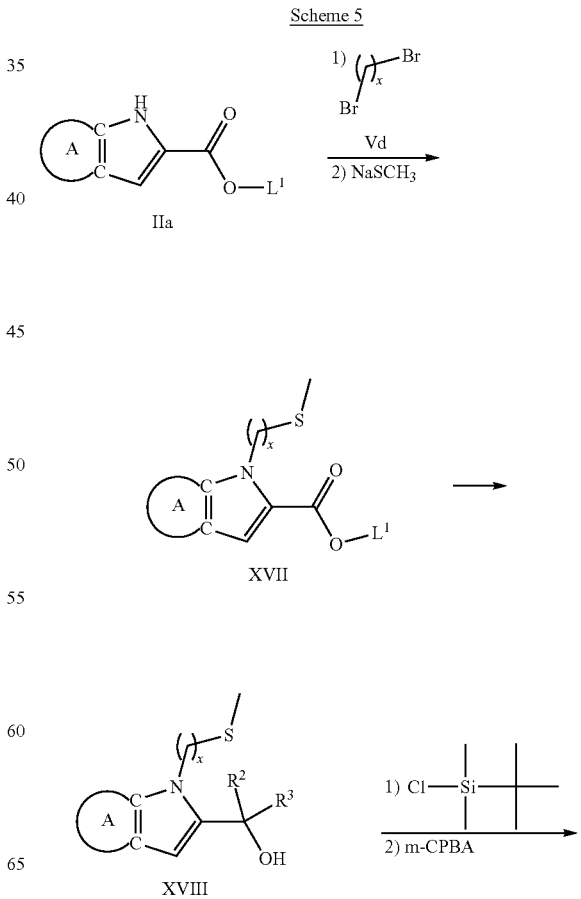

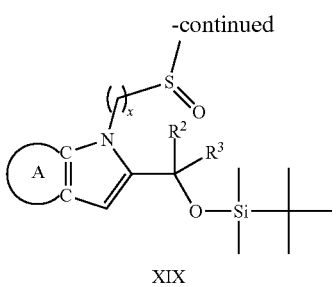

XIX

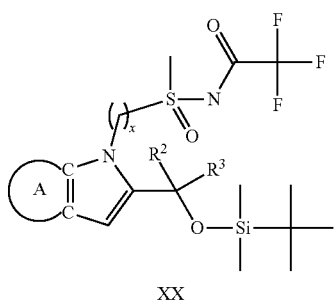

XX

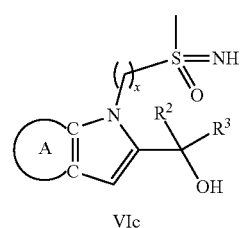

VIc

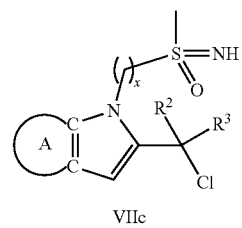

VIIc

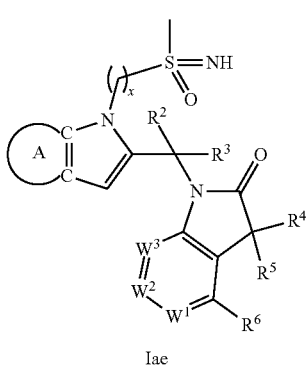

Iae

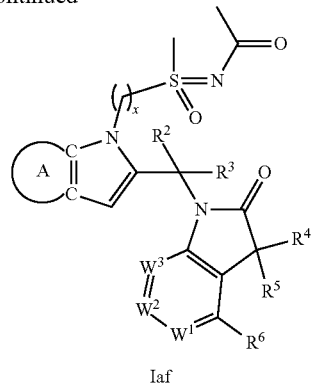

Iaf $L^1$ is $C_{1-6}$ alkyl.

Compounds of interest Iae and Iaf can be prepared according to Scheme 5.

Methylsulfanyl XVII can be prepared by reaction of indole IIa and bromide Vd and then followed by the reaction with sodium methanethiolate. The reaction of indole IIa and bromide Vd can be carried out in the presence of a base such as potassium carbonate or cesium carbonate in a suitable solvent such as acetone, acetonitrile or N,N-dimethylformamide at a temperature between 55° C. and 80° C. for several hours. The reaction of bromide with sodium methanethiolate can be carried out in ethanol at room temperature for several hours.

Hydroxymethyl indole XVIII can be prepared by reduction of ester XVII in the presence of lithium aluminum hydride or lithium aluminum deuteride in tetrahydrofuran at a temperature between 0° C. and room temperature for several hours.

Methylsulfoxide XIX can be prepared by reaction of hydroxymethyl indole XVIII and tert-butyl(chloro)dimethylsilane and then followed by oxidation of methylsulfanyl. The reaction of hydroxy XVIII with tert-butyl(chloro)dimethylsilane can be carried out in the presence of 4-dimethylaminopyridine and triethylamine in dichloromethane at a temperature between 0° C. and room temperature for several hours. Oxidation reaction can then be carried out with 3-chlorobenzene-1-carboperoxoic acid in dichloromethane at room temperature for several hours. Trifluoroacetyl sulfonimidoyl XX can be prepared by reaction of methylsulfoxide XIX and trifluoroacetamide. The reaction can be carried out in the presence of magnesium oxide and rhodium (II) acetate in an organic solvent such as dichloromethane at room temperature for several hours or overnight. Sulfonimidoyl VIc can be generated by removal of trifluoroacetyl and tert-butyl(dimethyl)silyl of trifluoroacetyl sulfonimidoyl XX in the presence of tetrabutylazanium fluoride and concentrated hydrochloric acid in a mixture of tetrahydrofuran and ethanol at a temperature between 50° C. and 80° C. for several hours or overnight.

Chloromethyl indole VIIc can be prepared by treating hydroxy VIc with thionyl chloride. The reaction can be carried out in dichloromethane at room temperature for several hours. Compound of interest Iae can be prepared by reaction of chloromethyl indole VIIc and amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

Compound of interest Iaf can be prepared by acetylation of sulfonimidoyl Compound Iae. The reaction can be carried out by treating sulfonimidoyl Iae with acyl chloride in the presence of a base such as triethylamine at room temperature for several hours.

General synthetic route for Compounds Iah, Iai, Iaj and Iak (Scheme 6)

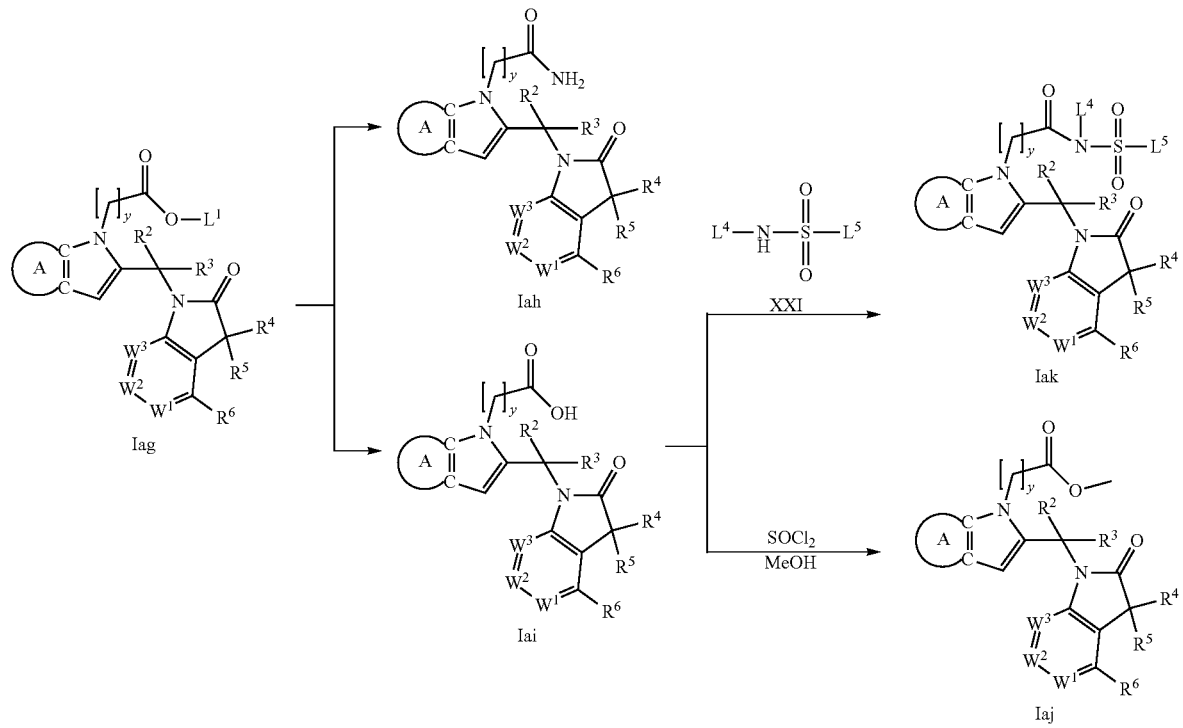

$L^1$ is $C_{1-6}$alkyl;
$L^4$ is hydrogen or $C_{1-6}$alkyl;
$L^5$ is $C_{1-6}$alkyl.

Compounds of interest Iah, Iai, Iaj and Iak can be prepared according to Scheme 6.

Ester Iag can be prepared according to Scheme 4.

Amide Iah can be prepared by ammonolysis of ester Iag in the presence of ammonia in an organic solvent such as methanol or ethanol at a temperature about 70° C. for several days.

Carboxylic acid Iai can be prepared by hydrolysis of ester Iag. The reaction can be carried out in the presence of a suitable base such as sodium hydroxide, potassium hydroxide or lithium hydroxide in a mixture of tetrahydrofuran and water at a temperature between room temperature and 80° C. for several hours.

Methyl ester Iaj can be prepared by reaction of carboxylic acid Iai in methanol. The reaction can be carried out in the presence of thionyl chloride in methanol at a temperature between 50° C. and 65° C. for several hours.

N—($C_{1-6}$ alkylsulfonyl)$C_{1-6}$alkylamide Iak can be prepared by reaction of carboxylic acid Iai and sulfonamide XXI. The reaction can be carried out in the presence of N-[3-(dimethylamino)propyl]-N'-ethylcarbodiimide hydrochloride and 4-dimethylamiopryidine in dichloromethane at room temperature for several hours.

General synthetic route for Compounds Iam and Ian (Scheme 7)

Scheme 7

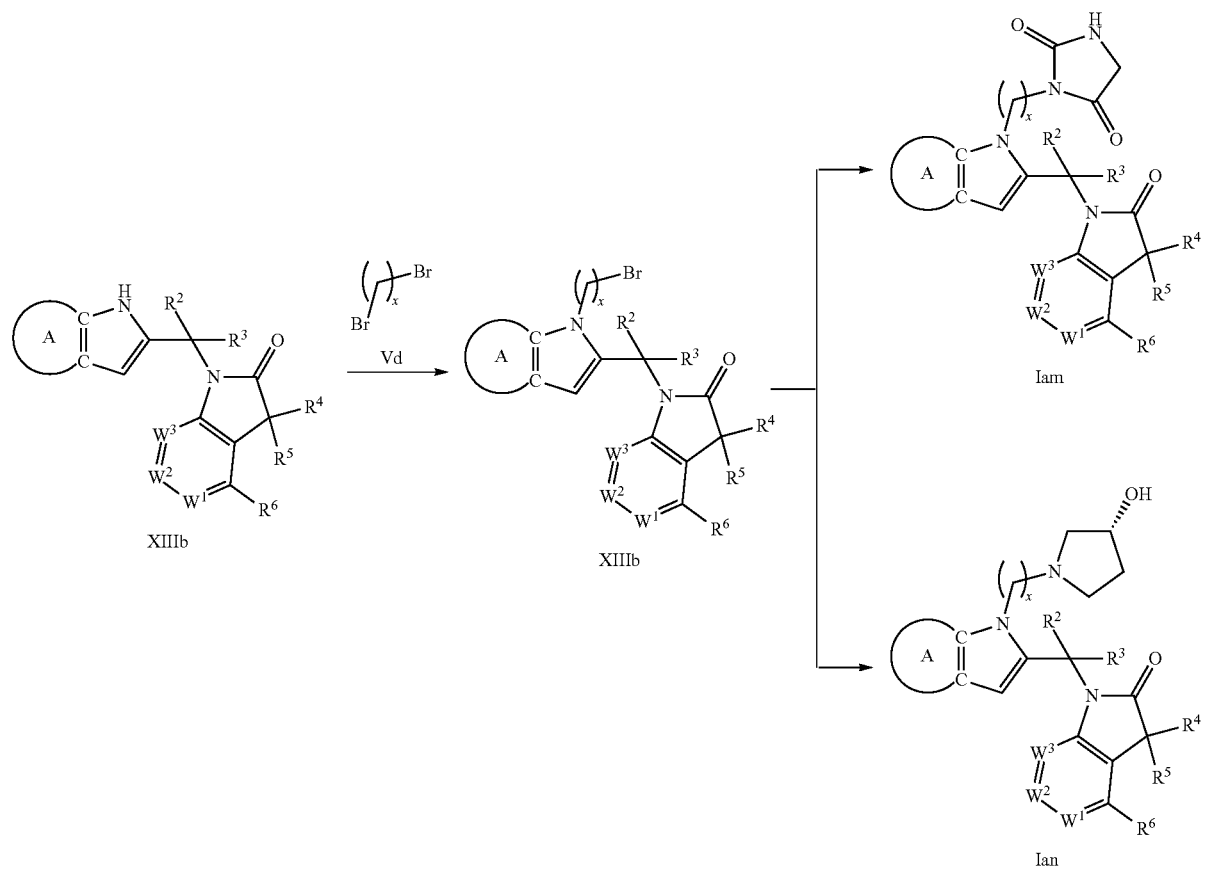

Compounds of interest Iam and Ian can be prepared according to Scheme 7.

XIIIb can be prepared in analogy to XIIIa in Scheme 3.

Bromide XXII can be prepared by reaction of XIIIb with dibromoalkane Vd. The reaction can be carried out in the presence of a suitable base such as potassium carbonate or cesium carbonate in an organic solvent such as acetonitrile or acetone at a temperature between 60° C. and 80° C. for several hours to several days.

Compound of interest Iam can be prepared by reaction of bromide XXII with imidazolidine-2,4-dione. The reaction can be carried out in the presence of a suitable base such as potassium carbonate or cesium carbonate and tetrabutylamine fluoride in an organic solvent such as tetrahydrofuran, acetonitrile or acetone at room temperature for several hours to several days.

Compound of interest Ian can be prepared by reaction of bromide XXII with (3R)-pyrrolidin-3-ol. The reaction can be carried out in the presence of a suitable base such as potassium carbonate or cesium carbonate in an organic solvent such as N,N-dimethylformamide, acetonitrile or acetone at a temperature between 60° C. and 80° C. for several hours.

General synthetic route for Compound Iao (Scheme 8)

Scheme 8

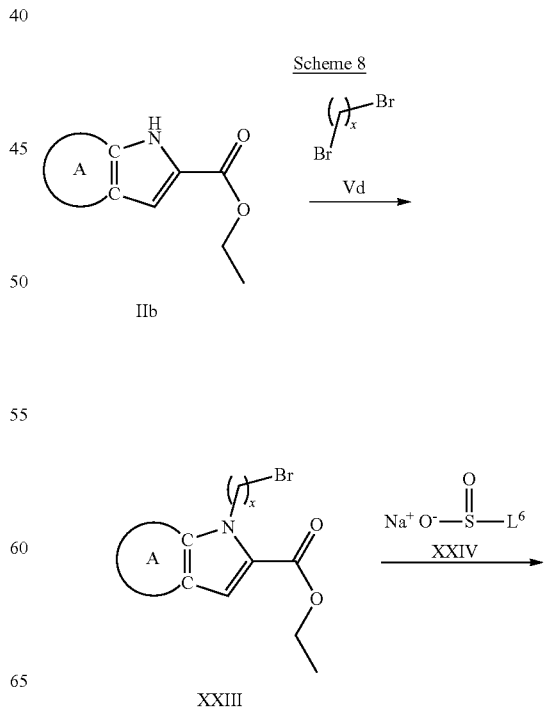

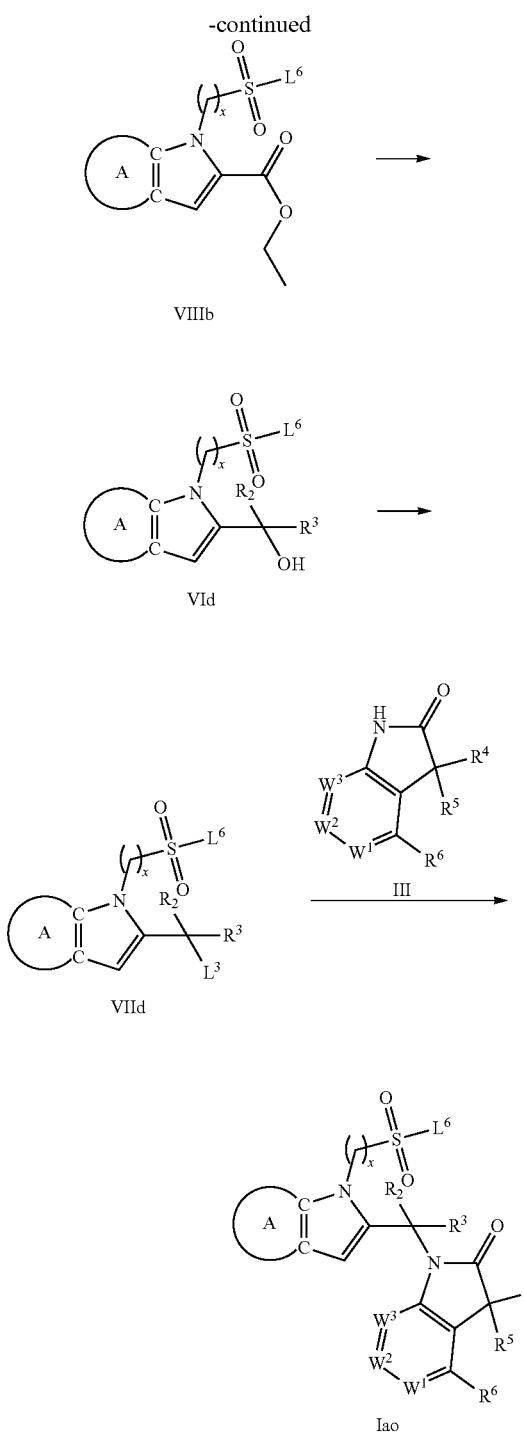

VIIIb

VId

VIId

Iao

L³ is chloro or —OSO₂CH₃;
L⁶ is $C_{1-6}$alkyl.

Compound of interest Iao can be prepared according to Scheme 8.

BromoC$_{1-6}$ alkyl indole XXIII can be prepared in analogy to bromide XXII in Scheme 7 by reaction of indole IIb with dibromoalkane Vd.

($C_{1-6}$ alkylsufonyl)$C_{1-6}$ alkyl indole VIIIb can be prepared by reaction of bromide XXIII and sodium $C_{1-6}$alkylsulfinate XXIV. The reaction can be carried out in N,N-dimethylformamide at a temperature between 50° C. and 100° C. for several hours.

Hydroxymethyl indole VId can be prepared by reduction of ethyl ester VIIIb in the presence of lithium aluminum hydride or lithium aluminum deuteride in tetrahydrofuran at a temperature between 0° C. and room temperature for several hours.

Intermediate VIId can be prepared by treating hydroxy VId with thionyl chloride or methanesulfonyl chloride. When L³ is chloro, the reaction can be carried out by treating hydroxy VId with thionyl chloride in dichloromethane at a temperature between room temperature and 60° C. for 30 minutes to several hours. When L³ is methanesulfonate, the reaction can be carried out by treating hydroxy VId with methanesulfonyl chloride in an organic base such as triethylamine or diisopropylethylamine in dichloromethane at a temperature between 0° C. and room temperature for one to several hours.

Compound of interest Iao can be prepared by reaction of intermediate VIId with amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

General Synthetic Route for Compound Iap (Scheme 9)

Scheme 9

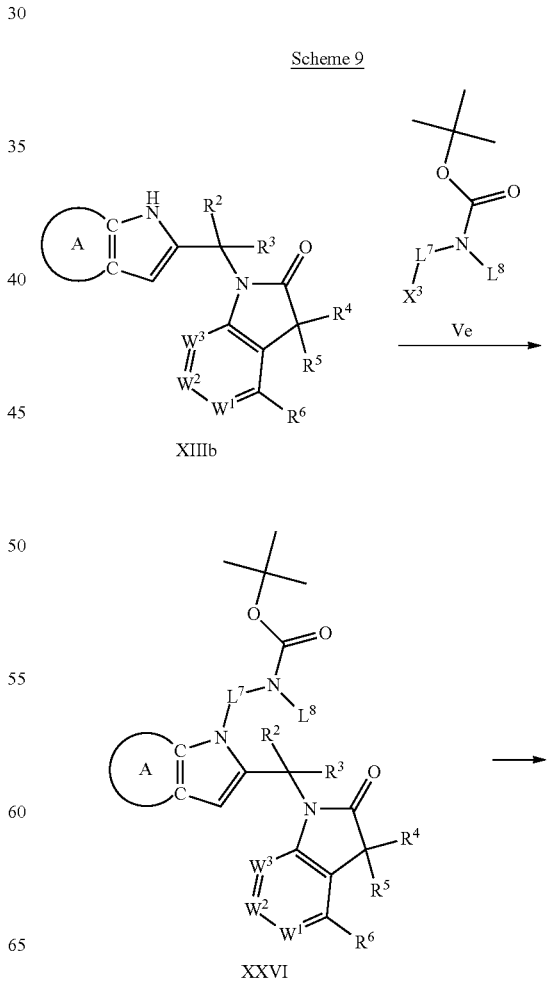

XIIIb

XXVI

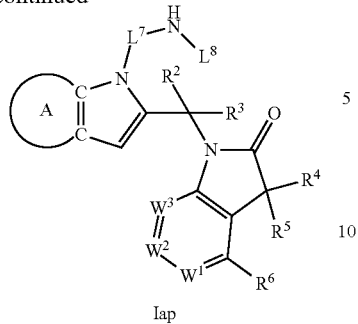

Iap $X^3$ is chloro or bromo;
$L^7$ is —$C_xH_{2x}$;
$L^8$ is hydrogen or $C_{1-6}$alkyl;
or $L^7$ and $L^8$, together with the nitrogen to which they are attached, form

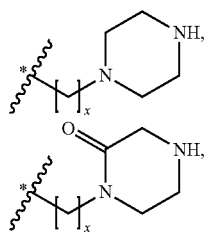

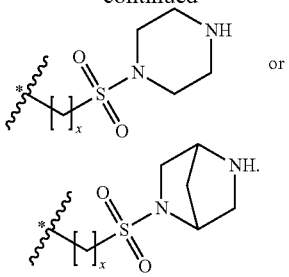

or

Compound of interest Iap can be prepared according to Scheme 9.

Intermediate XXVI can be prepared by reaction of indole XIIIb and halide Ve. The reaction can be carried out in the presence of a suitable base such as cesium carbonate, potassium carbonate or potassium tert-butoxide in an organic solvent such as acetone, acetonitrile or N,N-dimethylformamide at a temperature between room temperature and 0° C. for one to several hours.

Compound of interest Iap can be prepared by removal of tert-butyl carboxylate of Compound XXVI. The conversion can be achieved by treating of XXVI with hydrochloride in ethyl acetate or trifluoroacetic acid in dichloromethane at room temperature for several hours.

General Synthetic Route for Compounds Iar and Ias (Scheme 10)

Scheme 10

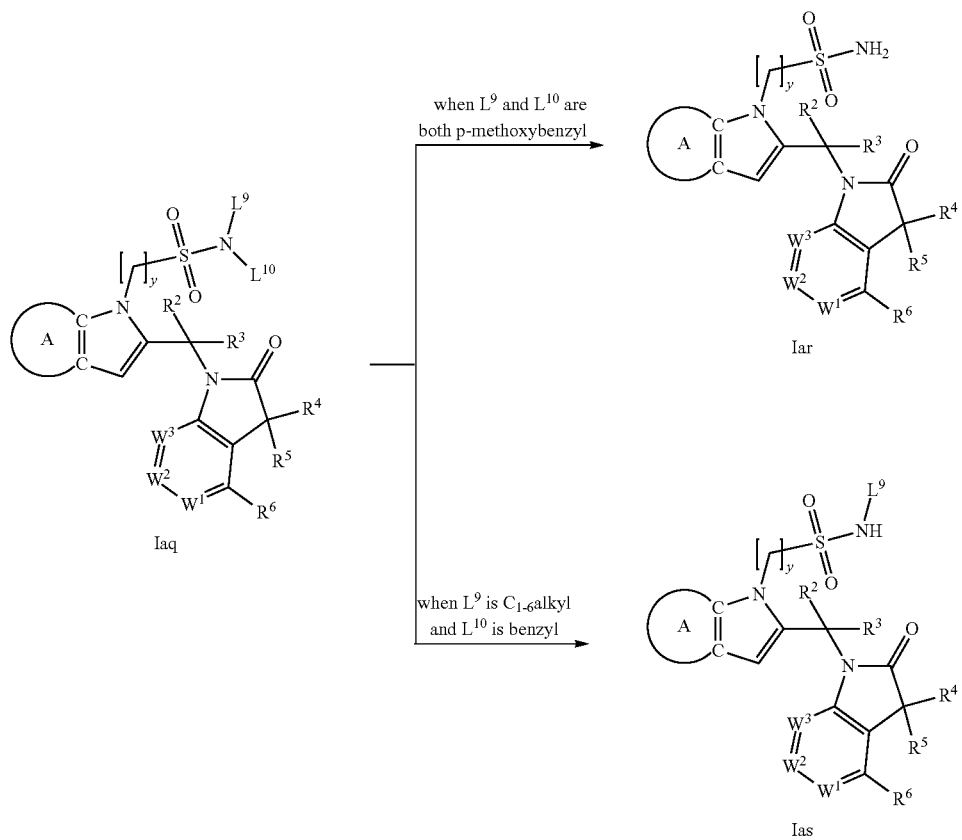

when $L^9$ is p-methoxybenzyl, $L^{10}$ is p-methoxybenzyl;
or when $L^9$ is $C_{1-6}$alky, $L^{10}$ is benzyl.

Compounds of interest Iar and Ias can be prepared according to Scheme 10.

Iaq can be prepared in analogy to Iab in Scheme 2.

Compound Ias can be prepared by removal of benzyl group of Compound Iaq wherein $L^9$ is $C_{1-6}$ alkyl and $L^{10}$ is benzyl. The conversion can be achieved by treating N-benzyl sulfonamides Iaq with concentrated sulfuric acid at 0° C. for several minutes to 1 hour.

Compound Iar can be prepared by removal of p-methoxybenzyl group of Compound Iaq wherein both $L^9$ and $L^{10}$ are p-methoxybenzyl. The conversion can be achieved by treating sulfonamides Iaq with trifluoroacetic acid at room temperature for several hours.

General Synthetic Route for Compounds Iau, Iay, Iaw, Iax and Iay (Scheme 11)

Scheme 11
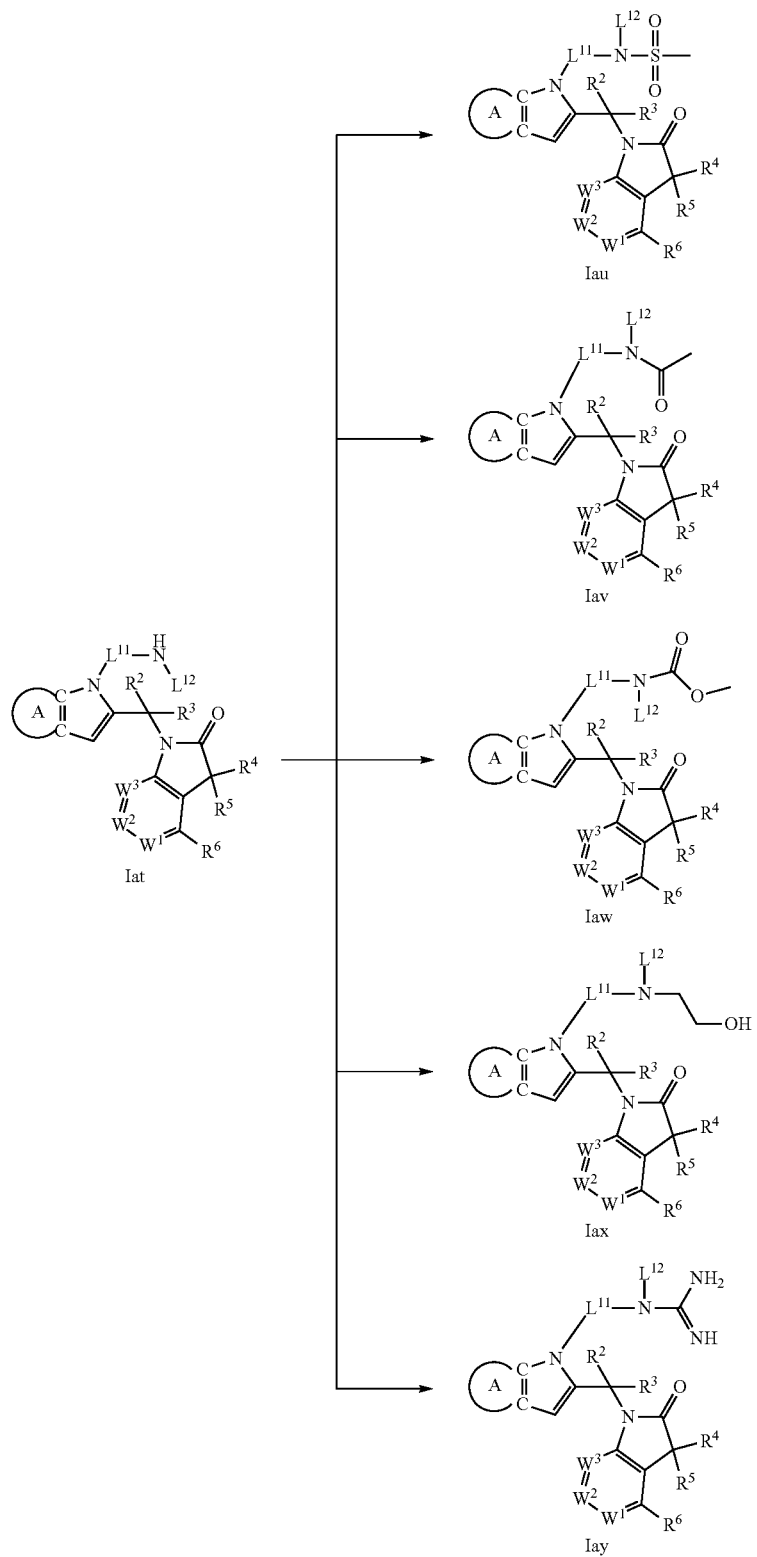
$L^{11}$ is ——$C_xH_{2x}$—— or ——$C_xH_{2x}$-sulfonyl;
$L^{12}$ is hydrogen or $C_{1-6}$alkyl;
or $L^{11}$ and $L^{12}$, together with the nitrogen to which they are attached, form

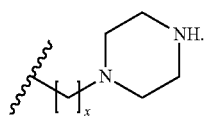

Compounds of interest Iau, Iay, Iaw, Iax and Iay can be prepared according to Scheme 11.

Amine Iat can be prepared in analogy to amine Iap in Scheme 9 or in analogy to sulfonamides Iar and Ias in Scheme 10.

Compound Iau can be prepared by reaction of amine Iat and methanesulfonyl chloride. The reaction can be carried out in the presence of a suitable base such as triethylamine in an organic solvent such as dichloromethane or N,N-dimethylformamide at a temperature between 0° C. and room temperature for several hours.

Compound Iav can be prepared by acetylation of amine Iat. The reaction can be carried out by treating amine Iat with acetic anhydride or acetyl chloride in the presence of a suitable base such as triethylamine or ethyldiisopropylamine in an organic solvent such as dichloromethane or N,N-dimethylformamide at a temperature between room temperature and 80° C. for several hours.

Compound Iaw can be prepared by reaction of amine Iat and methyl carbonochloridate. The reaction can be carried out in the presence of a base such as triethylamine in N,N-dimethylformamide at room temperature for several hours.

Compound Iax can be prepared by reaction of amine Iat and 2-bromoethanol. The reaction can be carried out in the presence of a suitable base such as cesium carbonate in an organic solvent such as acetonitrile or N,N-dimethylformamide at room temperature for several hours.

Compound Iay can be prepared by reaction of amine Iat and methyl carbamimidothioate. The reaction can be carried out in the presence of sulfuric acid in a mixture of ethanol and water at a temperature between 70° C. and 100° C. overnight.

General Synthetic Route for Compound Iba (Scheme 12)

Scheme 12

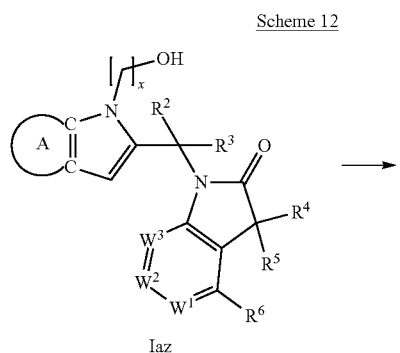

Iaz

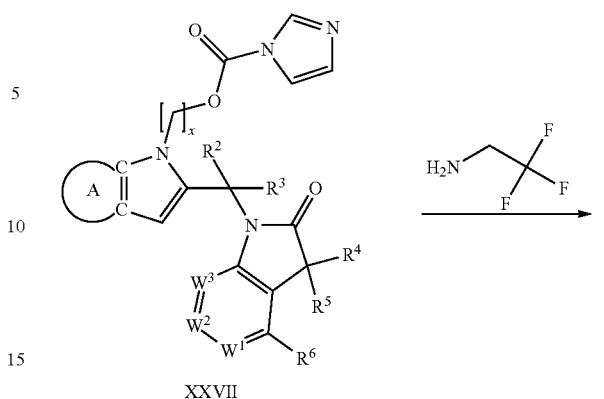

XXVII

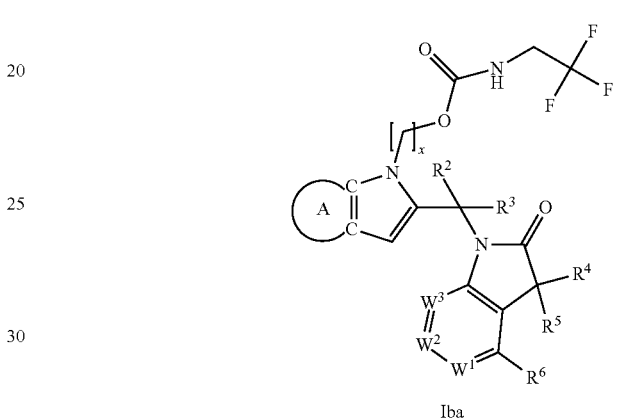

Iba

Compound of interest Iba can be prepared according to Scheme 12.

Hydroxy Iaz can be prepared in analogy to Compound Iac in Scheme 3.

Imidazol XXVII can be prepared by reaction of hydroxy Iaz with di-1H-imidazol-1-ylmethanone. The reaction can be carried out in the presence of a base such as cesium carbonate in tetrahydrofuran at room temperature for several hours or overnight.

Compound of interest Iba can be prepared by reaction of imidazol XXVII and trifluoroethanamine. The reaction can be carried out in the presence of a base such as cesium carbonate in tetrahydrofuran at room temperature for several hours or overnight.

General Synthetic Route for Compound Ibb (Scheme 13)

Scheme 13

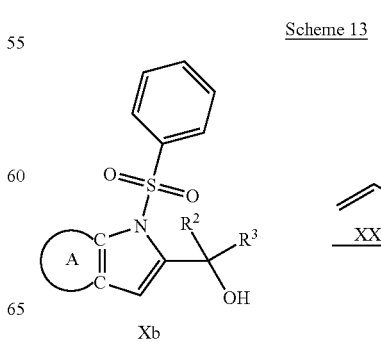

Xb

-continued

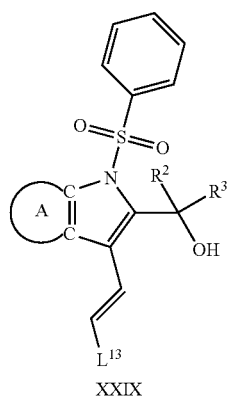
XXIX

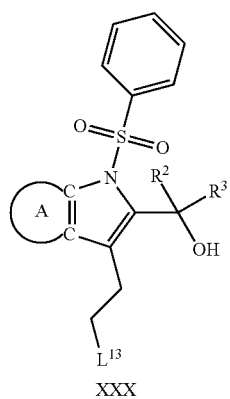
XXX

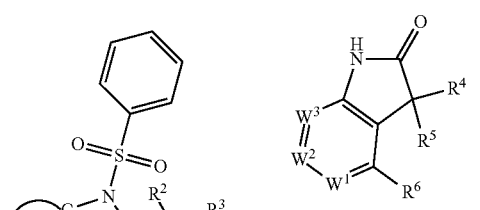
XXXI

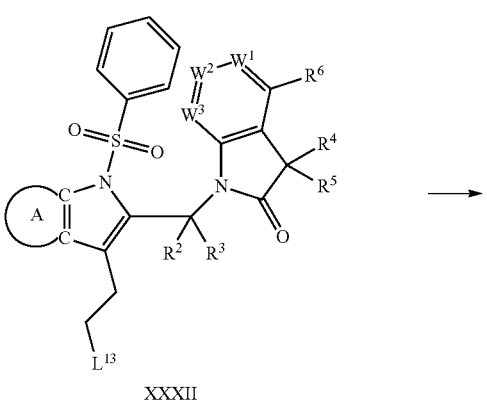
XXXII

-continued

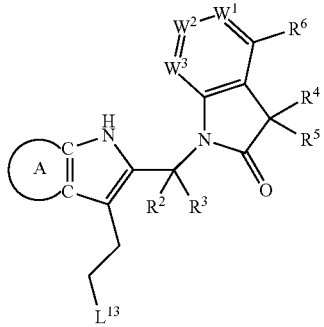
Ibb $L^3$ is chloro or -OSO$_2$CH$_3$;
$L^{13}$ is C$_{1-6}$alkoxycarbonyl or C$_{1-6}$alkylsulfonyl.

Compound of interest Ibb can be prepared according to Scheme 13.

Hydroxy Xb can be prepared in analogy to Xa in Scheme 3.

3-Ethenyl indole XXIX can be prepared via reaction of hydroxy Xb with ethene XXVIII. The reaction can be carried out in the presence of 2-dicyclohexylphosphino-2',6'-dimethoxy-1,1'-biphenyl, allylpalladium chloride dimmer and sodium acetate in a suitable solvent such as N,N-dimethylacetamide or N,N-dimethylformamide at a temperature between 100° C. and 150° C. under microwave irradiation for 15 minutes to several hours.

3-Ethyl indole XXX can be prepared by reduction of 3-ethenyl indole XXIX. The reaction can be carried out in the presence of sodium borohydride and nickel(II) chloride in methanol at 0° C. for several hours.

Intermediate XXXI can be prepared by treating hydroxy XXX with thionyl chloride or methanesulfonyl chloride. When $L^3$ is chloro, the reaction can be carried out by treating hydroxy XXX with thionyl chloride in dichloromethane at a temperature between room temperature and 60° C. for 30 minutes to several hours. When $L^3$ is methanesulfonate, the reaction can be carried out by treating hydroxy XXX with methanesulfonyl chloride in the presence of an organic base such as triethylamine or diisopropylethylamine in dichloromethane at a temperature between 0° C. and room temperature for one to several hours.

Compound XXXII can be prepared by reaction of intermediate XXXI and amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

Compound of interest Ibb can be prepared by removal of benzenesulfonyl of XXXII in the presence of tetrabutylammonium fluoride solution in tetrahydrofuran at room temperature for several hours.

General Synthetic Route for Compound Ibc (Scheme 14)

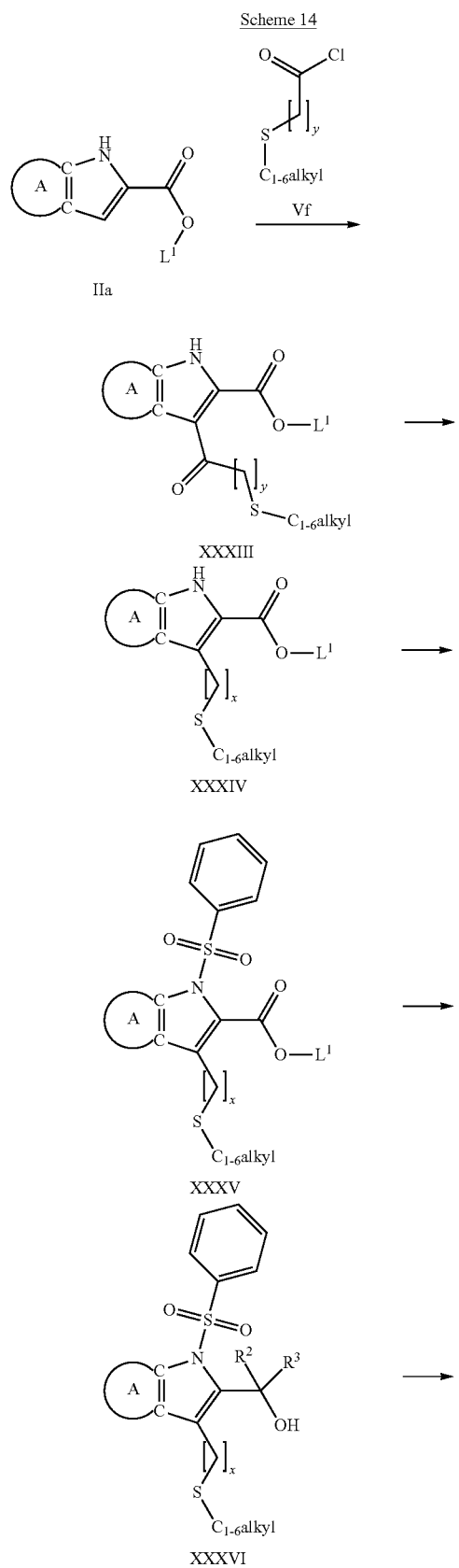

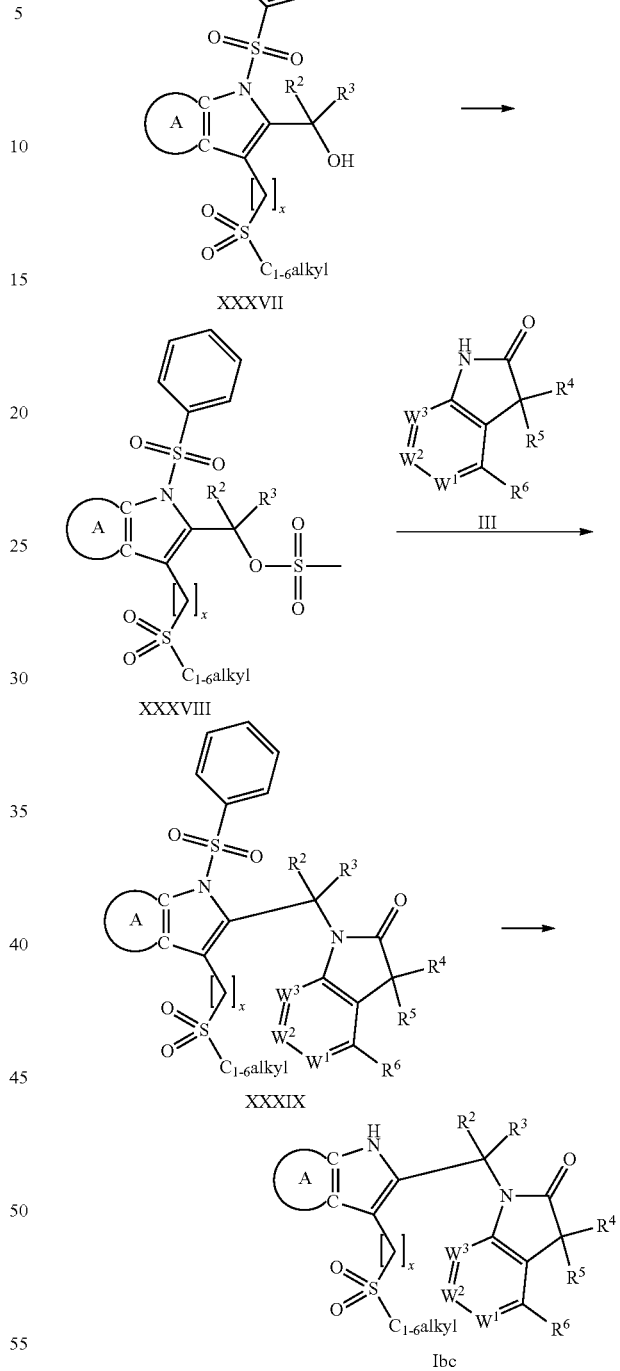

Compound of interest Ibc can be prepared according to Scheme 14.

3-(Methylsulfanyl)propanoyl indole XXXIII can be prepared by reaction of indole IIa with chloride Vf. The reaction can be carried out in the presence of ferric trichloride in 1,2-dichloroethane at 0° C. for several hours.

3-(Methylsulfanyl)propyl indole XXXIV can be prepared by reduction of 3-(methylsulfanyl)propyl XXXIII to 1-hydroxy-3-(methylsulfanyl)propyl and then followed by treating hydroxy with trifluoroacetic acid in triethylsilane. The reduction reaction can be carried out in the presence of sodium borohydride in methanol at room temperature for one to several hours. Then 3-(methylsulfanyl)propyl indole XXXIV can be generated by treating hydroxy with trifluoroacetic acid in triethylsilane. The reaction can be carried out at 0° C. for several hours.

N-Substituted indole XXXV can be prepared by reaction of indole XXXIV with benzenesulfonyl chloride. The reaction can be carried out in the presence of a base such as sodium hydride in N,N-dimethylformamide at a temperature between 0° C. and room temperature for several hours.

Hydroxymethyl indole XXXVI can be prepared by reduction of ester XXXV. Reduction reaction can be carried out by treating ester with lithium aluminium hydride or lithium aluminum deuteride in tetrahydrofuran at a temperature between 0° C. and room temperature for several hours or overnight.

Methylsulfone XXXVII can be prepared by oxidation of methylsulfanyl XXXVI. The reaction can be carried out by treating methylsulfanyl XXXVI with 3-chloro-peroxybenzoic acid in dichloromethane at a temperature between 0° C. and room temperature for several hours or overnight.

Methanesulfonate XXXVIII can be prepared by reaction of hydroxy XXXVII with methanesulfonyl chloride. The reaction can be carried out in the presence of a suitable base such as triethylamine in dichloromethane at 0° C. for one to several hours.

Intermediate XXXIX can be prepared by reaction of methanesulfonate XXXVIII and amide III. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

Compound of interest Ibc can be prepared by removal of benzenesulfonyl of intermediate XXXIX in the presence of tetrabutylammonium fluoride in tetrahydrofuran at room temperature for several hours or overnight.

General Synthetic Route for Compound Ibd (Scheme 15)

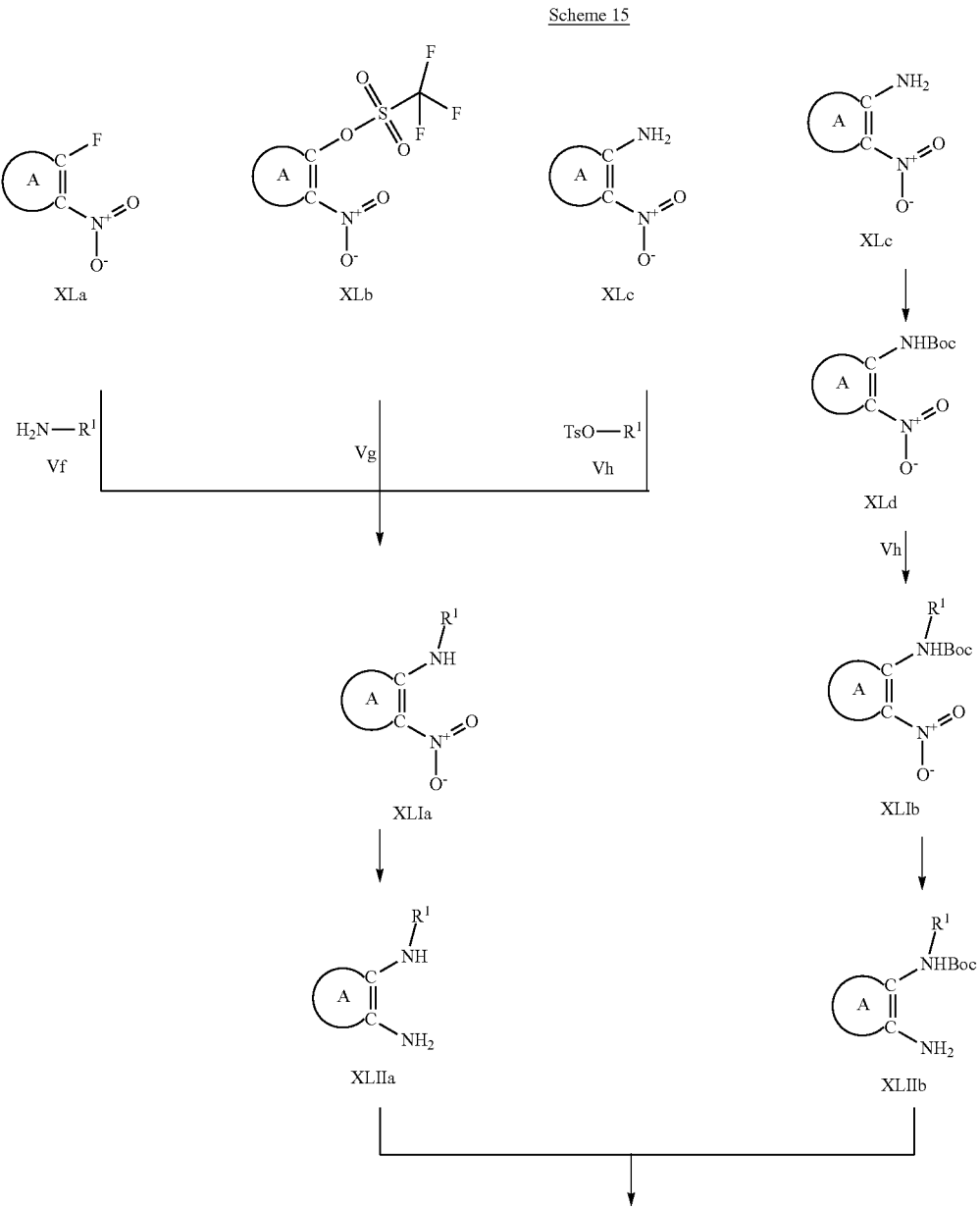

-continued

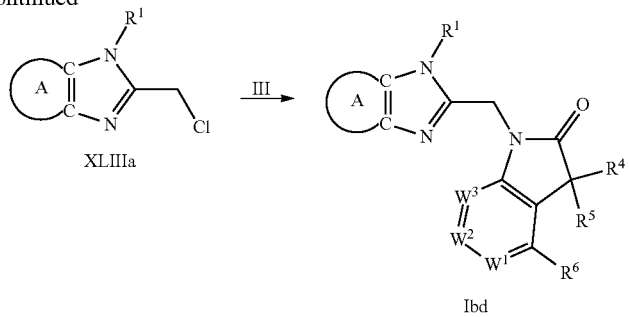

XLIIIa → Ibd

Compound of interest Ibd can be prepared according to Scheme 15.

N-Substituted aniline XLIa can be prepared by reaction of o-fluoro nitrobenzene XLa or o-nitrophenyl trifluoromethanesulfonate XLb with amine Vg. The reaction can be carried out in the presence of a suitable base such as triethylamine, N-ethyl-N-(propan-2-yl)propan-2-amine or potassium phosphate in an organic solvent such as tetrahydrofuran or acetonitrile at room temperature for several hours to several days.

N-Substituted aniline XLIa can also be prepared by reaction of o-nitro aniline XLc and p-methylbenzenesulfonate Vh. The reaction can be carried out in the presence or absence of tetrabutylamine iodide with a suitable base such as cesium carbonate or potassium carbonate in an organic solvent such as acetone or acetonitrile at a temperature between 50° C. and 80° C. for several hours to several days.

N-Substituted aniline XLIb can be prepared by reaction of N-Boc protected o-nitro aniline XLd and p-methylbenzenesulufonate Vh. The reaction can be carried out in the presence or absence of tetrabutylamine iodide with a suitable base such as cesium carbonate or potassium carbonate in an organic solvent such as acetone or acetonitrile at a temperature between 50° C. and 80° C. for several hours to several days.

Diamine XLIIa and XLIIb can be prepared by reduction of o-nitro aniline XLIa and o-nitro aniline XLIb separately. The reaction can be carried out in the presence of Raney nickel and hydrazine hydrate in an organic solvent such as methanol or ethanol at a temperature between room temperature and 80° C. for 10 minutes to several hours.

2-(Chloromethyl)benzimidazole XLIIIa can be prepared by reaction of diamine XLIIa or XLIIb with bromoacetic acid. The reaction can be carried out in an aqueous solution of hydrochloric acid at a concentration between 4 N and 12 N at a temperature between 100° C. and 150° C. for several hours to several days.

2-(Chloromethyl)benzimidazole XLIIIa also can be prepared by reaction of diamine XLIIa or XLIIb with 2-chloro-1,1,1-trimethoxyethane or 2-chloro-1,1,1-triethoxyethane. The reaction can be carried out by heating diamine XLIIa or XLIIb with 2-chloro-1,1,1-trimethoxyethane or 2-chloro-1,1,1-triethoxyethane in the presence or absence of 4-methylbenzenesulfonic acid with or without ethanol at a temperature between 50° C. and 80° C. for several hours. The reaction can also be carried out by heating the mixture of diamine XLIIa or XLIIb and 2-chloro-1,1,1-trimethoxyethane or 2-chloro-1,1,1-triethoxyethane with or without ethanol at a temperature between 100° C. and 120° C. for one to several hours under microwave irradiation.

Compound of interest Ibd can be prepared by reaction of 2-(chloromethyl)benzimidazole XLIIIa and amide III. The reaction can be carried out in the presence of a base such as cesium carbonate, sodium hydride or potassium tert-butoxide in an organic solvent such as acetonitrile or N,N-dimethylformamide at a temperature between 0° C. and room temperature for one to several hours.

General Synthetic Route for Compound Ibe (Scheme 16)

Scheme 16

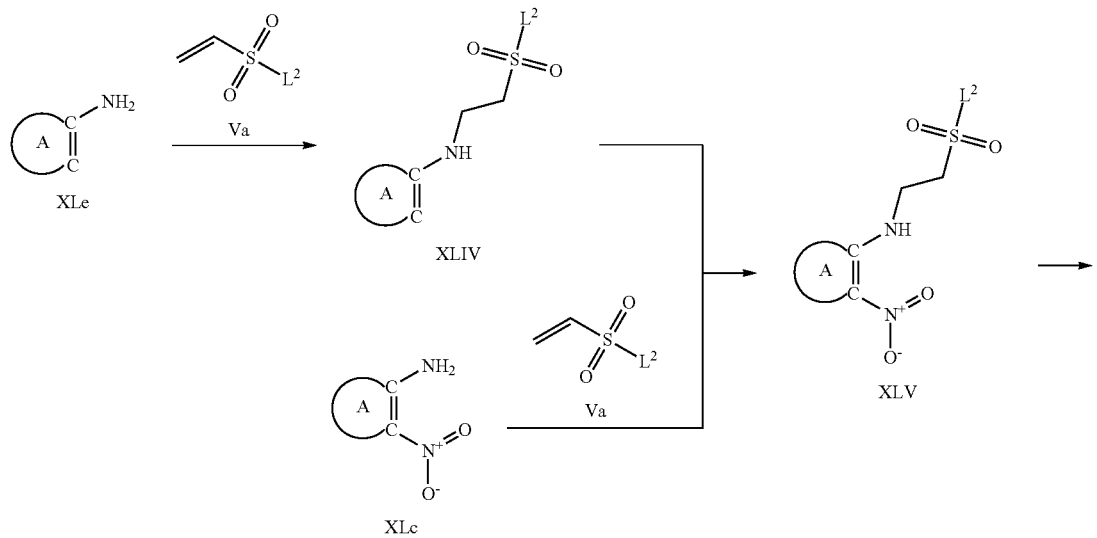

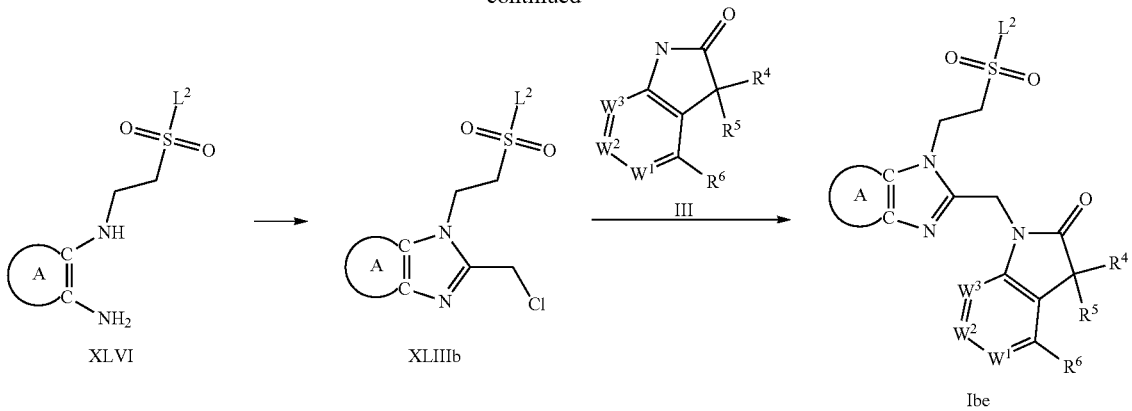

$L^2$ is $C_{1-6}$ alkyl.

Compound of interest Ibe can be prepared according to Scheme 16.

N-substituted aniline XLIV and o-nitro-N-substituted aniline XLV can be prepared by Michael addition of anilins XLc or XLe with ($C_{1-6}$ alkylsulfonyl)ethene Va. This Michael addition can be carried out in the presence of a base such as cesium carbonate in an organic solvent such as acetonitrile at about 80° C. for several hours or overnight.

o-Nitro-N-substituted aniline XLV can also be prepared by nitrification of N-substituted aniline XLIV. The conversion can be achieved by treating aniline XLIV with sulfuric acid and nitric acid at 0° C. for one to several hours.

Diamine XLVI can be prepared by reduction of nitro group of o-nitro-N-substituted aniline XLII. The reaction can be carried out in the presence of Raney nickel and hydrazine hydrate in an organic solvent such as methanol or ethanol at a temperature between room temperature and 80° C. for 10 minutes to several hours.

2-(Chloromethyl)benzimidazole XLIIIb can be prepared by reaction of diamine XLVI and bromoacetic acid. The reaction can be carried out in an aqueous solution of hydrochloric acid at a concentration between 4 N and 12 N at a temperature between 100° C. and 150° C. for several hours to several days.

2-(Chloromethyl)benzimidazole XLIIIb also can be prepared by reaction of diamine XLVI and 2-chloro-1,1,1-trimethoxyethane or 2-chloro-1,1,1-triethoxyethane. The reaction can be carried out by heating the mixture of diamine and 2-chloro-1,1,1-trimethoxyethane or 2-chloro-1,1,1-triethoxyethane in the presence or absence of 4-methylbenzenesulfonic acid with or without ethanol at a temperature between 50° C. and 80° C. for several hours. The reaction also can be carried out by heating diamine with 2-chloro-1,1,1-trimethoxyethane or 2-chloro-1,1,1-triethoxyethane with or without ethanol at a temperature between 100° C. and 120° C. for one to several hours under microwave irradiation.

Compound of interest Ibe can be prepared by reaction of 2-(chloromethyl)benzimidazole XLIIIb and amide III. The reaction can be carried out in the presence of a base such as cesium carbonate, sodium hydride or potassium tert-butoxide in an organic solvent such as acetonitrile or N,N-dimethylformamide at a temperature between 0° C. and room temperature for one to several hours.

General Synthetic Route for Compound Ibg (Scheme 17)

Scheme 17

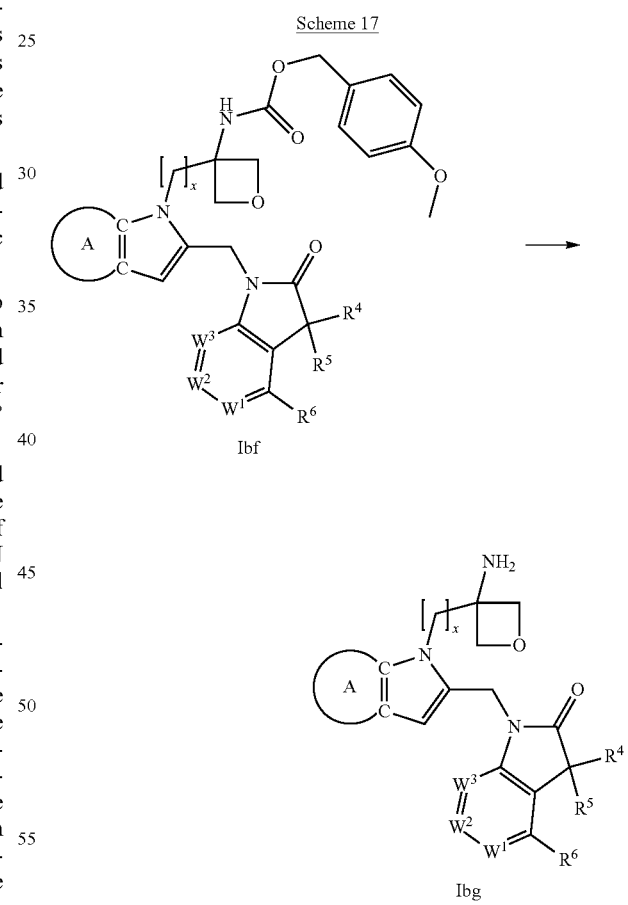

Compound of interest Ibg can be prepared according to Scheme 17. Compound Ibf can be prepared in analogous to Compound Ibd in Scheme 15. Treating Compound Ibf with an acid generates Compound of interest Ibg. The reaction can be carried out in the presence of trifluoroacetic acid in dichloromethane at room temperature for several hours.

This invention also relates to a process for the preparation of a compound of formula I comprising the reaction of (a) a compound of formula (A)

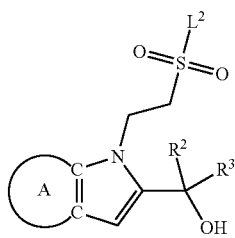

with

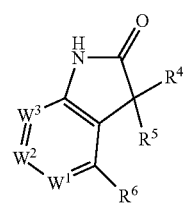

in the presence of a phosphine reagent and an azidocarbonyl reagent;
(b) a compound of formula (B)

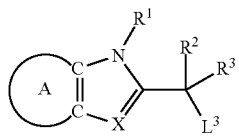

with

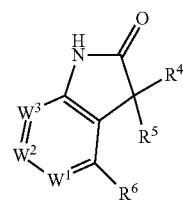

in the presence of a base;
(c) a compound of formula (C)

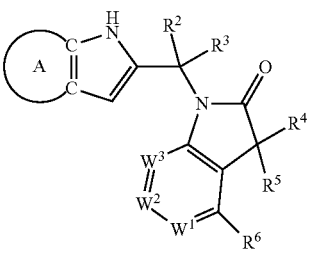

with $X^2$—$R^1$ in the presence of a base;

(d) a compound of formula (D)

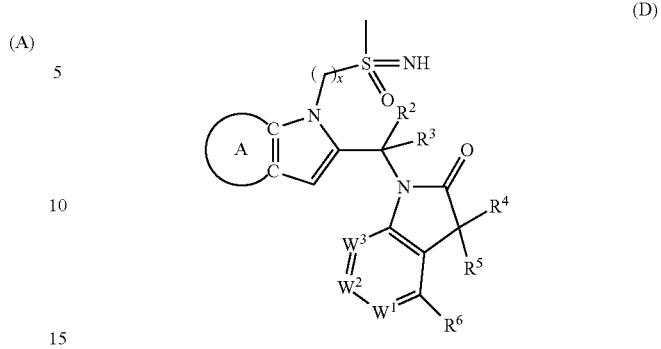

with acyl chloride in the presence of a base;
(e) a compound of formula (E)

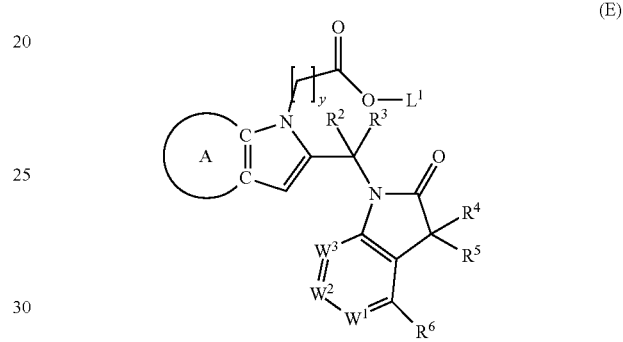

in the presence of a base;
(f) a compound of formula (F)

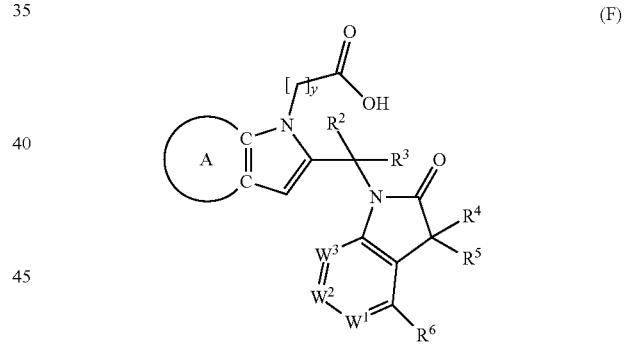

with thionyl chloride;
(g) a compound of formula (F)

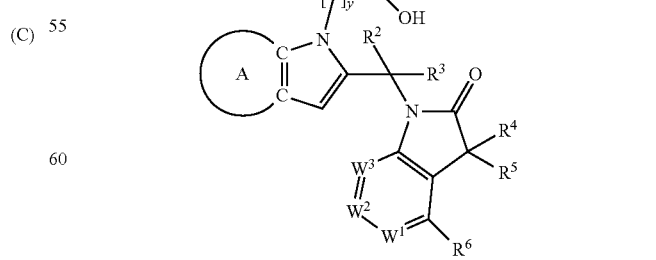

with sulfonamide in the presence of N-[3-(dimethylamino)propyl]-N'-ethylcarbodiimide hydrochloride and 4-dimethylamiopryidine;

(h) a compound of formula (G)

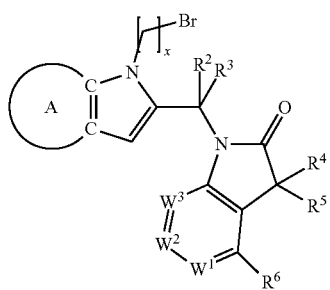

with imidazolidine-2,4-dione in the presence of a base;
(j) a compound of formula (G)

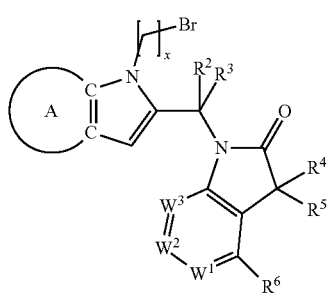

with (3R)-pyrrolidin-3-ol in the presence of a base;
(k) a compound of formula (J)

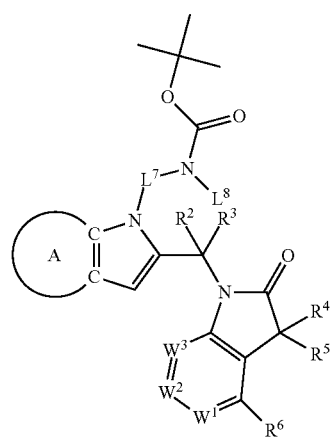

with hydrochloride or trifluoroacetic acid;
(l) a compound of formula (K)

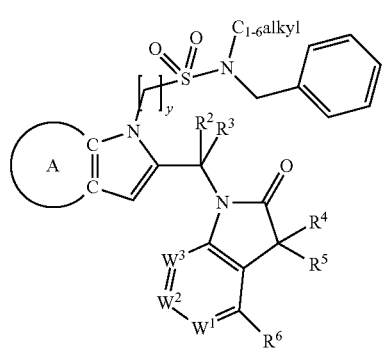

with concentrated sulfuric acid;

(m) a compound of formula (M)

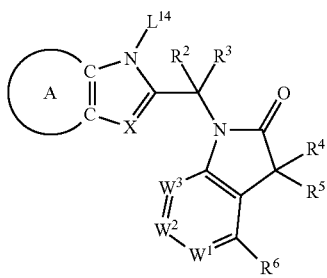

with trifluoroacetic acid;
(n) a compound of formula (N)

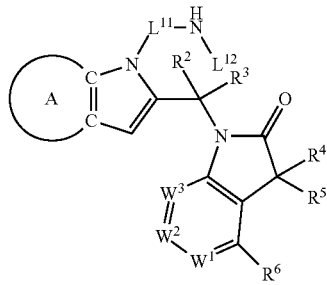

with methanesulfonyl chloride in the presence of a base;
(o) a compound of formula (N)

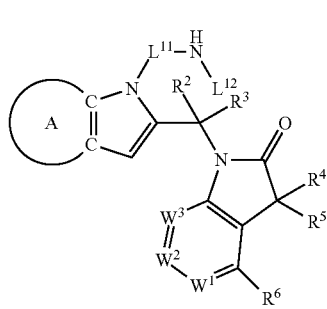

with acetic anhydride or acetyl chloride in the presence of a base;
(p) a compound of formula (N)

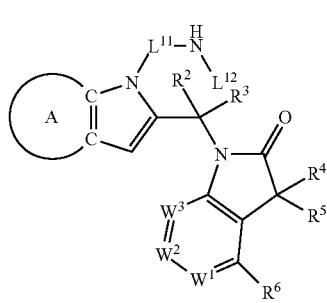

with methyl carbonochloridate in the presence of a base;

(q) a compound of formula (N)

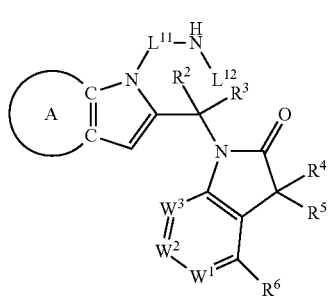

with 2-bromoethanol in the presence of a base;

(r) a compound of formula (N)

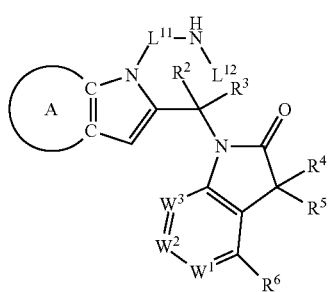

with methyl carbamimidothioate in the presence of an acid;

(s) a compound of formula (P)

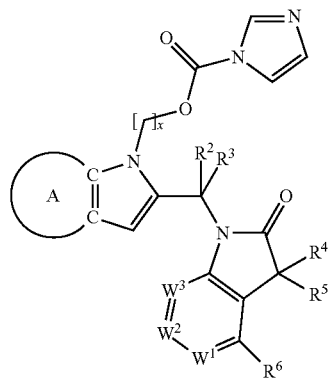

with

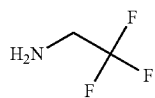

in the presence of a base;

(t) a compound of formula (Q)

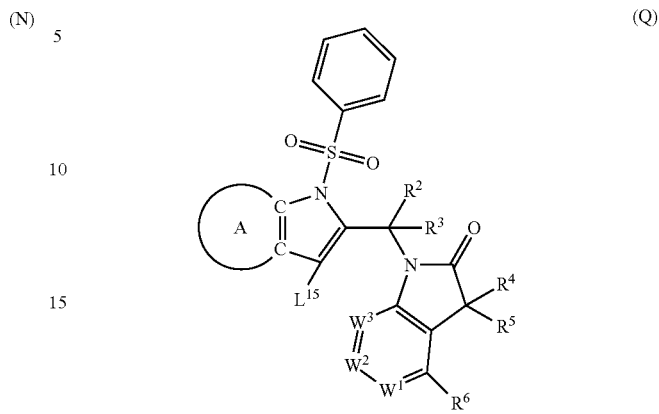

with tetrabutylammonium fluoride;

wherein $R^1$ to $R^6$, $W^1$ to $W^3$, X, A, x and y are defined above unless otherwise indicated; $X^2$ is chloro, bromo, iodo or 4-methylbenzenesulfonate; $L^1$ is $C_{1-6}$alkyl; $L^2$ is $C_{1-6}$alkyl; $L^3$ is chloro or $-OSO_2CH_3$; $L^7$ is $-C_xH_{2x}$; $L^8$ is hydrogen or $C_{1-6}$alkyl; or $L^7$ and $L^8$, together with the nitrogen, to which they are attached, form

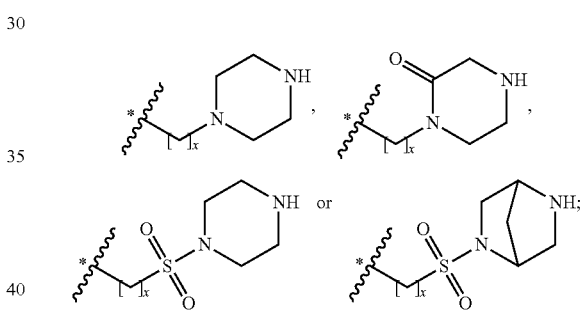

$L^{11}$ is $-C_xH_{2x}-$ or $-C_xH_{2x}$-sulfonyl; $L^{12}$ is hydrogen or $C_{1-6}$alkyl; or $L^{11}$ and $L^{12}$, is L together with the nitrogen, to which they are attached, form

$L^{14}$ is

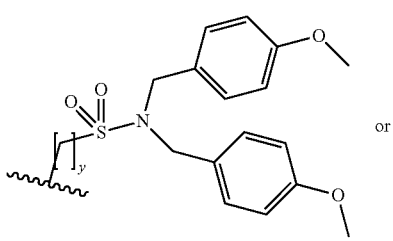

or

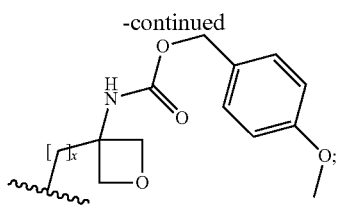

$L^{15}$ is $C_{1-6}$alkoxycarbonyl-$C_xH_{2x}$— or $C_{1-6}$ alkylsulfonyl-$C_xH_{2x}$—.

In step (a), the phosphine reagent can be for example triphenylphosphine or tributylphosphine; the azidocarbonyl reagent can be for example diethyl azodicarboxylate, diisopropyl azodicarboxylate, 1,1-(azodicarbonyl)dipiperidine or N,N,N',N'-tetarmethylazodicarboxamide;

In step (b), the base can be for example cesium carbonate, sodium hydride or sodium tert-butoxide;

In step (c), (h), (j), (q) or (s), the base can be for example potassium carbonate or cesium carbonate;

In step (d), (n), (p) or (o), the base can be for example triethylamine or ethyldiisopropylamine;

In step (e), the base can be for example ammonia, sodium hydroxide, potassium hydroxide or lithium hydroxide;

In step (r), the acid can be for example sulfuric acid.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit RSV fusion protein. For example, such amount may be below the amount that is toxic to normal cells, or the mammal as a whole.

In one example, the pharmaceutically effective amount of the compound of the invention administered parenterally per dose will be in the range of about 0.1 to about 50 mg/kg, alternatively about 0.1 to about 20 mg/kg of patient body weight per day, with the typical initial range of compound used being about 0.3 to about 15 mg/kg/day. In another embodiment, oral unit dosage forms, such as tablets and capsules, preferably contain from about 25 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg to about 500 mg of the compound of the invention compounded with about 90 to about 30 mg anhydrous lactose, about 5 to about 40 mg sodium croscarmellose, about 5 to about 30 mg polyvinylpyrrolidone (PVP) K30, and about 1 to about 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can be utilized to inhibit RSV fusion protein, therefore prevent the virus cell syncytial function. Accordingly, the compounds of the invention are useful for the treatment or prophylaxis of RSV infection.

The invention relates to the use of a compound of formula I for the treatment or prophylaxis of respiratory syncytial virus infection.

The use of a compound of formula I for the preparation of medicaments useful in the treatment or prophylaxis diseases that are related to RSV infection is an object of the invention.

The invention relates in particular to the use of a compound of formula I for the preparation of a medicament for the treatment or prophylaxis of RSV infection.

Another embodiment includes a method of treating or preventing RSV infection in a mammal in need of such treatment, wherein the method comprises administering to said mammal a therapeutically effective amount of a compound of Formula I, a stereoisomer, tautomer, prodrug or pharmaceutically acceptable salt thereof.

Combination Therapy

The compounds of the invention can be used in combination with other antiviral ingredients for the treatment or prophylaxis of RSV infection.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
AUC: area under the curve
CD$_3$OD: deuterated methanol
CDCl$_3$: deuterated chloroform
DMSO-d$_6$: deuterated dimethylsulfoxide
EC$_{50}$: the concentration of a compound where 50% of its maximal protection effect against viral induced CPE is observed
g: gram
HPLC: high performance liquid chromatography
Hz: Hertz
ICR: imprinting control region
J: coupling constants
LC/MS: Liquid chromatography/mass spectrometry
LongStrain: an A subtype RSV strain obtained from ATCC with catalog number VR-26
mg: milligram
MHz: megahertz
mL: milliliter
mm: millimeter
mmol: millimole
MS (ESI): mass spectroscopy (electron spray ionization)
NMR: nuclear magnetic resonance
obsd.: observed
PK: Pharmacokinetics
SDPK: single dose pharmacokinetics
Prep HPLC: preparative high performance liquid chromatography
TLC: thin layer chromatography
δ: chemical shift
ppm: parts per million General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):

Acidic condition: A: 0.1% formic acid in H$_2$O; B: 0.1% formic acid in acetonitrile;

Basic condition: A: 0.01% NH$_3$H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

PREPARATIVE EXAMPLES

Example 1-1

1'-({1-[2-(Methylsulfonyl)ethyl]-1H-indol-2-yl}methyl)spiro[cyclopropane-1,3'-pyrrolo[2,3-c]pyridin]-2'(1'H)-one Step 1: Preparation of 1H-indol-2-ylmethanol

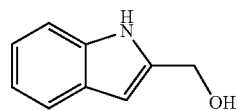 [SMILES: OCc1cc2ccccc2[nH]1]

To a slurry of lithium aluminum hydride (1.00 g, 26.3 mmol) in anhydrous tetrahydrofuran (50 mL) which was cooled to 0° C. was added a solution of ethyl 1H-indole-2-carboxylate (3.80 g, 20.0 mmol) in tetrahydrofuran (50 mL) dropwise at 0° C. while stirring. The temperature of the mixture was then warmed naturally to room temperature and the mixture was stirred at room temperature overnight. The resulting mixture was quenched with methanol, and then filtered through a celite pad. The filtrate was concentrated in vacuo to afford 1.5 g of 1H-indol-2-ylmethanol.

Step 2: Preparation of {1-[2-(methylsulfonyl)ethyl]-1H-indol-2-yl}methanol

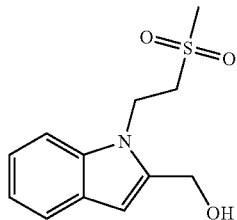 [SMILES: CS(=O)(=O)CCn1c(CO)cc2ccccc21]

To a cooled mixture of 1H-indol-2-ylmethanol (450 mg, 3.0 mmol), cesium carbonate (1.80 g, 6.0 mmol) in N,N-dimethylformamide (25 mL) was added (methylsulfonyl)ethene (293 mg, 3.0 mmol) in portions at 0° C. The reaction mixture was heated with stirring at 50° C. overnight. The resulting mixture was poured into ice-water (25 mL) and then extracted with ethyl acetate (30 mL×3). The combined organic layer was washed with brine (50 mL×2), and then dried over anhydrous sodium sulfate and then concentrated in vacuo to afford 150 mg of the crude {1-[2-(methylsulfonyl)ethyl]-1H-indol-2-yl}methanol.

Step 3: Preparation of 1'-({1-[2-(methylsulfonyl)ethyl]-1H-indol-2-yl}methyl)spiro[cyclopropane-1,3'-pyrrolo[2,3-c]pyridin]-2'(1'H)-one To a solution of {1-[2-(methylsulfonyl)ethyl]-1H-indol-2-yl}methanol (253 mg, 1.0 mmol), spiro[cyclopropane-1,3'-pyrrolo[2,3-c]pyridin]-2'(1'H)-one (160 mg, 1.0 mmol) and triphenylphosphane (800 mg, 3.0 mmol) in tetrahydrofuran (50 mL) was added diisopropyl azodicarboxylate (600 mg, 3.0 mmol) dropwise in an ice-water bath under nitrogen atmosphere. The reaction mixture was stirred at room temperature overnight. The resulting mixture was purified by preparative HPLC to afford 26 mg of the title product.

Example 1-2

1'-({5-Methoxy-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using ethyl 5-methoxy-1H-indole-2-carboxylate instead of ethyl 1H-indole-2-carboxylate.

Example 1-3

1-[2-(Methylsulfonyl)ethyl]-2-[(2'-oxospiro[cyclopropane-1,3'-pyrrolo[2,3-c]pyridin]-1'(2'H)-yl)methyl]-1H-indole-5-carbonitrile The title compound was prepared in analogy to Example 1-1 according to Scheme 1 by using ethyl 5-cyano-1H-indole-2-carboxylate instead of ethyl 1H-indole-2-carboxylate.

Example 1-4

1'-({5-Fluoro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using ethyl 5-fluoro-1H-indole-2-carboxylate instead of ethyl 1H-indole-2-carboxylate.

Example 1-5

1'-({5-Bromo-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using ethyl 5-bromo-1H-indole-2-carboxylate instead of ethyl 1H-indole-2-carboxylate.

Example 1-6

1'-({4-Chloro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 4-chloro-1H-indole-2-carboxylate instead of ethyl 1H-indole-2-carboxylate.

Example 1-7

1'-({7-Chloro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 7-chloro-1H-indole-2-carboxylate instead of ethyl 1H-indole-2-carboxylate.

Example 1-8

1'-({5-Ethyl-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5-ethyl-1H-indole-2-carboxylate instead of ethyl 1H-indole-2-carboxylate.

Example 1-9

1'-({5,7-Difluoro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5,7-difluoro-1H-indole-2-carboxylate instead of ethyl 1H-indole-2-carboxylate.

Example 1-10

1'-({1-[2-(Methylsulfonyl)ethyl]-5-(trifluoromethyl)-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5-(trifluoromethyl)-1H-indole-2-carboxylate instead of ethyl 1H-indole-2-carboxylate.

Example 1-11

1'-({5,6-Difluoro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5,6-difluoro-1H-indole-2-carboxylate instead of ethyl 1H-indole-2-carboxylate.

Example 1-12

1'-({5-Chloro-7-fluoro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5-chloro-7-fluoro-1H-indole-2-carboxylate instead of ethyl 1H-indole-2-carboxylate.

Example 1-13

1'-({5-Methyl-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 1-1 according to Scheme 1 by using methyl 5-methyl-1H-indole-2-carboxylate instead of ethyl 1H-indole-2-carboxylate.

Example 1-14

1'-({1-[2-(Methylsulfonyl)ethyl]-1H-pyrrolo[3,2-c]pyridin-2-yl}methyl)spiro[cyclopropane-1,3'-pyrrolo[2,3-c]pyridin]-2'(1'H)-one The title compound was prepared in analogy to Example 1-1 according to Scheme 1 by using methyl 1H-pyrrolo[3,2-c]pyridine-2-carboxylate instead of ethyl 1H-indole-2-carboxylate.

Example 2-1

1'-({5-Chloro-1-[2-(ethylsulfonyl)ethyl]-1H-indol-2-yl}methyl)spiro[cyclopropane-1,3'-pyrrolo[2,3-c]pyridin]-2'(1'H)-one Step 1: Preparation of {5-chloro-1-[2-(ethylsulfonyl)ethyl]-1H-indol-2-yl}methanol

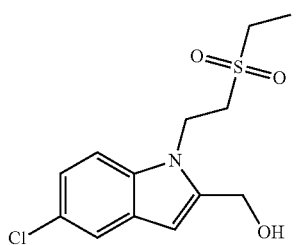 [SMILES: CCS(=O)(=O)CCn1c(CO)cc2cc(Cl)ccc21]

{5-Chloro-1-[2-(ethylsulfonyl)ethyl]-1H-indol-2-yl}methanol was prepared in analogy to {1-[2-(methylsulfonyl)ethyl]-1H-indol-2-yl}methanol in Example 1-1 according to Scheme 1 by using ethyl 5-chloro-1H-indole-2-carboxylate instead of ethyl 1H-indole-2-carboxylate. MS obsd. (ESI$^+$) [(M+H)$^+$]302.

Step 2: Preparation of {5-chloro-1-[2-(ethylsulfonyl)ethyl]-1H-indol-2-yl}methyl methanesulfonate

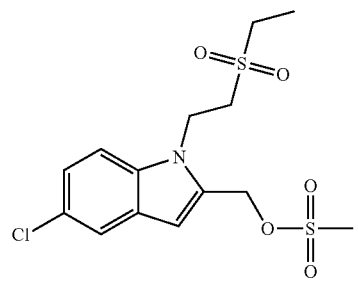 [SMILES: CCS(=O)(=O)CCn1c(COS(C)(=O)=O)cc2cc(Cl)ccc21]

To a solution of {5-chloro-1-[2-(ethylsulfonyl)ethyl]-1H-indol-2-yl}methanol (240 mg, 0.80 mmol) and triethylamine (0.34 mL, 2.4 mmol) in dichloromethane (20 mL) was added methanesulfonyl chloride (0.15 mL, 2.0 mmol) dropwise in an ice-water bath. After being stirred at 0° C. for 1 hour, the resulting mixture was neutralized with a saturated aqueous solution of sodium bicarbonate and then extracted with dichloromethane (20 mL×2). The combined organic layer was washed with a saturated aqueous solution of sodium bicarbonate (20 mL×2), and then dried over anhydrous sodium sulfate and then concentrated in vacuo to afford 303 mg of {5-chloro-1-[2-(ethylsulfonyl)ethyl]-1H-indol-2-yl}methyl methanesulfonate as a brown solid, which was used for next step without further purification.

Step 3: Preparation of 1'-({5-chloro-1-[2-(ethylsulfonyl)ethyl]-1H-indol-2-yl}methyl)spiro[cyclopropane-1,3'-pyrrolo[2,3-c]pyridin]-2'(1'H)-one A mixture of {5-chloro-1-[2-(ethylsulfonyl)ethyl]-1H-indol-2-yl}methyl methanesulfonate (303 mg, 0.80 mmol), cesium carbonate (521 mg, 1.6 mmol) and spiro[cyclopropane-1,3'-pyrrolo[2,3-c]pyridin]-2'(1'H)-one (128 mg, 0.80 mmol) in acetonitrile (20 mL) was heated with stirring at 85° C. for 2 hours. The resulting mixture was filtered and washed with acetonitrile (10 mL×2). The filtrate was concentrated in vacuo. The residue was purified by preparative HPLC to afford 130 mg of the product as a white solid.

Example 2-2

1'-({5-Chloro-1-[2-(ethylsulfonyl)ethyl]-1H-pyrrolo [2,3-b]pyridin-2-yl}methyl)spiro[cyclopropane-1,3'-pyrrolo[2,3-c]pyridin]-2'(1'H)-one The title compound was prepared in analogy to Example 2-1 according to Scheme 1 by using methyl 5-chloro-1H-pyrrolo[2,3-b]pyridine-2-carboxylate instead of ethyl 5-chloro-1H-indole-2-carboxylate.

Example 2-3

1'-({5-Chloro-1-[2-(ethylsulfonyl)ethyl]-1H-indol-2-yl}methyl)spiro[cyclopropane-1,3'-pyrrolo[2,3-b]pyridin]-2'(1'H)-one The title compound was prepared in analogy to Example 2-1 according to Scheme 1 by using spiro[cyclopropane-1,3'-pyrrolo[2,3-b]pyridin]-2'H-one instead of spiro[cyclopropane-1,3'-pyrrolo[2,3-c]pyridin]-2'(1'H)-one.

Example 2-4

1'-({5-Chloro-1-[2-(methylsulfonyl)ethyl]-1H-pyrrolo[2,3-b]pyridin-2-yl}methyl)spiro[cyclobutane-1,3'-pyrrolo[2,3-c]pyridin]-2'(1'H)-one The title compound was prepared in analogy to Example 2-1 according to Scheme 1 by using methyl 5-chloro-1H-pyrrolo[2,3-b]pyridine-2-carboxylate and spiro[cyclobutane-1,3'-pyrrolo[2,3-c]pyridin]-2'(1'H)-one instead of ethyl 5-chloro-1H-indole-2-carboxylate and spiro[cyclopropane-1,3'-pyrrolo[2,3-c]pyridin]-2'(1'H)-one.

Example 2-5

1'-({5-Chloro-1-[2-(methylsulfonyl)ethyl]-1H-indol-2-yl}methyl)spiro[cyclopropane-1,3'-pyrrolo[2,3-b]pyridin]-2'(1'H)-one The title compound was prepared in analogy to Example 2-1 according to Scheme 1 by using (methylsulfonyl)ethene and spiro[cyclopropane-1,3'-pyrrolo[2,3-b]pyridin]-2'(1'H)-one instead of (ethylsulfonyl)ethane and spiro[cyclopropane-1,3'-pyrrolo[2,3-c]pyridin]-2'(1'H)-one.

Example 2-6

1'-({5-Chloro-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 2-1 according to Scheme 1 by using methyl 5-chloro-1H-pyrrolo[2,3-b]pyridine-2-carboxylate and (methylsulfonyl) ethene instead of ethyl 5-chloro-1H-indole-2-carboxylate and (ethylsulfonyl)ethane.

Example 2-7

1'-({5-Chloro-1-[2-(methylsulfonyl)ethyl]-1H-pyrrolo[2,3-b]pyridin-2-yl}methyl)-5'-fluorospiro[cyclopropane-1,3'-indol]-2'(1'H)-one Step 1: Preparation of {5-chloro-1-[2-(methylsulfonyl)ethyl]-1H-pyrrolo[2,3-b]pyridin-2-yl}methyl methanesulfonate

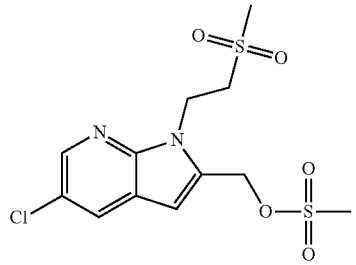 [SMILES: CS(=O)(=O)CCn1c(COS(C)(=O)=O)cc2cc(Cl)cnc21]

{5-Chloro-1-[2-(methylsulfonyl)ethyl]-1H-pyrrolo[2,3-b]pyridin-2-yl}methyl methanesulfonate was prepared in analogy to {5-chloro-1-[2-(ethylsulfonyl)ethyl]-1H-indol-2-yl}methyl methanesulfonate in Example 2-1 by using methyl 5-chloro-1H-pyrrolo[2,3-b]pyridine-2-carboxylate and (methylsulfonyl)ethene instead of ethyl 5-chloro-1H-indole-2-carboxylate and (ethylsulfonyl)ethane.

Step 2: Preparation of 1'-({5-chloro-1-[2-(methylsulfonyl)ethyl]-1H-pyrrolo[2,3-b]pyridin-2-yl}methyl)-5'-fluorospiro[cyclopropane-1,3'-indol]-2'(1'H)-one A mixture of {5-chloro-1-[2-(methylsulfonyl)ethyl]-1H-pyrrolo[2,3-b]pyridin-2-yl}methyl methanesulfonate (183 mg, 0.50 mmol), cesium carbonate (325 mg, 1.0 mmol) and 5'-fluorospiro[cyclopropane-1,3'-indol]-2'(1'H)-one (79 mg, 0.50 mmol) in N,N-dimethylformamide (5 mL) was heated with stirring at 60° C. for 30 minutes. The resulting mixture was purified by preparative HPLC to afford the title product.

Example 2-8

1'-({5-Chloro-1-[2-(methylsulfonyl)ethyl]-1H-pyrrolo[2,3-b]pyridin-2-yl}methyl)spiro[cyclopentane-1,3'-pyrrolo[2,3-c]pyridin]-2'(1'H)-one The title compound was prepared in analogy to Example 2-7 according to Scheme 1 by using spiro[cyclopentane-1,3'-pyrrolo[2,3-c]pyridin]-2'(1'H)-one instead of 5'-fluorospiro[cyclopropane-1,3'-indol]-2'(1'H)-one.

Example 2-9

1'-({5-Chloro-1-[2-(methylsulfonyl)ethyl]-1H-pyrrolo[3,2-b]pyridin-2-yl}methyl)spiro[cyclopropane-1,3'-pyrrolo[2,3-c]pyridin]-2'(1'H)-one Step 1: Preparation of {5-chloro-1-[2-(methylsulfonyl)ethyl]-1H-pyrrolo[3,2-b]pyridin-2-yl}methyl methanesulfonate

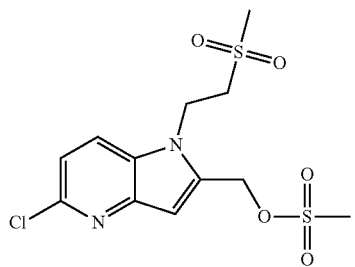 [SMILES: CS(=O)(=O)CCn1c(COS(C)(=O)=O)cc2nc(Cl)ccc21]

{5-Chloro-1-[2-(methylsulfonyl)ethyl]-1H-pyrrolo[3,2-b]pyridin-2-yl}methyl methanesulfonate was prepared in analogy to {5-chloro-1-[2-(ethylsulfonyl)ethyl]-1H-indol-2-yl}methyl methanesulfonate in Example 2-1 by using methyl 5-chloro-1H-pyrrolo[3,2-b]pyridine-2-carboxylate instead of methyl 5-chloro-1H-pyrrolo[2,3-b]pyridine-2-carboxylate.

Step 2: Preparation of 1'-({5-chloro-1-[2-(methylsulfonyl)ethyl]-1H-pyrrolo[3,2-b]pyridin-2-yl}methyl)spiro[cyclopropane-1,3'-pyrrolo[2,3-c]pyridin]-2'(1'H)-one A mixture of {5-chloro-1-[2-(methylsulfonyl)ethyl]-1H-pyrrolo[3,2-b]pyridin-2-yl}methyl methanesulfonate (376 mg, 1.03 mmol), sodium test-butoxide (105 mg, 1.09 mmol) and spiro[cyclopropane-1,3'-pyrrolo[2,3-c]pyridin]-2'(1'H)-one (165 mg, 1.03 mmol) in N,N-dimethylformamide (4 mL) was heated with stirring at 60° C. for 2 hours. The resulting mixture was purified by preparative HPLC to afford 130 mg of the title product as a white solid.

Example 3-1

1'-({5-Chloro-1-[2-(methylsulfonyl)ethyl]-1H-indol-2-yl}methyl)spiro[cyclopropane-1,3'-pyrrolo[3,2-c]pyridin]-2'(1'H)-one Step 1: Preparation of {5-chloro-1-[2-(methylsulfonyl)ethyl]-1H-indol-2-yl}methanol

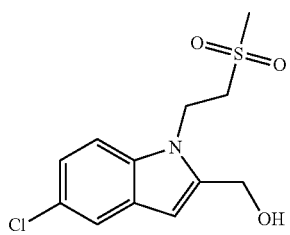 [SMILES: CS(=O)(=O)CCn1c(CO)cc2cc(Cl)ccc21]

{5-Chloro-1-[2-(methylsulfonyl)ethyl]-1H-indol-2-yl}methanol was prepared in analogy to [1-(2-methanesulfonyl-ethyl)-1H-indol-2-yl]-methanol in Example 1-1 according to Scheme 1 by using ethyl 5-chloro-1H-indole-2-carboxylate instead of ethyl 1H-indole-2-carboxylate. MS obsd. (ESI+) [(M+H)+] 288.

Step 2: Preparation of 5-chloro-2-(chloromethyl)-1-[2-(methylsulfonyl)ethyl]-1H-indole

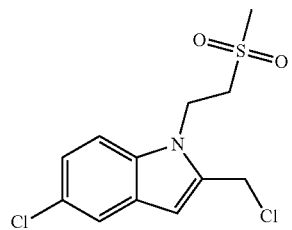 [SMILES: CS(=O)(=O)CCn1c(CCl)cc2cc(Cl)ccc21]

To a solution of {5-chloro-1-[2-(methylsulfonyl)ethyl]-1H-indol-2-yl}methanol (230 mg, 0.80 mmol) in dichloromethane (10 mL) was added thionyl chloride (0.2 mL) dropwise. After being stirred at room temperature for 2 hours, the resulting mixture was neutralized with a saturated aqueous solution of sodium bicarbonate and then extracted with dichloromethane (20 mL×2). The combined organic layer was washed with a saturated aqueous solution of sodium bicarbonate (20 mL×2), and then dried over anhydrous sodium sulfate and then concentrated in vacuo to afford the crude 5-chloro-2-(chloromethyl)-1-[2-(methylsulfonyl)ethyl]-1H-indole as a brown solid which was used for next step without further purification.

Step 3: Preparation of 1'-({5-chloro-1-[2-(methylsulfonyl)ethyl]-1H-indol-2-yl}methyl)spiro[cyclopropane-1,3'-pyrrolo[3,2-c]pyridin]-2'(1'H)-one A mixture of 5-chloro-2-(chloromethyl)-1-[2-(methylsulfonyl)ethyl]-1H-indole (140 mg, 0.46 mmol), cesium carbonate (200 mg, 0.62 mmol) and spiro[cyclopropane-1,3'-pyrrolo[3,2-c]pyridin]-2'(1'H)-one (50 mg, 0.31 mmol) in N,N-dimethylformamide (4 mL) was heated with stirring at 80° C. for 1 hour. The resulting mixture was purified by preparative HPLC to afford 17 mg of the title product.

Example 3-2

1'-({5-Chloro-1-[2-(methylsulfonyl)ethyl]-1H-indol-2-yl}methyl)spiro[cyclopentane-1,3'-pyrrolo[2,3-c]pyridin]-2'(1'H)-one The title compound was prepared in analogy to Example 3-1 according to Scheme 1 by using spiro[cyclopentane-1,3'-pyrrolo[2,3-c]pyridin]-2'(1'H)-one instead of spiro[cyclopropane-1,3'-pyrrolo[3,2-c]pyridin]-2'(1'H)-one.

Example 3-3

1'-({5-Chloro-1-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 3-1 according to Scheme 1 by using spiro[cyclopropane-1,3'-pyrrolo[2,3-c]pyridin]-2'(1'H)one instead of spiro[cyclopropane-1,3'-pyrrolo[3,2-c]pyridin]-2'(1'H)-one.

Example 4-1

1'-({5-Chloro-1-[4-(methylsulfonyl)butyl]-1H-indol-2-yl}methyl)spiro[cyclopropane-1,3'-pyrrolo[2,3-c]pyridin]-2'(1'H)-one

Step 1: Preparation of ethyl 5-chloro-1-[4-(methylsulfonyl)butyl]-1H-indole-2-carboxylate

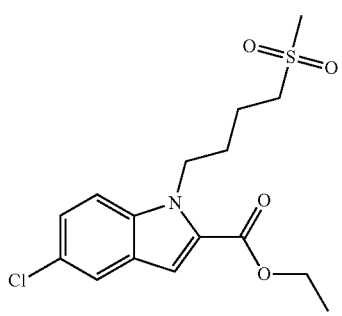 [SMILES: CCOC(=O)c1cc2cc(Cl)ccc2n1CCCCS(C)(=O)=O]

A mixture of ethyl 5-chloro-1H-indole-2-carboxylate (2.23 g, 10 mmol), 4-(methylsulfonyl)butyl 4-methylbenzenesulfonate (3.06 g, 10 mmol) and potassium carbonate (2.76 g, 20 mmol) in acetonitrile (30 mL) was heated with stirring at 80° C. overnight. The reaction mixture was diluted with water and then extracted with dichloromethane (30 mL×3). The combined organic layer was washed with water, and then dried over sodium sulfate and concentrated in vacuo. The residue was crystallized from ethyl acetate to afford 3.0 g of ethyl 5-chloro-1-[4-(methylsulfonyl)butyl]-1H-indole-2-carboxylate.

Step 2: Preparation of {5-chloro-1-[4-(methylsulfonyl)butyl]-1H-indol-2-yl}methanol

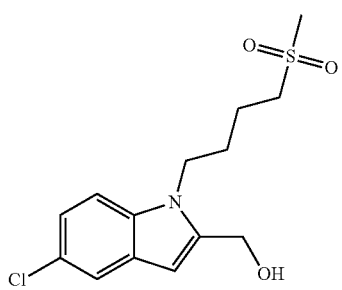 [SMILES: CS(=O)(=O)CCCCn1c(CO)cc2cc(Cl)ccc21]

{5-Chloro-1-[4-(methylsulfonyl)butyl]-1H-indol-2-yl}methanol was prepared in analogy to 1H-indol-2-yl-methanol in Example 1-1 according to Scheme 1 by using ethyl 5-chloro-1-[4-(methylsulfonyl)butyl]-1H-indole-2-carboxylate instead of ethyl 1H-indole-2-carboxylate.

Step 3: Preparation of 5-chloro-2-(chloromethyl)-1-[4-(methylsulfonyl)butyl]-1H-indole

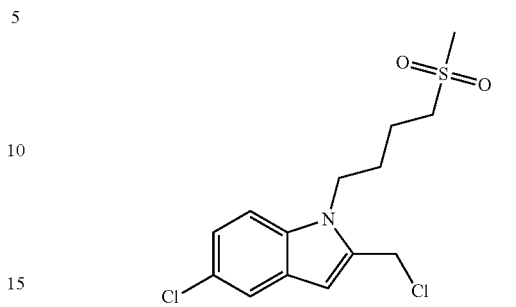

A solution of {5-chloro-1-[4-(methylsulfonyl)butyl]-1H-indol-2-yl}methanol (1.0 g, 3.17 mmol) in anhydrous dichloromethane was stirred with thionyl chloride (465 µL, 6.35 mmol) at room temperature for 2 hours. The resulting mixture was concentrated in vacuo. The residue was dissolved in ethyl acetate (60 mL). The solution was washed with a saturated aqueous solution of sodium bicarbonate (30 mL×2), and then dried over anhydrous sodium sulfate and then concentrated in vacuo to afford 900 mg of 5-chloro-2-(chloromethyl)-1-[4-(methylsulfonyl)butyl]-1H-indole as a yellow solid which was used for the next step without any purification.

Step 4: Preparation of 1'-({5-chloro-1-[4-(methylsulfonyl)butyl]-1H-indol-2-yl}methyl)spiro[cyclopropane-1,3'-pyrrolo[2,3-c]pyridin]-2'(1'H)-one A mixture of 5-chloro-2-(chloromethyl)-1-[4-(methylsulfonyl)butyl]-1H-indole (900 mg, 2.7 mmol), spiro[cyclopropane-1,3'-pyrrolo[2,3-c]pyridin]-2'(1'H)-one (480 mg 3.0 mmol) and cesium carbonate (1.95 g, 6.0 mmol) in anhydrous acetonitrile (20 mL) was heated with stirring at 70° C. for 2 hours. The resulting mixture was diluted with brine (30 mL) and then extracted with ethyl acetate (30 mL×3). The organic layers were combined, and then washed with brine (10 mL×2), then dried over anhydrous sodium sulfate and then concentrated in vacuo. The residue was purified by preparative HPLC to afford 200 mg of the title product as a white solid.

Example 4-2

1'-({5-Chloro-1-[4-(methylsulfonyl)benzyl]-1H-indol-2-yl}methyl)spiro[cyclopropane-1,3'-pyrrolo[2,3-c]pyridin]-2'(1'H)-one The title compound was prepared in analogy to Example 4-1 according to Scheme 2 by using 1-(bromomethyl)-4-(methylsulfonyl)benzene instead of 4-(methylsulfonyl)butyl 4-methylbenzenesulfonate.

Example 4-3

1'-({5-Chloro-1-[3-(methylsulfonyl)propyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 4-1 according to Scheme 2 by using methyl 5-chloro-1H-pyrrolo[2,3-b]pyridine-2-carboxylate and 3-(methylsulfonyl)propyl 4-methylbenzenesulfonate instead of ethyl 5-chloro-1H-indole-2-carboxylate and 4-(methylsulfonyl)butyl 4-methylbenzenesulfonate.

Example 4-4

1'-({5-Methyl-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 4-1 according to Scheme 2 by using methyl 5-methyl-1H-pyrrolo[2,3-b]pyridine-2-carboxylate and 2-(methylsulfonyl)ethyl 4-methylbenzenesulfonate instead of ethyl 5-chloro-1H-indole-2-carboxylate and 4-(methylsulfonyl)butyl 4-methylbenzenesulfonate.

Example 4-5

1'-({5-Chloro-1-[4-(methylsulfonyl)butyl]-1H-pyrrolo[3,2-b]pyridin-2-yl}methyl)spiro[cyclopropane-1,3'-pyrrolo[2,3-c]pyridin]-2'(1'H)-one The title compound was prepared in analogy to Example 4-1 according to Scheme 2 by using methyl 5-chloro-1H-pyrrolo[3,2-b]pyridine-2-carboxylate and (methylsulfonyl)butyl 4-methylbenzenesulfonate instead of ethyl 5-chloro-1H-indole-2-carboxylate and 4-(methylsulfonyl)butyl 4-methylbenzenesulfonate.

Example 4-6

1'-({5-Chloro-1-[3-(cyclopropylsulfonyl)propyl]-1H-pyrrolo[3,2-b]pyridin-2-yl}methyl)spiro[cyclopropane-1,3'-pyrrolo[2,3-c]pyridin]-2'(1'H)-one The title compound was prepared in analogy to Example 4-1 according to Scheme 2 by using methyl 5-chloro-1H-pyrrolo[3,2-b]pyridine-2-carboxylate and 3-(cyclopropylsulfonyl)propyl 4-methylbenzenesulfonate instead of ethyl 5-chloro-1H-indole-2-carboxylate and 4-(methylsulfonyl)butyl 4-methylbenzenesulfonate.

Example 4-7

1'-({5-Chloro-1-[4-(methylsulfonyl)butyl]-1H-pyrrolo[2,3-c]pyridin-2-yl}methyl)spiro[cyclopropane-1,3'-pyrrolo[2,3-c]pyridin]-2'(1'H)-one The title compound was prepared in analogy to Example 4-1 according to Scheme 2 by using ethyl 5-chloro-1H-pyrrolo[2,3-c]pyridine-2-carboxylate and (methylsulfonyl)butyl 4-methylbenzenesulfonate instead of ethyl 5-chloro-1H-indole-2-carboxylate and 4-(methylsulfonyl)butyl 4-methylbenzenesulfonate.

Example 4-8

N-Benzyl-3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide The title compound was prepared in analogy to Example 4-1 according to Scheme 2 by using methyl 5-chloro-1H-pyrrolo[2,3-b]pyridine-2-carboxylate and N-benzyl-3-chloro-N-methylpropane-1-sulfonamide instead of ethyl 5-chloro-1H-indole-2-carboxylate and 4-(methylsulfonyl)butyl 4-methylbenzenesulfonate.

Example 4-9

1'-({5-Chloro-1-[3-(cyclopropylsulfonyl)propyl]-1H-pyrrolo[2,3-c]pyridin-2-yl}methyl)spiro[cyclopropane-1,3'-pyrrolo[2,3-c]pyridin]-2'(1'H)-one Step 1: Preparation of 5-chloro-2-(chloromethyl)-1-[3-(cyclopropylsulfonyl)propyl]-1H-pyrrolo[2,3-c]pyridine

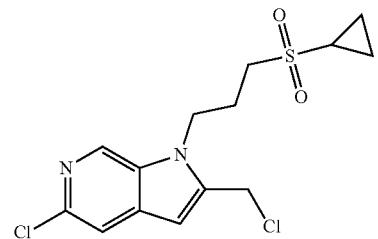 [SMILES: O=S(=O)(CCCn1c(CCl)cc2cc(Cl)ncc21)C1CC1]

5-Chloro-2-(chloromethyl)-1-[3-(cyclopropylsulfonyl)propyl]-1H-pyrrolo[2,3-c]pyridine was prepared in analogy to 5-chloro-2-(chloromethyl)-1-[4-(methylsulfonyl)butyl]-1H-indole in Example 4-1 according to Scheme 2 by using ethyl 5-chloro-1H-pyrrolo[2,3-c]pyridine-2-carboxylate and 3-(cyclopropylsulfonyl)propyl 4-methylbenzenesulfonate instead of ethyl 5-chloro-1H-indole-2-carboxylate and 4-(methylsulfonyl)butyl 4-methylbenzenesulfonate.

Step 2: Preparation of 1'-({5-chloro-1-[3-(cyclopropylsulfonyl)propyl]-1H-pyrrolo[2,3-c]pyridin-2-yl}methyl)spiro[cyclopropane-1,3'-pyrrolo[2,3-c]pyridin]-2'(1'H)-one To a cooled solution of 5-chloro-2-(chloromethyl)-1-[3-(cyclopropylsulfonyl)propyl]-1H-pyrrolo[2,3-c]pyridine (782 mg, 2.26 mmol) and spiro[cyclopropane-1,3'-pyrrolo[2,3-c]pyridin]-2'(1'H)-one (362 mg, 2.26 mmol) in N,N-dimethylformamide (10 mL) in an ice water bath was added sodium hydride (270 mg, 6.75 mmol) in portions. After the addition, the temperature was allowed to arise to room temperature and the mixture was stirred at room temperature overnight. The resulting mixture was purified by preparative HPLC to afford the title product.

Example 4-10

1'-({5-Chloro-1[2-(thietan-3-yl)ethyl]-1H-pyrrolo[2,3-c]pyridin-2-yl}methyl)spiro[cyclopropane-1,3'-pyrrolo[2,3-c]pyridin]-2'(1'H)-one Step 1: Preparation of ethyl thietan-3-ylideneacetate

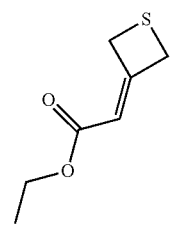

To a solution of thietane-3-one (5.0 g, 56.73 mmol) in dichloromethane (280 mL) was added ethyl 2-tri(phenyl) phosphoranylideneacetate (21.74 g, 62.41 mmol) in portions. After the mixture was stirred at room temperature for 24 hours, the solvent was removed in vacuo. The residue was purified by flash column chromatography (eluting with 0-30% ethyl acetate in petroleum ether) to give 7.8 g of ethyl thietan-3-ylideneacetate as colorless oil.

Step 2: Preparation of ethyl thietan-3-ylacetate

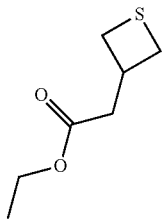

To a mixture of ethyl thietan-3-ylideneacetate (10 g, 63.2 mmol) and nickel (II) chloride hexahydrate (15.0 g, 63.2 mmol) in methanol (250 mL) was added sodium borohydride (12 g, 316.0 mmol) in portions at 0° C. After being stirred at room temperature for 30 minutes, the reaction mixture was filtered through a pad of silica gel. The filtrate was concentrated in vacuo. The residue was purified by column chromatography (eluting with 0-30% ethyl acetate in petroleum ether) to give 600 mg of ethyl thietan-3-ylacetate.

Step 3: Preparation of 2-(thietan-3-yl)ethanol

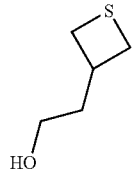

To a cooled solution of lithium aluminum hydride in tetrahydrofuran (5.0 mL, 1 M) was added a solution of ethyl thietan-3-ylacetate (784 mg, 4.9 mmol) in dry tetrahydrofuran (15 mL) dropwise at 0° C. The mixture was stirred for 2 hours while the temperature was allowed to arise to room temperature. The reaction was quenched by addition of water (10 mL). The resulting mixture was stirred for 10 minutes and then extracted with ethyl acetate (20 mL×3). The combined organic layer was washed with brine (40 mL×2), and then dried over anhydrous sodium sulfate and then concentrated in vacuo to afford 410 mg of 2-(thietan-3-yl)ethanol.

Step 4: Preparation of ethyl 5-chloro-1-[2-(thietan-3-yl)ethyl]-1H-pyrrolo[2,3-c]pyridine-2-carboxylate

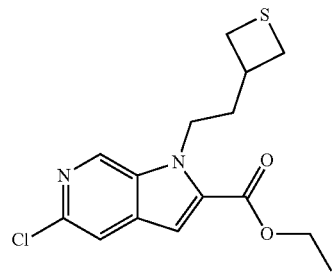 [SMILES: CCOC(=O)c1cc2cc(Cl)ncc2n1CCC1CSC1]

To a solution of 2-(thietan-3-yl)ethanol (200 mg, 1.69 mmol), tris(butyl)phosphine (6.84 g, 10% in hexane, 3.38 mmol) and 1,1'-(azodicarbonyl)dipiperidine (860 mg, 3.38 mmol) in anhydrous tetrahydrofuran (20 mL) was added ethyl 5-chloro-1H-pyrrolo[2,3-c]pyridine-2-carboxylate (380 mg, 1.69 mmol) under nitrogen atmosphere. The reaction mixture was stirred at room temperature for 3 hours. The resulting mixture was then concentrated in vacuo. The residue was purified by flash column (gradient eluting with 0-25% ethyl acetate in petroleum ether) to afford 400 mg of ethyl 5-chloro-1-[2-(thietan-3-yl)ethyl]-1H-pyrrolo[2,3-c]pyridine-2-carboxylate as a white solid.

Step 5: Preparation of 5-chloro-2-(chloromethyl)-1-[2-(thietan-3-yl)ethyl]-1H-pyrrolo[2,3-c]pyridine

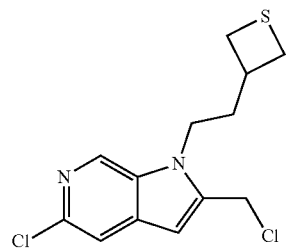 [SMILES: ClCc1cc2cc(Cl)ncc2n1CCC1CSC1]

5-Chloro-2-(chloromethyl)-1-[2-(thietan-3-yl)ethyl]-1H-pyrrolo[2,3-c]pyridine was prepared in analogy to 5-chloro-2-(chloromethyl)-1-[4-(methylsulfonyl)butyl]-1H-indole in Example 4-1 according to Scheme 2 by using ethyl 5-chloro-1-[2-(thietan-3-yl)ethyl]-1H-pyrrolo[2,3-c]pyridine-2-carboxylate instead of ethyl 5-chloro-1-[4-(methylsulfonyl)butyl]-1H-indole-2-carboxylate.

Step 6: Preparation of 1'-({5-chloro-1-[2-(thietan-3-yl)ethyl]-1H-pyrrolo[2,3-c]pyridin-2-yl}methyl) spiro[cyclopropane-1,3'-pyrrolo[2,3-c]pyridin]-2'(1'H)-one The title compound was prepared in analogy to Example 4-9 according to Scheme 2 by using 5-chloro-2-(chloromethyl)-1-[2-(thietan-3-yl)ethyl]-1H-pyrrolo[2,3-c]pyridine instead of 5-chloro-2-(chloromethyl)-1-[3-(cyclopropylsulfonyl)propyl]-1H-pyrrolo[2,3-c]pyridine.

Example 4-11

1'-({5-Chloro-1-[2-(1,1-dioxidothietan-3-yl)ethyl]-1H-pyrrolo[2,3-c]pyridin-2-yl}methyl)spiro[cyclopropane-1,3'-pyrrolo[2,3-c]pyridin]-2'(1'H)-one Step 1: Preparation of ethyl 5-chloro-1-[2-(1,1-dioxidothietan-3-yl)ethyl]-1H-pyrrolo[2,3-c]pyridine-2-carboxylate

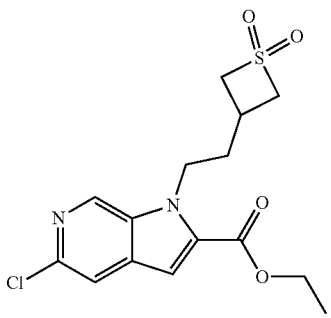 [SMILES: CCOC(=O)c1cc2cc(Cl)ncc2n1CCC1CS(=O)(=O)C1]

To a cooled solution of ethyl 5-chloro-1-[2-(thietan-3-yl)ethyl]-1H-pyrrolo[2,3-c]pyridine-2-carboxylate (163 mg, 0.50 mmol) in dichloromethane (10 mL) was added 3-chloroperbenzoic acid (247 mg, 1.0 mmol, 75% purity) slowly at 0° C. The reaction mixture was stirred for 1 hour while the temperature was allowed to arise to room temperature naturally. The resulting mixture was washed with a saturated aqueous solution of sodium carbonate (10 mL), and then dried over anhydrous sodium sulfate and then concentrated in vacuo to afford 182 mg of the crude ethyl 5-chloro-1-[2-(1,1-dioxidothietan-3-yl)ethyl]-1H-pyrrolo[2,3-c]pyridine-2-carboxylate as a light yellow semisolid.

Step 2: Preparation of 1'-({5-chloro-1-[2-(1,1-dioxidothietan-3-yl)ethyl]-1H-pyrrolo[2,3-c]pyridin-2-yl}methyl)spiro[cyclopropane-1,3'-pyrrolo[2,3-c]pyridin]-2'(1'H)-one The title compound was prepared in analogy to Example 4-10 according to Scheme 2 by using ethyl 5-chloro-1-[2-(1,1-dioxidothietan-3-yl)ethyl]-1H-pyrrolo[2,3-c]pyridine-2-carboxylate instead of ethyl 5-chloro-1-[2-(thietan-3-yl)ethyl]-1H-pyrrolo[2,3-c]pyridine-2-carboxylate.

Example 4-12

1'-({5-Chloro-1-[3-(methylsulfonyl)propyl]-1H-pyrrolo[2,3-b]pyridin-2-yl}methyl)spiro[cyclobutane-1,3'-pyrrolo[2,3-c]pyridin]-2'(1'H)-one The title compound was prepared in analogy to Example 4-9 according to Scheme 2 by using methyl 5-chloro-1H-pyrrolo[2,3-b]pyridine-2-carboxylate, 3-(methylsulfonyl)propyl 4-methylbenzenesulfonate and spiro[cyclobutane-1,3'-pyrrolo[2,3-c]pyridin]-2'(1'H)-one instead of ethyl 5-chloro-1-[3-(cyclopropylsulfonyl)propyl]-1H-indole-2-carboxylate and spiro[cyclopropane-1,3'-pyrrolo[2,3-c]pyridin]-2'(1'H)-one.

Example 4-13

1'-({5-Chloro-1-[3-(methylsulfonyl)propyl]-1H-pyrrolo[2,3-c]pyridin-2-yl}methyl)spiro[cyclopropane-1,3'-pyrrolo[2,3-c]pyridin]-2'(1'H)-one The title compound was prepared in analogy to Example 4-9 according to Scheme 2 by using 3-(methylsulfonyl)propyl 4-methylbenzenesulfonate instead of 3-(cyclopropylsulfonyl)propyl 4-methylbenzenesulfonate.

Example 4-14

1'-({5-Chloro-1-[2-(cyclopropylsulfonyl)ethyl]-1H-pyrrolo[3,2-b]pyridin-2-yl}methyl)spiro[cyclopropane-1,3'-pyrrolo[2,3-c]pyridin]-2'(1'H)-one The title compound was prepared in analogy to Example 4-9 according to Scheme 2 by using methyl 5-chloro-1H-pyrrolo[3,2-b]pyridine-2-carboxylate and 2-(cyclopropylsulfonyl)ethyl 4-methylbenzenesulfonate instead of ethyl 5-chloro-1H-pyrrolo[2,3-c]pyridine-2-carboxylate and 3-(cyclopropylsulfonyl)propyl 4-methylbenzenesulfonate.

Example 4-15

1'-({5-Chloro-1-[3-(methylsulfonyl)propyl]-1H-pyrrolo[3,2-b]pyridin-2-yl}methyl)spiro[cyclopropane-1,3'-pyrrolo[2,3-c]pyridin]-2'(1'H)-one Step 1: Preparation of 5-chloro-2-(chloromethyl)-1-[3-(methylsulfonyl)propyl]-1H-pyrrolo[3,2-b]pyridine

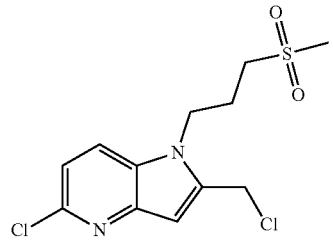 [SMILES: CS(=O)(=O)CCCn1c(CCl)cc2nc(Cl)ccc21]

5-Chloro-2-(chloromethyl)-1-[3-(methylsulfonyl)propyl]-1H-pyrrolo[3,2-b]pyridine was prepared in analogy to 5-chloro-2-(chloromethyl)-1-[4-(methylsulfonyl)butyl]-1H-indole in Example 4-1 by using methyl 5-chloro-1H-pyrrolo[3,2-b]pyridine-2-carboxylate and 3-(methylsulfonyl)propyl 4-methylbenzenesulfonate instead of ethyl 5-chloro-1H-indole-2-carboxylate and 4-(methylsulfonyl)butyl 4-methylbenzenesulfonate.

Step 2: Preparation of 1'-({5-chloro-1-[3-(methylsulfonyl)propyl]-1H-pyrrolo[3,2-b]pyridin-2-yl}methyl)spiro[cyclopropane-1,3'-pyrrolo[2,3-c]pyridin]-2'(1'H)-one To a cooled solution of 5-chloro-2-(chloromethyl)-1-[3-(methylsulfonyl)propyl]-1H-pyrrolo[3,2-b]pyridine (350 mg, 1.16 mmol) in N,N-dimethylformamide (2 mL) was added a mixture of spiro[cyclopropane-1,3'-pyrrolo[2,3-c]pyridin]-2'(1'H)-one (195 mg, 1.22 mmol) and sodium tert-buoxide (115 mg, 1.19 mmol) in N,N-dimethylformamide (2 mL) dropwise. The resulting mixture was heated with stirring at 60° C. for 2 hours. The resulting mixture was purified by preparative HPLC to afford the title product as a solid.

Example 4-16

1'-({5-Chloro-1-[4-(methylsulfonyl)butyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 4-15 according to Scheme 2 by using methyl 5-chloro-1H-pyrrolo[2,3-b]pyridine-2-carboxylate and 1-bromo-4-(methylsulfonyl)butane instead of methyl 5-chloro-1H-pyrrolo[3,2-b]pyridine-2-carboxylate and 3-(methylsulfonyl)propyl 4-methylbenzenesulfonate.

Example 5-1

1'-({5-Chloro-1-[3-(methylsulfinyl)propyl]-1H-indol-2-yl}methyl)spiro[cyclopropane-1,3'-pyrrolo[2,3-c]pyridin]-2'(1'H)-one Step 1: Preparation of {5-chloro-1[3-(methylsulfinyl)propyl]-1H-indol-2-yl}methanol

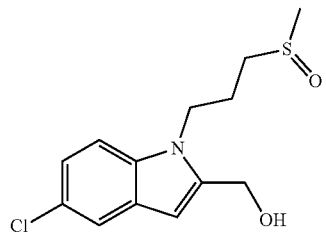 [SMILES: CS(=O)CCCn1c(CO)cc2cc(Cl)ccc21]

{5-Chloro-1[3-(methylsulfinyl)propyl]-1H-indol-2-yl}methanol was prepared in analogy to {5-chloro-1-[4-(methylsulfonyl)butyl]-1H-indol-2-yl}methanol in Example 4-1 according to Scheme 2 by using 3-(methylsulfinyl)propyl 4-methylbenzenesulfonate instead of 4-(methylsulfonyl)butyl 4-methylbenzenesulfonate.

Step 2: Preparation of {5-chloro-1[3-(methylsulfinyl)propyl]-1H-indol-2-yl}methyl methanesulfonate

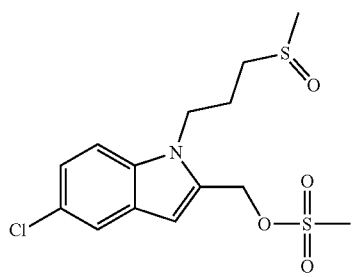 [SMILES: CS(=O)CCCn1c(COS(C)(=O)=O)cc2cc(Cl)ccc21]

{5-Chloro-1[3-(methylsulfinyl)propyl]-1H-indol-2-yl}methyl methanesulfonate was prepared in analogy to {5-chloro-1-[2-(ethylsulfonyl)ethyl]-1H-indol-2-yl}methyl methanesulfonate in Example 2-1 according to Scheme 2 by using {5-chloro-1-[3-(methylsulfinyl)propyl]-1H-indol-2-yl}methanol instead of {5-chloro-1-[2-(ethylsulfonyl)ethyl]-1H-indol-2-yl}methanol.

Step 3: Preparation of 1'-({5-chloro-1-[3-(methylsulfinyl)propyl]-1H-indol-2-yl}methyl)spiro[cyclopropane-1,3'-pyrrolo[2,3-c]pyridin]-2'(1'H)-one The title compound was prepared in analogy to Example 2-1 according to Scheme 2 by using {5-chloro-1-[3-(methylsulfinyl)propyl]-1H-indol-2-yl}methyl methanesulfonate instead of {5-chloro-1-[2-(ethylsulfonyl)ethyl]-1H-indol-2-yl}methyl methanesulfonate.

Example 5-2

1'-({5-Chloro-1-[2-(methylsulfonyl)ethyl]-1H-pyrrolo[2,3-c]pyridin-2-yl}methyl)spiro[cyclopropane-1,3'-pyrrolo[2,3-c]pyridin]-2'(1'H)-one The title compound was prepared in analogy to Example 5-1 according to Scheme 2 by using ethyl 5-chloro-1H-pyrrolo[2,3-c]pyridine-2-carboxylate and 2-(methylsulfonyl)ethyl 4-methylbenzenesulfonate instead of ethyl 5-chloro-1H-indole-2-carboxylate and 3-(methylsulfinyl)propyl 4-methylbenzenesulfonate.

Example 6

1'-({5-Chloro-1-[2-(ethylsulfonyl)ethyl]-1H-pyrrolo[3,2-b]pyridin-2-yl}methyl)spiro[cyclopropane-1,3'-pyrrolo[2,3-c]pyridin]-2'(1'H)-one Step 1: Preparation of methyl 5-chloro-1-(phenylsulfonyl)-1H-pyrrolo[3,2-b]pyridine-2-carboxylate

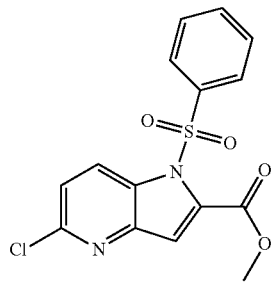 [SMILES: COC(=O)c1cc2nc(Cl)ccc2n1S(=O)(=O)c1ccccc1]

To a suspension of methyl 5-chloro-1H-pyrrolo[3,2-b]pyridine-2-carboxylate (7.56 g, 36 mmol) and sodium hydride (1.7 g, 43 mmol, 60% purity in mineral oil) in N,N-dimethylformamide (100 mL) was added benzenesulfonyl chloride (6.1 mL, 47 mmol) dropwise in an ice-water bath. After being stirred at room temperature for 2 hours, the mixture was then poured into ice water (100 mL). The resulting precipitate was collected by filtration, which was washed with petroleum ether (50 mL), and then dried in vacuo to afford 11.6 g of 5-chloro-1-(phenylsulfonyl)-1H-pyrrolo[3,2-b]pyridine-2-carboxylate as a pale white solid.

Step 2: Preparation of [5-chloro-1-(phenylsulfonyl)-1H-pyrrolo[3,2-b]pyridin-2-yl]methanol

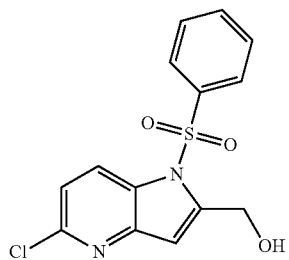 [SMILES: O=S(=O)(c1ccccc1)n1c(CO)cc2nc(Cl)ccc21]

To a suspension of lithium aluminium hydride (1.9 g, 50 mmol) in tetrahydrofuran (150 mL) at 0° C. was added methyl 5-chloro-1-(phenylsulfonyl)-1H-pyrrolo[3,2-b]pyridine-2-carboxylate (11.6 g, 33 mmol) in portions. After being stirred at room temperature for 3 hours, the resulting mixture was quenched with methanol, and then filtered through a celite pad. The filtrate was concentrated in vacuo to afford 9.7 g of the product as brown oil. MS obsd. (ESI$^+$) [(M+H)$^+$] 323.

Step 3: Preparation of 5-chloro-2-(chloromethyl)-1-(phenylsulfonyl)-1H-pyrrolo[3,2-b]pyridine

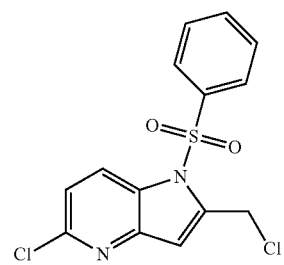 [SMILES: O=S(=O)(c1ccccc1)n1c(CCl)cc2nc(Cl)ccc21]

To a solution of [5-chloro-1-(phenylsulfonyl)-1H-pyrrolo[3,2-b]pyridin-2-yl]methanol (1.93 g, 6.0 mmol) in dichloromethane (150 mL) was added a solution of thionyl chloride (2.7 mL, 37 mmol) in dichloromethane (10 mL) in an ice-water bath. After being stirred at room temperature for 4 hours, the mixture was concentrated in vacuo to afford a light brown solid which was used for next step without further purification.

Step 4: Preparation of 1'-{[5-chloro-1-(phenylsulfonyl)-1H-pyrrolo[3,2-b]pyridin-2-yl]methyl}spiro[cyclopropane-1,3'-pyrrolo[2,3-c]pyridin]-2'(1'H)-one

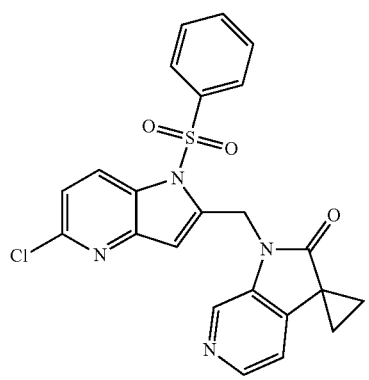 [SMILES: O=C1N(Cc2cc3nc(Cl)ccc3n2S(=O)(=O)c2ccccc2)c2cnccc2C12CC2]

To a suspension of spiro[cyclopropane-1,3'-pyrrolo[2,3-c]pyridin]-2'(1'14)-one (960 mg, 6.0 mmol) and sodium hydride (0.72 g, 18 mmol) in N,N-dimethylformamide (10 mL) was added a solution of 5-chloro-2-(chloromethyl)-1-(phenylsulfonyl)-1H-pyrrolo[3,2-b]pyridine (2.04 g, 6.0 mmol) in N,N-dimethylformamide (5 mL) dropwise in an ice-water bath. After being stirred at room temperature for 1 hour, the reaction mixture was then poured into ice-water (20 mL) and then extracted with dichloromethane (30 mL×2). The combined organic layer was dried over anhydrous sodium sulfate, and then concentrated in vacuo. The residue was purified by flash silica gel chromatography (eluting with 0-5% methanol in dichloromethane) to afford 600 mg of 1'-{[5-chloro-1-(phenylsulfonyl)-1H-pyrrolo[3,2-b]pyridin-2-yl]methyl}spiro[cyclopropane-1,3'-pyrrolo[2,3-c]pyridin]-2'(1'H)-one as a brown solid. MS obsd. (ESI$^+$) [(M+H)$^+$] 465.

Step 5: Preparation of 1'-[(5-chloro-1H-pyrrolo[3,2-b]pyridin-2-yl)methyl]spiro[cyclopropane-1,3'-pyrrolo[2,3-c]pyridin]-2'(1'H)-one

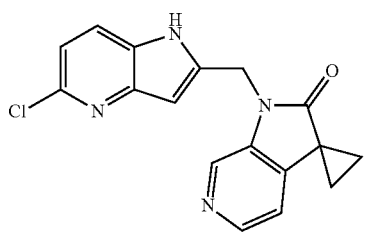 [SMILES: O=C1N(Cc2cc3nc(Cl)ccc3[nH]2)c2cnccc2C12CC2]

A mixture of 1'-{[5-chloro-1-(phenylsulfonyl)-1H-pyrrolo[3,2-b]pyridin-2-yl]methyl}spiro[cyclopropane-1,3'-pyrrolo[2,3-c]pyridin]-2'(1'H)-one (167 mg, 0.36 mmol) and tetrabutylammonium fluoride in tetrahydrofuran (1 mL, 1.0 M) in tetrahydrofuran (2 mL) was stirred at room temperature for 16 hours. The resulting mixture was concentrated in vacuo. The residue was extracted with ethyl acetate (20 mL×2). The organic layer was washed with a saturated aqueous solution of ammonium chloride (20 mL×2) and water (20 mL×2), and then dried over anhydrous sodium sulfate and then concentrated in vacuo. The residue was used for next step without further purification. MS obsd. (ESI$^+$) [(M+H)$^+$] 325.

Step 6: Preparation of 1'-({5-chloro-1-[2-(ethylsulfonyl)ethyl]-1H-pyrrolo[3,2-b]pyridin-2-yl}methyl)spiro[cyclopropane-1,3'-pyrrolo[2,3-c]pyridin]-2' (1'H)-one A mixture of 1'-[(5-chloro-1H-pyrrolo[3,2-b]pyridin-2-yl)methyl]spiro[cyclopropane-1,3'-pyrrolo[2,3-c]pyridin]-2'(1'H)-one (84 mg, 0.26 mmol), sodium tert-butoxide (90 mg, 1.0 mmol) and (ethylsulfonyl)ethene (63.5 mg, 0.52 mmol) in acetonitrile (5 mL) was stirred at room temperature for 6 hours. The resulting mixture was quenched with water, then filtered and washed with acetonitrile (10 mL×3). The filtrate was concentrated in vacuo. The residue was purified by preparative HPLC to afford 8.1 mg of the title product as colorless oil.

Example 7-1

3-{5-Chloro-2-[(2'-oxospiro[cyclopropane-1,3'-pyrrolo[2,3-c]pyridin]-1'(2'H)-yl)methyl]-1H-indol-1-yl}-N,N-dimethylpropane-1-sulfonamide Step 1: Preparation of 1'-[(5-chloro-1H-indol-2-yl)methyl]spiro[cyclopropane-1,3'-pyrrolo[2,3-c]pyridin]-2'(1'H)-one

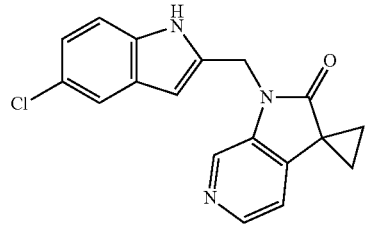 [SMILES: O=C1N(Cc2cc3cc(Cl)ccc3[nH]2)c2cnccc2C12CC2]

1'-[(5-Chloro-1H-indol-2-yl)methyl]spiro[cyclopropane-1,3'-pyrrolo[2,3-c]pyridin]-2'(1'H)-one was prepared in analogy to 1'-[(5-chloro-1H-pyrrolo[3,2-b]pyridin-2-yl)methyl]spiro[cyclopropane-1,3'-pyrrolo[2,3-c]pyridin]-2'(1'H)-one in Example 6 by using ethyl 5-chloro-1H-indole-2-carboxylate instead of methyl 5-chloro-1H-pyrrolo[3,2-b]pyridine-2-carboxylate.

Step 2: Preparation of 3-{5-chloro-2-[(2'-oxospiro[cyclopropane-1,3'-pyrrolo[2,3-c]pyridin]-1'(2'H)-yl)methyl]-1H-indol-1-yl}-N,N-dimethylpropane-1-sulfonamide A mixture of 1'-[(5-chloro-1H-indol-2-yl)methyl]spiro[cyclopropane-1,3'-pyrrolo[2,3-c]pyridin]-2'(1'H)-one (150 mg, 0.46 mmol), cesium carbonate (200 mg, 0.62 mmol) and 3-chloro-N,N-dimethylpropane-1-sulfonamide (90 mg, 0.49 mmol) in N,N-dimethylformamide (4 mL) was heated with stirring at 80° C. for 1 hour. The resulting mixture was purified by preparative HPLC to afford 6 mg of the title product.

Example 7-2

3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-dimethylpropane-1-sulfonamide The title compound was prepared in analogy to Example 7-1 according to Scheme 3 by using methyl 5-chloro-1H-pyrrolo[2,3-b]pyridine-2-carboxylate instead of ethyl 5-chloro-1H-indole-2-carboxylate.

Example 7-3

2-{5-Chloro-2-[(2'-oxospiro[cyclopropane-1,3'-pyrrolo[2,3-c]pyridin]-1'(2'H)-yl)methyl]-1H-indol-1-yl}-N,N-dimethylethanesulfonamide The title compound was prepared in analogy to Example 7-1 according to Scheme 3 by using 2-chloro-N,N-dimethylethanesulfonamide instead of 3-chloro-N,N-dimethylpropane-1-sulfonamide.

Example 7-4

1'-({5-Chloro-1-[3-(morpholin-4-ylsulfonyl)propyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 4-[(3-chloropropyl)sulfonyl]morpholine instead of 3-chloro-N,N-dimethylpropane-1-sulfonamide.

Example 7-5

1'-({5-Chloro-1-[3-(pyrrolidin-1-ylsulfonyl)propyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 1-[(3-chloropropyl)sulfonyl]pyrrolidine instead of 3-chloro-N,N-dimethylpropane-1-sulfonamide.

Example 7-6

1'-[(5-Chloro-1-{3-[(3-oxopiperazin-1-yl)sulfonyl]propyl}-1H-indol-2-yl)methyl]spiro[cyclopropane-1,3'-pyrrolo[2,3-c]pyridin]-2'(1'H)-one The title compound was prepared in analogy to Example 7-1 according to Scheme 3 by using 4-[(3-chloropropyl)sulfonyl]piperazin-2-one instead of 3-chloro-N,N-dimethylpropane-1-sulfonamide.

Example 7-7

1'-({5-Chloro-1-[2-(1,1-dioxido-1,2-thiazolidin-2-yl)ethyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 2-(2-bromoethyl)-1,2-thiazolidine 1,1-dioxide instead of 3-chloro-N,N-dimethylpropane-1-sulfonamide.

Example 7-8

1'-({5-Chloro-1-[4-(1,1-dioxido-1,2-thiazolidin-2-yl)butyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 2-(4-bromobutyl)-1,2-thiazolidine 1,1-dioxide instead of 3-chloro-N,N-dimethylpropane-1-sulfonamide.

Example 7-9

1'-({5-Chloro-1-[3-(1,1-dioxidothiomorpholin-4-yl)propyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 4-(3-bromopropyl)thiomorpholine 1,1-dioxide instead of 3-chloro-N,N-dimethylpropane-1-sulfonamide.

Example 7-10

1'-({5-Chloro-1-[3-(1,1-dioxido-1,2-thiazolidin-2-yl)propyl]-1H-indol-2-yl}methyl)spiro[cyclopropane-1,3'-pyrrolo[2,3-c]pyridin]-2'(1'H)-one The title compound was prepared in analogy to Example 7-1 according to Scheme 3 by using 2-(3-bromopropyl)-1,2-thiazolidine 1,1-dioxide instead of 3-chloro-N,N-dimethylpropane-1-sulfonamide.

Example 8

1'-{[5-Chloro-1-(3-hydroxypropyl)-1H-indol-2-yl]methyl}spiro[cyclopropane-1,3'-pyrrolo[2,3-c]pyridin]-2'(1'H)-one Step 1: Preparation of 1'-[(5-chloro-1H-indol-2-yl)methyl]spiro[cyclopropane-1,3'-pyrrolo[2,3-c]pyridin]-2'(1'H)-one

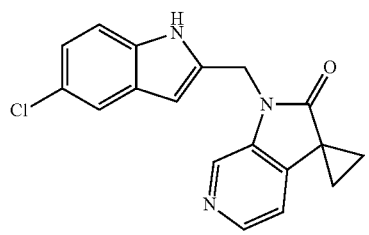 [SMILES: O=C1N(Cc2cc3cc(Cl)ccc3[nH]2)c2cnccc2C12CC2]

1'-[(5-chloro-1H-indol-2-yl)methyl]spiro[cyclopropane-1,3'-pyrrolo[2,3-c]pyridin]-2'(1'H)-one was prepared in analogy to 1'-[(5-chloro-1H-pyrrolo[3,2-b]pyridin-2-yl)methyl]spiro[cyclopropane-1,3'-pyrrolo[2,3-c]pyridin]-2'(1'H)-one in Example 6 by using ethyl 5-chloro-1H-indole-2-carboxylate instead of methyl 5-chloro-1H-pyrrolo[3,2-b]pyridine-2-carboxylate.

Step 2: Preparation of 1'-{[5-chloro-1-(3-hydroxypropyl)-1H-indol-2-yl]methyl}spiro[cyclopropane-1,3'-pyrrolo[2,3-c]pyridin]-2'(1'H)-one To a solution of 1'-[(5-chloro-1H-indol-2-yl)methyl]spiro[cyclopropane-1,3'-pyrrolo[2,3-c]pyridin]-2'(1'H)-one (163 mg, 0.50 mmol) in acetonitrile (5 mL) was added 3-bromopropan-1-ol (217 mg, 1.5 mmol), cesium carbonate (488 mg, 1.5 mmol) and tetrabutylammonium bromide (156 mg, 0.50 mmol). The resulting mixture was heated under reflux overnight. After being cooled to room temperature, the mixture was concentrated in vacuo. The residue was dissolved in dichloromethane (10 mL). The solution was washed with brine, and then drier over sodium sulfate and then concentrated in vacuo. The residue was purified by preparative HPLC to afford the title product.

Example 9

1'-[{5-Chloro-1-[2-(methylsulfonyl)ethyl]-1H-indol-2-yl}($^2$H$_2$)methyl]spiro[cyclopropane-1,3'-pyrrolo[2,3-c]pyridin]-2'(1'H)-one Step 1: Preparation of 1'-[(5-chloro-1H-indol-2-yl)($^2$H$_2$)methyl]spiro[cyclopropane-1,3'-pyrrolo[2,3-c]pyridin]-2'(1'H)-one

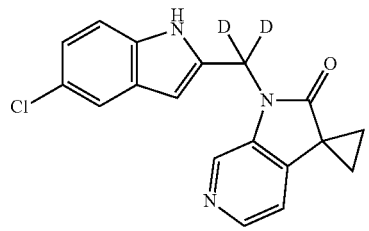 [SMILES: [2H]C([2H])(c1cc2cc(Cl)ccc2[nH]1)N1C(=O)C2(CC2)c2ccncc21]

1'-[(5-Chloro-1H-indol-2-yl)($^2$H$_2$)methyl]spiro[cyclopropane-1,3'-pyrrolo[2,3-c]pyridin]-2'(1'H)-one was prepared in analogy to 1'-[(5-chloro-1H-pyrrolo[3,2-b]pyridin-2-yl)methyl]spiro[cyclopropane-1,3'-pyrrolo[2,3-c]pyridin]-2'(1'H)-one in Example 6 in Scheme 3 by using ethyl 5-chloro-1H-indole-2-carboxylate and lithium aluminum deuteride instead of methyl 5-chloro-1H-pyrrolo[3,2-b]pyridine-2-carboxylate and lithium aluminum hydride.

Step 2: Preparation of 1'-[{5-chloro-1-[2-(methylsulfonyl)ethyl]-1H-indol-2-yl}($^2$H$_2$)methyl]spiro[cyclopropane-1,3'-pyrrolo[2,3-c]pyridin]-2'(1'H)-one The title compound was prepared in analogy to Example 6 according to Scheme 3 by using 1'-[(5-chloro-1H-indol-2-yl)($^2$H$_2$)methyl]spiro[cyclopropane-1,3'-pyrrolo[2,3-c]pyridin]-2'(1'H)-one and (methylsulfonyl)ethane instead of 1'-[(5-chloro-1H-pyrrolo[3,2-b]pyridin-2-yl)methyl]spiro[cyclopropane-1,3'-pyrrolo[2,3-c]pyridin]-2'(1'H)-one and (ethylsulfonyl)ethene.

Example 10

1'[{-5-Chloro-1-[3-(methylsulfonyl)propyl]-1H-indol-2-yl}($^2$H$_2$)methyl]spiro[cyclopropane-1,3'-pyrrolo[2,3-c]pyridin]-2'(1'H)-one The title compound was prepared in analogy to Example 7-1 according to Scheme 3 by using 1'-[(5-chloro-1H-indol-2-yl)($^2$H$_2$)methyl]spiro[cyclopropane-1,3'-pyrrolo[2,3-c]pyridin]-2'(1'H)-one and 3-(methylsulfonyl)propyl 4-methylbenzenesulfonate instead of ethyl 5-chloro-1H-indole-2-carboxylate, spiro[cyclopropane-1,3'-pyrrolo[2,3-c]pyridin]-2'(1'H)-one and 3-chloro-N,N-dimethylpropane-1-sulfonamide.

Example 11

Ethyl 3-{5-chloro-2-[(2'-oxospiro[cyclopropane-1, 3'-pyrrolo[2,3-c]pyridin]-1'(2'H)-yl)methyl]-1H-indol-1-yl}propanoate

Step 1: Preparation of (5-chloro-1H-indol-2-yl)methanol

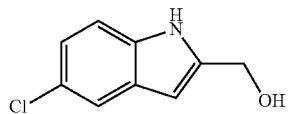 [SMILES: OCc1cc2cc(Cl)ccc2[nH]1]

(5-Chloro-1H-indol-2-yl)methanol was prepared in analogy to 1H-indol-2-ylmethanol in Example 1-1 by using ethyl 5-chloro-1H-indole-2-carboxylate instead of 1H-indole-2-carboxylate.

Step 2: Preparation of 2-({[tert-butyl(dimethyl)silyl]oxy}methyl)-5-chloro-1H-indole

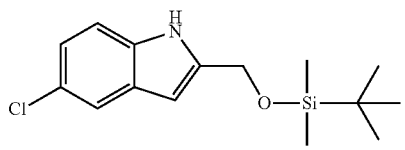 [SMILES: CC(C)(C)[Si](C)(C)OCc1cc2cc(Cl)ccc2[nH]1]

To a cooled solution of (5-chloro-1H-indol-2-yl)methanol (1.82 g, 10.0 mmol) in dichloromethane (20 mL) at 0° C. in an ice bath was added a solution of imidazole (1.0 g, 15.0 mmol) in dichloromethane (20 mL) slowly and then followed by addition of a solution of tert-butyl(chloro)dimethylsilane (2.26 g, 15.0 mol) in dichloromethane (10 mL) dropwise under nitrogen atmosphere. After being stirred for 15 minutes, the mixture was allowed to warm to room temperature and then stirred at room temperature overnight. The reaction mixture was then diluted with dichloromethane (50 mL) and then washed with water (50 mL) and brine (50 mL). The organic layer was dried over sodium sulfate and then concentrated in vacuo. The residue was purified by flash chromatography (eluting with 5% ethyl acetate in petroleum ether) to give 2.0 g of 2-({[tert-butyl(dimethyl)silyl]oxy}methyl)-5-chloro-1H-indole as a white solid.

Step 3: Preparation of ethyl 3-[2-({[tert-butyl(dimethyl)silyl]oxy}methyl)-5-chloro-1H-indol-1-yl]propanoate

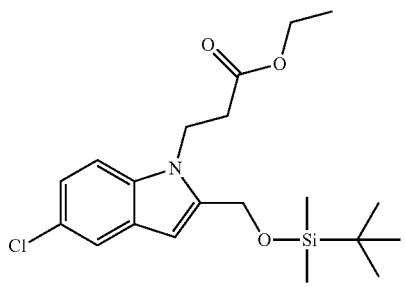 [SMILES: CCOC(=O)CCn1c(CO[Si](C)(C)C(C)(C)C)cc2cc(Cl)ccc21]

A mixture of 2-({[tert-butyl(dimethyl)silyl]oxy}methyl)-5-chloro-1H-indole (1.18 g, 4.0 mmol), cesium carbonate (2.6 g, 8.0 mmol) and ethyl 3-bromopropanoate (1 mL, 8.0 mmol) in N,N-dimethylformamide (10 mL) was heated with stirring at 100° C. for 2 hours. The resulting mixture was filtered. The filtrate was concentrated in vacuo. The residue was purified by flash silica gel chromatography (gradient eluting with 0-40% ethyl acetate in petroleum ether) to afford 1.38 g of ethyl 3-[2-{[tert-butyl(dimethyl)silyl]oxy}methyl)-5-chloro-1H-indol-1-yl]propanoate as a white solid. MS obsd. (ESI+) [(M+H)+] 396.

Step 4: Preparation of ethyl 3-[5-chloro-2-(hydroxymethyl)-1H-indol-1-yl]propanoate

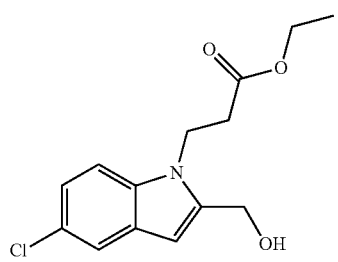 [SMILES: CCOC(=O)CCn1c(CO)cc2cc(Cl)ccc21]

A mixture of ethyl 3-[2-({[tert-butyl(dimethyl)silyl]oxy}methyl)-5-chloro-1H-indol-1-yl]propanoate (1.38 g, 3.5 mmol) and 1.0 M solution of tetrabutylammonium fluoride in tetrahydrofuran (5 mL) was stirred at 25° C. for 4 hours. The resulting mixture was quenched by adding 10 mL of saturated aqueous solution of ammonium chloride. The mixture was then extracted with ethyl acetate (20 mL×3), and then washed with a saturated aqueous ammonium chloride solution (50 mL×3) and brine. The organic layer was dried over anhydrous sodium sulfate and then concentrated in vacuo. The residue was purified by flash silica gel chromatography to afford 0.7 g of ethyl 3-[5-chloro-2-(hydroxymethyl)-1H-indol-1-yl]propanoate as a brown solid. MS obsd. (ESI+) [(M+H)+] 282.

Step 5: Preparation of ethyl 3-(5-chloro-2-{[(methylsulfonyl)oxy]methyl}-1H-indol-1-yl)propanoate

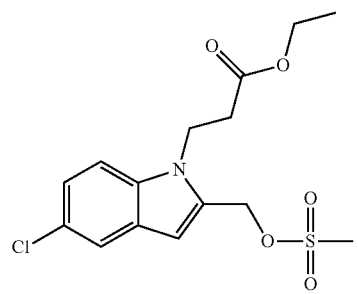 [SMILES: CCOC(=O)CCn1c(COS(C)(=O)=O)cc2cc(Cl)ccc21]

To a solution of ethyl 3-[5-chloro-2-(hydroxymethyl)-1H-indol-1-yl]propanoate (700 mg, 2.5 mmol) and triethylamine (1 mL, 7.5 mmol) in dichloromethane (20 mL) was added methanesulfonyl chloride (0.4 ml, 5 mmol) dropwise in an ice-water bath. After being stirred at 0° C. for 30 minutes, the resulting mixture was neutralized with a saturated aqueous solution of sodium bicarbonate and then extracted with dichloromethane (20 mL×2). The combined organic layer was washed with a saturated aqueous solution of sodium bicarbonate (20 mL×2), and then dried over anhydrous sodium sulfate and then concentrated in vacuo to afford 720 mg of ethyl 3-(5-chloro-2-{[(methylsulfonyl)

oxy]methyl}-1H-indol-1-yl)propanoate as a brown solid which was used for next step without further purification.

Step 6: Preparation of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate A mixture of ethyl 3-(5-chloro-2-{[(methylsulfonyl)oxy]methyl}-1H-indol-1-yl)propanoate (720 mg, 2.0 mmol), cesium carbonate (1.3 g, 4.0 mmol) and spiro[cyclopropane-1,3'-pyrrolo[2,3-c]pyridin]-2'(1R)-one (320 mg, 2.0 mmol) in acetonitrile (20 mL) was heated with stirring at 85° C. for 30 minutes. The mixture was then filtered and washed with acetonitrile (20 mL×2). The filtrate was concentrated in vacuo. The residue was purified by preparative HPLC to afford 480 mg of the title product as a white solid.

Example 12

1'-({5-Chloro-1-[2-(1,1-dioxidothietan-3-yl)ethyl]-1H-pyrrolo[2,3-b]pyridin-2-yl}methyl)spiro[cyclopropane-1,3'-pyrrolo[2,3-c]pyridin]-2'(1'H)-one Step 1: Preparation of 2-(1,1-dioxidothietan-3-yl)ethanol

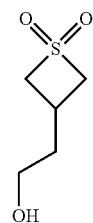

To a cooled solution of 2-(thietan-3-yl)ethanol (682 mg, 5.8 mmol) in dichloromethane was added 3-chloroperbenzoic acid (2.86 g, 11.6 mmol) in portions in an ice bath. The mixture was stirred for 2.5 hours while the temperature was allowed to arise to room temperature naturally. The resulting mixture was concentrated in vacuo. The residue was dissolved in ethyl acetate (50 mL). The organic solution was washed with a saturated aqueous solution of sodium carbonate (50 mL×3), and then dried over sodium sulfate and then concentrated in vacuo to afford 800 mg of viscous oil.

Step 2: Preparation of 2-(1,1-dioxidothietan-3-yl)ethyl 4-methylbenzenesulfonate

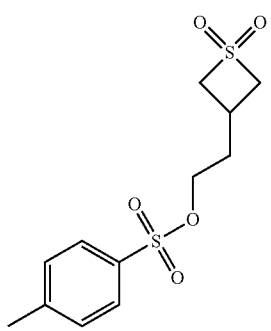 [SMILES: Cc1ccc(S(=O)(=O)OCCC2CS(=O)(=O)C2)cc1]

A mixture of 2-(1,1-dioxidothietan-3-yl)ethanol (150 mg, 1.0 mmol), 4-methylbenzenesulfonyl chloride (190.7 mg, 1.0 mmol) and triethylamine (139 μL, 1.0 mmol) was stirred at room temperature for 4 hours. The resulting mixture was concentrated in vacuo. The residue was purified by flash column (gradient eluting with 20-40% ethyl acetate in petroleum ether) to afford 190 mg of viscous oil.

Step 3: Preparation of 2-({[tert-butyl(dimethyl)silyl]oxy}methyl)-5-chloro-1H-pyrrolo[2,3-b]pyridine

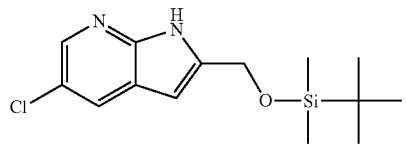 [SMILES: CC(C)(C)[Si](C)(C)OCc1cc2cc(Cl)cnc2[nH]1]

2-({[tert-Butyl(dimethyl)silyl]oxy}methyl)-5-chloro-1H-pyrrolo[2,3-b]pyridine was prepared in analogy to 2-({[tert-butyl(dimethyl)silyl]oxy}methyl)-5-chloro-1H-indole in Example 11 by using methyl 5-chloro-1H-pyrrolo[2,3-b]pyridine-2-carboxylate instead of ethyl 5-chloro-1H-indole-2-carboxylate.

Step 4: Preparation of 2-({[tert-butyl(dimethyl)silyl]oxy}methyl)-5-chloro-1-[2-(1,1-dioxidothietan-3-yl)ethyl]-1H-pyrrolo[2,3-b]pyridine

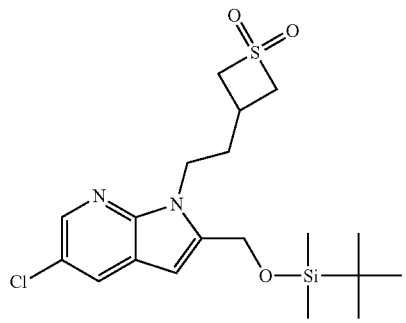 [SMILES: CC(C)(C)[Si](C)(C)OCc1cc2cc(Cl)cnc2n1CCC1CS(=O)(=O)C1]

A mixture of 2-(1,1-dioxidothietan-3-yl)ethyl 4-methylbenzenesulfonate (190 mg, 0.625 mg), 2-({[tert-butyl(dimethyl)silyl]oxy}methyl)-5-chloro-1H-pyrrolo[2,3-b]pyridine (185 mg, 0.625 mmol) and potassium carbonate (173 mg, 1.25 mmol) in acetonitrile (10 mL) was heated with stirring at 70° C. overnight. The resulting mixture was then concentrated in vacuo. The residue was purified by flash silica gel chromatography (gradient eluting with 0-5% methanol in dichloromethane) to afford 250 mg of 2-({[tert-butyl(dimethyl)silyl]oxy}methyl)-5-chloro-1-[2-(1,1-dioxidothietan-3-yl)ethyl]-1H-pyrrolo[2,3-b]pyridine as a brown viscous.

Step 5: Preparation of {5-chloro-1-[2-(1,1-dioxidothietan-3-yl)ethyl]-1H-pyrrolo[2,3-b]pyridin-2-yl}methanol

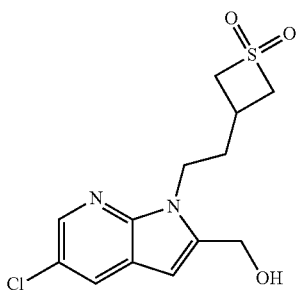 [SMILES: O=S1(=O)CC(CCn2c(CO)cc3cc(Cl)cnc32)C1]

A mixture of 2-({[tert-butyl(dimethyl)silyl]oxy}methyl)-5-chloro-1-[2-(1,1-dioxidothietan-3-yl)ethyl]-1H-pyrrolo[2,3-b]pyridine (270 mg, 0.63 mmol) and 1% of concentrated hydrochloric acid in ethanol (20 mL) was heated under reflux for 1 hour. After being cooled to room temperature, the mixture was basified with a saturated solution of sodium bicarbonate (20 mL) and then concentrated in vacuo to remove the organic solvent. The residual aqueous layer was extracted with dichloromethane (20 mL×2). The combined organic layer was dried over anhydrous sodium sulfate and then concentrated in vacuo. The residue was purified by flash silica gel chromatography (gradient eluting with 0-5% methanol in dichloromethane) to afford 90 mg of {5-chloro-1-[2-(1,1-dioxidothietan-3-yl)ethyl]-1H-pyrrolo[2,3-b]pyridin-2-yl}methanol.

Step 6: Preparation of 1'-({5-chloro-1-[2-(1,1-dioxidothietan-3-yl)ethyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 4-15 according to Scheme 4 by using {5-chloro-1-[2-(1,1-dioxidothietan-3-yl)ethyl]-1H-pyrrolo[2,3-b]pyridin-2-yl}methanol instead of {5-chloro-1-[3-(methylsulfonyl)propyl]-1H-pyrrolo[3,2-b]pyridine-2-yl}methanol.

Example 13

Ethyl 3-{5-chloro-7-fluoro-2-[(2'-oxospiro[cyclopropane-1,3'-pyrrolo[2,3-c]pyridin]-1'(2'H)-yl)methyl]-1H-indol-1-yl}propanoate Step 1: Preparation of 2-({[tert-butyl(dimethyl)silyl]oxy}methyl)-5-chloro-7-fluoro-1H-indole

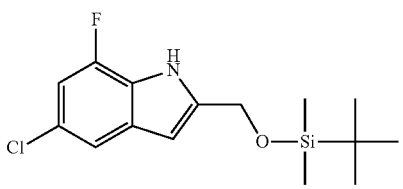 [SMILES: CC(C)(C)[Si](C)(C)OCc1cc2cc(Cl)cc(F)c2[nH]1]

2-({[tert-butyl(dimethyl)silyl]oxy}methyl)-5-chloro-7-fluoro-1H-indole was prepared in analogy to 2-({[tert-butyl (dimethyl)silyl]oxy}methyl)-5-chloro-1H-indole in Example 11 by using methyl 5-chloro-7-fluoro-1H-indole-2-carboxylate instead of ethyl 5-chloro-1H-indole-2-carboxylate.

Step 2: Preparation of ethyl 3-[2-({[tert-butyl(dimethyl)silyl]oxy}methyl)-5-chloro-7-fluoro-1H-indol-1-yl]propanoate

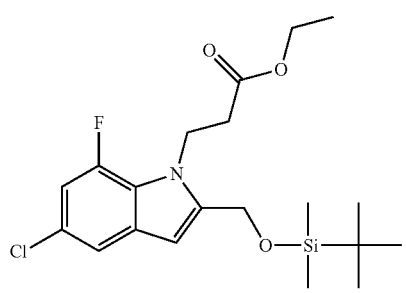 [SMILES: CCOC(=O)CCn1c(CO[Si](C)(C)C(C)(C)C)cc2cc(Cl)cc(F)c21]

To a mixture of 2-({[tert-butyl(dimethyl)silyl]oxy}methyl)-5-chloro-7-fluoro-1H-indole (100 mg, 0.40 mmol), cesium carbonate (221.6 mg, 0.68 mmol) and N,N-dimethylformamide (4 mL) was added ethyl prop-2-enoate (68.1 mg, 0.68 mmol) at room temperature. After being stirred overnight, the reaction mixture was diluted with ethyl acetate and washed with water. The organic layer was dried over sodium sulfate, and then concentrated in vacuo. The residue was purified by flash silica gel chromatography (gradient eluting with 0-40% ethyl acetate in petroleum ether) to give 80 mg of ethyl 3-[2-({[tert-butyl(dimethyl)silyl]oxy}methyl)-5-chloro-7-fluoro-1H-indol-1-yl]propanoate as colorless oil.

Step 3: Preparation of ethyl 3-[5-chloro-7-fluoro-2-(hydroxymethyl)-1H-indol-1-yl]propanoate

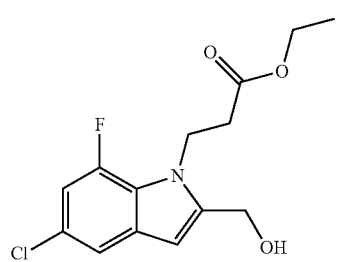 [SMILES: CCOC(=O)CCn1c(CO)cc2cc(Cl)cc(F)c21]

To a solution of ethyl 3-[2-({[tert-butyl(dimethyl)silyl]oxy}methyl)-5-chloro-7-fluoro-1H-indol-1-yl]propanoate (480 mg, 1.16 mmol) in tetrahydrofuran (10 mL) was added 1.0 M of tetrabutylammonium fluoride (3 mL) in tetrahydrofuran at 0° C. After being stirred for 1 hour, the mixture was diluted with a saturated aqueous solution of sodium bicarbonate (20 mL) and then extracted with ethyl acetate (20 mL). The organic layer was dried over sodium sulfate, and then concentrated in vacuo. The residue was purified by flash silica gel chromatography (gradient eluting with 0-5% methanol in dichloromethane) to afford 350 mg of ethyl 3-[5-chloro-7-fluoro-2-(hydroxymethyl)-1H-indol-1-yl]propanoate as a white solid.

Step 4: Preparation of ethyl 3-(5-chloro-7-fluoro-2-{[(methylsulfonyl)oxy]methyl}-1H-indol-1-yl)propanoate

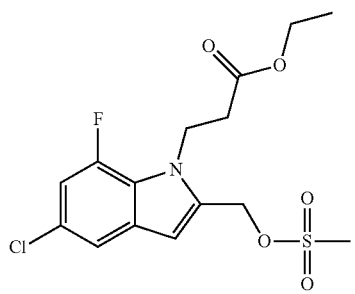 [SMILES: CCOC(=O)CCn1c(COS(C)(=O)=O)cc2cc(Cl)cc(F)c21]

To a solution of ethyl 3-[5-chloro-7-fluoro-2-(hydroxymethyl)-1H-indol-1-yl]propanoate (350 mg, 1.17 mmol) and triethylamine (355.2 mg, 3.51 mmol) in dichloromethane (10 mL) was added methanesulfonyl chloride (201.6 mg, 1.76 mmol) dropwise at 0° C. After being stirred at room temperature for 30 minutes, the reaction was quenched with a saturated aqueous solution of sodium bicarbonate (10 mL). The organic layer was separated, and then dried over sodium sulfate and then concentrated in vacuo to afford the crude ethyl 3-(5-chloro-7-fluoro-2-{[(methylsulfonyl)oxy]methyl}-1H-indol-1-yl)propanoate which was used for next step without further purification.

Step 5: Preparation of ethyl 3-{5-chloro-7-fluoro-2-[(2'-oxospiro[cyclopropane-1,3'-pyrrolo[2,3-c]pyridin]-1'(2'H)-yl)methyl]-1H-indol-1-yl}propanoate A mixture of ethyl 3-(5-chloro-7-fluoro-2-{[(methylsulfonyl)oxy]methyl}-1H-indol-1-yl)propanoate from Step 4, spiro[cyclopropane-1,3'-pyrrolo[2,3-c]pyridin]-2'(1'H)-one (160.2 mg, 1.0 mmol) and cesium carbonate (652 mg, 2.0 mmol) in acetonitrile (10 mL) was stirred at room temperature overnight, then at 80° C. for 1 hour. The reaction mixture was then diluted with dichloromethane and washed with water. The organic layer was dried over sodium sulfate and then concentrated in vacuo. The residue was purified by flash silica gel chromatography (gradient eluting with 0-5% methanol in dichloromethane) to afford 270 mg of the title product as a brown solid.

Example 14-1

1'-({5-Chloro-1-[3-(S-methylsulfonimidoyl)propyl]-1H-indol-2-yl}methyl)spiro[cyclopropane-1,3'-pyrrolo[2,3-c]pyridin]-2'(1'H)-one Step 1: Preparation of ethyl 1-(3-bromopropyl)-5-chloro-1H-indole-2-carboxylate

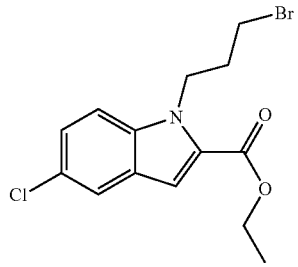 [SMILES: CCOC(=O)c1cc2cc(Cl)ccc2n1CCCBr]

A suspension of ethyl 5-chloro-1H-indole-2-carboxylate (40 g, 0.18 mol), 1,3-dibromo-propane (181 g, 0.90 mol) and potassium carbonate (49.68 g, 0.36 mol) in acetone (500 mL) was heated under reflux for 16 hours. The mixture was concentrated in vacuo to remove the solvent. The residue was diluted with water (1000 mL), and then extracted with ethyl acetate (300 mL×2). The combined organic layer was dried over sodium sulfated and then concentrated in vacuo. The residue was purified by flash silica gel chromatography (eluting with 0-10% ethyl acetate in petroleum ether) to afford 38.5 g of ethyl 1-(3-bromopropyl)-5-chloro-1H-indole-2-carboxylate.

Step 2: Preparation of ethyl 5-chloro-1-[3-(methylsulfanyl)propyl]-1H-indole-2-carboxylate

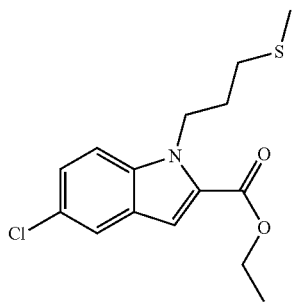 [SMILES: CCOC(=O)c1cc2cc(Cl)ccc2n1CCCSC]

A solution of ethyl 1-(3-bromopropyl)-5-chloro-1H-indole-2-carboxylate (38.5 g, 0.112 mol) and sodium methanethiolate (9.4 g, 0.135 mol) in ethanol (500 mL) was stirred at room temperature for 16 hours. The mixture was concentrated in vacuo. The residue was diluted with water (200 mL) and then extracted with ethyl acetate (100 mL×2). The combined organic layer was washed with brine (100 mL) and water (100 mL), and then dried over sodium sulfate and then concentrated in vacuo to afford 34.1 g of the crude ethyl 5-chloro-1-[3-(methylsulfanyl)propyl]-1H-indole-2-carboxylate, which was used without further purification.

Step 3: Preparation of {5-chloro-1[3-(methylsulfanyl)propyl]-1H-indol-2-yl}methanol

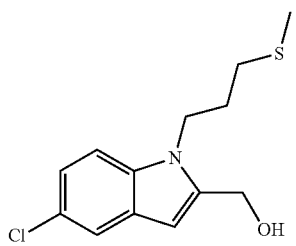 [SMILES: CSCCCn1c(CO)cc2cc(Cl)ccc21]

To a cooled suspension of lithium aluminum hydride (2.89 g, 0.076 mol) in tetrahydrofuran (250 mL) was added ethyl 5-chloro-1-[3-(methylsulfanyl)propyl]-1H-indole-2-carboxylate (15.9 g, 0.051 mol) in portions at 0° C. After the addition, the reaction mixture was stirred at room temperature for 4 hours. The reaction mixture was then cooled to 0° C. and the reaction was quenched by addition of methanol slowly. The resulting mixture was then filtered and the filter cake was washed with dichloromethane. The filtrate was concentrated in vacuo. The residue was purified by flash silica gel chromatography to afford 11.7 g of {5-chloro-1-[3-(methylsulfanyl)propyl]-1H-indol-2-yl}methanol.

Step 4: Preparation of 2-({[tert-butyl(dimethyl)silyl]oxy}methyl)-5-chloro-1-[3-(methylsulfanyl)propyl]-1H-indole

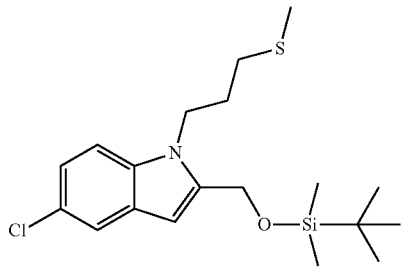 [SMILES: CSCCCn1c(CO[Si](C)(C)C(C)(C)C)cc2cc(Cl)ccc21]

To a cooled solution of {5-chloro-1-[3-(methylsulfanyl)propyl]-1H-indol-2-yl}methanol (5.38 g, 20 mmol), tert-butyl(chloro)dimethylsilane (3.24 g, 22 mmol) and 4-dimethylaminopyridine (0.244 g, 2.0 mmol) in dichloromethane (100 mL) was added triethylamine (3.03 g, 30 mmol) dropwise at 0° C. After being stirred for 15 minutes, the resulting mixture was allowed to warm to room temperature and stirred overnight. The reaction was quenched with methanol (30 mL) and the resulting mixture was concentrated in vacuo. The residue was purified by flash chromatography (eluting with 0-20% ethyl acetate in petroleum ether) to give 5.76 g of 2-({[tert-butyl(dimethyl)silyl]oxy}methyl)-5-chloro-1-[3-(methylsulfanyl)propyl]-1H-indole as a white solid.

Step 5: Preparation of 2-({[tert-butyl(dimethyl)silyl]oxy}methyl)-5-chloro-1-[3-(methylsulfinyl)propyl]-1H-indole

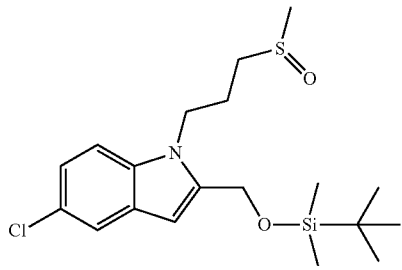 [SMILES: CS(=O)CCCn1c(CO[Si](C)(C)C(C)(C)C)cc2cc(Cl)ccc21]

To a cooled solution of 2-({[tert-butyl(dimethyl)silyl]oxy}methyl)-5-chloro-1-[3-(methylsulfanyl)propyl]-1H-indole (5.76 g, 15 mmol) in dichloromethane (150 mL) was added 3-chlorobenzene-1-carboperoxoic acid (3.3 g, 15 mmol, 85%) in portions at 0° C. The resulting mixture was then warmed naturally to room temperature and then stirred at room temperature for 16 hours. The reaction mixture was quenched by the addition of a saturated aqueous solution of sodium bicarbonate (50 mL) and a saturated aqueous solution of sodium thiosulfate (50 mL). The separated organic layer was washed with brine (50 mL), and then dried over sodium sulfate and then concentrated in vacuo. The residue was purified by flash column to afford 4.14 g of 2-({[tert-butyl(dimethyl)silyl]oxy}methyl)-5-chloro-1-[3-(methylsulfinyl)propyl]-1H-indole.

Step 6: Preparation of N-[{3-[2-({[tert-Butyl(dimethyl)silyl]oxy}methyl)-5-chloro-1H-indol-1-yl]propyl}(methyl)oxido-$\lambda^6$-sulfanylidene]-2,2,2-trifluoroacetamide

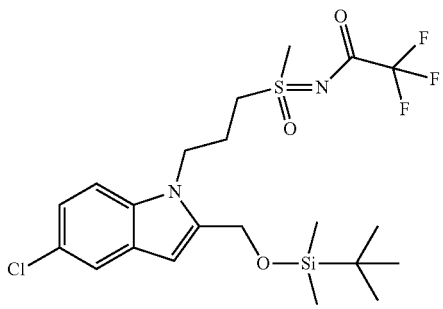 [SMILES: CC(C)(C)[Si](C)(C)OCc1cc2cc(Cl)ccc2n1CCCS(C)(=O)=NC(=O)C(F)(F)F]

To a suspension of 2-({[tert-butyl(dimethyl)silyl]oxy}methyl)-5-chloro-1-[3-(methylsulfinyl)propyl]-1H-indole (800 mg, 2.0 mmol), trifluoroacetamide (452 mg, 4.0 mmol), magnesium oxide (320 mg, 8.0 mmol), and rhodium (II) acetate (22 mg, 2.5 mol %) in dichloromethane (10 mL) was added bis(acetyloxy)(phenyl)-$\lambda^3$-iodane (966 mg, 3.0 mmol) at room temperature. The resulting mixture was stirred overnight and then concentrated in vacuo. The residue was purified by flash silica gel chromatography (gradient eluting with ethyl acetate in petroleum ether) to afford 510 mg of N-[{3-[2-({[tert-Butyl(dimethyl)silyl]oxy}methyl)-5-chloro-1H-indol-1-yl]propyl}(methyl)oxido-$\lambda^6$-sulfanylidene]-2,2,2-trifluoroacetamide. MS obsd. (ESI$^+$) [(M+H)$^+$] 511.

Step 7: Preparation of {5-chloro-1-[3-(S-methylsulfonimidoyl)propyl]-1H-indol-2-yl}methanol

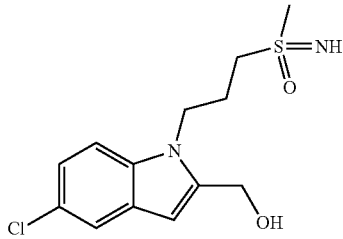 [SMILES: CS(=N)(=O)CCCn1c(CO)cc2cc(Cl)ccc21]

To a mixture of N-[{3-[2-({[tert-butyl(dimethyl)silyl]oxy}methyl)-5-chloro-1H-indol-1-yl]propyl}(methyl)oxido-$\lambda^6$-sulfanylidene]-2,2,2-trifluoroacetamide (511 mg, 1.0 mmol) in tetrahydrofuran (2 mL) was added 1% concentrated hydrochloric acid in ethanol (50 mL) dropwise. The resulting mixture was heated under reflux overnight and then concentrated in vacuo. The residue was dissolved in ethyl acetate (25 mL). The organic phase was washed with a saturated aqueous solution of sodium carbonate (25 mL) and brine (25 mL), and then dried over anhydrous sodium sulfate and then concentrated in vacuo. The residue was purified by flash silica gel chromatography (gradient eluting with ethyl acetate in petroleum ether) to afford 240 mg of {5-chloro-1-[3-(S-methylsulfonimidoyl)propyl]-1H-indol-2-yl}methanol.

177

Step 8: Preparation of 5-chloro-2-(chloromethyl)-1-[3-(S-methylsulfonimidoyl)propyl]-1H-indole

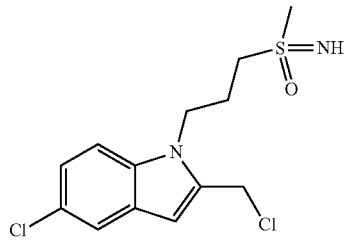 [SMILES: CS(=N)(=O)CCCn1c(CCl)cc2cc(Cl)ccc21]

To a solution of {5-chloro-1-[3-(S-methylsulfonimidoyl)propyl]-1H-indol-2-yl}methanol (200 mg, 0.67 mmol) in dichloromethane was added thionyl dichloride (96 mg, 0.80 mmol) slowly. The mixture was stirred at room temperature for 3 hours. The resulting mixture was concentrated in vacuo to afford the crude 5-chloro-2-(chloromethyl)-1-[3-(S-methylsulfonimidoyl)propyl]-1H-indole as a solid, which was used for next reaction without further purification.

Step 9: Preparation of 1'-({5-chloro-1-[3-(S-methylsulfonimidoyl)propyl]-1H-indol-2-yl}methyl)spiro[cyclopropane-1,3'-pyrrolo[2,3-c]pyridin]-2'(1'H)-one To a suspension of spiro[cyclopropane-1,3'-pyrrolo[2,3-c]pyridin]-2'(1'H)-one (115 mg, 0.66 mmol) and sodium hydride (80 mg, 1.98 mmol) in N,N-dimethylformamide (2 mL) was added 5-chloro-2-(chloromethyl)-1-[3-(S-methylsulfonimidoyl)propyl]-1H-indole (200 mg, 0.66 mmol) in N,N-dimethylformamide (1 mL) dropwise in an ice-water bath. After being stirred at room temperature for 1 hour, the reaction mixture was poured into ice-water (20 mL) and then extracted with dichloromethane (30 mL×2). The combined organic layer was dried over anhydrous sodium sulfate and then concentrated in vacuo. The residue was purified by flash silica gel chromatography (gradient eluting with 0-5% methanol in dichloromethane) to afford the title product.

Example 14-2

1'-({5-Chloro-1-[2-(S-methylsulfonimidoyl)ethyl]-1H-indol-2-yl}methyl)spiro[cyclopropane-1,3'-pyrrolo[2,3-c]pyridin]-2'(1'H)-one The title compound was prepared in analogy to Example 14-1 according to Scheme 5 by using 1,2-dibromoethane instead of 1,3-dibromo-propane.

Example 14-3

1'-({5-Chloro-1-[4-(S-methylsulfonimidoyl)butyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 14-1 according to Scheme 5 by using methyl 5-chloro-1H-pyrrolo[2,3-b]pyridine-2-carboxylate and 1,4-dibromobutane instead of ethyl 5-chloro-1H-indole-2-carboxylate and 1,3-dibromo-propane.

178

Example 14-4

1'-({5-Chloro-1-[2-(S-methylsulfonimidoyl)ethyl]-1H-pyrrolo[2,3-b]pyridin-2-yl}methyl)spiro[cyclopropane-1,3'-pyrrolo[2,3-c]pyridin]-2'(1'H)-one The title compound was prepared in analogy to Example 14-1 according to Scheme 5 by using methyl 5-chloro-1H-pyrrolo[2,3-b]pyridine-2-carboxylate and 1,2-dibromoethane instead of ethyl 5-chloro-1H-indole-2-carboxylate and 1,3-dibromo-propane.

Example 15

N-[(2-{5-Chloro-2-[(2'-oxospiro[cyclopropane-1,3'-pyrrolo[2,3-c]pyridin]-1'(2'H)-yl)methyl]-1H-indol-1-yl}ethyl)(methyl)oxido-$\lambda^6$-sulfanylidene]acetamide To a solution of 1'-({5-chloro-1-[2-(S-methylsulfonimidoyl)ethyl]-1H-indol-2-yl}methyl)spiro[cyclopropane-1,3'-pyrrolo[2,3-c]pyridin]-2'(1'H)-one (100 mg, 0.233 mmol) in dichloromethane (2 mL) was added triethylamine (42 µL, 0.303 mmol) at 0° C. and then followed by the addition of the acyl chloride (18.9 mg, 0.233 mmol) dropwise. After being stirred for about 1 hour at 0° C., the reaction mixture was warmed to room temperature and stirred overnight. The resulting mixture was then diluted with water (20 mL) and then extracted with dichloromethane (20 mL×2). The combined organic layer was dried over sodium sulfate and then concentrated in vacuo. The residue was purified by flash silica gel chromatography (gradient eluting with 0-5% methanol in dichloromethane) to afford the title product.

Example 16-1

3-{5-Chloro-2-[(2'-oxospiro[cyclopropane-1,3'-pyrrolo[2,3-c]pyridin]-1'(2'H)-yl)methyl]-1H-indol-1-yl}propanoic acid A mixture of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate (190 mg, 0.45 mmol) in tetrahydrofuran (5 mL) and 2.0 N of aqueous solution of lithium hydroxide (4 mL) was stirred at 25° C. for 3 hours. The resulting mixture was neutralized with a 3 N aqueous hydrochloric acid solution and then extracted with dichloromethane (20 mL×2). The combined organic layer was dried over anhydrous sodium sulfate and then concentrated in vacuo. The residue was purified by preparative HPLC to afford 38 mg of the title product as a light yellow solid.

Example 16-2

3-{5-Chloro-7-fluoro-2-[(2'-oxospiro[cyclopropane-1,3'-pyrrolo[2,3-c]pyridin]-1'(2'H)-yl)methyl]-1H-indol-1-yl}propanoic acid To a solution of ethyl 3-{5-chloro-7-fluoro-2-[(2'-oxospiro[cyclopropane-1,3'-pyrrolo[2,3-c]pyridin]-1'(2'H)-yl)methyl]-1H-indol-1-yl}propanoate (270 mg, 0.61 mmol) in tetrahydrofuran (10 mL) was added an aqueous solution of lithium hydroxide monohydrate (102.7 mg, 2.44 mmol, in 1 mL of water) at room temperature. After being stirred for 4 hours, the reaction was diluted with dichloromethane (10 mL) and then extracted with water (10 mL×2). The combined aqueous layer was acidified with 1 N hydrochloric acid to pH 3 and then extracted with dichloromethane (20 mL×2). The combined organic layer was dried over sodium sulfate and then concentrated in vacuo. The residue was stirred with methanol. The solid was collected by filtration and washed with methanol, and then dried in vacuo to afford 100 mg of the title product as a light yellow solid.

Example 17

Methyl 4-{5-chloro-2-[(2'-oxospiro[cyclopropane-1, 3'-pyrrolo[2,3-c]pyridin]-1'(2'H)-yl)methyl]-1H-indol-1-yl}butanoate Step 1: Preparation of ethyl 4-{5-chloro-2-[(2'-oxospiro[cyclopropane-1,3'-pyrrolo[2,3-c]pyridin]-1' (2'H)-yl)methyl]-1H-indol-1-yl}butanoate

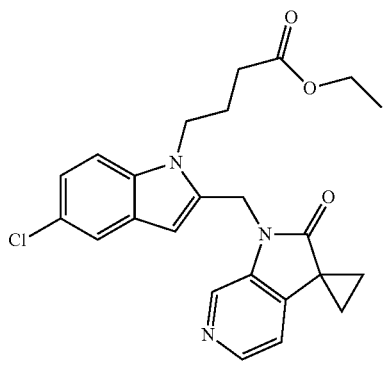 [SMILES: CCOC(=O)CCCn1c(CN2C(=O)C3(CC3)c3ccncc32)cc2cc(Cl)ccc21]

Ethyl 4-{5-chloro-2-[(2'-oxospiro[cyclopropane-1,3'-pyrrolo[2,3-c]pyridin]-1'(2'H)-yl)methyl]-1H-indol-1-yl}butanoate was prepared in analogy to Example 7-1 according to Scheme 3 by using ethyl 4-bromobutanoate instead of 3-chloro-N,N-dimethylpropane-1-sulfonamide.

Step 2: Preparation of 4-{5-chloro-2-[(2'-oxospiro [cyclopropane-1,3'-pyrrolo[2,3-c]pyridin]-1'(2'H)-yl) methyl]-1H-indol-1-yl}butanoic acid

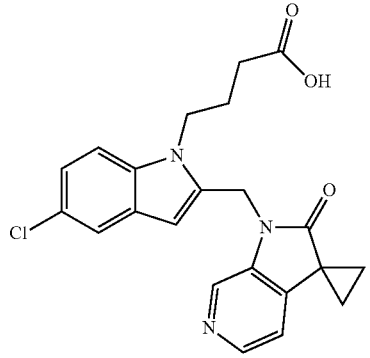 [SMILES: O=C(O)CCCn1c(CN2C(=O)C3(CC3)c3ccncc32)cc2cc(Cl)ccc21]

4-{5-Chloro-2-[(2'-oxospiro[cyclopropane-1,3'-pyrrolo[2,3-c]pyridin]-1'(2'H)-yl)methyl]-1H-indol-1-yl}butanoic acid was prepared in analogy to Example 16-1 according to Scheme 6 by using ethyl 4-{5-chloro-2-[(2'-oxospiro[cyclopropane-1,3'-pyrrolo[2,3-c]pyridin]-1'(2'H)-yl)methyl]-1H-indol-1-yl}butanoate instead of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate.

Step 3: Preparation of methyl 4-{5-chloro-2-[(2'-oxospiro[cyclopropane-1,3'-pyrrolo[2,3-c]pyridin]-1' (2'H)-yl)methyl]-1H-indol-1-yl}butanoate To a solution of 4-{5-chloro-2-[(2'-oxospiro[cyclopropane-1,3'-pyrrolo[2,3-c]pyridin]-1'(2'H)-yl)methyl]-1H-indol-1-yl}butanoic acid (41.0 mg, 0.10 mmol) in methanol (20 mL) was added thionyl chloride (0.3 mL) in an ice-water bath. The mixture was stirred at 50° C. for 2 hours and then concentrated in vacuo. The residue was purified by preparative HPLC to afford 5 mg of the title product as a white solid.

Example 18-1

3-{5-Chloro-2-[(2'-oxospiro[cyclopropane-1,3'-pyrrolo[2,3-c]pyridin]-1'(2'H)-yl)methyl]-1H-indol-1-yl}propanamide A mixture of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate (190 mg, 0.45 mmol) in methanol (10 mL) and 7 N solution of ammonia in methanol (5 mL) was heated with stirring at 80° C. for 16 hours. The mixture was concentrated in vacuo. The residue was purified by preparative HPLC to afford 16 mg of the title product as a white solid.

Example 18-2

3-{5-Chloro-2-[(2'-oxospiro[cyclopropane-1,3'-pyrrolo[2,3-b]pyridin]-1'(2'H)-yl)methyl]-1H-indol-1-yl}propanamide Step 1: Preparation of methyl 3-{5-chloro-2-[(2'-oxospiro[cyclopropane-1,3'-pyrrolo[2,3-b]pyridin]-1' (2'H)-yl)methyl]-1H-indol-1-yl}propanoate

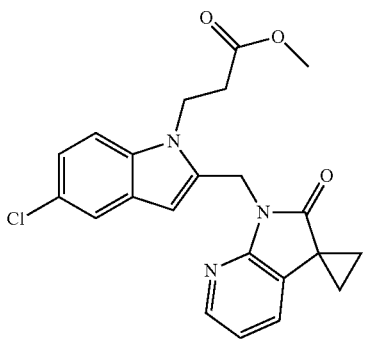 [SMILES: COC(=O)CCn1c(CN2C(=O)C3(CC3)c3cccnc32)cc2cc(Cl)ccc21]

Methyl 3-{5-chloro-2-[(2'-oxospiro[cyclopropane-1,3'-pyrrolo[2,3-b]pyridin]-1'(2'H)-yl)methyl]-1H-indol-1-yl}propanoate was prepared in analogy to Example 6 by using ethyl 5-chloro-1H-indole-2-carboxylate, spiro[cyclopropane-1,3'-pyrrolo[2,3-b]pyridin]-2'(1'H)-one and methyl prop-2-enoate instead of methyl 5-chloro-1H-pyrrolo[3,2-b]pyridine-2-carboxylate, spiro[cyclopropane-1,3'-pyrrolo[2,3-c]pyridin]-2'(1'H)-one and (ethylsulfonyl)ethene.

Step 2: Preparation of 3-{5-chloro-2-[(2'-oxospiro [cyclopropane-1,3'-pyrrolo[2,3-b]pyridin]-1'(2'H)-yl) methyl]-1H-indol-1-yl}propanamide The title compound was prepared in analogy to Example 18-1 according to Scheme 6 by using methyl 3-{5-chloro-2-[(2'-oxospiro[cyclopropane-1,3'-pyrrolo[2,3-b]pyridin]-1' (2'H)-yl)methyl]-1H-indol-1-yl}propanoate instead of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate.

Example 18-3

4-{5-Chloro-2-[(2'-oxospiro[cyclopropane-1,3'-pyrrolo[2,3-c]pyridin]-1'(2'H)-yl)methyl]-1H-indol-1-yl}butanamide The title compound was prepared in analogy to Example 18-1 according to Scheme 6 by using methyl 4-{5-chloro-2-[(2'-oxospiro[cyclopropane-1,3'-pyrrolo[2,3-c]pyridin]-1' (2'H)-yl)methyl]-1H-indol-1-yl}butanoate instead of ethyl 3-{5-chloro-2-[(2'-oxospiro[cyclopropane-1,3'-pyrrolo[2,3-c]pyridin]-1'(2'H)-yl)methyl]-1H-indol-1-yl}propanoate.

Example 19-1

3-{5-Chloro-2-[(2'-oxospiro[cyclopropane-1,3'-pyrrolo[2,3-c]pyridin]-1'(2'H)-yl)methyl]-1H-indol-1-yl}-N-(cyclopropylsulfonyl)propanamide A mixture of 3-{5-chloro-2-[(2'-oxospiro[cyclopropane-1,3'-pyrrolo[2,3-c]pyridin]-1'(2'H)-yl)methyl]-1H-indol-1-yl}propanoic acid (200 mg, 0.5 mmol), cyclopropanesulfonamide (121 mg, 1.0 mmol), N-[3-(dimethylamino)propyl]-N'-ethylcarbodiimide hydrochloride (192 mg, 1.0 mmol), and 4-dimethylamiopryidine (13 mg, 0.1 mmol) in dichloromethane (6 mL) was stirred at room temperature for 16 hours. The mixture was concentrated in vacuo. The residue was purified by preparative HPLC to afford 12 mg of the product as a light yellow solid.

Example 19-2

3-{5-Chloro-2-[(2'-oxospiro[cyclopropane-1,3'-pyrrolo[2,3-c]pyridin]-1'(2'H)-yl)methyl]-1H-indol-1-yl}-N-(cyclopropylsulfonyl)-N-methylpropanamide The title compound was prepared in analogy to Example 19-1 according to Scheme 6 by using N-methyl(cyclopropane)methanesulfonamide instead of cyclopropanesulfonamide.

Example 19-3

3-{5-Chloro-2-[(2'-oxospiro[cyclopropane-1,3'-pyrrolo[2,3-c]pyridin]-1'(2'H)-yl)methyl]-1H-indol-1-yl}-N-methyl-N-(methylsulfonyl)propanamide The title compound was prepared in analogy to Example 19-1 according to Scheme 6 by using N-methylmethanesulfonamide instead of cyclopropanesulfonamide.

Example 20

3-(2-{5-Chloro-2-[(2'-oxospiro[cyclopropane-1,3'-pyrrolo[2,3-c]pyridin]-1'(2'H)-yl)methyl]-1H-indol-1-yl}ethyl)imidazolidine-2,4-dione Step 1: Preparation of 1'-[(5-chloro-1H-indol-2-yl) methyl]spiro[cyclopropane-1,3'-pyrrolo[2,3-c]pyridin]-2'(1'H)-one

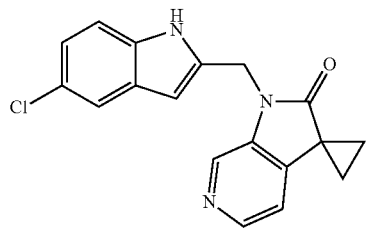 [SMILES: O=C1N(Cc2cc3cc(Cl)ccc3[nH]2)c2cnccc2C12CC2]

1'-[(5-Chloro-1H-indol-2-yl)methyl]spiro[cyclopropane-1,3'-pyrrolo[2,3-c]pyridin]-2'(1'H)-one was prepared in analogy to 1'-[(5-chloro-1H-pyrrolo[3,2-b]pyridin-2-yl) methyl]spiro[cyclopropane-1,3'-pyrrolo[2,3-c]pyridin]-2' (1'1)-one in Example 6 according to Scheme 3 by using ethyl 5-chloro-1H-indole-2-carboxylate instead of methyl 5-chloro-1H-pyrrolo[3,2-b]pyridine-2-carboxylate.

Step 2: Preparation of 1'-{[1-(2-bromoethyl)-5-chloro-1H-indol-2-yl]methyl}spiro[cyclopropane-1, 3'-pyrrolo[2,3-c]pyridin]-2'(1'H)-one

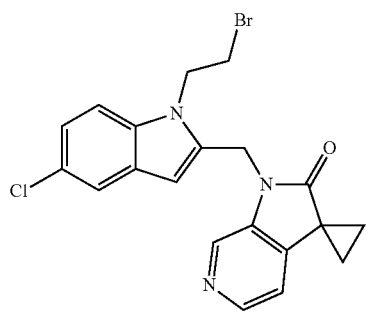 [SMILES: O=C1N(Cc2cc3cc(Cl)ccc3n2CCBr)c2cnccc2C12CC2]

A mixture of 1'-[(5-chloro-1H-indol-2-yl)methyl]spiro [cyclopropane-1,3'-pyrrolo[2,3-c]pyridin]-2'(1'H)-one (550 mg, 1.7 mmol), 1,2-dibromoethane (1.6 g, 8.5 mmol) and potassium carbonate (1.2 g, 8.5 mmol) in acetone (100 mL) was stirred at 70° C. for 96 hours. The suspension was filtered and the filtrate was concentrated in vacuo. The residue was purified by flash silica gel chromatography (eluting with 33% ethyl acetate in petroleum ether) to afford 0.2 g of 1'-{[1-(2-bromoethyl)-5-chloro-1H-indol-2-yl] methyl}spiro[cyclopropane-1,3'-pyrrolo[2,3-c]pyridin]-2' (1'H)-one.

Step 3: Preparation of 3-(2-{5-chloro-2-[(2'-oxospiro[cyclopropane-1,3'-pyrrolo[2,3-c]pyridin]-1' (2'H)-yl)methyl]-1H-indol-1-yl}ethyl)imidazolidine-2,4-dione A mixture of 1'-{[1-(2-bromoethyl)-5-chloro-1H-indol-2-yl]methyl}spiro[cyclopropane-1,3'-pyrrolo[2,3-c]pyridin]-

2'(1'H)-one (50 mg, 0.12 mmol), imidazolidine-2,4-dione (58 mg, 0.58 mmol), tetrabutylazanium fluoride (3.2 mg) and potassium carbonate (80 mg, 0.58 mmol) in tetrahydrofuran (8 mL) was stirred at room temperature for 72 hours. The reaction mixture was filtered and the filtrate was concentrated in vacuo. The residue was purified by preparative HPLC to afford 2.0 mg of the title product.

Example 21

1'-[(5-Chloro-1-{3-[(3R)-3-hydroxypyrrolidin-1-yl]propyl}-1H-indol-2-yl)methyl]spiro[cyclopropane-1,3'-pyrrolo[2,3-c]pyridin]-2'(1'H)-one Step 1: Preparation of 1'-{[1-(3-bromopropyl)-5-chloro-1H-indol-2-yl]methyl}spiro[cyclopropane-1,3'-pyrrolo[2,3-c]pyridin]-2'(1'H)-one

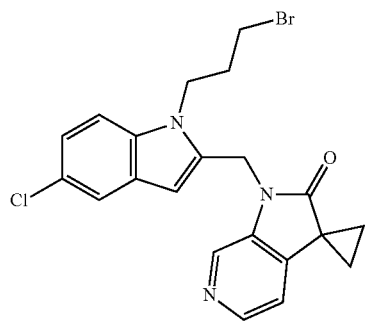 [SMILES: O=C1N(Cc2cc3cc(Cl)ccc3n2CCCBr)c2cnccc2C12CC2]

A mixture of 1'-[(5-chloro-1H-indol-2-yl)methyl]spiro[cyclopropane-1,3'-pyrrolo[2,3-c]pyridin]-2'(1'H)-one (50 mg, 0.15 mmol), cesium carbonate (250 mg, 0.77 mmol) and 1,3-dibromo-propane (1.0 g, 5.0 mmol) in acetonitrile (4 mL) was heated with stirring at 80° C. for 1 hour, and then the reaction mixture was concentrated in vacuo. The residue was purified by flash silica gel chromatography (eluting with 33% ethyl acetate in petroleum ether) to afford 70 mg of 1'-{[1-(3-bromopropyl)-5-chloro-1H-indol-2-yl]methyl}spiro[cyclopropane-1,3'-pyrrolo[2,3-c]pyridin]-2'(1'H)-one.

Step 2: Preparation of 1'-[(5-chloro-1-{3-[(3R)-3-hydroxypyrrolidin-1-yl]propyl}-1H-indol-2-yl)methyl]spiro[cyclopropane-1,3'-pyrrolo[2,3-c]pyridin]-2'(1'H)-one A mixture of 1'-{[1-(3-bromopropyl)-5-chloro-1H-indol-2-yl]methyl}spiro[cyclopropane-1,3'-pyrrolo[2,3-c]pyridin]-2'(1'H)-one (70 mg, 016 mmol), cesium carbonate (250 mg) and (3R)-pyrrolidin-3-ol (150 mg, 1.7 mmol) in N,N-dimethylformamide (4 mL) was heated with stirring at 80° C. for 1 hour, and then the reaction mixture was concentrated in vacuo. The residue was purified by preparative HPLC to afford 2.0 mg of the title product.

Example 22-1

1'-({5-Chloro-1-[3-(ethylsulfonyl)propyl]-1H-indol-2-yl}methyl)spiro[cyclopropane-1,3'-pyrrolo[2,3-c]pyridin]-2'(1'H)-one Step 1: Preparation of ethyl 5-chloro-1-[3-(ethylsulfonyl)propyl]-1H-indole-2-carboxylate

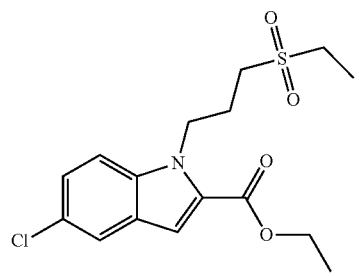 [SMILES: CCOC(=O)c1cc2cc(Cl)ccc2n1CCCS(=O)(=O)CC]

A mixture of ethyl 1-(3-bromopropyl)-5-chloro-1H-indole-2-carboxylate (1.0 g, 2.9 mmol) and sodium ethanesulfinate (1.0 g, 8.7 mmol) in N,N-dimethylformamide (10 mL) was heated with stirring at 80° C. overnight. The reaction mixture was cooled and then diluted with ethyl acetate (40 mL), and then washed with brine. The organic layer was dried over sodium sulfate and then concentrated in vacuo. The residue was purified by flash silica gel chromatography (eluting with 33% ethyl acetate in petroleum ether) to afford 680 mg of ethyl 5-chloro-1-[3-(ethylsulfonyl)propyl]-1H-indole-2-carboxylate.

Step 2: Preparation of {5-chloro-1-[3-(ethylsulfonyl)propyl]-1H-indol-2-yl}methanol

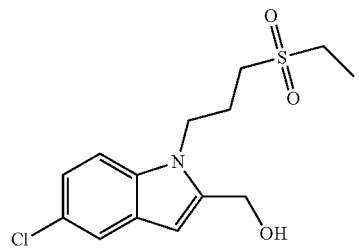 [SMILES: CCS(=O)(=O)CCCn1c(CO)cc2cc(Cl)ccc21]

To a slurry of lithium aluminium hydride (96 mg, 2.5 mmol) in anhydrous tetrahydrofuran (5 mL), which was cooled to 0° C., was added a solution of ethyl 5-chloro-1-[3-(ethylsulfonyl)propyl]-1H-indole-2-carboxylate (600 mg, 1.68 mmol) in anhydrous tetrahydrofuran (10 mL) dropwise. After being stirred at 0° C. for 1 hour, the reaction was quenched by addition of 1N hydrochloric acid (10 mL) slowly. After being stirred for 10 minutes, the mixture was basified by the addition of a saturated aqueous solution of sodium bicarbonate (10 mL) and then filtered through a celite pad. The filter cake was washed with dichloromethane (50 mL). The organic layer was separated and the aqueous layer was extracted with dichloromethane (20 mL×3). The combined organic layer was dried over sodium sulfate and then concentrated in vacuo. The residue was purified by flash silica gel chromatography (eluting with 0-50% ethyl acetate in petroleum ether) to afford 420 mg of {5-chloro-1-[3-(ethylsulfonyl)propyl]-1H-indol-2-yl}methanol.

Step 3: Preparation of {5-chloro-1-[3-(ethylsulfonyl)propyl]-1H-indol-2-yl}methyl methanesulfonate

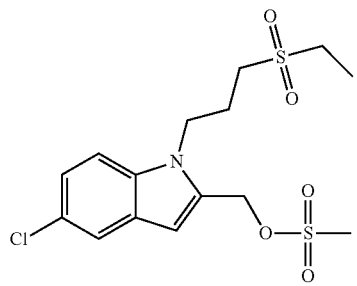 [SMILES: CCS(=O)(=O)CCCn1c(COS(C)(=O)=O)cc2cc(Cl)ccc21]

To a solution of {5-chloro-1-[3-(ethylsulfonyl)propyl]-1H-indol-2-yl}methanol (400 mg, 1.27 mmol) in dichloromethane (10 mL) was added methanesulfonyl chloride (219 mg, 1.9 mmol) and triethylamine (0.353 ml, 2.54 mmol) slowly at 0° C. The mixture was stirred at 0° C. for 2 hours and then diluted with dichloromethane (10 mL). The organic layer was washed with water, and then dried over sodium sulfate and then concentrated in vacuo to afford 415 mg of the crude {5-chloro-1-[3-(ethylsulfonyl)propyl]-1H-indol-2-yl}methyl methanesulfonate which was used for the next step without any purification.

Step 4: Preparation of 1'-({5-chloro-1-[3-(ethylsulfonyl)propyl]-1H-indol-2-yl}methyl)spiro[cyclopropane-1,3'-pyrrolo[2,3-c]pyridin]-2'(1'H)-one A mixture of {5-chloro-1-[3-(ethylsulfonyl)propyl]-1H-indol-2-yl}methyl methanesulfonate (415 mg, the crude product from the Step 3), spiro[cyclopropane-1,3'-pyrrolo[2,3-c]pyridin]-2'(1'H)-one (203 mg, 1.27 mmol) and 2-(tert-butylimino)-N,N-diethyl-1,3-dimethyl-1,3,2λ$^5$-diazaphosphinan-2-amine (522 mg, 1.91 mmol) in acetonitrile (10 mL) was heated with stirring at 80° C. for 30 minutes. The resulting mixture was concentrated in vacuo. The residue was dissolved in ethyl acetate (30 mL). The organic layer was washed with water, and then dried over sodium sulfate and then concentrated in vacuo. The residue was purified by preparative HPLC to afford 80 mg of the title product.

Example 22-2

1'-({5-Chloro-1-[3-(methylsulfonyl)propyl]-1H-indol-2-yl}methyl)spiro[cyclopropane-1,3'-pyrrolo[2,3-b]pyridin]-2'(1'H)-one The title compound was prepared in analogy to Example 22-1 according to Scheme 8 by using spiro[cyclopropane-1,3'-pyrrolo[2,3-b]pyridin]-2'(1'H)-one instead of spiro[cyclopropane-1,3'-pyrrolo[2,3-c]pyridin]-2'(1'H)-one.

Example 22-3

1'-({5-Chloro-1-[3-(methylsulfonyl)propyl]-1H-indol-2-yl}methyl)spiro[cyclopropane-1,3'-pyrrolo[2,3-c]pyridin]-2'(1'H)-one The title compound was prepared in analogy to Example 22-1 according to Scheme 8 by using spiro[cyclopropane-1,3'-pyrrolo[2,3-c]pyridin]-2'(1'H)-one instead of spiro[cyclopropane-1,3'-pyrrolo[2,3-c]pyridin]-2'(1'H)-one.

Example 23

1'-({5-Chloro-1-[3-(ethylsulfonyl)propyl]-1H-pyrrolo[2,3-b]pyridin-2-yl}methyl)spiro[cyclopropane-1,3'-pyrrolo[2,3-c]pyridin]-2'(1'H)-one Step 1: Preparation of {5-chloro-1-[3-(ethylsulfonyl)propyl]-1H-pyrrolo[2,3-b]pyridin-2-yl}methanol

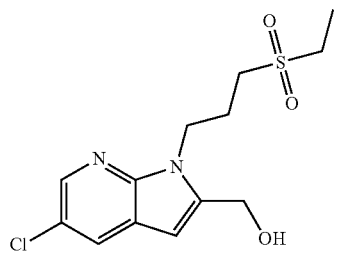 [SMILES: CCS(=O)(=O)CCCn1c(CO)cc2cc(Cl)cnc21]

{5-Chloro-1-[3-(ethylsulfonyl)propyl]-1H-pyrrolo[2,3-b]pyridin-2-yl}methanol was prepare in analogy to {5-chloro-1-[3-(ethylsulfonyl)propyl]-1H-indol-2-yl}methanol in Example 22-1 by using methyl 5-chloro-1H-pyrrolo[2,3-b]pyridine-2-carboxylate instead of ethyl 5-chloro-1H-indole-2-carboxylate.

Step 2: Preparation of 5-chloro-2-(chloromethyl)-1-[3-(ethylsulfonyl)propyl]-1H-pyrrolo[2,3-b]pyridine

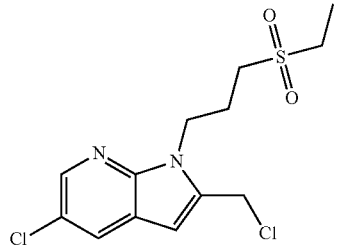 [SMILES: CCS(=O)(=O)CCCn1c(CCl)cc2cc(Cl)cnc21]

A solution of {5-chloro-1-[3-(ethylsulfonyl)propyl]-1H-pyrrolo[2,3-b]pyridin-2-yl}methanol (474 mg, 1.5 mmol) in anhydrous dichloromethane was added thionyl dichloride (155 μL, 3.0 mmol). The reaction mixture was stirred at room temperature for 2 hours. The resulting mixture was concentrated in vacuo. The residue was dissolved in ethyl acetate (20 mL). The solution was washed with a saturated aqueous solution of sodium bicarbonate (20 mL). The organic layer was dried over anhydrous sodium sulfate and then concentrated in vacuo to afford 427 mg of 5-chloro-2-(chloromethyl)-1-[3-(ethylsulfonyl)propyl]-1H-pyrrolo[2,3-b]pyridine as a yellow solid which was used for the next step without any purification.

Step 3: Preparation of 1'-({5-chloro-1-[3-(ethylsulfonyl)propyl]-1H-pyrrolo[2,3-b]pyridin-2-yl}methyl)spiro[cyclopropane-1,3'-pyrrolo[2,3-c]pyridin]-2'(1'H)-one To a cooled solution of 5-chloro-2-(chloromethyl)-1-[3-(ethylsulfonyl)propyl]-1H-pyrrolo[2,3-b]pyridine and spiro

[cyclopropane-1,3'-pyrrolo[2,3-c]pyridin]-2'(1'H)-one (240 mg 1.5 mmol) in anhydrous N,N-dimethylformamide (10 mL) at 0° C. was added sodium hydride (90 mg, 2.25 mmol) in portions. The reaction mixture was stirred for 3 hours while the temperature was raised to room temperature naturally. The resulting mixture was diluted with brine (30 mL) and then extracted with ethyl acetate (30 mL×3). The combined organic layer was washed with brine (40 mL×2), and then dried over anhydrous sodium sulfate and then concentrated in vacuo. The residue was purified by preparative HPLC to afford 318.6 mg of the title product as a white solid.

Example 24-1

1'-({5-Chloro-1-[2-(piperazin-1-yl)ethyl]-1H-indol-2-yl}methyl)spiro[cyclopropane-1,3'-pyrrolo[2,3-c]pyridin]-2'(1'H)-one Step 1: Preparation of tert-butyl 4-(2-{5-chloro-2-[(2'-oxospiro[cyclopropane-1,3'-pyrrolo[2,3-c]pyridin]-1'(2'H)-yl)methyl]-1H-indol-1-yl}ethyl)piperazine-1-carboxylate

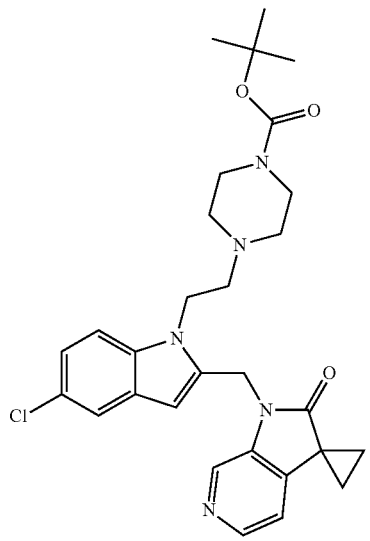 [SMILES: CC(C)(C)OC(=O)N1CCN(CCn2c(CN3C(=O)C4(CC4)c4ccncc43)cc3cc(Cl)ccc32)CC1]

To a solution of tert-butyl 4-(2-bromoethyl)piperazine-1-carboxylate (130 mg, 0.44 mmol) in acetone (20 mL) was added 1'-[(5-chloro-1H-indol-2-yl)methyl]spiro[cyclopropane-1,3'-pyrrolo[2,3-c]pyridin]-2'(1'H)-one (142 mg, 0.44 mmol) and potassium carbonate (182 mg, 1.32 mmol). The reaction was heated under reflux for 48 hours. The reaction mixture was filtered and the filtrate was concentrated in vacuo. The residue was purified by preparative TLC (10% methanol in dichloromethane) to afford 130 mg of tert-butyl 4-(2-{5-chloro-2-[(2'-oxospiro[cyclopropane-1,3'-pyrrolo[2,3-c]pyridin]-1'(2'H)-yl)methyl]-1H-indol-1-yl}ethyl)piperazine-1-carboxylate.

Step 2: Preparation of 1'-({5-chloro-1-[2-(piperazin-1-yl)ethyl]-1H-indol-2-yl}methyl)spiro[cyclopropane-1,3'-pyrrolo[2,3-c]pyridin]-2'(1'H)-one To a cooled solution of tert-butyl 4-(2-{5-chloro-2-[(2'-oxospiro[cyclopropane-1,3'-pyrrolo[2,3-c]pyridin]-1'(2'H)-yl)methyl]-1H-indol-1-yl}ethyl)piperazine-1-carboxylate (130 mg, 0.24 mmol) in ethyl acetate (10 mL) was added hydrochloride solution in ethyl acetate (100 mL) at 0° C. After being stirred at room temperature overnight, the reaction mixture was concentrated in vacuo. The residue was purified by preparative HPLC. The combined eluent from preparative HPLC was concentrated in vacuo and then basified with sodium bicarbonate to pH>7. The residue was extracted by dichloromethane (20 mL×3). The combined organic layer was dried over sodium sulfate, and then filtered and then concentrated in vacuo. The residue was added a few drops of methanol and 1 mL of water, and then was dried by lyophilization to afford 19.1 mg of the title product.

Example 24-2

1'-({5-Chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one Step 1: Preparation of tert-butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate

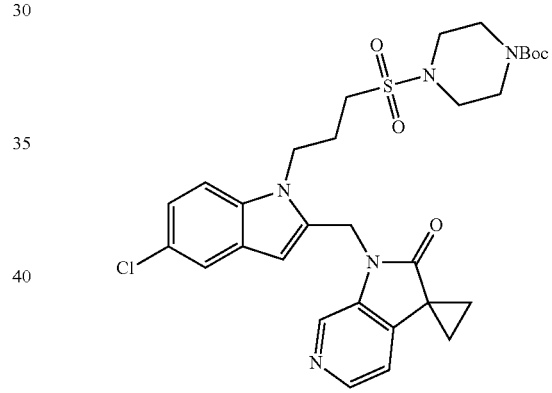

tert-Butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate was prepared in analogy to Example 7-1 according to Scheme 3 by using tert-butyl 4-[(3-chloropropyl)sulfonyl]piperazine-1-carboxylate instead of 3-chloro-N,N-dimethylpropane-1-sulfonamide.

Step 2: Preparation of 1'-({5-chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one A solution of tert-butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate (31.2 mg, 0.05 mmol) in dichloromethane (2 mL) was added trifluoroacetic acid (0.5 mL). The reaction mixture was stirred at room temperature for 2 hours. The resulting mixture was concentrated in vacuo. The residue was purified by preparative HPLC to afford 10 mg of 1'-({5-chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one.

Example 24-3

1'-[(5-Chloro-1-{3-[(1R,4R)-2,5-diazabicyclo[2.2.1]hept-2-ylsulfonyl]propyl}-1H-indol-2-yl)methyl]spiro[cyclopropane-1,3'-pyrrolo[2,3-c]pyridin]-2'(1'H)-one Step 1: Preparation of tert-butyl(1R,4R)-5-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]-2,5-diazabicyclo[2.2.1]heptane-2-carboxylate

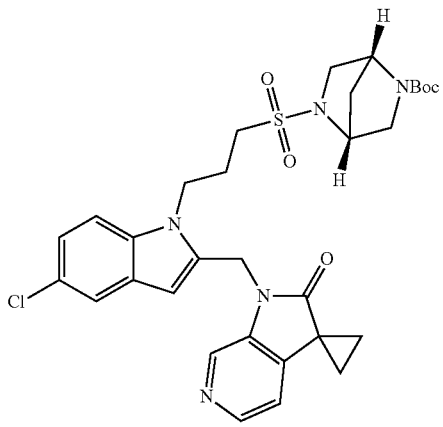 [SMILES: CC(C)(C)OC(=O)N1C[C@H]2C[C@@H]1CN2S(=O)(=O)CCCn1c(CN2C(=O)C3(CC3)c3ccncc32)cc2cc(Cl)ccc21]

tert-Butyl(1R,4R)-5-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]-2,5-diazabicyclo[2.2.1]heptane-2-carboxylate was prepared in analogy to Example 7-1 according to Scheme 3 by using tert-butyl(1R,4R)-5-[(3-chloropropyl)sulfonyl]-2,5-diazabicyclo[2.2.1]heptane-2-carboxylate instead of 3-chloro-N,N-dimethylpropane-1-sulfonamide.

Step 2: Preparation of 1'-[(5-chloro-1-{3-[(1R,4R)-2,5-diazabicyclo[2.2.1]hept-2-ylsulfonyl]propyl}-1H-indol-2-yl)methyl]spiro[cyclopropane-1,3'-pyrrolo[2,3-c]pyridin]-2'(1'H)-one The title compound was prepared in analogy to Example 24-2 according to Scheme 9 by using tert-butyl(1R,4R)-5-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]-2,5-diazabicyclo[2.2.1]heptane-2-carboxylate instead of tert-butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate.

Example 24-4

1'-({5-Chloro-1-[3-(2-oxopiperazin-1-yl)propyl]-1H-indol-2-yl}methyl)spiro[cyclopropane-1,3'-pyrrolo[2,3-c]pyridin]-2'(1'H)-one Step 1: Preparation of tert-butyl 4-(3-{5-chloro-2-[(2'-oxospiro[cyclopropane-1,3'-pyrrolo[2,3-c]pyridin]-1'(2'H)-yl)methyl]-1H-indol-1-yl}propyl)-3-oxopiperazine-1-carboxylate

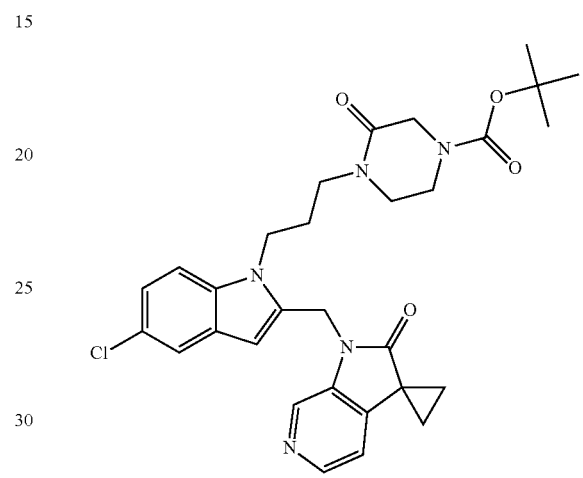

A mixture of tert-butyl 3-oxopiperazine-1-carboxylate (240 mg, 1.2 mmol), 1,3-dibromopropane (264 mg, 1.2 mmol) and potassium tert-butoxide (172 mg, 1.8 mmol) in N,N-dimethylformamide (2 mL) was stirred at room temperature for 1 hour. Then 1'-[(5-chloro-1H-indol-2-yl)methyl]spiro[cyclopropane-1,3'-pyrrolo[2,3-c]pyridin]-2'(1'14)-one (96.9 mg, 0.3 mmol) and another batch of potassium tert-butoxide(115 mg, 1.2 mmol) were added to the reaction mixture. The resulting mixture was stirred at room temperature for another one hour. The reaction mixture was diluted with water (10 mL) and then extracted with ethyl acetate (20 mL). The organic layer was dried over sodium sulfate and then concentrated in vacuo to afford the crude tert-butyl 4-(3-{5-chloro-2-[(2'-oxospiro[cyclopropane-1,3'-pyrrolo[2,3-c]pyridin]-1'(2'H)-yl)methyl]-1H-indol-1-yl}propyl)-3-oxopiperazine-1-carboxylate which was used for the next step without any purification.

Step 2: Preparation of 1'-({5-chloro-1-[3-(2-oxopiperazin-1-yl)propyl]-1H-indol-2-yl}methyl)spiro[cyclopropane-1,3'-pyrrolo[2,3-c]pyridin]-2'(1'H)-one The title compound was prepared in analogy to Example 24-2 according to Scheme 9 by using tert-butyl 4-(3-{5-chloro-2-[(2'-oxospiro[cyclopropane-1,3'-pyrrolo[2,3-c]pyridin]-1'(2'H)-yl)methyl]-1H-indol-1-yl}propyl)-3-oxopiperazine-1-carboxylate instead of tert-butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate.

Example 24-5

1'-{[1-(2-Aminoethyl)-5-chloro-1H-indol-2-yl]methyl}spiro[cyclopropane-1,3'-pyrrolo[2,3-c]pyridin]-2'(1'H)-one

Step 1: Preparation of tert-butyl(2-{5-chloro-2-[(2'-oxospiro[cyclopropane-1,3'-pyrrolo[2,3-c]pyridin]-1'(2'H)-yl)methyl]-1H-indol-1-yl}ethyl)carbamate

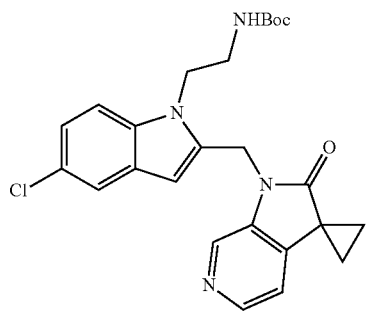 [SMILES: CC(C)(C)OC(=O)NCCn1c(CN2C(=O)C3(CC3)c3ccncc32)cc2cc(Cl)ccc21]

tert-Butyl(2-{5-chloro-2-[(2'-oxospiro[cyclopropane-1,3'-pyrrolo[2,3-c]pyridin]-1'(2'H)-yl)methyl]-1H-indol-1-yl}ethyl)carbamate was prepared in analogy to Example 7-1 in Scheme 3 by using tert-butyl(2-bromoethyl)carbamate instead of 3-chloro-N,N-dimethylpropane-1-sulfonamide.

Step 2: Preparation of 1'-{[1-(2-aminoethyl)-5-chloro-1H-indol-2-yl]methyl}spiro[cyclopropane-1,3'-pyrrolo[2,3-c]pyridin]-2'(1'H)-one The title compound was prepared in analogy to Example 24-2 according to Scheme 9 by using tert-butyl(2-{5-chloro-2-[(2'-oxospiro[cyclopropane-1,3'-pyrrolo[2,3-c]pyridin]-1'(2'H)-yl)methyl]-1H-indol-1-yl}ethyl)carbamate instead of tert-butyl 4-[(3-{5-chloro-2-[(2'-oxospiro[cyclopropane-1,3'-pyrrolo[2,3-c]pyridin]-1'(2'H)-yl)methyl]-1H-indol-1-yl}propyl)sulfonyl]piperazine-1-carboxylate.

Example 25-1

3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide To a flask containing cooled concentrated sulfuric acid (2 mL) was added N-benzyl-3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide (60 mg, 0.11 mol) at 0° C. The resulting mixture was stirred at 0° C. for 15 minutes, then basified with 4 N aqueous solution of sodium hydroxide to pH>7 at 0° C. The mixture was extracted with ethyl acetate (20 mL). The organic layer was dried over sodium sulfate and then concentrated in vacuo. The residue was purified by preparative HPLC to afford the title product.

Example 25-2

3-{5-Chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide

Step 1: Preparation of N-benzyl-3-{5-chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide

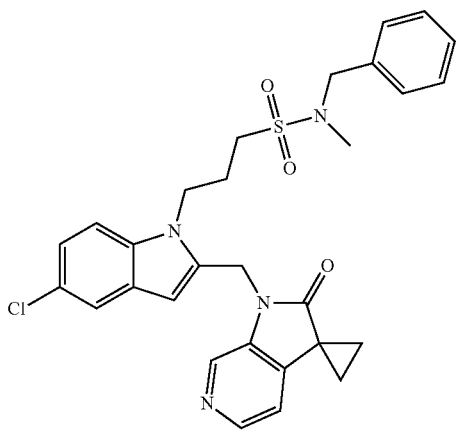 [SMILES: CN(Cc1ccccc1)S(=O)(=O)CCCn1c(CN2C(=O)C3(CC3)c3ccncc32)cc2cc(Cl)ccc21]

N-Benzyl-3-{5-chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide was prepared in analogy to Example 4-8 according to Scheme 2 by using ethyl 5-chloro-1H-indole-2-carboxylate instead of methyl 5-chloro-1H-pyrrolo[2,3-b]pyridine-2-carboxylate.

Step 2: Preparation of 3-{5-chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide The title compound was prepared in analogy to Example 25-1 according to Scheme 10 by using N-benzyl-3-{5-chloro-2-[(2'-oxospiro[cyclopropane-1,3'-pyrrolo[2,3-c]pyridin]-1'(2'H)-yl)methyl]-1H-indol-1-yl}-N-methylpropane-1-sulfonamide instead of N-benzyl-3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide.

Example 25-3

3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propane-1-sulfonamide Step 1: Preparation of 3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-bis(4-methoxybenzyl)propane-1-sulfonamide

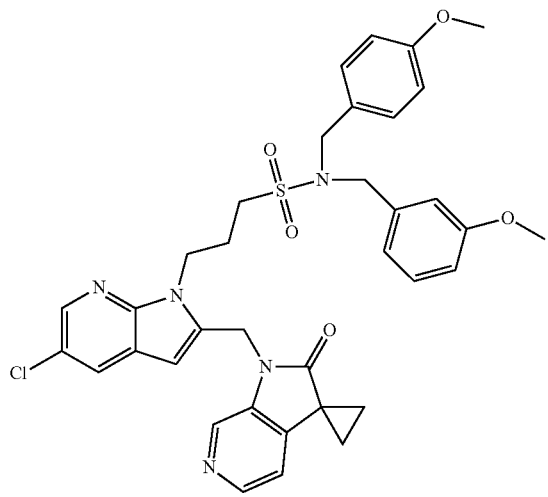 [SMILES: COc1ccc(CN(Cc2cccc(OC)c2)S(=O)(=O)CCCn2c(CN3C(=O)C4(CC4)c4ccncc43)cc3cc(Cl)cnc32)cc1]

3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-bis(4-methoxybenzyl)propane-1-sulfonamide was prepared in analogy to Example 4-8 according to Scheme 2 by using N,N-bis(4-methoxybenzyl)propane-1-sulfonamide instead of N-benzyl-3-chloro-N-methylpropane-1-sulfonamide.

Step 2: Preparation of 3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propane-1-sulfonamide A mixture of 3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-bis(4-methoxybenzyl)propane-1-sulfonamide (300 mg, 0.43 mmol) and trifluoroacetic acid (3 mL) was stirred at room temperature for 3 hours. The resulting mixture was basified with 4 N aqueous solution of sodium hydroxide to pH>7 at 0° C. and then extracted with ethyl acetate (20 mL). The organic layer was dried over sodium sulfate and then concentrated in vacuo. The residue was purified by preparative HPLC to afford the title product.

Example 26-1

1'-({1-[2-(4-Acetylpiperazin-1-yl)ethyl]-5-chloro-1H-indol-2-yl}methyl)spiro[cyclopropane-1,3'-pyrrolo[2,3-c]pyridin]-2'(1'H)-one To a cooled solution of 1'-({5-chloro-1-[2-(piperazin-1-yl)ethyl]-1H-indol-2-yl}methyl)spiro[cyclopropane-1,3'-pyrrolo[2,3-c]pyridin]-2'(1'H)-one (100 mg, 0.23 mmol) in dichloromethane (20 mL) was added triethylamine (70 mg, 0.69 mmol) and acetic anhydride (70 mg, 0.69 mmol) at 0° C. After being stirred at room temperature overnight, the reaction mixture was washed with water (20 mL). The organic layer was dried over sodium sulfate and then concentrated in vacuo. The residue was purified by preparative HPLC to afford 16.1 mg of the title product.

Example 26-2

N-[(3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propyl)sulfonyl]acetamide A mixture of 3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}propane-1-sulfonamide (50 mg, 0.11 mmol), acetic anhydride (45 mg, 0.44 mmol) and ethyldiisopropylamine (57 mg, 0.44 mmol) in N,N-dimethylformamide (4 mL) was heated with stirring at 80° C. for 4 hours. The resulting mixture was purified by preparative HPLC to afford 16.1 mg of the title product.

Example 26-3

N-(2-{5-Chloro-2-[(2'-oxospiro[cyclopropane-1,3'-pyrrolo[2,3-c]pyridin]-1'(2'H)-yl)methyl]-1H-indol-1-yl}ethyl)acetamide To a cooled solution of 1'-{[1-(2-aminoethyl)-5-chloro-1H-indol-2-yl]methyl}spiro[cyclopropane-1,3'-pyrrolo[2,3-c]pyridin]-2'(1'H)-one (100 mg, 0.27 mmol) and triethylamine (50 mg, 0.50 mmol) in N,N-dimethylformamide (5 mL) was added acetyl chloride (23.4 mg, 0.30 mmol) at 0° C. After being stirred at room temperature for 2 hours, the mixture was concentrated in vacuo. The residue was purified by preparative HPLC to afford 10 mg of the title product.

Example 27-1

1'-[(5-Chloro-1-{2-[4-(methylsulfonyl)piperazin-1-yl]ethyl}-1H-indol-2-yl)methyl]spiro[cyclopropane-1,3'-pyrrolo[2,3-c]pyridin]-2'(1'H)-one To a cooled solution of 1'-({5-chloro-1-[2-(piperazin-1-yl)ethyl]-1H-indol-2-yl}methyl)spiro[cyclopropane-1,3'-pyrrolo[2,3-c]pyridin]-2'(1'H)-one (100 mg, 0.23 mmol) in dichloromethane (20 mL) was added triethylamine (70 mg, 0.69 mmol) and methanesulfonyl chloride (0.510 g, 4.4 mmol) at 0° C. After being stirred at room temperature overnight, the reaction mixture was washed with water (20 mL). The organic layer was dried over sodium sulfate and then concentrated in vacuo. The residue was purified by preparative HPLC to afford 8.6 mg of the title product.

Example 27-2

N-(2-{5-Chloro-2-[(2'-oxospiro[cyclopropane-1,3'-pyrrolo[2,3-c]pyridin]-1'(2'H)-yl)methyl]-1H-indol-1-yl}ethyl)methanesulfonamide The title compound was prepared in analogy to Example 27-1 according to Scheme 11 by using 1'-{[1-(2-aminoethyl)-5-chloro-1H-indol-2-yl]methyl}spiro[cyclopropane-1,3'-pyrrolo[2,3-c]pyridin]-2'(1'H)-one instead of 1'-({5- chloro-1-[2-(piperazin-1-yl)ethyl]-1H-indol-2-yl}methyl) spiro[cyclopropane-1,3'-pyrrolo[2,3-c]pyridin]-2'(1'H)-one.

Example 27-3

N-(3-{5-Chloro-2-[(2'-oxospiro[cyclopropane-1,3'-pyrrolo[2,3-c]pyridin]-1'(2'H)-yl)methyl]-1H-indol-1-yl}propyl)methanesulfonamide Step 1: Preparation of 1'-{[1-(3-aminopropyl)-5-chloro-1H-indol-2-yl]methyl}spiro[cyclopropane-1,3'-pyrrolo[2,3-c]pyridin]-2'(1'H)-one

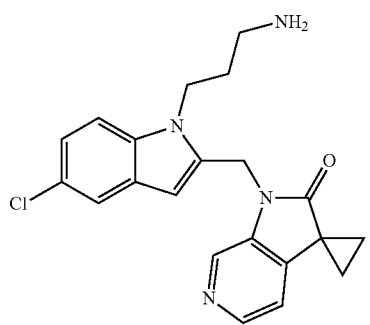 [SMILES: NCCCn1c(CN2C(=O)C3(CC3)c3ccncc32)cc2cc(Cl)ccc21]

1'-{[1-(3-Aminopropyl)-5-chloro-1H-indol-2-yl] methyl}spiro[cyclopropane-1,3'-pyrrolo[2,3-c]pyridin]-2' (1'H)-one was prepared in analogy to Example 24-5 by using tert-butyl(3-bromopropyl)carbamate instead of tert-butyl(2-bromoethyl)carbamate.

Step 2: Preparation of N-(3-{5-chloro-2-[(2'-oxospiro[cyclopropane-1,3'-pyrrolo[2,3-c]pyridin]-1' (2'H)-yl)methyl]-1H-indol-1-yl}propyl)methanesulfonamide The title compound was prepared in analogy to Example 27-1 according to Scheme 11 by using 1'-{[1-(3-aminopropyl)-5-chloro-1H-indol-2-yl]methyl}spiro[cyclopropane-1,3'-pyrrolo[2,3-c]pyridin]-2'(1'H)-one instead of 1'-({5-chloro-1-[2-(piperazin-1-yl)ethyl]-1H-indol-2-yl}methyl) spiro[cyclopropane-1,3'-pyrrolo[2,3-c]pyridin]-2'(1'H)-one.

Example 28

1-(2-{5-Chloro-2-[(2'-oxospiro[cyclopropane-1,3'-pyrrolo[2,3-c]pyridin]-1'(2'H)-yl)methyl]-1H-indol-1-yl}ethyl)urea A solution of 1'-{[1-(2-aminoethyl)-5-chloro-1H-indol-2-yl]methyl}spiro[cyclopropane-1,3'-pyrrolo[2,3-c]pyridin]-2'(1'H)-one (100 mg, 0.27 mmol), methyl carbamimidothioate and sulfuric acid (94 mg, 0.50 mmol) in a mixture of ethanol (5 mL) and water (5 mL) was heated under reflux overnight. The resulting mixture was concentrated in vacuo. The residue was purified by preparative HPLC to afford 15 mg of the title product.

Example 29

1'-[(5-Chloro-1-{3-[(2-hydroxyethyl)amino]propyl}-1H-indol-2-yl)methyl]spiro[cyclopropane-1,3'-pyrrolo[2,3-c]pyridin]-2'(1'H)-one A mixture of 1'-{[1-(3-aminopropyl)-5-chloro-1H-indol-2-yl]methyl}spiro[cyclopropane-1,3'-pyrrolo[2,3-c]pyridin]-2'(1'H)-one (70 mg, 0.18 mmol), 2-bromoethanol (22.5 mg, 0.18 mmol) and cesium carbonate (97.5 mg, 0.30 mmol) in dry acetonitrile (10 mL) was stirred at room temperature overnight. The resulting mixture was filtered. The filtrate was concentrated in vacuo. The residue was purified by preparative HPLC to afford 7 mg of the title product.

Example 30

Methyl(3-{5-chloro-2-[(2'-oxospiro[cyclopropane-1,3'-pyrrolo[2,3-c]pyridin]-1'(2'H)-yl)methyl]-1H-indol-1-yl}propyl)carbamate To a solution of 1'-{[1-(3-aminopropyl)-5-chloro-1H-indol-2-yl]methyl}spiro[cyclopropane-1,3'-pyrrolo[2,3-c]pyridin]-2'(1'H)-one (70 mg, 0.18 mmol) and triethylamine (40 mg, 0.40 mmol) in N,N-dimethylformamide (5 mL) was added methyl carbonochloridate (18.8 mg, 0.20 mmol) at 0° C. The mixture was stirred at room temperature for 2 hours and then concentrated in vacuo. The residue was purified by preparative HPLC to afford 22 mg of the title product.

Example 31

3-{5-Chloro-2-[(2'-oxospiro[cyclopropane-1,3'-pyrrolo[2,3-c]pyridin]-1'(2'H)-yl)methyl]-1H-indol-1-yl}propyl(2,2,2-trifluoroethyl)carbamate Step 1: Preparation of 1'-{[5-chloro-1-(3-hydroxypropyl)-1H-indol-2-yl]methyl}spiro[cyclopropane-1,3'-pyrrolo[2,3-c]pyridin]-2'(1'H)-one

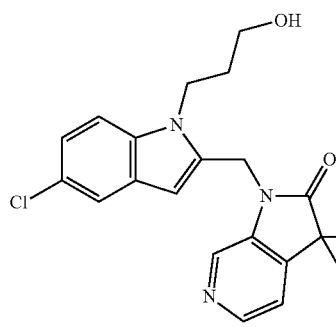

A mixture of 1'-[(5-chloro-1H-indol-2-yl)methyl]spiro [cyclopropane-1,3'-pyrrolo[2,3-c]pyridin]-2'(1'H)-one (50 mg, 0.15 mmol), cesium carbonate (250 mg, 0.76 mmol) and 3-bromopropan-1-ol (150 mg, 1.09 mmol) in acetonitrile (4 mL) was heated with stirring at 80° C. for 1 hour. The reaction mixture was concentrated in vacuo. The residue was purified by flash chromatography on silica gel (eluting with 20-40% ethyl acetate in petroleum ether) to afford 50 mg of 1'-{[5-chloro-1-(3-hydroxypropyl)-1H-indol-2-yl] methyl}spiro[cyclopropane-1,3'-pyrrolo[2,3-c]pyridin]-2' (1'H)-one.

Step 2: Preparation of 3-{5-chloro-2-[(2'-oxospiro [cyclopropane-1,3'-pyrrolo[2,3-c]pyridin]-1'(2'H)-yl) methyl]-1H-indol-1-yl}propyl(2,2,2-trifluoroethyl) carbamate A mixture of 1'-{[5-chloro-1-(3-hydroxypropyl)-1H-indol-2-yl]methyl}spiro[cyclopropane-1,3'-pyrrolo[2,3-c] pyridin]-2'(1'H)-one (50 mg, 0.13 mmol), cesium carbonate (250 mg, 0.77 mmol) and di-1H-imidazol-1-ylmethanone (87 mg, 0.43 mmol) in tetrahydrofuran (4 mL) was stirred at room temperature overnight. Then 2,2,2-trifluorethanamine (200 mg, 2.0 mmol) was added to the reaction mixture. The mixture was stirred at room temperature overnight. The resulting mixture was purified by preparative HPLC to afford 10 mg of the title product.

Example 32-1

1'-({6-Chloro-3-[2-(ethylsulfonyl)ethyl]-1H-indol-2-yl}methyl)spiro[cyclopropane-1,3'-pyrrolo[2,3-b]pyridin]-2'(1'H)-one Step 1: Preparation of [6-chloro-1-(phenylsulfonyl)-1H-indol-2-yl]methanol

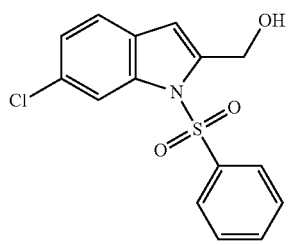 [SMILES: O=S(=O)(c1ccccc1)n1c(CO)cc2ccc(Cl)cc21]

[6-Chloro-1-(phenylsulfonyl)-1H-indol-2-yl]methanol was prepared in analogy to [5-chloro-1-(phenylsulfonyl)-1H-pyrrolo[3,2-b]pyridin-2-yl]methanol in Example 6 by using ethyl 5-chloro-1H-indole-2-carboxylate instead of methyl 5-chloro-1-(phenylsulfonyl)-1H-pyrrolo[3,2-b]pyridine-2-carboxylate.

Step 2: Preparation of {6-chloro-3-[(E)-2-(ethylsulfonyl)ethenyl]-1-(phenylsulfonyl)-1H-indol-2-yl}methanol

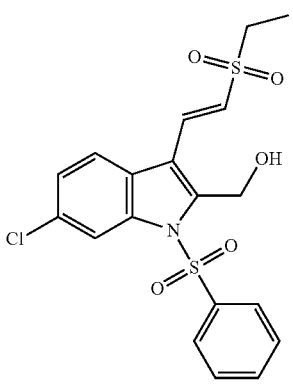 [SMILES: CCS(=O)(=O)/C=C/c1c(CO)n(S(=O)(=O)c2ccccc2)c2cc(Cl)ccc12]

A mixture of [6-chloro-1-(phenylsulfonyl)-1H-indol-2-yl]methanol (2.68 g, 6.0 mmol), ethanesulfonyl-ethene (1.56 mL, 15 mmol), 2-dicyclohexylphosphino-2',6'-dimethoxy-1,1'-biphenyl (252 mg, 0.60 mmol), allylpalladium chloride dimmer (222 mg, 0.60 mmol) and sodium acetate (984 mg, 12 mmol) in N,N-dimethylacetamide (15 mL) was heated to microwave irradiation for 25 minutes at 130° C. The mixture was diluted with ethyl acetate (100 mL), and then washed with water (50 mL×2). The organic layer was dried over anhydrous sodium sulfate and then concentrated in vacuo to afford 2.4 g of {6-chloro-3-[(E)-2-(ethylsulfonyl)ethenyl]-1-(phenylsulfonyl)-1H-indol-2-yl}methanol as a yellow solid.

Step 3: Preparation of {6-chloro-3-[2-(ethylsulfonyl)ethyl]-1-(phenylsulfonyl)-1H-indol-2-yl}methanol

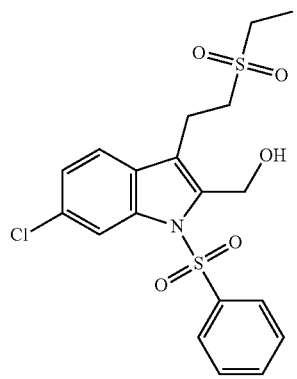 [SMILES: CCS(=O)(=O)CCc1c(CO)n(S(=O)(=O)c2ccccc2)c2cc(Cl)ccc12]

To a suspension of nickel(II) chloride (680 mg, 5.24 mmol) in methanol (150 mL) was added sodium borohydride (198 mg, 5.24 mmol) in an ice bath. After the mixture was stirred at 0° C. for 15 minutes, a solution of {6-chloro-3-[(E)-2-(ethylsulfonyl)ethenyl]-1-(phenylsulfonyl)-1H-indol-2-yl}methanol (2.3 g, 5.24 mmol) in methanol (50 mL) was added slowly to the mixture. After the resulting mixture was stirred at 0° C. for another 15 minutes, sodium borohydride (396 mg, 10.48 mmol) was added in one portion. The reaction mixture was then stirred at 0° C. for 7 hours. The reaction was quenched with water (50 mL). The mixture was filtered. The filtrate was concentrated in vacuo to remove the organic solvent. The residual aqueous phase was extracted with dichloromethane. The organic layer was washed with brine, and then dried over anhydrous sodium sulfate and then concentrated in vacuo to afford 1.68 g of {6-chloro-3-[2-(ethylsulfonyl)ethyl]-1-(phenylsulfonyl)-1H-indol-2-yl}methanol as a yellow solid, which was used for next step without further purification. MS obsd. (ESI$^+$) [(M+H)$^+$] 424.

Step 4: Preparation of {6-chloro-3-[2-(ethylsulfonyl)ethyl]-1-(phenylsulfonyl)-1H-indol-2-yl}methyl methanesulfonate

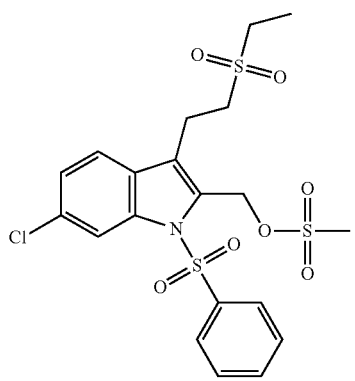 [SMILES: CCS(=O)(=O)CCc1c(COS(C)(=O)=O)n(S(=O)(=O)c2ccccc2)c2cc(Cl)ccc12]

To a cooled solution of {6-chloro-3-[2-(ethylsulfonyl)ethyl]-1-(phenylsulfonyl)-1H-indol-2-yl}methanol (441 mg, 1.0 mmol) and triethylamine (0.42 mL, 3.0 mmol) in dichloromethane (50 mL) was added methanesulfonyl chloride (0.3 mL, 3.9 mmol) dropwise in an ice bath. After being stirred at 0° C. for 3 hours, the mixture was neutralized with a saturated aqueous solution of sodium bicarbonate and then extracted with dichloromethane (30 mL×2). The combined organic layer was washed with a saturated aqueous sodium bicarbonate solution (30 mL×2), and then dried over anhydrous sodium sulfate and then concentrated in vacuo to afford 0.5 g of {6-chloro-3-[2-(ethylsulfonyl)ethyl]-1-(phenylsulfonyl)-1H-indol-2-yl}methyl methanesulfonate as a light yellow solid, which was used for next step without further purification.

Step 5: Preparation of 1'-({6-chloro-3-[2-(ethylsulfonyl)ethyl]-1-(phenylsulfonyl)-1H-indol-2-yl}methyl)spiro[cyclopropane-1,3'-pyrrolo[2,3-b]pyridin]-2'(1'H)-one

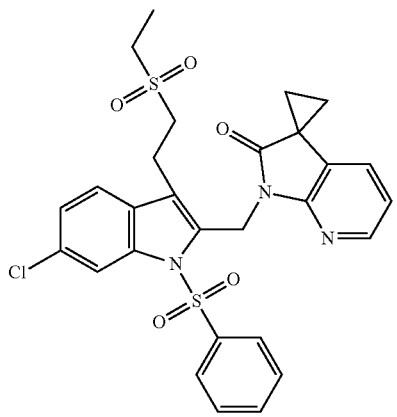 [SMILES: CCS(=O)(=O)CCc1c(CN2C(=O)C3(CC3)c3cccnc32)n(S(=O)(=O)c2ccccc2)c2cc(Cl)ccc12]

A mixture of {6-chloro-3-[2-(ethylsulfonyl)ethyl]-1-(phenylsulfonyl)-1H-indol-2-yl}methyl methanesulfonate (415 mg, 0.8 mmol), cesium carbonate (521 mg, 1.6 mmol) and spiro[cyclopropane-1,3'-pyrrolo[2,3-b]pyridin]-2'(1'H)-one (128 mg, 0.8 mmol) in acetonitrile (8 mL) was heated at 85° C. for 16 hours. The mixture was filtered. The filtrate was concentrated in vacuo to afford 362 mg of 1'-({6-chloro-3-[2-(ethylsulfonyl)ethyl]-1-(phenylsulfonyl)-1H-indol-2-yl}methyl)spiro[cyclopropane-1,3'-pyrrolo[2,3-b]pyridin]-2'(1'H)-one as a brown solid, which was used for next step without further purification. MS obsd. (ESI+) [(M+H)+] 584.

Step 6: Preparation of 1'-({6-chloro-3-[2-(ethylsulfonyl)ethyl]-1H-indol-2-yl}methyl)spiro[cyclopropane-1,3'-pyrrolo[2,3-b]pyridin]-2'(1'H)-one A mixture of 1'-({6-chloro-3-[2-(ethylsulfonyl)ethyl]-1-(phenylsulfonyl)-1H-indol-2-yl}methyl)spiro[cyclopropane-1,3'-pyrrolo[2,3-b]pyridin]-2'(1'H)-one (360 mg, 0.61 mmol) and a solution of tetrabutylammonium fluoride in tetrahydrofuran (1.0 M, 4 mL) in tetrahydrofuran (2 mL) was stirred at room temperature for 16 hours. Then the mixture was concentrated in vacuo. The residue was extracted with ethyl acetate (30 mL×2). The combined organic layer was washed with a saturated aqueous solution of ammonium chloride (30 mL×3) and water (30 mL×3), and then dried over anhydrous sodium sulfate and then concentrated in vacuo. The residue was purified by preparative HPLC to afford 60 mg of the title product as a white solid.

Example 32-2

1'-({6-Chloro-3-[2-(methylsulfonyl)ethyl]-1H-indol-2-yl}methyl)spiro[cyclopropane-1,3'-pyrrolo[2,3-c]pyridin]-2'(1'H)-one The title compound was prepared in analogy to Example 32-1 according to Scheme 13 by using (methylsulfonyl)ethene and spiro[cyclopropane-1,3'-pyrrolo[2,3-c]pyridin]-2'(1'H)-one instead of (ethylsulfonyl)ethane and spiro[cyclopropane-1,3'-pyrrolo[2,3-b]pyridin]-2'(1'H)-one.

Example 33

1'-({6-Chloro-3-[3-(methylsulfonyl)propyl]-1H-indol-2-yl}methyl)spiro[cyclopropane-1,3'-pyrrolo[2,3-c]pyridin]-2'(1'H)-one Step 1: Preparation of ethyl 6-chloro-3-[3-(methylsulfanyl)propanoyl]-1H-indole-2-carboxylate

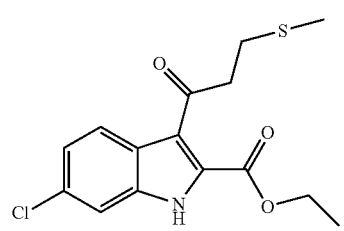 [SMILES: CCOC(=O)c1[nH]c2cc(Cl)ccc2c1C(=O)CCSC]

To a suspension of ferric trichloride (3.9 g, 24 mmol) in 1,2-dichloroethane (50 mL) was added 3-(methylsulfanyl)propanoyl chloride (2.77 mL, 24 mmol) in an ice-water bath. After the mixture was stirred at 0° C. for 10 minutes under an argon atmosphere, a solution of ethyl 6-chloro-1H-indole-2-carboxylate (4.5 g, 20 mmol) in 1,2-dichloro-ethane (50 mL) was added dropwise to the mixture in an ice-water bath. The mixture was stirred at 0° C. for 1 hour, then poured into ice-water (50 mL) and extracted with ethyl acetate (50 mL×3). The combined organic layer was washed with a saturated aqueous solution of sodium bicarbonate (50 mL×3), and then dried over anhydrous sodium sulfate and then concentrated in vacuo. The residue was purified by flash silica gel chromatography (eluting with 0-30% ethyl acetate in petroleum ether) to afford 2.9 g of ethyl 6-chloro-3-[3-(methylsulfanyl)propanoyl]-1H-indole-2-carboxylate as a light yellow solid. MS obsd. (ESI+) [(M+H)+] 326.

Step 2: Preparation of ethyl 6-chloro-3-[1-hydroxy-3-(methylsulfanyl)propyl]-1H-indole-2-carboxylate

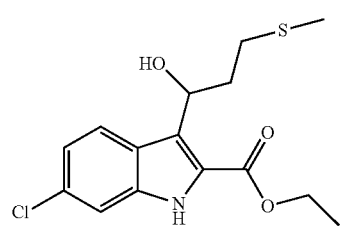 [SMILES: CCOC(=O)c1[nH]c2cc(Cl)ccc2c1C(O)CCSC]

To a solution of ethyl 6-chloro-3-[3-(methylsulfanyl)propanoyl]-1H-indole-2-carboxylate (2.5 g, 7.7 mmol) in methanol (100 mL) was added sodium borohydride (440 mg, 11.5 mmol) in portions. After the reaction mixture was stirred at room temperature for 1 hour, the reaction was quenched by water (20 mL). The organic solvent was removed by concentration in vacuo. The residue was extracted with ethyl acetate (50 mL×3). The combined organic layer was washed with brine (30 mL×3), and then dried over anhydrous sodium sulfate and then concentrated in vacuo to afford 2.5 g of the crude ethyl 6-chloro-3-[1-hydroxy-3-(methylsulfanyl)propyl]-1H-indole-2-carboxylate as a white solid. MS obsd. (ESI⁺) [(M+H)⁺] 310.

Step 3: Preparation of ethyl 6-chloro-3-[3-(methylsulfanyl)propyl]-1H-indole-2-carboxylate

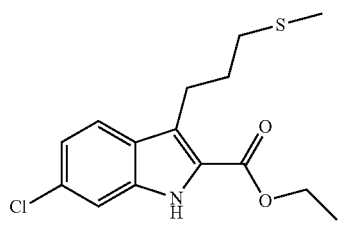 [SMILES: CCOC(=O)c1[nH]c2cc(Cl)ccc2c1CCCSC]

To a mixture of ethyl 6-chloro-3-[1-hydroxy-3-(methylsulfanyl)propyl]-1H-indole-2-carboxylate (2.0 g, 6.0 mmol) and triethylsilane (30 mL) was added trifluoroacetic acid (10 mL) dropwise in an ice-water bath. After being stirred at 0° C. for 2 hours, the mixture was neutralized with a saturated aqueous solution of sodium bicarbonate and then extracted with ethyl acetate (100 mL×2). The combined organic layer was washed with a saturated aqueous solution of sodium bicarbonate (50 mL×3), and then dried over anhydrous sodium sulfate and then concentrated in vacuo. The residue was purified by flash silica gel chromatography (eluting with 0-30% ethyl acetate in petroleum ether) to afford 1.5 g of ethyl 6-chloro-3-[3-(methylsulfanyl)propyl]-1H-indole-2-carboxylate as a white solid. MS obsd. (ESI⁺) [(M+H)⁺] 312.

Step 4: Preparation of ethyl 6-chloro-3-[3-(methylsulfanyl)propyl]-1-(phenylsulfonyl)-1H-indole-2-carboxylate

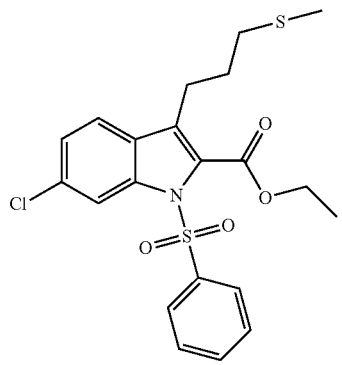 [SMILES: CCOC(=O)c1c(CCCSC)c2ccc(Cl)cc2n1S(=O)(=O)c1ccccc1]

To a suspension of ethyl 6-chloro-3-[3-(methylsulfanyl)propyl]-1H-indole-2-carboxylate (1.26 g, 4 mmol) and sodium hydride (0.24 g, 6.0 mmol, 60% in mineral oil) in N,N-dimethylformamide (30 mL) was added benzenesulfonyl chloride (0.62 mL, 4.8 mmol) dropwise in an ice-water bath. The mixture was stirred at room temperature for 4 hours, and then poured into ice-water (100 mL). The resulting precipitate was collected by filtration, which was washed with petroleum ether (50 mL), and then dried in vacuo to afford 1.5 g of ethyl 6-chloro-3-[3-(methylsulfanyl)propyl]-1-(phenylsulfonyl)-1H-indole-2-carboxylate as a pale white solid. MS obsd. (ESI⁺) [(M+H)⁺] 452.

Step 5: Preparation of {6-chloro-3-[3-(methylsulfanyl)propyl]-1-(phenylsulfonyl)-1H-indol-2-yl}methanol

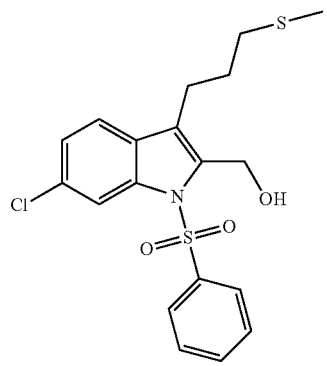 [SMILES: CSCCCc1c(CO)n(S(=O)(=O)c2ccccc2)c2cc(Cl)ccc12]

To a cooled suspension of lithium aluminium hydride (0.18 g, 4 mmol) in tetrahydrofuran (100 mL) was added ethyl 6-chloro-3-[3-(methylsulfanyl)propyl]-1-(phenylsulfonyl)-1H-indole-2-carboxylate (0.902 g, 2 mmol) at 0° C. The mixture was stirred at room temperature for 16 hours. The reaction was quenched with methanol. The resulting mixture was then filtered through a celite pad. The filtrate was concentrated in vacuo to afford 0.5 g of {6-chloro-3-[3-(methylsulfanyl)propyl]-1-(phenylsulfonyl)-1H-indol-2-yl}methanol as brown oil. MS obsd. (ESI⁺) [(M+H)⁺] 392.

Step 6: Preparation of {6-chloro-3-[3-(methylsulfonyl)propyl]-1-(phenylsulfonyl)-1H-indol-2-yl}methanol

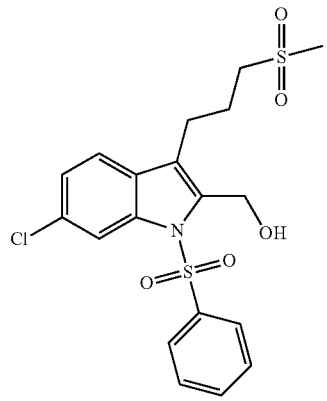 [SMILES: CS(=O)(=O)CCCc1c(CO)n(S(=O)(=O)c2ccccc2)c2cc(Cl)ccc12]

To a solution of {6-chloro-3-[3-(methylsulfanyl)propyl]-1-(phenylsulfonyl)-1H-indol-2-yl}methanol (0.5 g, 1.28 mmol) in dichloromethane (20 mL) was added 3-chloroperoxybenzoic acid (0.55 g, 3.2 mmol) at 0° C. The mixture was then stirred at room temperature for 4 hours. The resulting mixture was neutralized with a saturated aqueous solution of sodium sulfite and then extracted with dichloromethane (30 mL×2). The combined organic layer was washed successively with a saturated aqueous solution of sodium sulfite (30 mL×2), a saturated aqueous solution of sodium bicarbonate (30 mL×2), and water (30 mL×2), and then dried over anhydrous sodium sulfate and then concentrated in vacuo. The residue was purified by flash silica gel chromatography (eluting with 0-10% methanol in dichloromethane) to afford 0.32 g of {6-chloro-3-[3-(methylsulfonyl)propyl]-1-(phenylsulfonyl)-1H-indol-2-yl}methanol as colorless oil. MS obsd. (ESI$^+$) [(M+H)$^+$] 424.

Step 7: Preparation of {6-chloro-3-[3-(methylsulfonyl)propyl]-1-(phenylsulfonyl)-1H-indol-2-yl}methyl methanesulfonate

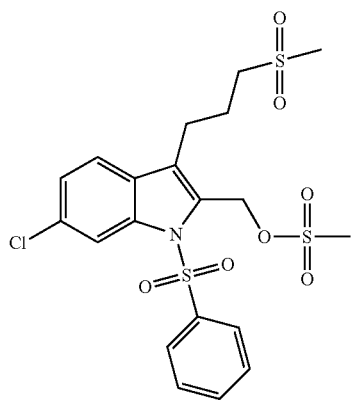 [SMILES: CS(=O)(=O)CCCc1c(COS(C)(=O)=O)n(S(=O)(=O)c2ccccc2)c2cc(Cl)ccc12]

To a solution of {6-chloro-3-[3-(methylsulfonyl)propyl]-1-(phenylsulfonyl)-1H-indol-2-yl}methanol (320 mg, 0.7 mmol) and triethylamine (0.59 ml, 4.2 mmol) in dichloromethane (20 mL) was added methanesulfonyl chloride (0.17 ml, 2.1 mmol) dropwise in an ice-water bath. After being stirred at 0° C. for 1 hour, the resulting mixture was neutralized with a saturated aqueous solution of sodium bicarbonate and then extracted with dichloromethane (30 mL×2). The combined organic layer was washed with a saturated aqueous solution of sodium bicarbonate (30 mL×2), and then dried over anhydrous sodium sulfate and then concentrated in vacuo to afford 363 mg of {6-chloro-3-[3-(methylsulfonyl)propyl]-1-(phenylsulfonyl)-1H-indol-2-yl}methyl methanesulfonate as a light yellow solid which was used for next step without further purification.

Step 8: Preparation of 1'-({6-chloro-3-[3-(methylsulfonyl)propyl]-1-(phenylsulfonyl)-1H-indol-2-yl}methyl)spiro[cyclopropane-1,3'-pyrrolo[2,3-c]pyridin]-2'(1'H)-one

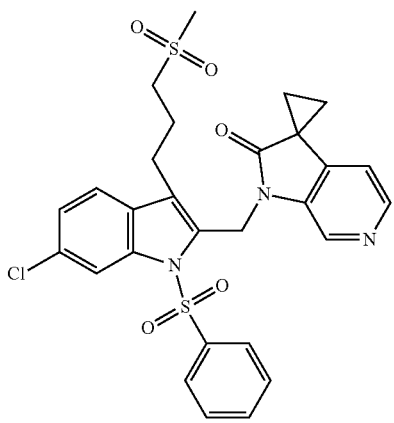 [SMILES: CS(=O)(=O)CCCc1c(CN2C(=O)C3(CC3)c3ccncc32)n(S(=O)(=O)c2ccccc2)c2cc(Cl)ccc12]

A suspension of {6-chloro-3-[3-(methylsulfonyl)propyl]-1-(phenylsulfonyl)-1H-indol-2-yl}methyl methanesulfonate (364 mg, 0.7 mmol), cesium carbonate (684 mg, 2.1 mmol) and spiro[cyclopropane-1,3'-pyrrolo[2,3-c]pyridin]-2'(1'H)-one (90 mg, 0.56 mmol) in acetonitrile (10 mL) was heated with stirring at 85° C. for 20 minutes. The mixture was filtered. The filtrate was concentrated in vacuo to afford 300 mg of 1'-({6-chloro-3-[3-(methylsulfonyl)propyl]-1-(phenylsulfonyl)-1H-indol-2-yl}methyl)spiro[cyclopropane-1,3'-pyrrolo[2,3-c]pyridin]-2'(1'H)-one as a brown solid which was used for next step without further purification. MS obsd. (ESI$^+$) [(M+H)$^+$] 584.

Step 9: Preparation of 1'-({6-chloro-3-[3-(methylsulfonyl)propyl]-1H-indol-2-yl}methyl)spiro[cyclopropane-1,3'-pyrrolo[2,3-c]pyridin]-2'(1'H)-one A mixture of 1'-({6-chloro-3-[3-(methylsulfonyl)propyl]-1-(phenylsulfonyl)-1H-indol-2-yl}methyl), spiro[cyclopropane-1,3'-pyrrolo[2,3-c]pyridin]-2'(1'H)-one (300 mg, 0.51 mmol), 1.0 M tetrabutylammonium fluoride in tetrahydrofuran (2 mL) and tetrahydrofuran (2 mL) was stirred at room temperature for 24 hours. The resulting mixture was concentrated in vacuo. The residue was dissolved with ethyl acetate (60 mL). The solution was washed with a saturated aqueous solution of ammonium chloride (30 mL×3) and water (30 mL×3), and then dried over anhydrous sodium sulfate and then concentrated in vacuo. The residue was purified by preparative HPLC to afford 125 mg of the title product as a light yellow solid.

Example 34-1

1'-({5-Chloro-1-[2-(methylsulfonyl)ethyl]-1H-benzimidazol-2-yl}methyl)spiro[cyclopropane-1,3'-pyrrolo[2,3-c]pyridin]-2'(1'H)-one Step 1: Preparation of 4-chloro-N-[2-(methylsulfonyl)ethyl]-2-nitroaniline

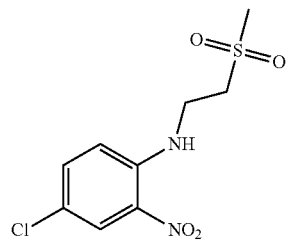

A mixture of 4-chloro-2-nitroaniline (3.44 g, 20.0 mmol), (methylsulfonyl)ethene (2.0 mL, 22.8 mmol) and cesium carbonate (9.78 g, 30.0 mmol) in acetonitrile (40 mL) was heated with stirring at 80° C. for 1.5 hours. The resulting mixture was concentrated in vacuo. The residue was purified by flash chromatography on silica gel (eluting with 0-8% methanol in dichloromethane) to afford 4.70 g of 4-chloro-N-[2-(methylsulfonyl)ethyl]-2-nitroaniline as an orange solid.

Step 2: Preparation of 4-chloro-N¹[2-(methylsulfonyl)ethyl]benzene-1,2-diamne

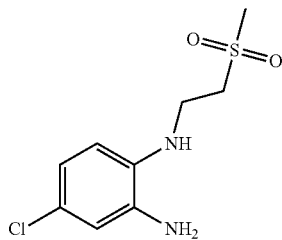 [SMILES: CS(=O)(=O)CCNc1ccc(Cl)cc1[N+](=O)[O-]]

A mixture of 4-chloro-N-[2-(methylsulfonyl)ethyl]-2-nitroaniline (3.0 g, 10.8 mmol), Raney nickel (1.0 g of suspension in water) and hydrazine hydrate (2 mL, 85% aqueous solution) in methanol (25 mL) was heated with stirring under reflux for 1.5 hours. The resulting mixture was filtered and the filtrate was concentrated in vacuo. The residue was stirred with dichloromethane (20 mL) and then filtered to afford 1.8 g of 4-chloro-N¹-[2-(methylsulfonyl)ethyl]benzene-1,2-diamne as a pale solid.

Step 3: Preparation of 5-chloro-2-(chloromethyl)-1-[2-(methylsulfonyl)ethyl]-1H-benzimidazole

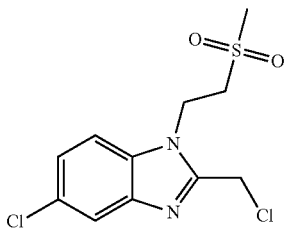 [SMILES: CS(=O)(=O)CCn1c(CCl)nc2cc(Cl)ccc21]

A mixture of 4-chloro-N¹[2-(methylsulfonyl)ethyl]benzene-1,2-diamine (1.25 g, 5.0 mmol), bromoacetic acid (700 mg, 5.0 mmol) and 6 N hydrochloric acid (10 mL) was heated under reflux for 5 hours. The mixture was then cooled to room temperature, and then basified with sodium bicarbonate. The mixture was extracted with ethyl acetate (20 mL×3). The combined organic layer was dried over sodium sulfate and then concentrated in vacuo to afford 1.24 g of the crude 5-chloro-2-(chloromethyl)-1-[2-(methylsulfonyl)ethyl]-1H-benzimidazole as a yellow semi-solid.

Step 4: Preparation of 1'-({5-chloro-1-[2-(methylsulfonyl)ethyl]-1H-benzimidazol-2-yl}methyl)spiro[cyclopropane-1,3'-pyrrolo[2,3-c]pyridin]-2'(1'H)-one To a cooled solution of spiro[cyclopropane-1,3'-pyrrolo[2,3-c]pyridin]-2'(1'H)-one (360 mg, 2.25 mmol) in N,N-dimethylformamide (3 mL) was added sodium tert-butoxide (240 mg, 2.5 mmol) at 0° C. After being stirred at 0° C. for 10 minutes, a solution of 5-chloro-2-(chloromethyl)-1-[2-(methylsulfonyl)ethyl]-1H-benzimidazole (620 mg, 2.01 mmol) in N,N-dimethylformamide (2 mL) was added to the reaction mixture at 0° C. The resulting mixture was stirred at room temperature for 10 minutes, and then diluted with ethyl acetate (20 mL). The organic layer was washed with brine (15 mL), and then dried over sodium sulfate and then concentrated in vacuo. The residue was purified by preparative HPLC to afford 80 mg of the title product as a light brown solid.

Example 34-2

1'-({5-Chloro-1-[2-(methylsulfonyl)ethyl]-1H-benzimidazol-2-yl}methyl)-4'-fluorospiro[cyclopropane-1,3'-indol]-2'(1'H)-one The title compound was prepared in analogy to Example 34-1 according to Scheme 16 by using 5-chloro-2-(chloromethyl)-1-[2-(methylsulfonyl)ethyl]-1H-benzimidazole and 4'-fluorospiro[cyclopropane-1,3'-indol]-2'(1'H)-one instead of 5-chloro-2-(chloromethyl)-1-[2-(methylsulfonyl)ethyl]-1H-benzimidazole and spiro[cyclopropane-1,3'-pyrrolo[2,3-c]pyridin]-2'(1'H)-one.

Example 34-3

4'-Chloro-1'-({5-chloro-1-[2-(methylsulfonyl)ethyl]-1H-benzimidazol-2-yl}methyl)spiro[cyclopropane-1,3'-indol]-2'(1'H)-one The title compound was prepared in analogy to Example 34-1 according to Scheme 16 by using 4'-chlorospiro[cyclopropane-1,3'-indol]-2'(1'H)-one instead of spiro[cyclopropane-1,3'-pyrrolo[2,3-c]pyridin]-2'(1'H)-one.

Example 34-4

4'-Bromo-1'-({5-chloro-1-[2-(methylsulfonyl)ethyl]-1H-benzimidazol-2-yl}methyl)spiro[cyclopropane-1,3'-indol]-2'(1'H)-one The title compound was prepared in analogy to Example 34-1 according to Scheme 16 by using 4'-bromospiro[cyclopropane-1,3'-indol]-2'(1'H)-one instead of spiro[cyclopropane-1,3'-pyrrolo[2,3-c]pyridin]-2'(1'74)-one.

Example 34-5

1'-({5-Chloro-1-[2-(ethylsulfonyl)ethyl]-1H-benzimidazol-2-yl}methyl)spiro[cyclopropane-1,3'-pyrrolo[2,3-c]pyridin]-2'(1'H)-one The title compound was prepared in analogy to Example 34-1 according to Scheme 16 by using 5-chloro-2-(chloromethyl)-1-[2-(ethylsulfonyl)ethyl]-1H-benzimidazole instead of 5-chloro-2-(chloromethyl)-1-[2-(methylsulfonyl)ethyl]-1H-benzimidazole.

Example 35

1'-({5-Chloro-1-[2-(1,1-dioxidothietan-3-yl)ethyl]-1H-benzimidazol-2-yl}methyl)spiro[cyclopropane-1,3'-pyrrolo[2,3-c]pyridin]-2'(1'H)-one Step 1: Preparation of tert-butyl(4-chloro-2-nitrophenyl)carbamate

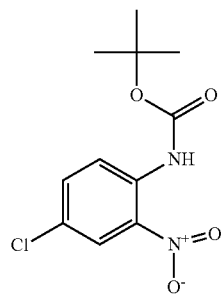 [SMILES: CC(C)(C)OC(=O)Nc1ccc(Cl)cc1[N+](=O)[O-]]

A mixture of 4-chloroaniline (5.0 g, 28.97 mmol), di-tert-butyldicarbonate (12.65 mmol, 57.94 mmol) and 4-dimehylaminopyridine (35 mg, 0.29 mmol) in tetrahydrofuran (150 mL) was heated under reflux for 1 hour. After being cooled to room temperature, the mixture was concentrated in vacuo. The residue was stirred with potassium carbonate (12.0 g, 87.0 mmol) in methanol (150 mL) at room temperature for 2 hours. The resulting mixture was diluted with water (120 mL) and then extracted with ethyl acetate (150 mL×2). The combined organic layer was washed with brine, and then dried over sodium sulfate and then concentrated in vacuo. The residue was purified by flash column to afford 6.3 g of tert-butyl(4-chloro-2-nitrophenyl)carbamate.

Step 2: Preparation of tert-butyl(4-chloro-2-nitrophenyl)[2-(1,1-dioxidothietan-3-yl)ethyl]carbamate

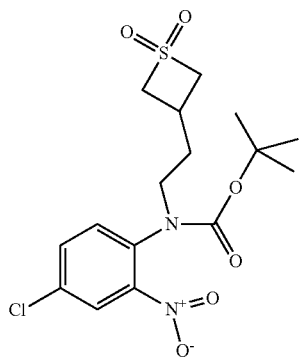 [SMILES: CC(C)(C)OC(=O)N(CCC1CS(=O)(=O)C1)c1ccc(Cl)cc1[N+](=O)[O-]]

A mixture of tert-butyl(4-chloro-2-nitrophenyl)carbamate (176 mg, 0.67 mmol), 2-(1,1-dioxidothietan-3-yl)ethyl 4-methylbenzenesulfonate (204 mg, 0.67 mmol), potassium carbonate (138 mg, 1.0 mmol), tetrabutylamine iodide (40 mg) and acetonitrile (20 mL) was stirred under reflux overnight. The resulting mixture was concentrated in vacuo. The residue was purified by flash column to afford 213 mg of tert-butyl(4-chloro-2-nitrophenyl)[2-(1,1-dioxidothietan-3-yl)ethyl]carbamate.

Step 3: Preparation of tert-butyl(2-amino-4-chlorophenyl)[2-(1,1-dioxidothietan-3-yl)ethyl]carbamate

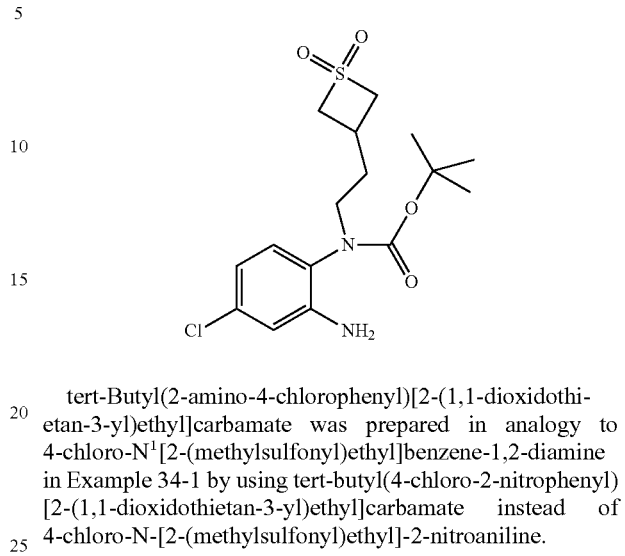

tert-Butyl(2-amino-4-chlorophenyl)[2-(1,1-dioxidothietan-3-yl)ethyl]carbamate was prepared in analogy to 4-chloro-N¹[2-(methylsulfonyl)ethyl]benzene-1,2-diamine in Example 34-1 by using tert-butyl(4-chloro-2-nitrophenyl)[2-(1,1-dioxidothietan-3-yl)ethyl]carbamate instead of 4-chloro-N-[2-(methylsulfonyl)ethyl]-2-nitroaniline.

Step 4: Preparation of 1'-({5-chloro-1-[2-(1,1-dioxidothietan-3-yl)ethyl]-1H-benzimidazol-2-yl}methyl)spiro[cyclopropane-1,3'-pyrrolo[2,3-c]pyridin]-2'(1'H)-one The title compound was prepared in analogy to Example 34-1 according to Scheme 15 by using tert-butyl(2-amino-4-chlorophenyl)[2-(1,1-dioxidothietan-3-yl)ethyl]carbamate instead of 4-chloro-N¹[2-(methylsulfonyl)ethyl]benzene-1,2-diamine.

Example 36-1

1'-({5-Chloro-1-[3-(methylsulfonyl)propyl]-1H-benzimidazol-2-yl}methyl)spiro[cyclopropane-1,3'-pyrrolo[2,3-c]pyridin]-2'(1'H)-one Step 1: Preparation of 4-chloro-N-[2-(methylsulfonyl)propyl]-2-nitroaniline A mixture of 4-chloro-2-nitroaniline (3.44 g, 20.0 mmol), 3-(methylsulfonyl)propyl 4-methylbenzenesulfonate (5.53 g, 20.0 mmol) and cesium carbonate (9.78 g, 30.0 mmol) in acetonitrile (40 mL) was heated with stirring under reflux overnight. The resulting mixture was concentrated in vacuo. The residue was purified by flash chromatography on silica gel (eluting with 0-8% methanol in dichloromethane) to afford 4.60 g of 4-chloro-N-[2-(methylsulfonyl)propyl]-2-nitroaniline as an orange solid.

Step 2: Preparation of 1'-({5-chloro-1-[3-(methylsulfonyl)propyl]-1H-benzimidazol-2-yl}methyl)spiro[cyclopropane-1,3'-pyrrolo[2,3-c]pyridin]-2'(1'H)-one The title compound was prepared in analogy to Example 34-1 according to Scheme 15 by using 4-chloro-N-[2-(methylsulfonyl)propyl]-2-nitroaniline instead of 4-chloro-N-[2-(methylsulfonyl)ethyl]-2-nitroaniline.

Example 36-2

1'-({5-Chloro-1-[2-(cyclopropylsulfonyl)ethyl]-1H-benzimidazol-2-yl}methyl)spiro[cyclopropane-1,3'-pyrrolo[2,3-c]pyridin]-2'(1'H)-one The title compound was prepared in analogy to Example 36-1 according to Scheme 15 by using 3-(cyclopropylsulfonyl)ethyl 4-methylbenzenesulfonate instead of 3-(methylsulfonyl)propyl 4-methylbenzenesulfonate.

Example 37-1

1'-({5-Chloro-7-fluoro-1-[2-(methylsulfonyl)ethyl]-1H-benzimidazol-2-yl}methyl)spiro[cyclopropane-1,3'-pyrrolo[2,3-c]pyridin]-2'(1'H)-one Step 1: Preparation of 4-chloro-2-fluoro-N-[2-(methylsulfonyl)ethyl]aniline

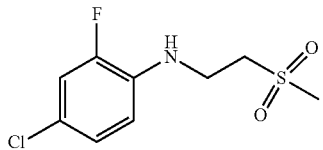

To a solution of 4-chloro-2-fluoroaniline (55 g, 375 mmol) in acetonitrile (60 mL) was added (methylsulfonyl)ethene (36 mL, 412 mmol) and cesium carbonate (243 g, 750 mmol). The reaction mixture was refluxed overnight, and then filtered. The filtrate was concentrated in vacuo. The residue was purified by flash chromatography (eluting with 33% ethyl acetate in petroleum ether) to afford 66 g of 4-chloro-2-fluoro-N-[2-(methylsulfonyl)ethyl]aniline.

Step 2: Preparation of 4-chloro-2-fluoro-N-[2-(methylsulfonyl)ethyl]-6-nitroaniline

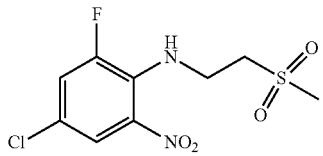 [SMILES: CS(=O)(=O)CCNc1c(F)cc(Cl)cc1[N+](=O)[O-]]

To a three-necked bottle containing sulfuric acid (400 mL) was added 4-chloro-2-fluoro-N-[2-(methylsulfonyl)ethyl]aniline (50 g, 200 mmol) in portions. After the mixture was cooled to 0° C., nitric acid (21.6 g, 240 mmol, 70% w/w) was added dropwise. After being stirred at 0° C. for 1 hour, the mixture was poured into ice-water (1000 mL), and then extracted with ethyl acetate (500 mL×3). The combined organic layer was washed with water (1000 mL) and brine (1000 mL), and then dried over sodium sulfate and filtered. The filtrate was concentrated in vacuo. The residue was purified by flash chromatography (eluting with 20-33% ethyl acetate in petroleum ether) to afford 23.7 mg of 4-chloro-2-fluoro-N-[2-(methylsulfonyl)ethyl]-6-nitroaniline.

Step 3: Preparation of 5-chloro-3-fluoro-$N^2$-[2-(methylsulfonyl)ethyl]benzene-1,2-diamine

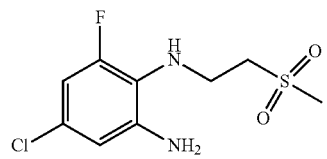 [SMILES: CS(=O)(=O)CCNc1c(N)cc(Cl)cc1F]

A solution of 4-chloro-2-fluoro-N-[2-(methylsulfonyl)ethyl]-6-nitroaniline (23 g, 78 mmol) in methanol (500 mL) was hydrogenated with Raney nickel (5 g) under hydrogen atmosphere at room temperature for 30 minutes. The resulting mixture was filtered through silica gel to afford 14 g of 5-chloro-3-fluoro-$N^2$-[2-(methylsulfonyl)ethyl]benzene-1,2-diamine.

Step 4: Preparation of 5-chloro-2-(chloromethyl)-7-fluoro-1-[2-(methylsulfonyl)ethyl]-1H-benzimidazole

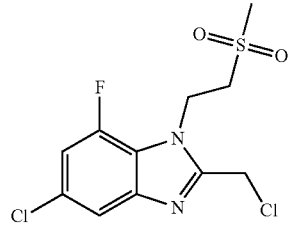 [SMILES: CS(=O)(=O)CCn1c(CCl)nc2cc(Cl)cc(F)c21]

A mixture of 5-chloro-3-fluoro-$N^2$-[2-(methylsulfonyl)ethyl]benzene-1,2-diamine (14 g, 52.4 mmol), bromoacetic acid (36.5 g, 262 mmol) and concentrated hydrochloric acid (100 mL) was heated at 110° C. for 2 hours. The reaction mixture was poured into ice-water (80 g) and then neutralized with sodium bicarbonate. The precipitate was collected by filtration and then dried in vacuo to afford 14.5 g of 5-chloro-2-(chloromethyl)-7-fluoro-1-[2-(methylsulfonyl)ethyl]-1H-benzimidazole.

Step 5: Preparation of 1'-({5-chloro-7-fluoro-1-[2-(methylsulfonyl)ethyl]-1H-benzimidazol-2-yl}methyl)spiro[cyclopropane-1,3'-pyrrolo[2,3-c]pyridin]-2'(1'H)-one To a solution of spiro[cyclopropane-1,3'-pyrrolo[2,3-c]pyridin]-2'(1'H)-one (7.16 g, 44.7 mmol) in N,N-dimethylformamide (80 mL) was added sodium tert-butoxide (4.5 g, 47 mmol) and the resulting mixture was stirred for 30 minutes to obtain a clear solution. Then this clear solution was added dropwise into a cooled solution of 5-chloro-2-

(chloromethyl)-7-fluoro-1-[2-(methylsulfonyl)ethyl]-1H-benzimidazole (14.5 g, 44.7 mmol) in N,N-dimethylformamide (60 mL) at 0° C. After the addition, the resulting solution was stirred at 0° C. for 30 minutes. The reaction mixture was diluted with ice water (1500 mL) and then stirred for 15 minutes. The precipitate was collected by filtration, and then washed with water (20 mL×3) and methanol (10 mL×2). The collected solid was dissolved in a mixture of ethyl acetate (50 mL) and methanol (5 mL). The mixture was refluxed for 10 minutes and filtered to afford 11.5 g of the title product.

Example 37-2

1'-({5,7-Dichloro-1-[2-(methylsulfonyl)ethyl]-1H-benzimidazol-2-yl}methyl)spiro[cyclopropane-1,3'-pyrrolo[2,3-c]pyridin]-2'(1'H)-one The title compound was prepared in analogy to Example 37-1 according to Scheme 16 by using 2,4-dichloroaniline instead of 4-chloro-2-fluoroaniline.

Example 38-1

1'-{[5-Chloro-1-(oxetan-3-ylmethyl)-1H-benzimidazol-2-yl]methyl}spiro[cyclopropane-1,3'-pyrrolo[2,3-c]pyridin]-2'(1'H)-one Step 1: Preparation of 4-chloro-2-nitro-N-(oxetan-3-ylmethyl)aniline

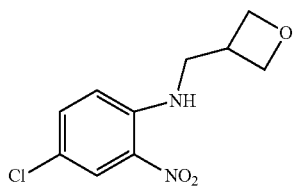 [SMILES: O=[N+]([O-])c1cc(Cl)ccc1NCC1COC1]

A mixture of oxetan-3-ylmethanamine (250 mg, 2.87 mmol), 4-chloro-1-fluoro-2-nitrobenzene (503 mg, 2.87 mmol) and N-ethyl-N-isopropylpropan-2-amine (1.10 g, 8.52 mmol) in tetrahydrofuran (10 mL) was stirred at room temperature for 3 days. The reaction mixture was concentrated in vacuo. The residue was purified by flash column (eluting with 0-50% ethyl acetate in petroleum ether) to afford 300 mg of 4-chloro-2-nitro-N-(oxetan-3-ylmethyl)aniline.

Step 2: Preparation of 4-chloro-N¹-(oxetan-3-ylmethyl)benzene-1,2-diamine

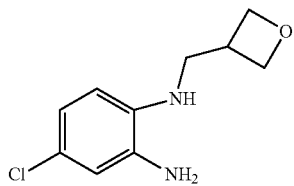 [SMILES: Nc1cc(Cl)ccc1NCC1COC1]

A mixture of 4-chloro-2-nitro-N-(oxetan-3-ylmethyl)aniline (300 mg, 1.24 mmol) and Raney Nickel (100 mg) in methanol (10 mL) was stirred under hydrogen atmosphere at room temperature for 2 hours. The reaction mixture was filtered through silica pad and the filtrate was concentrated in vacuo. The residue was purified by preparative TLC (ethyl acetate: petroleum ether=1:1) to afford 200 mg of 4-chloro-N¹-(oxetan-3-ylmethyl)benzene-1,2-diamine.

Step 3: Preparation of 5-chloro-2-(chloromethyl)-1-(oxetan-3-ylmethyl)-1H-benzimidazole

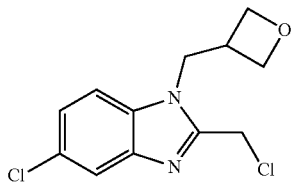 [SMILES: ClCc1nc2cc(Cl)ccc2n1CC1COC1]

A mixture of 4-chloro-N¹-(oxetan-3-ylmethyl)benzene-1,2-diamine (200 mg, 0.94 mmol) and 2-chloro-1,1,1-trimethoxyethane (800 mg, 5.17 mmol) in ethanol (10 mL) was heated under reflux for 2 hours. The resulting mixture was concentrated in vacuo. The residue was purified by preparative TLC (ethyl acetate: petroleum ether=1:1) to afford 200 mg of 5-chloro-2-(chloromethyl)-1-(oxetan-3-ylmethyl)-1H-benzimidazole.

Step 4: Preparation of 1'-{[5-chloro-1-(oxetan-3-ylmethyl)-1H-benzimidazol-2-yl]methyl}spiro[cyclopropane-1,3'-pyrrolo[2,3-c]pyridin]-2'(1'H)-one A mixture of 5-chloro-2-(chloromethyl)-1-(oxetan-3-ylmethyl)-1H-benzimidazole (200 mg, 0.74 mmol), spiro[cyclopropane-1,3'-pyrrolo[2,3-c]pyridin]-2'(1'H)-one (118 mg, 0.74 mmol) and cesium carbonate (287 mg, 0.81 mmol) in acetonitrile (5 mL) was stirred at room temperature overnight. The reaction mixture was filtered and the filtrate was concentrated in vacuo. The residue was purified by preparative HPLC to afford 165 mg of the title product.

Example 38-2

1'-({5-Chloro-1-[2-(oxetan-3-yl)ethyl]-1H-benzimidazol-2-yl}methyl)spiro[cyclopropane-1,3'-pyrrolo[2,3-c]pyridin]-2'(1'H)-one Step 1: Preparation of oxetan-3-ylideneacetonitrile

To a cooled slurry of sodium hydride (5.56 g, 139 mmol) in tetrahydrofuran (150 mL) was added a solution of diethyl (cyanomethyl)phosphonate (24.6 g, 139 mmol) in tetrahydrofuran (20 mL) dropwise in an ice-water bath. The mixture was stirred at 0° C. for 30 minutes. To the resulting mixture was added a solution of oxetan-3-one (10.0 g, 139 mmol) in tetrahydrofuran (30 mL) dropwise in an ice-water bath. The mixture was warmed naturally to room temperature and then stirred overnight. The resulting reaction mixture was poured into water (200 mL) and then extracted with ethyl acetate (200 mL×2). The combined organic layer was washed with brine, and then dried over sodium sulfate and then concentrated in vacuo. The residue was purified by flash column (eluting with 0-50% ethyl acetate in petroleum ether) to afford 7.0 g of oxetan-3-ylideneacetonitrile.

Step 2: Preparation of 2-(oxetan-3-yl)-ethylamine

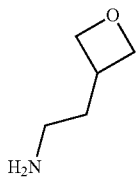

A mixture of oxetan-3-ylideneacetonitrile (3.0 g, 31.5 mmol) and 7 N ammonia in methanol (200 mL) was stirred with 10% palladium on carbon (600 mg) and platinum(IV) oxide (600 mg) under 50 psi of hydrogen overnight. The reaction mixture was filtered through silica pad and the filtrate was concentrated in vacuo to afford the crude 2-(oxetan-3-yl)-ethylamine which was used directly into next step without any further purification.

Step 3: Preparation of 1'-({5-chloro-1-[2-(oxetan-3-yl)ethyl]-1H-benzimidazol-2-yl}methyl)spiro[cyclopropane-1,3'-pyrrolo[2,3-c]pyridin]-2'(1'H)-one The title compound was prepared in analogy to Example 38-1 according to Scheme 15 by using 2-(oxetan-3-yl)-ethylamine instead of oxetan-3-ylmethanamine.

Example 38-3

1'-{[5-Chloro-7-fluoro-1-(oxetan-3-ylmethyl)-1H-benzimidazol-2-yl]methyl}spiro[cyclopropane-1,3'-pyrrolo[2,3-c]pyridin]-2'(1'H)-one Step 1: Preparation of 4-chloro-2-fluoro-6-nitro-N-(oxetan-3-ylmethyl)aniline

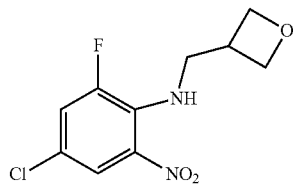

A mixture of oxetan-3-ylmethanamine (179 mg, 2.00 mmol, 97% purity), 4-chloro-2-fluoro-6-nitrophenyl trifluoromethanesulfonate (650 mg, 2.00 mmol) and potassium phosphate (424 mg, 2.00 mmol) in acetonitrile (20 mL) was stirred at room temperature overnight under nitrogen atmosphere. The reaction mixture was concentrated in vacuo. The residue was purified by flash column (eluting with 0-50% ethyl acetate in petroleum ether) to afford 165 mg of 4-chloro-2-fluoro-6-nitro-N-(oxetan-3-ylmethyl)aniline.

Step 2: Preparation of 1'-{[5-chloro-7-fluoro-1-(oxetan-3-ylmethyl)-1H-benzimidazol-2-yl]methyl}spiro[cyclopropane-1,3'-pyrrolo[2,3-c]pyridin]-2'(1'H)-one The title compound was prepared in analogy to Example 38-1 according to Scheme 15 by using 4-chloro-2-fluoro-6-nitro-N-(oxetan-3-ylmethyl)aniline instead of 4-chloro-2-nitro-N-(oxetan-3-ylmethyl)aniline.

Example 39-1

1'-({1-[(3-Aminooxetan-3-yl)methyl]-5-chloro-1H-benzimidazol-2-yl}methyl)spiro[cyclopropane-1,3'-pyrrolo[2,3-c]pyridin]-2'(1'H)-one Step 1: Preparation of 4-methoxybenzyl(3-{[5-chloro-2-{2'-oxospiro[cyclopropane-1,3'-pyrrolo[2,3-c]pyridin]-1'(2'H)-yl)methyl}-1H-benzo[d]imidazol-1-yl]methyl}oxetan-3-yl)carbamate

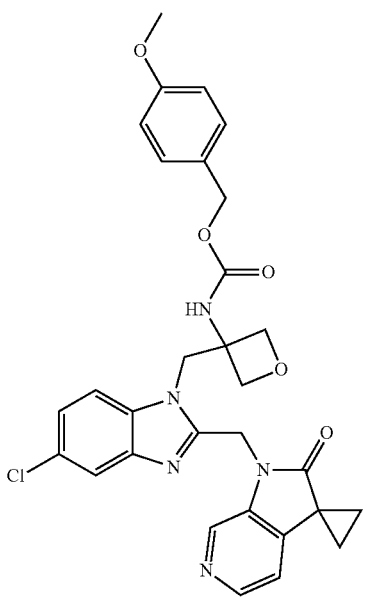 [SMILES: COc1ccc(COC(=O)NC2(Cn3c(CN4C(=O)C5(CC5)c5ccncc54)nc4cc(Cl)ccc43)COC2)cc1]

4-Methoxybenzyl(3-{[5-chloro-2-{2'-oxospiro[cyclopropane-1,3'-pyrrolo[2,3-c]pyridin]-1'(2'H)-yl)methyl}-1H-benzo[d]imidazol-1-yl]methyl}oxetan-3-yl)carbamate was prepared in analogy to Example 38-1 according to Scheme 15 by using 4-methoxybenzyl[3-(aminomethyl)oxetan-3-yl]carbamate instead of oxetan-3-ylmethanamine.

Step 2: Preparation of 1'-({1-[(3-aminooxetan-3-yl)methyl]-5-chloro-1H-benzimidazol-2-yl}methyl)spiro[cyclopropane-1,3'-pyrrolo[2,3-c]pyridin]-2' (1'H)-one A solution of 4-methoxybenzyl(3-{[5-chloro-2-{2'-oxospiro[cyclopropane-1,3'-pyrrolo[2,3-c]pyridin]-1'(2'H)-yl)methyl}-1H-benzo[d]imidazol-1-yl]methyl}oxetan-3-yl)carbamate (573 mg, 1.0 mmol) in dichloromethane (10 mL) was added trifluoroacetic acid (2.5 mL). The reaction mixture was stirred for 2 hours and then diluted with dichloromethane (20 mL) and then washed with saturated aqueous solution of sodium carbonate (20 mL). The separated aque-

215 ous layer was extracted with dichloromethane (20 mL). The combined organic layer was dried over sodium sulfate and then concentrated in vacuo. The residue was purified by preparative HPLC to afford 230 mg of the title product as a white solid.

Example 39-2

1'-({1-[(3-Aminooxetan-3-yl)methyl]-5-chloro-7-fluoro-1H-benzimidazol-2-yl}methyl)spiro[cyclopropane-1,3'-pyrrolo[2,3-c]pyridin]-2'(1'H)-one The title compound was prepared in analogous to Example 39-1 according to Scheme 17 by using 4-chloro-2-fluoro-6-nitrophenyl trifluoromethanesulfonate instead of 4-chloro-1-fluoro-2-nitrobenzene.

BIOLOGICAL EXAMPLES

Example 40

Viral Cytopathic Effect (CPE) Assay

To measure anti-RSV activity of compounds, 96-well plates are seeded with 6×10³ cells per well in Dulbecco's modified Eagle's medium (DMEM) containing 10% fetal bovine serum (FBS). Cells are infected the next day with sufficient RSV Long strain (ATCC) to produce an approximately 80-90% cytopathic effect after 6 days, in the presence of serial half-log diluted compound in a total volume of 200 μA per well. The viability of cells is assessed after 6 days using Cell Counting kit-8 (Dojindo Molecular Technologies). The absorbance at 450 nm and referenced at 630 nm is measured to determine 50% effective concentration ($EC_{50}$)

The compounds of the present invention were tested for their anti-RSV activity, and the activation as described herein. The Examples were tested in the above assay and found to have $EC_{50}$ of about 0.0001 μM to about 10 μM. Particular compound of formula (I) were found to have $EC_{50}$ of about 0.0001 μM to about 1 μM. Further particular compound of formula (I) were found to have $EC_{50}$ of about 0.0001 μM to about 0.1 μM.

Results of CPE assays are given in Table 1.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. Compounds of formula (I)

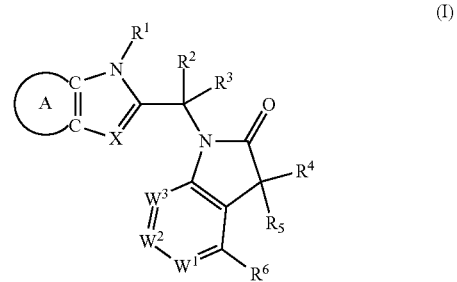

wherein

A is phenyl or pyridinyl, which is unsubstituted or substituted by $C_{1-6}$alkyl, $C_{1-6}$alkoxy, halogen, trifluoromethyl or cyano;

X is nitrogen, —CH or —CR⁷; provided that when X is —CR⁷, R¹ is hydrogen, wherein R⁷ is $C_{1-6}$alkylsulfonyl-$C_yH_{2y}$—;

when X is nitrogen or —CH, R¹ is $C_{1-6}$alkylsulfonylphenyl-$C_yH_{2y}$—, thietan-3-yl-$C_yH_{2y}$—, dioxothietan-3-yl-$C_yH_{2y}$—, oxetan-3-yl-$C_yH_{2y}$—, aminooxetan-3-yl-$C_xH_{2x}$—, $C_{1-6}$alkylsufinyl-$C_yH_{2y}$—,

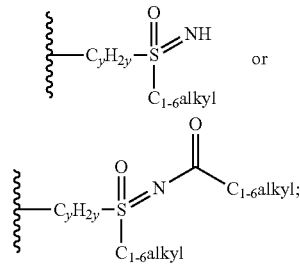

or R¹ is —$C_yH_{2y}$—SO₂R⁸, wherein R⁸ is $C_{1-6}$alkyl, cycloalkyl, $C_{1-6}$alkylcarbonylamino, $C_{1-6}$alkylamino, di$C_{1-6}$alkylamino, amino, morpholinyl, pyrrolidinyl, piperazinyl,

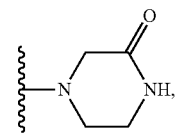

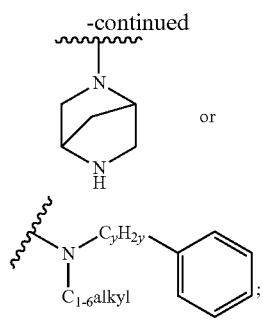

or

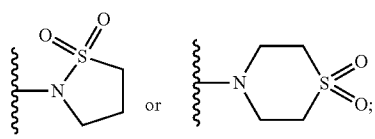 [SMILES: *N1CCCS1(=O)=O ; *N1CCS(=O)(=O)CC1]

or $R^1$ is —$C_yH_{2y}$—$COR^9$, wherein $R^9$ is cycloalkylsulfonylamino, cycloalkylsulfonylamino($C_{1-6}$alkyl) or $C_{1-6}$alkylsulfonylamino($C_{1-6}$alkyl); or $R^1$ is —$C_xH_{2x}$—$NR^{10}R^{11}$, wherein $R^{10}$ and $R^{11}$, together with the nitrogen atom, to which they are attached, form or $R^2$ and $R^3$ are hydrogen or deuterium simultaneously;
$R^4$ and $R^5$, with the carbon atom to which they are attached, form cyclopropyl;
$R^6$ is hydrogen or halogen;
$W^1$ is nitrogen or —$CR^{12}$, wherein $R^{12}$ is hydrogen or halogen;
$W^2$ is —CH or nitrogen;
$W^3$ is —CH or nitrogen; provided that at most one of $W^1$, $W^2$ and $W^3$ is nitrogen;
x is 2-6;
y is 1-6;
or a pharmaceutically acceptable salt thereof.

2. A compound according to claim 1, wherein
A is phenyl, which is unsubstituted or once or twice substituted by $C_{1-6}$alkyl, $C_{1-6}$alkoxy, halogen, trifluoromethyl or cyano; or pyridinyl, which is unsubstituted or once substituted by $C_{1-6}$alkyl or halogen or pharmaceutically acceptable salt thereof.

3. A compound according to claim 1, wherein
A is phenyl, which is unsubstituted or once or twice substituted by methyl, ethyl, fluoro, chloro, bromo, methoxy, trifluoromethyl or cyano; or pyridinyl, which is unsubstituted or once substituted by methyl or chloro;
X is nitrogen, —CH or —$CR^7$; provided that
when X is —$CR^7$, $R^1$ is hydrogen, wherein $R^7$ is ethylsulfonylethyl, methylsulfonylethyl or methylsulfonylpropyl;
when X is nitrogen or —CH, $R^1$ is aminosulfonylpropyl, cyclopropylsulfonylaminocarbonylethyl, cyclopropylsulfonylamino(methyl)carbonylethyl, cyclopropylsulfonylethyl, cyclopropylsulfonylpropyl, dimethylaminosulfonylethyl, dimethylaminosulfonylpropyl, ethylsulfonylethyl, ethylsulfonylpropyl, methylaminosulfonylpropyl, methylsulfinylpropyl, methylsulfonylamino(methyl)carbonylethyl, methylsulfonylaminoethyl, methylsulfonylaminopropyl, methylsulfonylbutyl, methylsulfonylethyl, methylsulfonylphenylmethyl, 4-(methylsulfonyl)piperazin-1-ylethyl, methylsulfonylpropyl, piperazin-1-ylsulfonylpropyl, thietan-3-ylethyl,

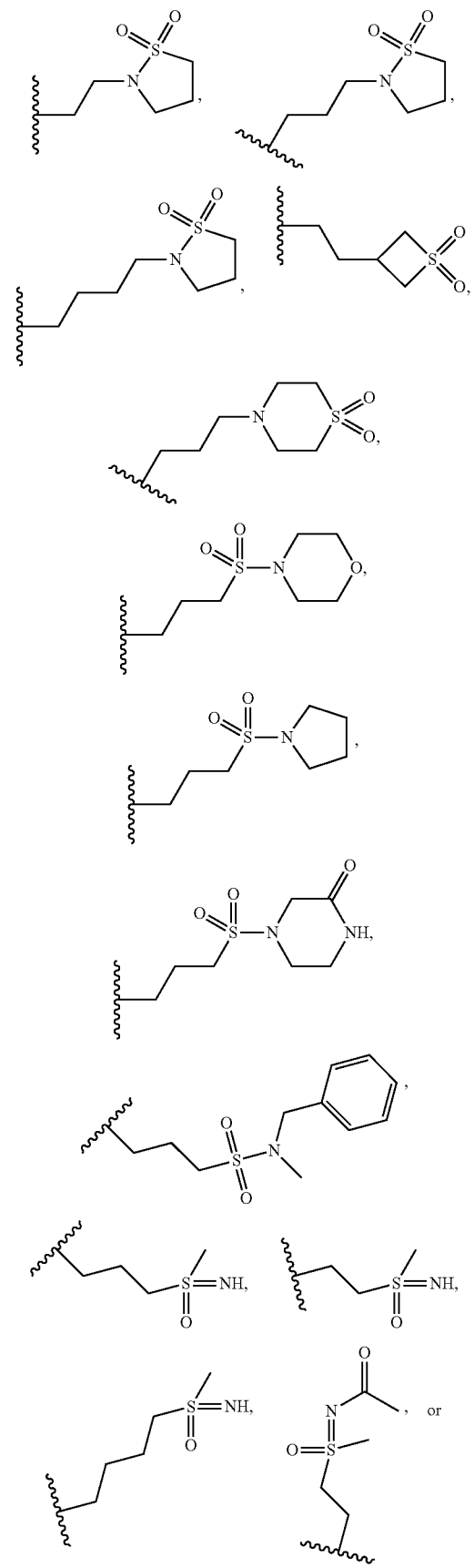

-continued

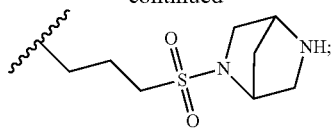

R² and R³ are hydrogen or deuterium simultaneously;
R⁶ is hydrogen, fluoro, chloro or bromo;
W¹ is nitrogen, —CH or —CF;
W² is —CH or nitrogen;
W³ is —CH or nitrogen; provided that at most one of W¹, W² and W³ is nitrogen;
or pharmaceutically acceptable salt thereof.

4. A compound according to claim 2, wherein
R⁶ is hydrogen;
W¹ is —CH;
W² is nitrogen; and
W³ is —CH.

5. A compound according to claim 3, wherein
R⁶ is hydrogen;
W¹ is —CH;
W² is nitrogen; and
W³ is —CH.

6. A compound according to claim 2, wherein
A is phenyl or pyridinyl, which is once substituted by halogen;
X is nitrogen, —CH or —CR⁷; provided that
when X is —CR⁷, R¹ is hydrogen, wherein R⁷ is $C_{1-6}$alkylsulfonyl-$C_yH_{2y}$—;
when X is nitrogen or —CH, R¹ is $C_{1-6}$alkylsulfonyl-$C_yH_{2y}$—;
R² is hydrogen;
R³ is hydrogen;
R⁶ is hydrogen or halogen;
W¹ is nitrogen or —CR¹², wherein R¹² is hydrogen or halogen;
W² is —CH;
W³ is —CH or nitrogen; provided that W¹ and W³ are not nitrogen simultaneously;
x is 2-6;
y is 1-6.

7. A compound according to claim 2, wherein
A is

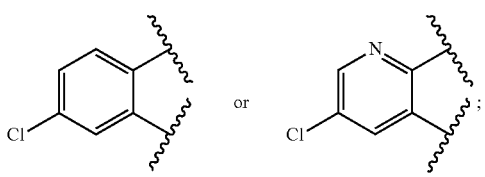 [SMILES: *c1ccc(Cl)cc1* ; *c1cc(Cl)cnc1*]

X is nitrogen, —CH or —CR⁷; provided that
when X is —CR⁷, R¹ is hydrogen, wherein R⁷ is ethylsulfonylethyl;
when X is nitrogen or —CH, R¹ is ethylsulfonylethyl, methylsulfonylethyl, or methylsulfonylpropyl;
R² is hydrogen;
R³ is hydrogen;
R⁶ is hydrogen, fluoro, chloro or bromo;
W¹ is nitrogen, —CH or —CF;
W² is —CH;
W³ is —CH or nitrogen;
provided that W¹ and W³ are not nitrogen simultaneously.

8. A compound having formula:
1'-({1-[2-(Methylsulfonyl)ethyl]-1H-indol-2-yl}methyl)spiro[cyclopropane-1,3'-pyrrolo[2,3-c]pyridin]-2'(1'H)-one;
1'-({5-Methoxy-1-[2-(methylsulfonyl)ethyl]-1H-indol-2-yl}methyl)spiro[cyclopropane-1,3'-pyrrolo[2,3-c]pyridin]-2'(1'H)-one;
1-[2-(Methylsulfonyl)ethyl]-2-[(2'-oxospiro[cyclopropane-1,3'-pyrrolo[2,3-c]pyridin]-1'(2'H)-yl)methyl]-1H-indole-5-carbonitrile;
1'-({5-Fluoro-1-[2(methylsulfonyl)ethyl]-1H-indol-2-yl}methyl)spiro[cyclopropane-1,3'-pyrrolo[2,3-c]pyridin]-2'(1'H)-one;
1'-({5-Bromo-1-[2-(methylsulfonyl)ethyl]-1H-indol-2-yl}methyl)spiro[cyclopropane-1,3'-pyrrolo[2,3-c]pyridin]-2'(1'H)-one;
1'-({4-Chloro-1-[2-(methylsulfonyl)ethyl]-1H-indol-2-yl}methyl)spiro[cyclopropane-1,3'-pyrrolo[2,3-c]pyridin]-2'(1'H)-one;
1'-({7-Chloro-1-[2-(methylsulfonyl)ethyl]-1H-indol-2-yl}methyl)spiro[cyclopropane-1,3'-pyrrolo[2,3-c]pyridin]-2'(1'H)-one;
1'-({5-Ethyl-1-[2-(methylsulfonyl)ethyl]-1H-indol-2-yl}methyl)spiro[cyclopropane-1,3'-pyrrolo[2,3-c]pyridin]-2"(1'H)-one;
1'({5,7-Difluoro-1-[2-(methylsulfonyl)ethyl]-1H-indol-2-yl}methyl)spiro[cyclopropane-1,3'-pyrrolo[2,3-c]pyridin]-2'(1'H)-one;
1'-({1-[2-(Methylsulfonyl)ethyl]-5-(trifluoromethyl)-1H-indol-2-yl}methyl)spiro[cyclopropane-1,3'-pyrrolo[2,3-c]pyridin]-2'(1'H)-one;
1'-({5,6-Difluoro-1-[2-(methylsulfonyl)ethyl]-1H-indol-2-yl}methyl)spiro[cyclopropane-1,3'-pyrrolo[2,3-c]pyridin]-2'(1'H)-one;
1'-({5-Chloro-7-fluoro-1-[2-(methylsulfonyl)ethyl]-1H-indol-2-yl}methyl)spiro[cyclopropane-1,3'-pyrrolo[2,3-c]pyridin]-2'(1'H)-one;
1'-({5-Methyl-1-[2-(methylsulfonyl)ethyl]-1H-indol-2-yl}methyl)spiro[cyclopropane-1,3'-pyrrolo[2,3-c]pyridin]-2'(1'H)-one;
1'-({1-[2-(Methylsulfonyl)ethyl]-1H-pyrrolo[3,2-c]pyridin-2-yl}methyl)spiro[cyclopropane-1,3'-pyrrolo[2,3-c]pyridin]-2'(1'H)-one;
1'-({5-Chloro-1-[2-(ethylsulfonyl)ethyl]-1H-indol-2-yl}methyl)spiro[cyclopropane-1,3'-pyrrolo[2,3-c]pyridin]-2'(1'H)-one;
1'-({5-Chloro-1-[2-(ethylsulfonyl)ethyl]-1H-pyrrolo[2,3-b]pyridin-2-yl}methyl)spiro[cyclopropane-1,3'-pyrrolo[2,3-c]pyridin]-2'(1'H)-one;
1'-({5-Chloro-1-[2-(ethylsulfonyl)ethyl]-1H-indol-2-yl}methyl)spiro[cyclopropane-1,3'-pyrrolo[2,3-b]pyridin]-2'(1'H)-one;
1'-({5-Chloro-1-[2-(methylsulfonyl)ethyl]-1H-indol-2-yl}methyl)spiro[cyclopropane-1,3'-pyrrolo[2,3-b]pyridin]-2'(1'H)-one;
1'-({5-Chloro-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one;
1'-({5-Chloro-1-[2-(methylsulfonyl)ethyl]-1H-pyrrolo[2,3-b]pyridin-2-yl}methyl)-5'-fluorospiro[cyclopropane-1,3'-indol]-2'(1'H)-one;
1'-({5-Chloro-1-[2-(methylsulfonyl)ethyl]-1H-pyrrolo[3,2-b]pyridin-2-yl}methyl)spiro[cyclopropane-1,3'-pyrrolo[2,3-c]pyridin]-2'(1'H)-one;
1'-({5-Chloro-1-[2-(methylsulfonyl)ethyl]-1H-indol-2-yl}methyl)spiro[cyclopropane-1,3'-pyrrolo[3,2-c]pyridin]-2'(1'H)-one;

1'-({5-Chloro-1-[2-(methylsulfonyl)ethyl]-1H-indol-2-yl}methyl)spiro[cyclopropane-1,3'-pyrrolo[2,3-c]pyridin]-2'(1'H)-one;

1'-({5-Chloro-1-[4-(methylsulfonyl)butyl]-1H-indol-2-yl}methyl)spiro[cyclopropane-1,3'-pyrrolo[2,3-c]pyridin]-2'(1'H)-one;

1'-({5-Chloro-1-[4-(methylsulfonyl)benzyl]-1H-indol-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-pyrrolo[2,3-b]pyridin-2-yl}methyl)spiro[cyclopropane-1,3'-pyrrolo[2,3-c]pyridin]-2'(1'H)-one;

1'-({5-Methyl-1-[2-(methylsulfonyl)ethyl]-1H-pyrrolo[2,3-b]pyridin-2-yl}methyl)spiro[cyclopropane-1,3'-pyrrolo[2,3-c]pyridin]-2'(1'H)-one;

1'-({5-Chloro-1-[4-(methylsulfonyl)butyl]-1H-pyrrolo[3,2-b]pyridin-2-yl}methyl)spiro[cyclopropane-1,3'-pyrrolo[2,3-c]pyridin]-2'(1'H)-one;

1'-({5-Chloro-1-[3-(cyclopropylsulfonyl)propyl]-1H-pyrrolo[3,2-b]pyridin-2-yl}methyl)spiro[cyclopropane-1,3'-pyrrolo[2,3-c]pyridin]-2'(1'H)-one;

1'-({5-Chloro-1-[4-(methylsulfonyl)butyl]-1H-pyrrolo[2,3-c]pyridin-2-yl}methyl)spiro[cyclopropane-1,3'-pyrrolo[2,3-c]pyridin]-2'(1'H)-one;

N-Benzyl-3-{5-chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N-methylpropane-1-sulfonamide;

1'-({5-Chloro-1-[3-(cyclopropylsulfonyl)propyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[2(thietan-3-yl)ethyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[2-(1,1-dioxidothietan-3-yl)ethyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[2-(cyclopropylsulfonyl)ethyl]-1H-pyrrolo[3,2-b]pyridin-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-pyrrolo[3,2-b]pyridin-2-yl}methyl)spiro[cyclopropane-1,3'-pyrrolo[2,3-c]pyridin]-2'(1'H)-one;

1'-({5-Chloro-1-[4-(methylsulfonyl)butyl]-1H-pyrrolo[2,3-b]pyridin-2-yl}methyl)spiro[cyclopropane-1,3'-pyrrolo[2,3-c]pyridin]-2'(1'H)-one;

1'-({5-Chloro-1-[3-(methylsulfinyl)propyl]-1H-indol-2-yl}methyl)spiro[cyclopropane-1,3'-pyrrolo[2,3-c]pyridin]-2'(1'H)-one;

1'-({5-Chloro-1-[2-(methylsulfonyl)ethyl]-1H-pyrrolo[2,3-c]pyridin-2-yl}methyl)spiro[cyclopropane-1,3'-pyrrolo[2,3-c]pyridin]-2'(1'H)-one;

1'-({5-Chloro-1-[2-(ethylsulfonyl)ethyl]-1H-pyrrolo[3,2-b]pyridin-2-yl}methyl)spiro[cyclopropane-1,3'-pyrrolo[2,3-c]pyridin]-2'(1'H)-one;

3-{5-Chloro-2-[(2'-oxospiro[cyclopropane-1,3'-pyrrolo[2,3-c]pyridin]-1'(2'H)-yl)methyl]-1H-indol-1-yl}-N,N-dimethylpropane-1-sulfonamide;

3-{5-Chloro-2-[(2'-oxospiro[cyclopropane-1,3'-pyrrolo[2,3-c]pyridin]-1'(2'H)-yl)methyl]-1H-pyrrolo[2,3-b]pyridin-1-yl}-N,N-dimethylpropane-1-sulfonamide;

2-{5-Chloro-2-[(2'-oxospiro[cyclopropane-1,3'-pyrrolo[2,3-c]pyridin]-1'(2'H)-yl)methyl]-1H-indol-1-yl}-N,N-dimethylethanesulfonamide;

1'-({5-Chloro-1-[3-(morpholin-4-ylsulfonyl)propyl]-1H-indol-2-yl}methyl)spiro[cyclopropane-1,3'-pyrrolo[2,3-c]pyridin]-2'(1'H)-one;

1'-({5-Chloro-1-[3-(pyrrolidin-1-ylsulfonyl)propyl]-1H-indol-2-yl}methyl)spiro[cyclopropane-1,3'-pyrrolo[2,3-c]pyridin]-2'(1'H)-one;

1'-[(5-Chloro-1-{3-[(3-oxopiperazin-1-yl)sulfonyl]propyl}-1H-indol-2-yl)methyl]spiro[cyclopropane-1,3'-pyrrolo[2,3-c]pyridin]-2'(1'H)-one;

1'-({5-Chloro-1-[2-(1,1-dioxido-1,2-thiazolidin-2-yl)ethyl]-1H-indol-2-yl}methyl)spiro[cyclopropane-1,3'-pyrrolo[2,3-c]pyridin]-2'(1'H)-one;

1'-({5-Chloro-1-[4-(1,1-dioxido-1,2-thiazolidin-2-yl)butyl]-1H-indol-2-yl}methyl)spiro[cyclopropane-1,3'-pyrrolo[2,3-c]pyridin]-2'(1'H)-one;

1'-({5-Chloro-1[3-(1,1-dioxidothiomorpholin-4-yl)propyl]-1H-indol-2-yl}methyl)spiro[cyclopropane-1,3'-pyrrolo[2,3-c]pyridin]-2'(1'H)-one;

1'-({5-Chloro-1[3-(1,1-dioxido-1,2-thiazolidin-2-yl)propyl]-1H-indol-2-yl}methyl)spiro[cyclopropane-1,3'-pyrrolo[2,3-c]pyridin]-2'(1'H)-one;

1'-{[5-Chloro-1-(3-hydroxypropyl)-1H-indol-2-yl]methyl}spiro[cyclopropane-1,3'-pyrrolo[2,3-c]pyridin]-2'(1'H)-one;

1'-[{5-Chloro-1-[2-(methylsulfonyl)ethyl]-1H-indol2-yl}($^{2}H_2$)1,3'-pyrrolo[2,3-c]pyridin]-2'(1'H)-one-1,3'-pyrrolo[2,3-c]pyridin]-2'(1'H)-one 1'-[{5-Chloro-1-[3-(methylsulfonyl)propyl]-1H-indol-2-yl}($^{2}H_2$)methyl]spiro[cyclopropane-1,3'-pyrrolo[2,3-c]pyridin]-2'(1'H)-one;

Ethyl 3-{5-chloro-2-[(2'-oxospiro[cyclopropane-1,3'-pyrrolo[2,3-c]pyridin]-1'(2'H)-yl)methyl]-1H-indol-1-yl}propanoate;

1'-({5-Chloro-1-[1,1-dioxidothietan-3-yl)ethyl]-1H-pyrrolo[2,3-b]pyridin-2-yl}methyl)spiro[cyclopropane-1,3'-pyrrolo[2,3-c]pyridin]-2'(1'H)-one;

Ethyl 3-{5-chloro-7-fluoro-2-[(2'-oxospiro[cyclopropane-1,3'-pyrrolo[2,3-c]pyridin]-1'(2H)-yl)methyl]-1H-indol-1-yl}propanoate;

1'-({5-Chloro-1[3-(S-methylsulfonimidoyl)propyl]-1H-indol-2-yl}methyl)spiro[cyclopropane-1,3'-pyrrolo[2,3-c]pyridin]-2'(1'H)-one;

1'-({5-Chloro-1-[2-(S-methylsulfonimidoyl)ethyl]-1H-indol-2-yl}methyl)spiro[cyclopropane-1,3'-pyrrolo[2,3-c]pyridin]-2'(1'H)-one;

1'-({5-Chloro-1-[4-(S-methylsulfonimidoyl)butyl]-1H-pyrrolo[2,3-b]pyridin-2-yl}methyl)spiro[cyclopropane-1,3'-pyrrolo[2,3-c]pyridin]-2'(1'H)-one;

1'-({5-Chloro-1-[2-(S-methylsulfonimidoyl)ethyl]-1H-pyrrolo[2,3-b]pyridin-2-yl}methyl)spiro[cyclopropane-1,3'-pyrrolo[2,3-c]pyridin]-2'(1'H)-one;

N-[(2-{5-Chloro-2-[(2'-oxospiro[cyclopropane-1,3'-pyrrolo[2,3-c]pyridin]-1'(2'H)-yl)methyl]-1H-indol-1-yl}ethyl)(methyl)oxido-$\lambda^6$-sulfanylidene]acetamide;

3-{5-Chloro-2-[(2'-oxospiro[cyclopropane-1,3'-pyrrolo[2,3-c]pyridin]-1'(2H)-yl)methyl]-1H-indol-1-yl}propanoic acid;

3-{5-Chloro-7-fluoro-2-[(2'-oxospiro[cyclopropane-1,3'-pyrrolo[2,3-c]pyridin]-1'(2H)-yl)methyl]-1H-indol-1-yl}propanoic acid;

Methyl 4-{5-chloro-2-[(2'-oxospiro[cyclopropane-1,3'-pyrrolo[2,3-c]pyridin]-1'(2'H)-yl)methyl]-1H-indol-1-yl}butanoate;

3-{5-Chloro-2-[(2'-oxospiro[cyclopropane-1,3'-pyrrolo[2,3-c]pyridin]-1'(2H)-yl)methyl]-1H-indol-1-yl}propanamide;

3-{5-Chloro-2-[(2'-oxospiro[cyclopropane-1,3'-pyrrolo[2,3-b]pyridin]-1'(2H)-yl)methyl]-1H-indol-1-yl}propanamide;

4-{5-Chloro-2-[(2'-oxospiro[cyclopropane-1,3'-pyrrolo[2,3-c]pyridin]-1'(2H)-yl)methyl]-1H-indol-1-yl}butanamide;

3-{5-Chloro-2-[(2'-oxospiro[cyclopropane-1,3'-pyrrolo[2,3-c]pyridin]-1'(2H)-yl)methyl]-1H-indol-1-yl}-N-(cyclopropylsulfonyl)propanamide;

3-{5-Chloro-2-[(2'-oxospiro[cyclopropane-1,3'-pyrrolo[2,3-c]pyridin]-1'(2H)-yl)methyl]-1H-indol-1-yl}-N-(cyclopropylsulfonyl)-N-methylpropanamide;

3-{5-Chloro-2-[(2'-oxospiro[cyclopropane-1,3'-pyrrolo[2,3-c]pyridin]-1'(2H)-yl)methyl]-1H-indol-1-yl}-N-methyl-N-(methylsulfonyl)propanamide;

3-(2-{5-Chloro-2-[(2'-oxospiro[cyclopropane-1,3'-pyrrolo[2,3-c]pyridin]-1'(2'H)-yl)methyl]-1H-indol-1-yl}ethyl)imidazolidine-2,4-dione;

1'-[(5-Chloro-1-{3-[(3R)-3-hydroxypyrrolidin-1-yl]propyl}-1H-indol-2-yl)methyl]spiro[cyclopropane-1,3'-pyrrolo[2,3-c]pyridin]-2'(1'H)-one;

1'-({5-Chloro-1-[3-(ethylsulfonyl)propyl]-1H-indol-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-indol-2-yl}methyl)spiro[cyclopropane-1,3'-pyrrolo[2,3-b]pyridin]-2'(1'H)-one;

1'-({5-Chloro-1-[3-(methylsulfonyl)propyl]-1H-indol-2-yl}methyl)spiro[cyclopropane-1,3'-pyrrolo[2,3-c]pyridin]-2'(1'H)-one;

1'-({5-Chloro-1-[3-(ethylsulfonyl)propyl]-1H-pyrrolo[2,3-b]pyridin-2-yl}methyl)spiro[cyclopropane-1,3'-pyrrolo[2,3-c]pyridin]-2'(1'H)-one;

1'-({5-Chloro-1-[2-(piperazin-1-yl)ethyl]-1H-indol-2-yl}methyl)spiro[cyclopropane-1,3'-pyrrolo[2,3-c]pyridin]-2'(1'H)-one;

1'-({5-Chloro-1-[3-(piperazin-1-ylsulfonyl)propyl]-1H-indol-2-yl}methyl)spiro[cyclopropane-1,3'-pyrrolo[2,3-c]pyridin]-2'(1'H)-one;

1'-[(5-Chloro-1-{3-[(1R,4R)-2,5-diazabicyclo[2.2.1]hept-2-ylsulfonyl]propyl}-1H-indol-2-yl)methyl]spiro[cyclopropane-1,3'-pyrrolo[2,3-c]pyridin]-2'(1'H)-one;

1'-({5-Chloro-1-[3-(2-oxopiperazin-1-yl)propyl]-1H-indol-2-yl}methyl)spiro[cyclopropane-1,3'-pyrrolo[2,3-c]pyridin]-2'(1'H)-one;

1'-{[1-(2-Aminoethyl)-5-chloro-1H-indol-2-yl]methyl}spiro[cyclopropane-1,3'-pyrrolo[2,3-c]pyridin]-2'(1'H)-one;

3-{5-Chloro-2-[(2'-oxospiro[cyclopropane-1,3'-pyrrolo[2,3-c]pyridin]-1'(2H)-yl)methyl]-1H-pyrrolo[2,3-b]pyridin-1-yl}-N-methylpropane-1-sulfonamide;

3-{5-Chloro-2-[(2'-oxospiro[cyclopropane-1,3'-pyrrolo[2,3-c]pyridin]-1'(2H)-yl)methyl]-1H-indol-1-yl}-N-methylpropane-1-sulfonamide;

3-{5-Chloro-2-[(2'-oxospiro[cyclopropane-1,3'-pyrrolo[2,3-c]pyridin]-1'(2H)-yl)methyl]-1H-pyrrolo[2,3-b]pyridin-1-yl}propane-1-sulfonamide;

1'-({1-[2-(4-Acetylpiperazin-1-yl)ethyl]-5-chloro-1H-indol-2-yl}methyl)spiro[cyclopropane-1,3'-pyrrolo[2,3-c]pyridin]-2'(1'H)-one;

N-[(3-{5-Chloro-2-[(2'-oxospiro[cyclopropane-1,3'-pyrrolo[2,3-c]pyridin]-1'(2H)-yl)methyl]-1H-pyrrolo[2,3-b]pyridin-1-yl}propyl)sulfonyl]acetamide;

N-(2-{5-Chloro-2-[(2'-oxospiro[cyclopropane-1,3'-pyrrolo[2,3-c]pyridin]-1'(2H)-yl)methyl]-1H-indol-1-yl}ethyl)acetamide;

1'-[(5-Chloro-1-{2-[4-(methylsulfonyl)piperazin-1-yl]ethyl}-1H-indol-2-yl)methyl]spiro[cyclopropane-1,3'-pyrrolo[2,3-c]pyridin]-2'(1'H)-one;

N-(2-{5-Chloro-2-[(2'-oxospiro[cyclopropane-1,3'-pyrrolo[2,3-c]pyridin]-1'(2'H)-yl)methyl]-1H-indol-1-yl}ethyl)methanesulfonamide;

N-(3-{5-Chloro-2-[(2'-oxospiro[cyclopropane-1,3'-pyrrolo[2,3-c]pyridin]-1'(2'H)-yl)methyl]-1H-indol-1-yl}propyl)methanesulfonamide;

1-(2-{5-Chloro-2-[(2'-oxospiro[cyclopropane-1,3'-pyrrolo[2,3-c]pyridin]-1'(2H)-yl)methyl]-1H-indol-1-yl}ethyl)urea;

1'-[(5-Chloro-1-{3-[(2-hydroxyethyl)amino]propyl}-1H-indol-2-yl)methyl]spiro[cyclopropane-1,3'-pyrrolo[2,3-c]pyridin]-2'(1'H)-one;

Methyl (3-{5-chloro-2-[(2'-oxospiro[cyclopropane-1,3'-pyrrolo[2,3-c]pyridin]-1'(2'H)-yl)methyl]-1H-indol-1-yl}propyl)carbamate;

3-{5-Chloro-2-[(2'-oxospiro[cyclopropane-1,3'-pyrrolo[2,3-c]pyridin]-1'(2H)-yl)methyl]-1H-indol-1-yl}propyl(2,2,2-trifluoroethyl)carbamate;

1'-({6-Chloro-3-[2-(ethylsulfonyl)ethyl]-1H-indol-2-yl}methyl)spiro[cyclopropane-1,3'-pyrrolo[2,3-b]pyridin]-2'(1'H)-one;

1'-({6-Chloro-3-[2-(methylsulfonyl)ethyl]-1H-indol-2-yl}methyl)spiro[cyclopropane-1,3'-pyrrolo[2,3-c]pyridin]-2'(1'H)-one;

1'-({6-Chloro-3-[3-(methylsulfonyl)propyl]-1H-indol-2-yl}methyl)spiro[cyclopropane-1,3'-pyrrolo[2,3-c]pyridin]-2'(1'H)-one;

1'-({5-Chloro-1-[2-(methylsulfonyl)ethyl]-1H-benzimidazol-2-yl}methyl)spiro[cyclopropane-1,3'-pyrrolo[2,3-c]pyridin]-2'(1'H)-one;

1'-({5-Chloro-1-[2-(methylsulfonyl)ethyl]-1H-benzimidazol-2-yl}methyl)-4'-fluorospiro[cyclopropane-1,3'-indol]-2'(1'H)-one;

4'-Chloro-1'-({5-chloro-1-[2-(methylsulfonyl)ethyl]-1H-benzimidazol-2-yl}methyl)spiro[cyclopropane-1,3'-indol]-2'(1'H)-one;

4'-Bromo-1'-({5-chloro-1-[2-(methylsulfonyl)ethyl]-1H-benzimidazol-2-yl}methyl)spiro[cyclopropane-1,3'-indol]-2'(1'H)-one;

1'-({5-Chloro-1-[2-(ethylsulfonyl)ethyl]-1H-benzimidazol-2-yl}methyl)spiro[cyclopropane-1,3'-pyrrolo[2,3-c]pyridin]-2'(1'H)-one;

1'-({5-Chloro-1-[2-(1,1-dioxidothietan-3-yl)ethyl]-1H-benzimidazol-2-yl}methyl)spiro[cyclopropane-1,3'-pyrrolo[2,3-c]pyridin]-2'(1'H)-one;

1'-({5-Chloro-1-[3-(methylsulfonyl)propyl]-1H-benzimidazol-2-yl}methyl)spiro[cyclopropane-1,3'-pyrrolo[2,3-c]pyridin]-2'(1'H)-one;

1'-({5-Chloro-1-[2-(cyclopropylsulfonyl)ethyl]-1H-benzimidazol-2-yl}methyl)spiro[cyclopropane-1,3'-pyrrolo[2,3-c]pyridin]-2'(1'H)-one;

1l'-({5-Chloro-7-fluoro-1-[2-(methylsulfonyl)ethyl]-1H-benzimidazol-2-yl}methyl)spiro[cyclopropane-1,3'-pyrrolo[2,3-c]pyridin]-2'(1'H)-one;

1'-({5,7-Dichloro-1-[2-(methylsulfonyl)ethyl]-1H-benzimidazol-2-yl}methyl)spiro[cyclopropane-1,3'-pyrrolo[2,3-c]pyridin]-2'(1'H)-one;

1'-{[5-Chloro-1-(oxetan-3-ylmethyl)-1H-benzimidazol-2-yl]methyl}spiro[cyclopropane-1,3'-pyrrolo[2,3-c]pyridin]-2'(1'H)-one;

1'-({5-Chloro-1-[2-(oxetan-3-yl)ethyl]-1H-benzimidazol-2-yl}methyl)spiro[cyclopropane-1,3'-pyrrolo[2,3-c]pyridin]-2'(1'H)-one;

1'-{[5-Chloro-7-fluoro-1-(oxetan-3-ylmethyl)-1H-benzimidazol-2-yl]methyl}spiro[cyclopropane-1,3'-pyrrolo[2,3-c]pyridin]-2'(1'H)-one;

1'-({1-[(3-Aminooxetan-3-yl)methyl]-5-chloro-1H-benzimidazol-2-yl}methyl)spiro[cyclopropane-1,3'-pyrrolo[2,3-c]pyridin]-2'(1'H)-one; and 1'-({1-[(3-Aminooxetan-3-yl)methyl]-5-chloro-7-fluoro-1H-benzimidazol-2-yl}methyl)spiro[cyclopropane-1,3'-pyrrolo[2,3-c]pyridin]-2'(1'H)-one.

9. A process for the preparation of a compound of formula (I):

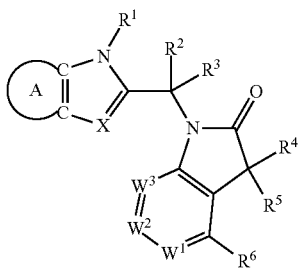

wherein,

A is phenyl or pyridinyl, which is unsubstituted or substituted by $C_{1-6}$alkyl, $C_{1-6}$alkoxy, halogen, trifluoromethyl or cyano;

X is nitrogen, —CH or —CR$^7$; provided that when X is —CR$^7$, R$^1$ is hydrogen, wherein R$^7$ is $C_{1-6}$alkylsulfonyl-C$_y$H$_{2y}$—;

when X is nitrogen or —CH, R$^1$ is $C_{1-6}$alkylsulfonylphenyl-C$_y$H$_{2y}$—, thietan-3-yl-C$_y$H$_{2y}$—, dioxothietan-3-yl-C$_y$H$_{2y}$—, oxetan-3-yl-C$_y$H$_{2y}$—, aminooxetan-3-yl-C$_x$H$_{2x}$—, hydroxy-C$_x$H$_{2x}$—, $C_{1-6}$alkylsufinyl-C$_y$H$_{2y}$—, trifluoromethyl-C$_y$H$_{2y}$-aminocarbonyl-O-C$_x$H$_{2x}$—,

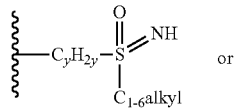 or

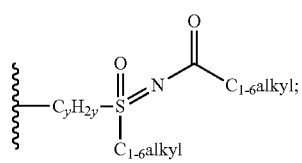

or R$^1$ is —C$_y$H$_{2y}$—SO$_2$R$^8$, wherein R$^8$ is $C_{1-6}$alkyl, cycloalkyl, $C_{1-6}$alkylcarbonylamino, $C_{1-6}$alkylamino, diC$_{1-6}$alkylamino, amino, morpholinyl, pyrrolidinyl, piperazinyl,

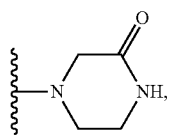

-continued

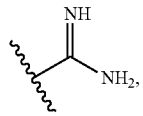

or R$^1$ is —C$_y$H$_{2y}$—COR$^9$, wherein R$^9$ is $C_{1-6}$alkoxy, amino, hydroxy, cycloalkylsulfonylamino, cycloalkylsulfonylamino(C$_{1-6}$alkyl) or $C_{1-6}$alkylsulfonylamino (C$_{1-6}$alkyl); or R$^1$ is —C$_x$H$_{2y}$—NR$^{10}$R$^{11}$, wherein R$^{10}$ is hydrogen, R$^{11}$ is hydrogen, $C_{1-6}$alkoxycarbonyl, $C_{1-6}$alkylcarbonyl, $C_{1-6}$alkylsulfonyl, hydroxy-C$_x$H$_{2x}$— or

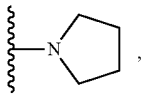

R$^{10}$ and R$^{11}$, together with the nitrogen atom, to which they are attached, form

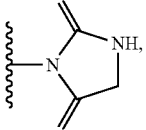

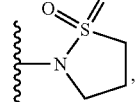

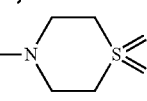

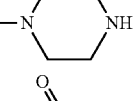

which is unsubstituted or substituted by hydroxy, $C_{1-6}$alkylcarbonyl or $C_{1-6}$alkylsulfonyl;

R$^2$ and R$^3$ are hydrogen or deuterium simultaneously;

R$^4$ and R$^5$, with the carbon atom to which they are attached, form cyclopropyl;

$R^6$ is hydrogen or halogen;
$W^1$ is nitrogen or $-CR^{12}$, wherein $R^{12}$ is hydrogen or halogen;
$W^2$ is $-CH$ or nitrogen;
$W^3$ is $-CH$ or nitrogen; provided that at most one of $W^1$, $W^2$ and $W^3$ is nitrogen;
x is 2-6;
y is 1-6;
the process comprising the reaction of:
(a) a compound of formula (A)

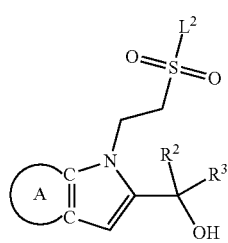

(A)

wherein $L^2$ is $C_{1-6}$alkyl, with

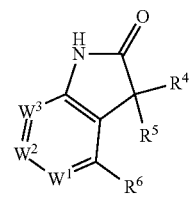

in the presence of a phosphine reagent and an azidocarbonyl reagent to form a compound of formula (Iaa)

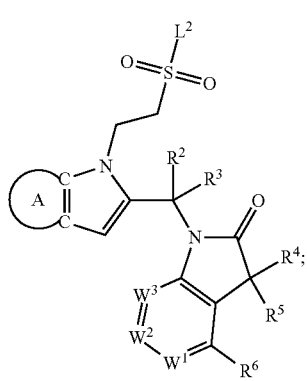

(Iaa)

or
(b) a compound of formula (B)

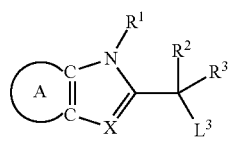

(B)

wherein $L^3$ is chloro or $-OSO_2CH_3$, with

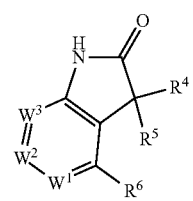

in the presence of a base to form a compound of formula (Iab),

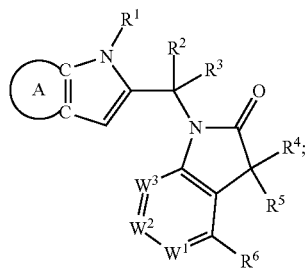

(Iab)

or
(c) a compound of formula (C)

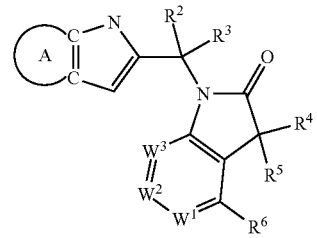

(C)

with $X^2-R^1$, wherein $X^2$ is chloro, bromo, iodo or 4-methylbenzenesulfonate, in the presence of a base to form a compound of formula (Iac)

(Iac)

or
(d) a compound of formula (D)

(D)

with acetyl chloride in the presence of a base to form a compound of formula (Iaf)

(Iaf)

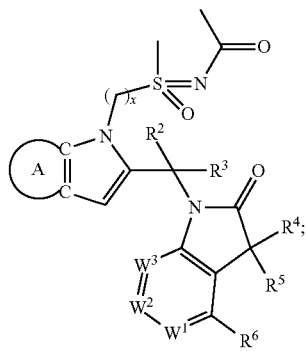

or
(e) a compound of formula (E)

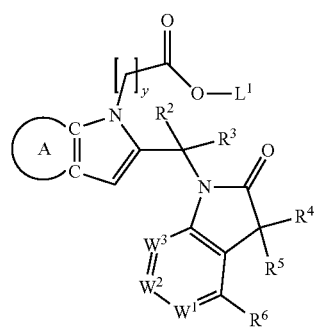
(E)

wherein $L^1$ is $C_{1-6}$alkyl, in the presence of a base to form a compound of formula (Iai),

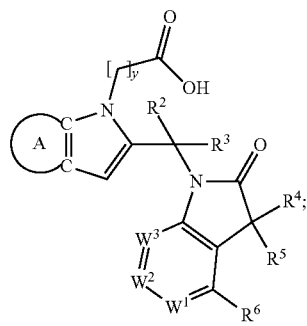
(Iai)

or
(f) a compound of formula (F)

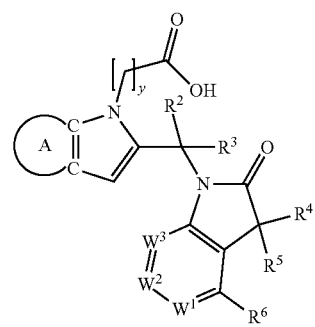
(F)

with thionyl chloride in the presence of methanol to form a compound of formula (Iaj)

(Iaj)

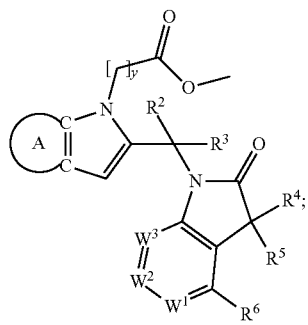

or
(g) a compound of formula (F)

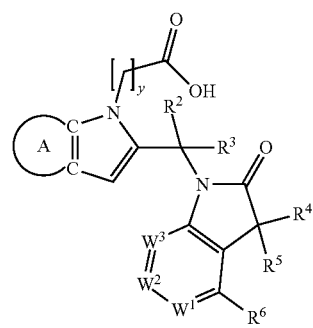
(F)

with a sulfonamide having the formula $L^4$-NH—S(O)$_2$-$L^5$, wherein $L^4$ is hydrogen or $C_{1-6}$alkyl and $L^5$ is $C_{1-6}$alkyl in the presence of N-[3-(dimethylamino)propyl]-N'-ethylcarbodiimide hydrochloride and 4-dimethylamiopryidine to form a compound of formula (Iak)

(Iak)

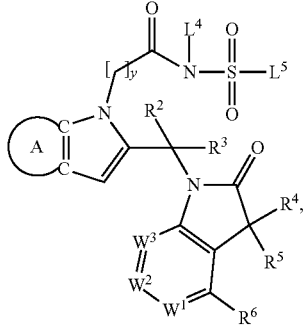

or
(h) a compound of formula (G)

(G)

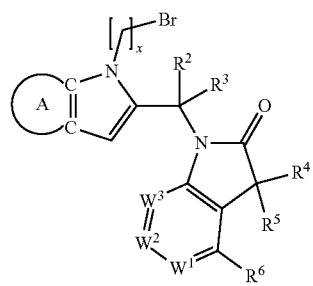

with imidazolidine-2,4-dione in the presence of a base to form a compound of formula (Iam)

(Iam)

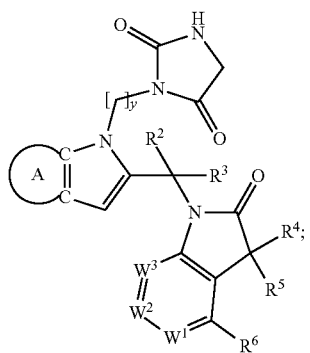

or
(j) a compound of formula (G)

(G)

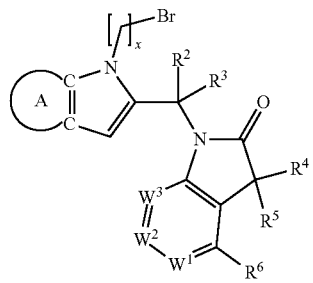

with (3R)-pyrrolidin-3-ol in the presence of a base to form a compound of formula (Ian)

(Ian)

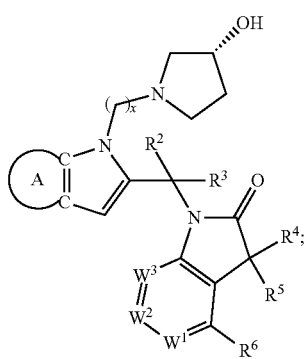

or
(k) a compound of formula (J)

(J)

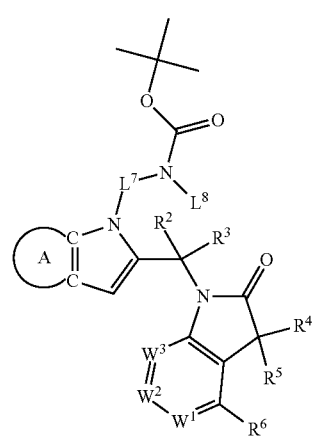

wherein $L^7$ is —$C_xH_{2x}$ and $L^8$ is hydrogen or $C_{1-6}$alkyl; or $L^7$ and $L^8$, together with the nitrogen, to which they are attached, form

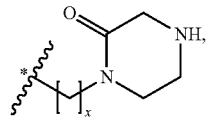

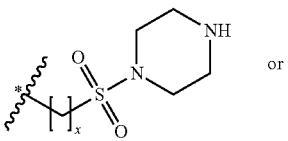

or

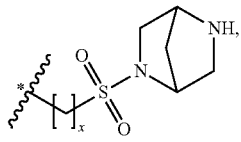

with hydrochloride or trifluoroacetic acid to form a compound of formula (Iap), (Iap)

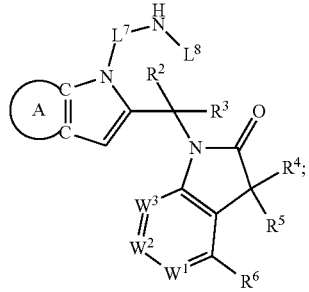

or
(l) a compound of formula (K)

(K)

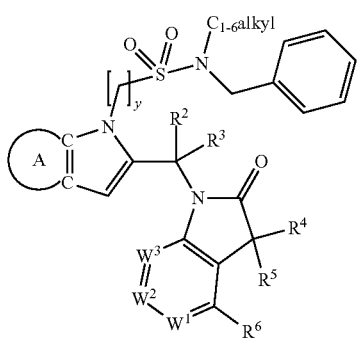

with concentrated sulfuric acid to form a compound of formula (Ias)

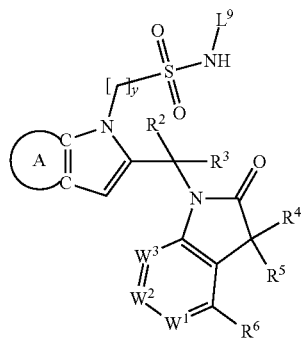

wherein $L^9$ is $C_{1-6}$alkyl; or
(m) a compound of formula (M)

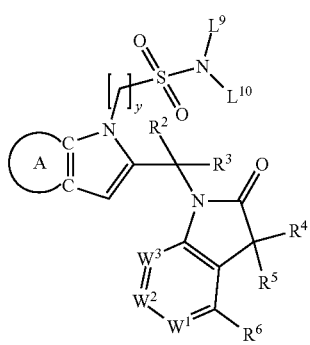

wherein $L^9$ and $L^{10}$ are independently p-methoxybenzyl, with trifluoroacetic acid to form a compound of formula (Iar);

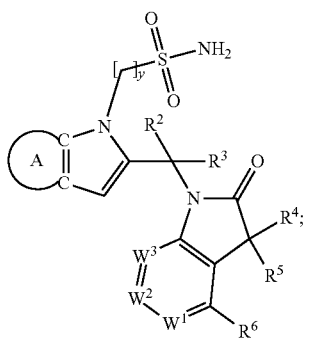

or
(n) a compound of formula (N)

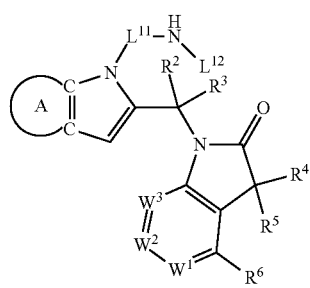

wherein $L^{11}$ is —$C_xH_{2x}$— or —$C_xH_{2x}$-sulfonyl; and $L^{12}$ is hydrogen or $C_{1-6}$alkyl; with methanesulfonyl chloride in the presence of a base to form a compound of formula (Iau),

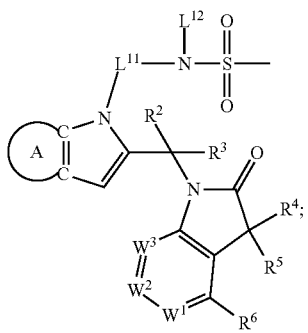

or
(o) a compound of formula (N)

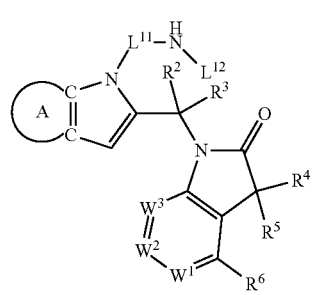

wherein $L^{11}$ is —$C_xH_{2x}$— or —$C_xH_{2x}$-sulfonyl; and $L^{12}$ is hydrogen or $C_{1-6}$alkyl; with acetic anhydride or acetyl chloride in the presence of a base to form a compound of formula (Iav),

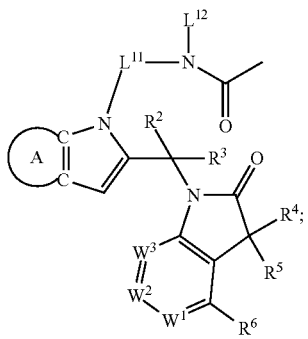

or
(p) a compound of formula (N)

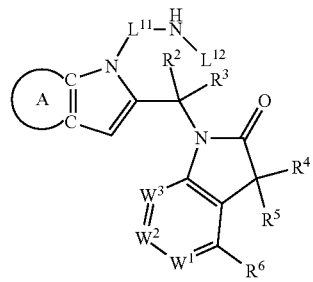

wherein $L^{11}$ is —$C_xH_{2x}$— or —$C_xH_{2x}$-sulfonyl; and $L^{12}$ is hydrogen or $C_{1-6}$alkyl; with methyl carbonochloridate in the presence of a base to form a compound of formula (Iaw),

235

(Iaw)
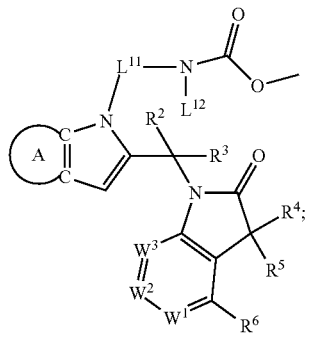

or (q) a compound of formula (N)

(N)
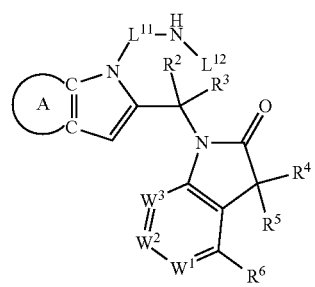

wherein $L^{11}$ is —$C_xH_{2x}$— or —$C_xH_{2x}$-sulfonyl; and $L^{12}$ is hydrogen or $C_{1-6}$alkyl; with 2-bromoethanol in the presence of a base to form a compound of formula (Iax), (Iax)
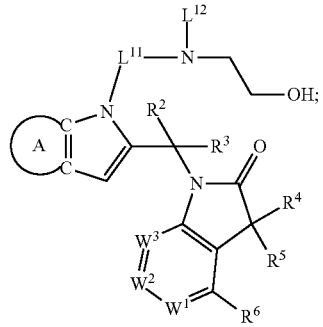

or (r) a compound of formula (N)

(N)
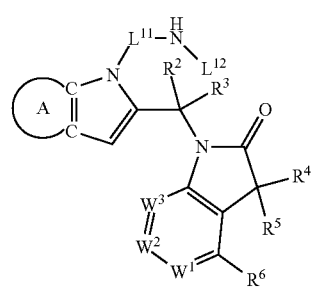

wherein $L^{11}$ is —$C_xH_{2x}$— or —$C_xH_{2x}$-sulfonyl; and $L^{12}$ is hydrogen or $C_{1-6}$alkyl; with methyl carbamimidothioate in the presence of sulfuric acid to form a compound of formula (Iay),

236

(Iay)
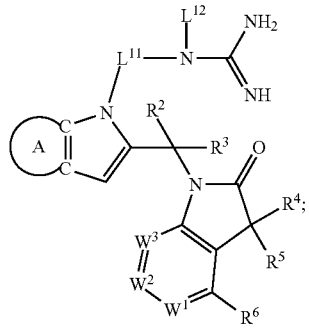

or (s) a compound of formula (P)

(P)
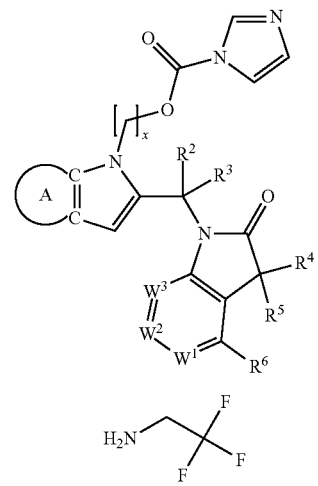

with $H_2N$—$CF_3$ (2,2,2-trifluoroethylamine)

in the presence of a base to form a compound of formula (Iba)

(Iba)
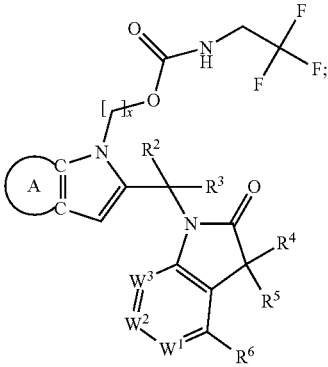

or (t) a compound of formula (Q)

(Q)
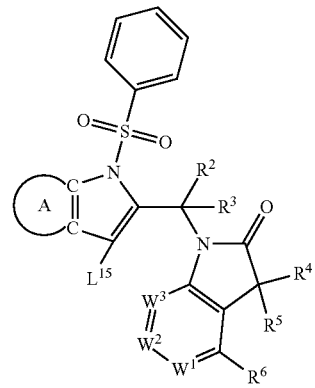

wherein $L^{15}$ is $C_{1-6}$alkylsulfonyl-$C_xH_{2x}$—, with tetrabutylammonium fluoride to form a compound of formula (Ibc),

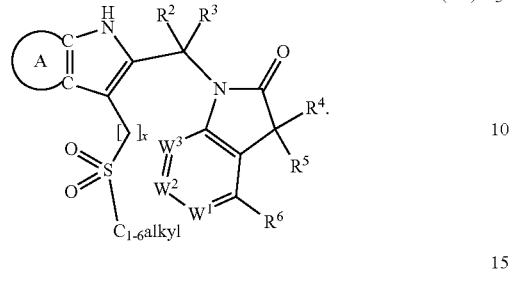

(Ibc)

10. A pharmaceutical composition comprising a compound in accordance with claim 1 and a therapeutically inert carrier.

11. A method for the treatment or prophylaxis of respiratory syncytial virus infection, which method comprises administering an effective amount of a compound as defined in claim 1.

* * * * *